(12) United States Patent
Stone et al.

(10) Patent No.: US 9,605,319 B2
(45) Date of Patent: Mar. 28, 2017

(54) GENE SIGNATURES FOR CANCER DIAGNOSIS AND PROGNOSIS

(75) Inventors: Steven Stone, Salt Lake City, UT (US); Alexander Gutin, Salt Lake City, UT (US); Susanne Wagner, Salt Lake City, UT (US); Julia Reid, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 695 days.

(21) Appl. No.: 13/819,963

(22) PCT Filed: Aug. 30, 2011

(86) PCT No.: PCT/US2011/049760
§ 371 (c)(1),
(2), (4) Date: Jun. 11, 2013

(87) PCT Pub. No.: WO2012/030840
PCT Pub. Date: Mar. 8, 2012

(65) Prior Publication Data
US 2013/0302242 A1    Nov. 14, 2013

Related U.S. Application Data

(60) Provisional application No. 61/378,220, filed on Aug. 30, 2010, provisional application No. 61/407,791, filed on Oct. 28, 2010.

(51) Int. Cl.
*C12Q 1/68* (2006.01)
*G01N 33/50* (2006.01)
*G06F 19/20* (2011.01)

(52) U.S. Cl.
CPC ...... *C12Q 1/6886* (2013.01); *C12Q 2600/118* (2013.01); *C12Q 2600/158* (2013.01); *C12Q 2600/16* (2013.01); *G06F 19/20* (2013.01)

(58) Field of Classification Search
None
See application file for complete search history.

(56) References Cited

U.S. PATENT DOCUMENTS

| | | |
|---|---|---|
| 5,993,388 A | 11/1999 | Kattan et al. |
| 6,409,664 B1 | 6/2002 | Kattan et al. |
| 7,056,674 B2 | 6/2006 | Baker et al. |
| 7,081,340 B2 | 7/2006 | Baker et al. |
| 7,569,345 B2 | 8/2009 | Cobleigh et al. |

(Continued)

FOREIGN PATENT DOCUMENTS

| | | |
|---|---|---|
| WO | WO 2004/065583 | 8/2004 |
| WO | WO 2004-074518 | 9/2004 |

(Continued)

OTHER PUBLICATIONS

Freije et al. Cancer Research (2004) 64: 6503-6510.*

(Continued)

*Primary Examiner* — Joseph G Dauner
(74) *Attorney, Agent, or Firm* — Myriad Genetics, Inc. IP Dept.

(57) ABSTRACT

Biomarkers and methods using the biomarkers for molecular detection and classification of disease and, particularly, molecular markers for cancer diagnosis and prognosis and methods of use thereof are provided.

8 Claims, 18 Drawing Sheets

(56) References Cited

U.S. PATENT DOCUMENTS

| | | |
|---|---|---|
| 7,598,031 B2 | 10/2009 | Liew et al. |
| 7,622,251 B2 | 11/2009 | Baker et al. |
| 7,666,595 B2 | 2/2010 | Rubin et al. |
| 7,695,913 B2 | 4/2010 | Cowens et al. |
| 7,723,033 B2 | 5/2010 | Baker et al. |
| 7,767,391 B2 | 8/2010 | Scott et al. |
| 7,871,769 B2 | 1/2011 | Baker et al. |
| 7,914,988 B1 | 3/2011 | Chudin et al. |
| 7,930,104 B2 | 4/2011 | Baker et al. |
| 8,110,363 B2 | 2/2012 | Chudin et al. |
| 8,338,109 B2 | 12/2012 | Vasmatzis et al. |
| 2003/0235816 A1 | 12/2003 | Slawin et al. |
| 2005/0064455 A1 | 3/2005 | Baker et al. |
| 2005/0244872 A1 | 11/2005 | Harris |
| 2005/0272644 A1 | 12/2005 | Chung et al. |
| 2007/0059720 A9* | 3/2007 | Fuqua ............... C12Q 1/6886 435/6.16 |
| 2007/0099209 A1 | 5/2007 | Clarke et al. |
| 2007/0128599 A1 | 6/2007 | Ridder et al. |
| 2007/0128636 A1 | 6/2007 | Baker et al. |
| 2007/0253953 A1 | 11/2007 | Chen et al. |
| 2008/0275652 A1 | 11/2008 | Sotiriou et al. |
| 2009/0123925 A1 | 5/2009 | Collie-Duguid et al. |
| 2009/0215054 A1 | 8/2009 | Carter et al. |
| 2009/0258795 A1 | 10/2009 | Cowens et al. |
| 2009/0297500 A1 | 12/2009 | Nakamura et al. |
| 2009/0305277 A1 | 12/2009 | Baker et al. |
| 2009/0311702 A1 | 12/2009 | Shak et al. |
| 2010/0130377 A1 | 5/2010 | Vasmatzis et al. |
| 2010/0184041 A1 | 7/2010 | Baker et al. |
| 2010/0184063 A1 | 7/2010 | Tsao et al. |
| 2010/0222229 A1 | 9/2010 | Cobleigh et al. |
| 2010/0267032 A1 | 10/2010 | Baker et al. |
| 2010/0284908 A1 | 11/2010 | Rohlff et al. |
| 2011/0123990 A1 | 5/2011 | Baker et al. |
| 2011/0129833 A1 | 6/2011 | Baker et al. |
| 2011/0166838 A1 | 7/2011 | Gehrmann et al. |
| 2011/0178374 A1 | 7/2011 | Baker et al. |
| 2012/0028264 A1 | 2/2012 | Shak et al. |
| 2012/0039805 A1 | 2/2012 | Lisanti et al. |
| 2012/0041274 A1 | 2/2012 | Stone et al. |
| 2012/0053842 A9 | 3/2012 | Gehrmann et al. |
| 2012/0108453 A1 | 5/2012 | Smit et al. |
| 2012/0109535 A1 | 5/2012 | Chudin et al. |
| 2012/0190565 A1 | 7/2012 | Lisanti et al. |

FOREIGN PATENT DOCUMENTS

| | | |
|---|---|---|
| WO | WO 2004-111603 | 12/2004 |
| WO | WO 2005-007830 | 1/2005 |
| WO | WO 2005-039382 | 5/2005 |
| WO | WO 2005-100606 | 10/2005 |
| WO | WO 2006-052731 | 5/2006 |
| WO | WO 2006-052862 | 5/2006 |
| WO | WO 2006-119593 | 11/2006 |
| WO | WO 2006-135886 | 12/2006 |
| WO | WO 2007-067672 | 6/2007 |
| WO | WO 2007-070621 | 6/2007 |
| WO | WO 2008-058018 | 5/2008 |
| WO | WO 2008-077165 | 7/2008 |
| WO | WO 2008/103971 | 8/2008 |
| WO | WO 2008-115419 | 9/2008 |
| WO | WO 2009-032915 | 3/2009 |
| WO | WO 2009-045115 | 4/2009 |
| WO | WO 2009-114836 | 9/2009 |
| WO | WO 2009-140304 | 11/2009 |
| WO | WO 2009-158620 | 12/2009 |
| WO | WO 2010-003771 | 1/2010 |
| WO | WO 2010-080933 | 7/2010 |
| WO | WO 2010-119126 | 10/2010 |
| WO | WO 2010-127322 | 11/2010 |
| WO | WO 2011-063274 | 5/2011 |
| WO | 2011097509 | 8/2011 |
| WO | WO 2012-152811 | 11/2011 |
| WO | WO 2012-006447 | 1/2012 |
| WO | WO 2012-012225 | 1/2012 |
| WO | 2012106718 | 8/2012 |
| WO | WO 2012-122626 | 9/2012 |
| WO | WO 2012-135008 | 10/2012 |
| WO | WO 2012-152800 | 11/2012 |
| WO | WO2012-030840 | 3/2013 |
| WO | 2014078700 | 5/2014 |

OTHER PUBLICATIONS

Affymetrix website search results. Retrieved on May 8, 2015 from: https://www.affymetrix.com/analysis/netaffx/xmlquery. affx?netaffx=netaffx4_annot&_requestid=118226#.*

Paik et al. NEJM (2004) 351: 28174-2826.*

Yu et al. Journal of Clinical Oncology. 2004. 22(14): 2790-2799.*

Affymetrix U95 Set. Retrieved on Oct. 22, 2015 from the internet: https://www.affymetrix.com/user/login.jsp?toURL=/analysis/netaffx/showresults.affx#.*

Holzbeierlein et al. Am J Pathol. 2004. 164: 217-227.*

Michiels et al. Lancet. 2005. 365: 488-492.*

Slonim et al. Nature Genetics Supplemental. 2002. 32: 502-508.*

Simon et al. Journal of Clinical Oncology. 2005. 23(29): 7332-7341.*

Yanaihara et al. Cancer Cell. 2006 9: 189-198.*

Beer et al. Nature Medicine. 2002. 8(8): 816-824.*

Ho et al. Lung Cancer. 2008. 59: 105-110.*

McDoniels-Silvers et al. Neoplasia. 2002. 4(2): 141-150.*

McDoniels-Silvers et al. Clinical Cancer Research. 2002. 8: 1127-1138.*

Kuner et al. Lung Cancer. 2009. 63: 32-38.*

Shore et al. The Journal of Urology. 2016. 195:612-618.*

Paik et al. N Engl J Med. 2004. 2817-2826.*

Galea et al. Breast Cancer Research and Treatment. 1992. 22:207-219.*

Foley et al. Endocrine-Related Cancer. 2004. 11:477-488.*

Whitfield et al, "Identification of Genes Periodically Expressed in the Human Cell Cycle and Their Expression in Tumors", Molecular Biology of the Cell, Jun. 2002, 13:1977-2000.

Willman et al. (The Prostate, vol. 42, pp. 280-286, 2000).

Wu et al., "Cdc6 and Cyclin E2 Are PTEN-Regulated Genes Associated with Human Prostate Cancer Metastasis1", Neoplasia, Jan. 2009, 11(1):66-76.

Yoshimoto et al., "FISH analysis of 107 prostate cancers shows that PTEN genomic deletion is associated with poor clinical outcome", British Journal of Cancer, 2007, 97:678-685.

Zhu et al., "Rad9 Has Functional Role in Human Prostate Carcinogenesis", Cancer Research, Mar. 1, 2008, 68 (5):1267-1274.

Cooperberg et al., "Validation of a Cell-Cycle Progression Gene Panel to Improve Risk-Stratification in a Contemporary Prostatectom Cohort", Journal of Urology, vol. 187, No. 4, Suppl. S, Apr. 2012, p. E850, XP002720976.

Freedland et al., "Prognostic Utility of Cell Cycle Progression Score in Men with Prostate Cancer After Primary External Beam Radiation Therapy", Internation al Journal of Radiation, vol. 86, No. 5, Aug. 1, 2013, pp. 848-853.

International Search Report and Written Opinionfrom Application No. PCT/US2013/070373, dated Apr. 1, 2014.

Romanuik et al., "Novel Biomarkers for Prostate Cancer Including Noncoding Transcripts", American Journal of Pathology, vol. 175, Dec. 1, 2009, pp. 2264-2276.

Stone et al., "PTEN expression predicts biochemical recurrrence in prostate cancer", American Association for Cancer Research, vol. 51, Apr. 1, 2010, p. 287, XP009174127.

Wistuba et al., "Validation of a Proliferation-Based Expression Signature as Prognostic Marker in Early Stage Lung Adenocarcinoma", Clinical Cancer Research, vol. 19, No. 22, Nov. 15, 2013, pp. 6261-6271.

Wu, C-L. et al., PNAS USA, vol. 110, pp. 6121-6125 + Supplement pp. 1-9 (2013).

(56) References Cited

OTHER PUBLICATIONS

Bedolla et al., "Determining Risk of Biochemical Recurrence in Prostate Cancer by Immunohistochemical Detection of PTEN Expression and Akt Activation", Clinical Cancer Research, 2007, 13(13):3860-3867.

Beresford et al., "Measuring proliferation in breast cancer: practicalities and applications," Breast Cancer Research, Nov. 30, 2006, Retrieved from internet: URL: http://www.ncbi.nlm.nih.gov/pmc/articles/pmc1797032/pdf/bcr1618.pdf, p. 4.

Bibikova et al., "Expression signatures that correlated with Gleason score and relapse in prostate cancer", Genomics, 2007, 89:666-672.

Carter et al., "A signature of chromosomal instability inferred from gene expression profiles predicts clinical outcome in multiple human cancers", Nature Genetics, Sep. 2006, 38(9):1043-1048.

Cuzick, J. et al, "Prognostic value of an RNA expressive signature derived from cell cycle proliferation genes in patients with prostate cancer: a retrospective study," The Lancet, Mar. 1, 2011, vol. 12, pp. 245-255.

Cuzick, J. et al., "Prognostic value of a cell cycle progression signature for prostate cancer death in a conservatively managed needle biopsy cohort," British Journal of Cancer, Mar. 13, 2012, vol. 106, No. 6, pp. 1095-1099.

Dai et al., "A Cell Proliferation Signature Is a Marker of Extremely Poor Outcome in a Subpopulation of Breast Cancer Patients", Cancer Research, May 15, 2005, 65(10):4059-4066.

European Search Report and Annex from Application No. 10729525.5, dated Nov. 30, 2012.

European Search Report and Annex from Application No. 11804357.9, dated Nov. 14, 2013.

European Search Report and Annex from Application No. 11822498.9, dated Dec. 17, 2013.

Foley, R. et al., "Molecular pathology of prostate cancer: the key to identifying new biomarkers of disease," European Journal of Cancer, Apr. 1, 2005, vol. 41, No. 6, pp. 858-887.

Glinsky, G. V. et al., "Gene expression profiling predicts clinical outcome of prostate cancer," Journal of Clinical Investigation, Mar. 1, 2004, vol. 113, No. 6, pp. 913-923.

Habel et al., "A population-based study of tumor gene expression and risk of breast cancer death among lymph node-negative patients", Breast Cancer Research, 2006, 8(3):1-15.

Halvorsen et al., "Combined Loss of PTEN and p27 Expression Is Associated with Tumor Cell Proliferation by Ki-67 and Increased Risk of Recurrent Disease in Localized Prostate Cancer", Clinical Cancer Research, Apr. 2003, 9:1474-1479.

Henshall, S. et al., "Survival Analysis of Genome-Wide Gene Expression Profiles of Prostate Cancers Identifies New Prognostic Targets of Disease Relapse," Cancer Research, Jul. 15, 2003, vol. 63, pp. 4196-4203.

Hess et al., "Pharmacogenomic Predictor of Sensitivity to Preoperative Chemotherapy With Paclitaxel and Fluorouracil, Doxorubicin, and Cyclophosphamide in Breast Cancer", Journal of Clinical Oncology, Sep. 10, 2006, 24(26):4236-4244.

Hughes et al. (J. Clin. Pathol. vol. 59, pp. 721-724, 2006).

International Search Report and Witten Opinion from Application No. PCT/US2010/020397, dated Feb. 10, 2010.

International Search Report and Written Opinion from Application No. PCT/US2011/043228, dated Feb. 24, 2012.

International Search Report and Written Opinion from Application No. PCT/US2013/021839, dated May 27, 2013.

International Search Report and Written Opinionfrom Application No. PCT/US2012/051447, dated Feb. 21, 2013.

Ishibashi et al., "Detection of significant prognostic factors using gene-expression profiling in patients with esophageal squamous cell carcinoma," Gastroenterology, Apr. 1, 2007, vol. 132, No. 4, Suppl. 2, p. A852.

Kerner et al., "Expression of cell cycle regulatory proteins in ovaries prophylactically removed from Jewish Ashkenazi BRCA1 and BRCA2 mutation carriers: Correlation with histopathology", Gynecol. Oncol., Nov. 2005, 99(2):367-75. Abstract.

Kosari et al., "Identification of Prognostic Biomarkers for Prostate Cancer", Clinical Cancer Research, Mar. 15, 2008, 14(6):1734-1743.

LaTulippe et al. (Cancer Research, vol. 62, pp. 4499-4506, Aug. 2002).

Lauss, M. et al., "Consensus genes of the literature to predict breast cancer recurrence," Breast Cancer Research and Treatment, Sep. 26, 2007, vol. 110, No. 2, pp. 235-244.

Lee et al., "Targeting prostate cancer based on signal transduction and cell cycle pathways", Cell Cycle, Jun. 15, 2008, 7(12):1745-1762.

Liu et al., "Identification of a gene signature in cell cycle pathway for breast cancer prognosis using gene expression profiling data," BMC Medial Genomics, Sep. 11, 2008, vol. 1, No. 1, pp. 1-12.

Liu et al., "Quantitative analysis of a panel of gene expression in prostate cancer—with emphasis on NPY expression analysis", Journal of Zhejiang University Science B, 2007, 8(12):853-859.

McCall, P. et al., "Is PTEN loss associated with clinical outcome measures in human prostate cancer?" British Journal of Cancer, Oct. 21, 2008, vol. 99, No. 8, pp. 1296-1301.

Miller et al., "Utilizing Nottingham Prognostic Index in microarray gene expression profiling of breast carcinomas", Modern Pathology, Jul. 2004, 17(7):756-764.

Mosley & Keri, "Cell cycle correlated genes dictate the prognostic power of breast cancer gene lists", MBC Medical Genomics, Apr. 25, 2008, 3 pages: Abstract.

Nakopoulou et al. (J. Clin. Pathol. vol. 54, pp. 309-313, 2001).

Oligo Ge Array. Human Breast Cancer Biomarkers Microarray. Jul. 16, 2006 [online]. [retrieved on Feb. 9, 2010]. Retrieved from the internet: URL:http://web.archive.org/web/20060716064356/www.superarray.com/gene_array_product/HTML/OHS-402.html. Especially p. 1 cell cycle genes.

Porter et al., "Prognostic value of cell cycle regulators p27 and cyclin E: Tissue microarray analysis of 1753 women enrolled in SWOG breast cancer trial 9313", Journal of Clinical Oncology, 2005 ASCO Annual Meeting Proceedings, Jun. 1, 2005, vol. 23, No. 16S, Abstract: 507. Abstract only.

Quinn, D. I. et al., "Molecular markers of prostate cancer outcome," European Journal of Cancer, Apr. 1, 2005, vol. 41, No. 6, pp. 858-887.

Schmidt et al., "Asynchronous Growth of Prostate Cancer Is Reflected by Circulating Tumor Cells Delivered from Distinct, Even Small Foci, Harboring Loss of Heterozygosity of the PTEN Gene", Cancer Research, Sep. 15, 2006, 66(18):8959-8965.

Scholmm et al., "Value of Cell Cycle Progression (CCP) Score to Predict Biochemical Recurrence and Definitive Post-Surgical Pathology," Journal of Urology, Apr. 1, 2013, vol. 189, No. 4, p. E404.

Shariat et al., "542 Improved Prediction of Clinical Outcomes in Patients With Advanced Bladder Cancer Using a Panel of Four Cell Cycle Regulators ," European Urology Supplements, Mar. 1, 2009, vol. 8, No. 4, p. 256.

Sheikh et al., "Predictive Value of PTEN and AR Coexpression of Sustained Responsiveness to Hormonal Therapy in Prostate Cancer—A Pilot Study", Neoplasia, Sep. 2008, 10(9):949-953.

Simon et al., "Diagnostic and prognostic prediction using gene expression profiles in high-dimensional microarray data," British Journal of Cancer, Jan. 1, 2003, vol. 89, No. 9, p. 1599-1604.

Sotiriou et al, "Gene Expression Profiling in Breast Cancer: Understanding the Molecular Basis of Histologic Grade to Improve Prognosis", Journal of the National Cancer Institute, Feb. 15, 2006, 98(4):262-272.

Stephenson et al., "Integration of Gene Expression Profiling and Clinical Variables to Predict Prostate Carcinoma Recurrence after Radical Prostatectomy", American Cancer Society, 2005, 104:290-298.

Stephenson et al., "Postoperative Nomogram Predicting the 10-Year Probability of Prostate Cancer Recurrence After Radical Prostatectomy", Journal of Clinical Oncology, Oct. 1, 2005, 23(28):7005-7012.

Tabach et al., "The promoters of human cell cycle genes integrate signals from two tumor suppressive pathways during cellular transformation", Molecular Systems Biology, 2005, pp. 1-15.

(56) References Cited

OTHER PUBLICATIONS

Teschendorff et al., "A consensus prognostic gene expression classifier for ER positive breast cancer", Genome Biology, Oct. 31, 2006, 7:R101.

Toillon et al., "Estrogens decrease •ray-induced senescence and maintain cell cycle progression in breast cancer cells independently of p53" International Journal of Radiation Oncology, Biology, Physics, vol. 67, No. 4, pp. 1187-1200 (Mar. 15, 2007) See abstract and table 1.

Vandevijver et al., "A Gene-Expression Signature as a Predictor of Survival in Breast Cancer", The New England Journal of Medicine, Dec. 19, 2002, 347(25):1999-2009.

Wang et al., "Gene networks and microRNAs implicated in aggressive prostate cancer," Cancer Research, Dec. 15, 2009, vol. 69, No. 24, pp. 9490-9497.

Wang et al., "Gene-expression profiles to predict distant metastasis of lymph-node-negative primary breast cancer", The Lancet, Feb. 19, 2005, 365:671-679.

European Communication from Application No. 10729525.5, dated Jan. 2, 2014.

European Communication from Application No. 10729525.5, dated Jun. 11, 2015.

European Communication from Application No. 10729525.5, dated Nov. 13, 2015.

European Search Report and Annex from Application No. 12825690.6, dated Mar. 3, 2015.

International Preliminary Report on Patentability from Application No. PCT/US11/043228, dated Jan. 17, 2013.

International Preliminary Report on Patentability from Application No. PCT/US2011/049760, dated Mar. 14, 2013.

International Preliminary Report on Patentability from Application No. PCT/US2012/051447, dated Mar. 6, 2014.

International Preliminary Report on Patentability from Application No. PCT/US2013/021839, dated Jul. 31, 2014.

International Preliminary Report on Patentability from Application No. PCT/US2013/070373, dated May 28, 2015.

International Preliminary Report on Patentability from Application No. PCT/US2014/017706, dated Sep. 3, 2015.

International Search Report and Written Opinion from Application No. PCT/US2011/049760, dated Apr. 26, 2012.

International Search Report and Written Opinion from Application No. PCT/US2014/017706, dated Jun. 25, 2014.

International Search Report and Written Opinion from Application No. PCT/US2014/068628, dated Apr. 16, 2015.

International Search Report and Written Opinion from Application No. PCT/US2015/030617, dated Aug. 20, 2015.

Ma et al., "Diagnostic and Prognostic Score System for Prostate Cancer Using Urine and Plasma Biomarkers" Genetic Testing and Molecular Biomarkers, vol. 18, No. 3, Mar. 1, 2014.

Oligo Ge Array. Human Cell Cycle Microarray., Jun. 11, 2006 [online]. [retrieved on Feb. 9, 2010]. Retrieved from the internet: <URL:http://web.archive.org!web/200611 05215154/www.superarray . comlgene_array_producVHTMUOHS-020.html >.

Response to European Communication from Application No. 10729525.5, dated May 9, 2014.

Response to European Communication from Application No. 10729525.5, dated Oct. 16, 2015.

Response to European Communication from Application No. 10729525.5, dated Jun. 19, 2013.

Response to European Communication from Application No. 11804357.9, dated Jun. 20, 2014.

Response to European Communication from Application No. 11822498.9, dated Jul. 24, 2014.

Response to European Communication from Application No. 12825690.6, dated Sep. 22, 2015.

Aman et al., "Up-regulation of microRNA-21 correlates with lower kidney cancer survival" PLoS One, vol. 7, No. 2, e31060 (internal pp. 1-9).

Chan et al. G&P magazine. 2006. 6(3): 20-26.

European Communication from Application No. 11822498.9, dated Jun. 3, 2016.

Foley et al., Endocrine-Related Cancer, 2004, vol. 11, pp. 477-488.

Galea et al., Breast Cancer Research and Treatment, 1992, vol. 22, pp. 207-219.

* cited by examiner

GENE SIGNATURES FOR CANCER DIAGNOSIS AND PROGNOSIS

CROSS REFERENCE TO RELATED APPLICATIONS

This application is the U.S. national phase entry of International Application no. PCT/US11/49760 filed Aug. 30, 2011 (publication no. WO2012/030840) and further claims the priority benefit of U.S. Provisional Application Ser. No. 61/378,220 (filed on Aug. 30, 2010) and U.S. Provisional Application Ser. No. 61/407,791 (filed on Oct. 28, 2010), the contents of each of which is hereby incorporated by reference in its entirety.

FIELD OF THE INVENTION

The invention generally relates to molecular detection and classification of disease and particularly to molecular markers for cancer diagnosis and prognosis and methods of use thereof.

BACKGROUND OF THE INVENTION

Cancer is a major public health problem, accounting for nearly one out of every four deaths in the United States. American Cancer Society, Facts and Figures 2010. Patient prognosis generally improves with earlier detection of cancer. Indeed, more readily detectable cancers such as breast cancer have a substantially better survival rate than cancers that are more difficult to detect (e.g., ovarian cancer).

Though many treatments have been devised for various cancers, these treatments often vary in severity of side effects. It is useful for clinicians to know how aggressive a patient's cancer is in order to determine how aggressively to treat the cancer. For example, most patients with early-stage asymptomatic prostate cancer are treated with radical prostatectomy or radiotherapy and optionally adjuvant therapy (e.g., hormone or chemotherapy), all of which have severe side effects. For many of these patients, however, these treatments and their associated side effects and costs are unnecessary because the cancer in these patients is not aggressive (i.e., grows slowly and is unlikely to cause mortality or significant morbidity during the patient's lifetime). In other patients the cancer is virulent (i.e., more likely to recur) and aggressive treatment is necessary to save the patient's life.

Thus, there is a serious need for novel and improved tools for both diagnosing cancer and predicting cancer recurrence.

SUMMARY OF THE INVENTION

The present invention is based in part on the surprising discovery that the expression of those genes whose expression closely tracks the cell cycle ("cell-cycle progression" or "CCP" genes, as further defined below) is particularly useful in diagnosing and determining the prognosis of selected cancers.

Accordingly, in a first aspect of the present invention, a method is provided for determining gene expression in a sample from a patient. Generally, the method includes at least the following steps: (1) obtaining a sample from the patient; (2) determining the expression of a panel of genes in said tumor sample including at least 4 cell-cycle progression genes; and (3) providing a test value by (a) weighting the determined expression of each of a plurality of test genes selected from said panel of genes with a predefined coefficient, and (b) combining the weighted expression to provide said test value, wherein at least 50%, at least 75% or at least 90% of said plurality of test genes are cell-cycle progression genes. In some embodiments the patient is suspected of having prostate cancer, lung cancer, bladder cancer or brain cancer. In some embodiments the patient is identified as having having prostate cancer, lung cancer, bladder cancer or brain cancer.

In some embodiments, the plurality of test genes includes at least 6 cell-cycle progression genes, or at least 7, 8, 9, 10, 15, 20, 25 or 30 cell-cycle progression genes. In some embodiments, all of the test genes are cell-cycle progression genes. In some embodiments the cell-cycle genes are weighted to contribute at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the test value.

In some embodiments, the step of determining the expression of the panel of genes in the tumor sample comprises measuring the amount of mRNA in the tumor sample transcribed from each of from 4 to about 200 cell-cycle progression genes; and measuring the amount of mRNA of one or more housekeeping genes in the tumor sample.

In another aspect of the present invention, a method is provided for diagnosing cancer in a patient comprising determining in a sample the expression of at least 6, 8 or 10 cell-cycle progression genes, and correlating overexpression of said at least 6, 8 or 10 cell-cycle progression genes to a diagnosis of cancer or an increased likelihood of cancer.

In one embodiment, the diagnosis method comprises (1) determining in a sample the expression of a panel of genes including at least 4 or at least 8 cell-cycle progression genes; (2) providing a test value by (a) weighting the determined expression of each of a plurality of test genes selected from the panel of genes with a predefined coefficient, and (b) combining the weighted expression to provide the test value, wherein at least 25%, at least 50%, at least 75% or at least 85% of the plurality of test genes are cell-cycle progression genes, and (3) correlating an increased level (e.g., overall) of expression of the plurality of test genes to a diagnosis of cancer or an increased likelihood of cancer. In some embodiments a confirmatory test (e.g., imaging, biopsy, etc.) is recommended, prescribed, and/or performed if there is an increased level of expression of the plurality of test genes correlating to a diagnosis of an increased likelihood of cancer. In some embodiments, no increase in the expression of the test genes correlates to a diagnosis of no cancer or a decreased likelihood of cancer. In some embodiments, no increase in the expression of the test genes correlates to indolent (e.g., not aggressive) cancer (e.g., a decreased likelihood of recurrence or progression).

In some embodiments, the diagnosis method further includes a step of comparing the test value provided in step (2) above to one or more reference values, and correlating the test value to the presence or absence of cancer. Optionally cancer is indicated if the test value is greater than the reference value. In some embodiments the cell-cycle genes are weighted to contribute at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the test value.

In another aspect of the present invention, a method is provided for determining the prognosis of prostate cancer, lung cancer, bladder cancer or brain cancer, which comprises determining in a tumor sample from a patient diagnosed of prostate cancer, lung cancer, bladder cancer or brain cancer, the expression of at least 6, 8 or 10 cell-cycle progression genes, and correlating overexpression of said at least 6, 8 or 10 cell-cycle progression genes to a poor prognosis or an increased likelihood of recurrence of cancer in the patient.

In one embodiment, the prognosis method comprises (1) determining in a tumor sample from a patient diagnosed with prostate cancer, lung cancer, bladder cancer or brain cancer, the expression of a panel of genes in said tumor sample including at least 4 or at least 8 cell-cycle progression genes; and (2) providing a test value by (a) weighting the determined expression of each of a plurality of test genes selected from the panel of genes with a predefined coefficient, and (b) combining the weighted expression to provide the test value, wherein at least 50%, at least 75% or at least 85% of the plurality of test genes are cell-cycle progression genes, and wherein an increased level (e.g., overall) of expression of the plurality of test genes indicates a poor prognosis, whereas if there is no increase (e.g., overall) in the expression of the test genes, it would indicate a good prognosis or a low likelihood of recurrence of cancer in the patient.

In some embodiments, the prognosis method further includes a step of comparing the test value provided in step (2) above to one or more reference values, and correlating the test value to a risk of cancer progression or risk of cancer recurrence. Optionally an increased likelihood of poor prognosis is indicated if the test value is greater than the reference value.

In yet another aspect, the present invention also provide a method of treating cancer in a patient identified as having prostate cancer, lung cancer, bladder cancer or brain cancer, comprising: (1) determining in a tumor sample from a patient diagnosed of prostate cancer, lung cancer, bladder cancer or brain cancer, the expression of a panel of genes in the tumor sample including at least 4 or at least 8 cell-cycle progression genes; (2) providing a test value by (a) weighting the determined expression of each of a plurality of test genes selected from said panel of genes with a predefined coefficient, and (b) combining the weighted expression to provide said test value, wherein at least 50% or 75% or 85% of the plurality of test genes are cell-cycle progression genes, wherein an increased level of expression of the plurality of test genes indicates a poor prognosis, and no increased level of expression of the plurality of test genes indicates a good prognosis; and recommending, prescribing or administering a treatment regimen or watchful waiting based at least in part on the prognosis provided in step (2). In some embodiments the cell-cycle genes are weighted to contribute at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the test value.

The present invention further provides a diagnostic kit useful in the above methods, the kit generally comprising, in a compartmentalized container, a plurality of oligonucleotides hybridizing to at least 8 test genes, wherein less than 10%, 30% or less than 40% of all of the at least 8 test genes are non-cell-cycle progression genes; and one or more oligonucleotide hybridizing to at least one housekeeping gene. In one emobidment the invention provides a diagnostic kit for diagnosing cancer in a patient comprising the above components. In another emobidment the invention provides a diagnostic kit for prognosing cancer in a patient diagnosed of prostate cancer, lung cancer, bladder cancer or brain cancer, comprising the above components. The oligonucleotides can be hybridizing probes for hybridization with the test genes under stringent conditions or primers suitable for PCR amplification of the test genes. In one embodiment, the kit consists essentially of, in a compartmentalized container, a first plurality of PCR reaction mixtures for PCR amplification of from 5 or 10 to about 300 test genes, wherein at least 25%, at least 50%, at least 60% or at least 80% of such test genes are cell-cycle progression genes, and wherein each reaction mixture comprises a PCR primer pair for PCR amplifying one of the test genes; and a second plurality of PCR reaction mixtures for PCR amplification of at least one housekeeping gene.

The present invention also provides the use of (1) a plurality of oligonucleotides hybridizing to at least 4 or at least 8 cell-cycle progression genes; and (2) one or more oligonucleotides hybridizing to at least one housekeeping gene, for the manufacture of a diagnostic product. In one embodiment the diagnostic product is for determining the expression of the test genes in a sample from a patient to diagnose cancer, wherein an increased level (e.g., overall) of the expression of the test genes indicates the patient has cancer. In another embodiment the diagnostic product is for determining the expression of the test genes in a tumor sample from a patient diagnosed of prostate cancer, lung cancer, bladder cancer or brain cancer, to predict the prognosis of cancer, wherein an increased level of the overall expression of the test genes indicates a poor prognosis or an increased likelihood of recurrence of cancer in the patient, whereas if there is no increase in the overall expression of the test genes, it would indicate a good prognosis or a low likelihood of recurrence of cancer in the patient. In some embodiments, the oligonucleotides are PCR primers suitable for PCR amplification of the test genes. In other embodiments, the oligonucleotides are probes hybridizing to the test genes under stringent conditions. In some embodiments, the plurality of oligonucleotides are probes for hybridization under stringent conditions to, or are suitable for PCR amplification of, from 4 to about 300 test genes, at least 50%, 70% or 80% or 90% of the test genes being cell-cycle progression genes. In some other embodiments, the plurality of oligonucleotides are hybridization probes for, or are suitable for PCR amplification of, from 20 to about 300 test genes, at least 30%, 40%, 50%, 70% or 80% or 90% of the test genes being cell-cycle progression genes.

The present invention further provides systems related to the above methods of the invention. In one embodiment the invention provides a system for determining gene expression in a tumor sample, comprising: (1) a sample analyzer for determining the expression levels of a panel of genes in a sample including at least 4 cell-cycle progression genes, wherein the sample analyzer contains the sample, mRNA from the sample and expressed from the panel of genes, or cDNA synthesized from said mRNA; (2) a first computer program for (a) receiving gene expression data on at least 4 test genes selected from the panel of genes, (b) weighting the determined expression of each of the test genes with a predefined coefficient, and (c) combining the weighted expression to provide a test value, wherein at least 50%, at least at least 75% of at least 4 test genes are cell-cycle progression genes; and optionally (3) a second computer program for comparing the test value to one or more reference values each associated with a predetermined degree of risk of cancer. In another embodiment the invention provides a system for determining gene expression in a tumor sample, comprising: (1) a sample analyzer for determining the expression levels of a panel of genes in a tumor sample including at least 4 cell-cycle progression genes, wherein the sample analyzer contains the tumor sample which is from a patient identified as having prostate cancer, lung cancer, bladder cancer or brain cancer, or cDNA molecules from mRNA expressed from the panel of genes; (2) a first computer program for (a) receiving gene expression data on at least 4 test genes selected from the panel of genes, (b) weighting the determined expression of each of the test genes with a predefined coefficient, and (c) combining the weighted expression to provide a test value, wherein at least 50%, at least at least 75% of at least 4 test genes are cell-cycle progression genes; and optionally (3) a second computer program for comparing the test value to one or more reference values each associated with a predetermined degree of risk of cancer recurrence or progression of the prostate cancer, lung cancer, bladder cancer or brain cancer. In some embodiments, the system further comprises a display module displaying the comparison between the test value and the one or more reference values, or displaying a result of the comparing step. In some embodiments the cell-cycle genes are weighted to contribute at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the test value.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following Detailed Description, and from the Claims.

DETAILED DESCRIPTION OF THE INVENTION

I. Determining Cell-Cycle Gene Expression

Figure 1:
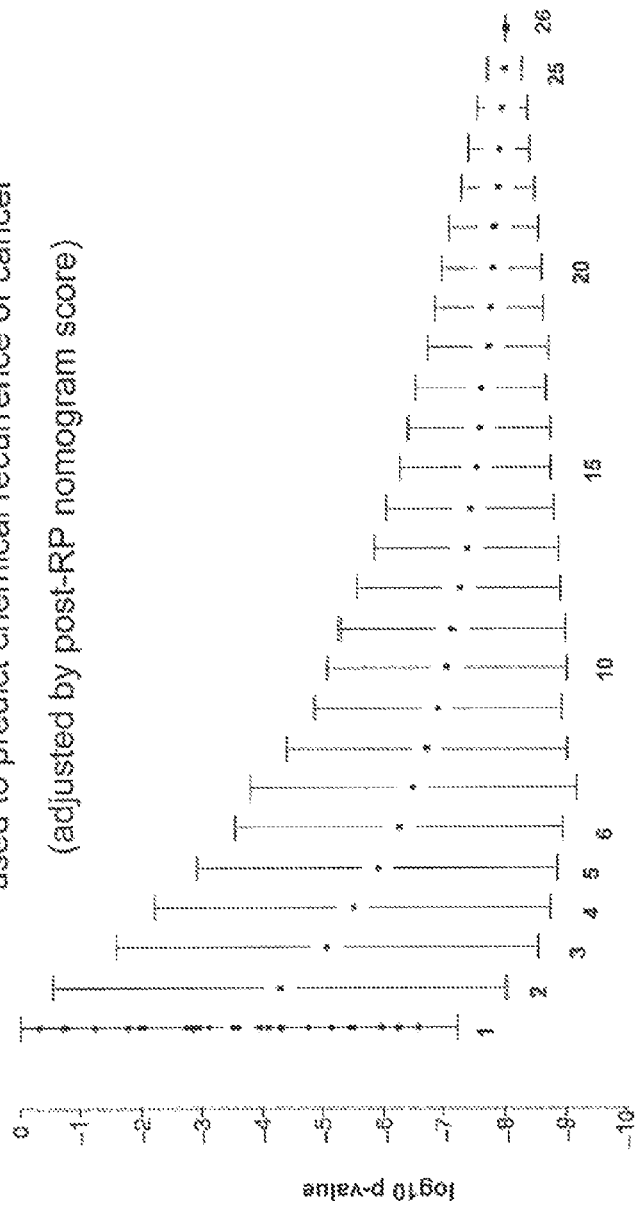
FIG. 1 is an illustration of the predictive power over nomogram for CCP panels of different sizes.

The present invention is based in part on the discovery that genes whose expression closely tracks the cell cycle ("cell-cycle progression genes," "CCP genes," "cell-cycle genes," or sometimes "CCGs") are particularly powerful genes for diagnosing cancer and for classifying selected cancers including prostate cancer, lung cancer, bladder cancer, brain cancer and breast cancer, but not other types of cancer such as certain colorectal cancer.

"Cell-cycle gene," "CCG," "Cell-cycle progression gene," and "CCP gene" herein refer to a gene whose expression level closely tracks the progression of the cell through the cell-cycle. See, e.g., Whitfield et al., MOL. BIOL. CELL (2002) 13:1977-2000. More specifically, CCP genes show periodic increases and decreases in expression that coincide with certain phases of the cell cycle—e.g., STK15 and PLK show peak expression at G2/M. Id. Often CCP genes have clear, recognized cell-cycle related function—e.g., in DNA synthesis or repair, in chromosome condensation, in cell-division, etc. However, some CCP genes have expression levels that track the cell-cycle without having an obvious, direct role in the cell-cycle—e.g., UBE2S encodes a ubiquitin-conjugating enzyme, yet its expression closely tracks the cell-cycle. Thus a CCP according to the present invention need not have a recognized role in the cell-cycle. Exemplary CCP genes are listed in Tables 1, 2, 3, 9, 11, 16, 25, 26, 28, 29 and 30 and Panels A, B, C, D, E, F, and G.

Whether a particular gene is a CCP gene may be determined by any technique known in the art, including that taught in Whitfield et al., MOL. BIOL. CELL (2002) 13:1977-2000. For example, a sample of cells, e.g., HeLa cells, can be synchronized such that they all progress through the different phases of the cell cycle at the same time. Generally this is done by arresting the cells in each phase—e.g., cells may be arrested in S phase by using a double thymidine block or in mitosis with a thymidine-nocodazole block. See, e.g., Whitfield et al., MOL. CELL. BIOL. (2000) 20:4188-4198. RNA is extracted from the cells after arrest in each phase and gene expression is quantitated using any suitable technique—e.g., expression microarray (genome-wide or specific genes of interest), real-time quantitative PCR™ (RTQ-PCR). Finally, statistical analysis (e.g., Fourier Transform) is applied to determine which genes show peak expression during particular cell-cycle phases. Genes may be ranked according to a periodicity score describing how closely the gene's expression tracks the cell-cycle—e.g., a high score indicates a gene very closely tracks the cell cycle. Finally, those genes whose periodicity score exceeds a defined threshold level (see Whitfield et al., MOL. BIOL. CELL (2002) 13:1977-2000) may be designated CCP genes. A large, but not exhaustive, list of nucleic acids associated with CCP genes (e.g., genes, ESTs, cDNA clones, etc.) is given in Table 1. See Whitfield et al., MOL. BIOL. CELL (2002) 13:1977-2000. All of the CCP genes in Table 2 below form a panel of CCP genes ("Panel A") useful in the methods of the invention.

TABLE 2

| Gene Symbol | Entrez GeneID | ABI Assay ID | RefSeq Accession Nos. |
|---|---|---|---|
| APOBEC3B* | 9582 | Hs00358981_m1 | NM_004900.3 |
| ASF1B* | 55723 | Hs00216780_m1 | NM_018154.2 |
| ASPM* | 259266 | Hs00411505_m1 | NM_018136.4 |
| ATAD2* | 29028 | Hs00204205_m1 | NM_014109.3 |
| BIRC5* | 332 | Hs00153353_m1; Hs03043576_m1 | NM_001012271.1; NM_001012270.1; NM_001168.2 |
| BLM* | 641 | Hs00172060_m1 | NM_000057.2 |
| BUB1 | 699 | Hs00177821_m1 | NM_004336.3 |
| BUB1B* | 701 | Hs01084828_m1 | NM_001211.5 |
| C12orf48* | 55010 | Hs00215575_m1 | NM_017915.2 |
| C18orf24* | 220134 | Hs00536843_m1 | NM_145060.3; NM_001039535.2 |
| C1orf135* | 79000 | Hs00225211_m1 | NM_024037.1 |
| C21orf45* | 54069 | Hs00219050_m1 | NM_018944.2 |
| CCDC99* | 54908 | Hs00215019_m1 | NM_017785.4 |
| CCNA2* | 890 | Hs00153138_m1 | NM_001237.3 |
| CCNB1* | 891 | Hs00259126_m1 | NM_031966.2 |
| CCNB2* | 9133 | Hs00270424_m1 | NM_004701.2 |
| CCNE1* | 898 | Hs01026536_m1 | NM_001238.1; NM_057182.1 |
| CDC2* | 983 | Hs00364293_m1 | NM_033379.3; NM_001130829.1; NM_001786.3 |
| CDC20* | 991 | Hs03004916_g1 | NM_001255.2 |
| CDC45L* | 8318 | Hs00185895_m1 | NM_003504.3 |
| CDC6* | 990 | Hs00154374_m1 | NM_001254.3 |
| CDCA3* | 83461 | Hs00229905_m1 | NM_031299.4 |
| CDCA8* | 55143 | Hs00983655_m1 | NM_018101.2 |
| CDKN3* | 1033 | Hs00193192_m1 | NM_001130851.1; NM_005192.3 |
| CDT1* | 81620 | Hs00368864_m1 | NM_030928.3 |
| CENPA | 1058 | Hs00156455_m1 | NM_001042426.1; NM_001809.3 |
| CENPE* | 1062 | Hs00156507_m1 | NM_001813.2 |
| CENPF* | 1063 | Hs00193201_m1 | NM_016343.3 |
| CENPI* | 2491 | Hs00198791_m1 | NM_006733.2 |
| CENPM* | 79019 | Hs00608780_m1 | NM_024053.3 |
| CENPN* | 55839 | Hs00218401_m1 | NM_018455.4; NM_001100624.1; NM_001100625.1 |
| CEP55* | 55165 | Hs00216688_m1 | NM_018131.4; NM_001127182.1 |
| CHEK1* | 1111 | Hs00967506_m1 | NM_001114121.1; NM_001114122.1; NM_001274.4 |
| CKAP2* | 26586 | Hs00217068_m1 | NM_018204.3; NM_001098525.1 |
| CKS1B* | 1163 | Hs01029137_g1 | NM_001826.2 |
| CKS2* | 1164 | Hs01048812_g1 | NM_001827.1 |
| CTPS* | 1503 | Hs01041851_m1 | NM_001905.2 |
| CTSL2* | 1515 | Hs00952036_m1 | NM_001333.2 |
| DBF4* | 10926 | Hs00272696_m1 | NM_006716.3 |
| DDX39* | 10212 | Hs00271794_m1 | NM_005804.2 |
| DLGAP5/ DLG7* | 9787 | Hs00207323_m1 | NM_014750.3 |
| DONSON* | 29980 | Hs00375083_m1 | NM_017613.2 |
| DSN1* | 79980 | Hs00227760_m1 | NM_024918.2 |
| DTL* | 51514 | Hs00978565_m1 | NM_016448.2 |
| E2F8* | 79733 | Hs00226635_m1 | NM_024680.2 |
| ECT2* | 1894 | Hs00216455_m1 | NM_018098.4 |
| ESPL1* | 9700 | Hs00202246_m1 | NM_012291.4 |
| EXO1* | 9156 | Hs00243513_m1 | NM_130398.2; NM_003686.3; NM_006027.3 |

TABLE 2-continued

| Gene Symbol | Entrez GeneID | ABI Assay ID | RefSeq Accession Nos. |
|---|---|---|---|
| EZH2* | 2146 | Hs00544830_m1 | NM_152998.1; NM_004456.3 |
| FANCI* | 55215 | Hs00289551_m1 | NM_018193.2; NM_001113378.1 |
| FBXO5* | 26271 | Hs03070834_m1 | NM_001142522.1; NM_012177.3 |
| FOXM1* | 2305 | Hs01073586_m1 | NM_202003.1; NM_202002.1; NM_021953.2 |
| GINS1* | 9837 | Hs00221421_m1 | NM_021067.3 |
| GMPS* | 8833 | Hs00269500_m1 | NM_003875.2 |
| GPSM2* | 29899 | Hs00203271_m1 | NM_013296.4 |
| GTSE1* | 51512 | Hs00212681_m1 | NM_016426.5 |
| H2AFX* | 3014 | Hs00266783_s1 | NM_002105.2 |
| HMMR* | 3161 | Hs00234864_m1 | NM_001142556.1; NM_001142557.1; NM_012484.2; NM_012485.2 |
| HN1* | 51155 | Hs00602957_m1 | NM_001002033.1; NM_001002032.1; NM_016185.2 |
| KIAA0101* | 9768 | Hs00207134_m1 | NM_014736.4 |
| KIF11 | 3832 | Hs00189698_m1 | NM_004523.3 |
| KIF15* | 56992 | Hs00173349_m1 | NM_020242.2 |
| KIF18A* | 81930 | Hs01015428_m1 | NM_031217.3 |
| KIF20A* | 10112 | Hs00993573_m1 | NM_005733.2 |
| KIF20B/ MPHOSPH1* | 9585 | Hs01027505_m1 | NM_016195.2 |
| KIF23* | 9493 | Hs00370852_m1 | NM_138555.1; NM_004856.4 |
| KIF2C* | 11004 | Hs00199232_m1 | NM_006845.3 |
| KIF4A* | 24137 | Hs01020169_m1 | NM_012310.3 |
| KIFC1* | 3833 | Hs00954801_m1 | NM_002263.3 |
| KPNA2 | 3838 | Hs00818252_g1 | NM_002266.2 |
| LMNB2* | 84823 | Hs00383326_m1 | NM_032737.2 |
| MAD2L1 | 4085 | Hs01554513_g1 | NM_002358.3 |
| MCAM* | 4162 | Hs00174838_m1 | NM_006500.2 |
| MCM10* | 55388 | Hs00960349_m1 | NM_018518.3; NM_182751.1 |
| MCM2* | 4171 | Hs00170472_m1 | NM_004526.2 |
| MCM4* | 4173 | Hs00381539_m1 | NM_005914.2; NM_182746.1 |
| MCM6* | 4175 | Hs00195504_m1 | NM_005915.4 |
| MCM7* | 4176 | Hs01097212_m1 | NM_005916.3; NM_182776.1 |
| MELK | 9833 | Hs00207681_m1 | NM_014791.2 |
| MKI67* | 4288 | Hs00606991_m1 | NM_002417.3 |
| MYBL2* | 4605 | Hs00231158_m1 | NM_002466.2 |
| NCAPD2* | 9918 | Hs00274505_m1 | NM_014865.3 |
| NCAPG* | 64151 | Hs00254617_m1 | NM_022346.3 |
| NCAPG2* | 54892 | Hs00375141_m1 | NM_017760.5 |
| NCAPH* | 23397 | Hs01010752_m1 | NM_015341.3 |
| NDC80* | 10403 | Hs00196101_m1 | NM_006101.2 |
| NEK2* | 4751 | Hs00601227_mH | NM_002497.2 |
| NUSAP1* | 51203 | Hs01006195_m1 | NM_018454.6; NM_001129897.1; NM_016359.3 |
| OIP5* | 11339 | Hs00299079_m1 | NM_007280.1 |
| ORC6L* | 23594 | Hs00204876_m1 | NM_014321.2 |
| PAICS* | 10606 | Hs00272390_m1 | NM_001079524.1; NM_001079525.1; NM_006452.3 |
| PBK* | 55872 | Hs00218544_m1 | NM_018492.2 |
| PCNA* | 5111 | Hs00427214_g1 | NM_182649.1; NM_002592.2 |
| PDSS1* | 23590 | Hs00372008_m1 | NM_014317.3 |
| PLK1* | 5347 | Hs00153444_m1 | NM_005030.3 |
| PLK4* | 10733 | Hs00179514_m1 | NM_014264.3 |
| POLE2* | 5427 | Hs00160277_m1 | NM_002692.2 |
| PRC1* | 9055 | Hs00187740_m1 | NM_199413.1; NM_199414.1; NM_003981.2 |
| PSMA7* | 5688 | Hs00895424_m1 | NM_002792.2 |
| PSRC1* | 84722 | Hs00364137_m1 | NM_032636.6; NM_001005290.2; NM_001032290.1; NM_001032291.1 |

TABLE 2-continued

| Gene Symbol | Entrez GeneID | ABI Assay ID | RefSeq Accession Nos. |
|---|---|---|---|
| PTTG1* | 9232 | Hs00851754_u1 | NM_004219.2 |
| RACGAP1* | 29127 | Hs00374747_m1 | NM_013277.3 |
| RAD51* | 5888 | Hs00153418_m1 | NM_133487.2; NM_002875.3 |
| RAD51AP1* | 10635 | Hs01548891_m1 | NM_001130862.1; NM_006479.4 |
| RAD54B* | 25788 | Hs00610716_m1 | NM_012415.2 |
| RAD54L* | 8438 | Hs00269177_m1 | NM_001142548.1; NM_003579.3 |
| RFC2* | 5982 | Hs00945948_m1 | NM_181471.1; NM_002914.3 |
| RFC4* | 5984 | Hs00427469_m1 | NM_181573.2; NM_002916.3 |
| RFC5* | 5985 | Hs00738859_m1 | NM_181578.2; NM_001130112.1; NM_001130113.1; NM_007370.4 |
| RNASEH2A* | 10535 | Hs00197370_m1 | NM_006397.2 |
| RRM2* | 6241 | Hs00357247_g1 | NM_001034.2 |
| SHCBP1* | 79801 | Hs00226915_m1 | NM_024745.4 |
| SMC2* | 10592 | Hs00197593_m1 | NM_001042550.1; NM_001042551.1; NM_006444.2 |
| SPAG5* | 10615 | Hs00197708_m1 | NM_006461.3 |
| SPC25* | 57405 | Hs00221100_m1 | NM_020675.3 |
| STIL* | 6491 | Hs00161700_m1 | NM_001048166.1; NM_003035.2 |
| STMN1* | 3925 | Hs00606370_m1; Hs01033129_m1 | NM_005563.3; NM_203399.1 |
| TACC3* | 10460 | Hs00170751_m1 | NM_006342.1 |
| TIMELESS* | 8914 | Hs01086966_m1 | NM_003920.2 |
| TK1* | 7083 | Hs01062125_m1 | NM_003258.4 |
| TOP2A* | 7153 | Hs00172214_m1 | NM_001067.2 |
| TPX2* | 22974 | Hs00201616_m1 | NM_012112.4 |
| TRIP13* | 9319 | Hs01020073_m1 | NM_004237.2 |
| TTK* | 7272 | Hs00177412_m1 | NM_003318.3 |
| TUBA1C* | 84790 | Hs00733770_m1 | NM_032704.3 |
| TYMS* | 7298 | Hs00426591_m1 | NM_001071.2 |
| UBE2C | 11065 | Hs00964100_g1 | NM_181799.1; NM_181800.1; NM_181801.1; NM_181802.1; NM_181803.1; NM_007019.2 |
| UBE2S | 27338 | Hs00819350_m1 | NM_014501.2 |
| VRK1* | 7443 | Hs00177470_m1 | NM_003384.2 |
| ZWILCH* | 55055 | Hs01555249_m1 | NM_017975.3; NR_003105.1 |
| ZWINT* | 11130 | Hs00199952_m1 | NM_032997.2; NM_001005413.1; NM_007057.3 |

*124-gene subset of CCP genes useful in the invention ("Panel B").
ABI Assay ID means the catalogue ID number for the gene expression assay commercially available from Applied Biosystems Inc. (Foster City, CA) for the particular gene.

Accordingly, in a first aspect of the present invention, a method is provided for determining gene expression in a sample. Generally, the method includes at least the following steps: (1) obtaining a sample from a patient; (2) determining the expression of a panel of genes in the sample including at least 2, 4, 6, 8 or 10 cell-cycle progression genes; and (3) providing a test value by (a) weighting the determined expression of each of a plurality of test genes selected from said panel of genes with a predefined coefficient, and (b) combining the weighted expression to provide said test value, wherein at least 20%, 50%, at least 75% or at least 90% of said plurality of test genes are cell-cycle progression genes.

In some embodiments, said plurality of test genes comprises at least 2 CCP genes, and the combined weight given to said at least 2 CCP genes is at least 40% of the total weight given to the expression of all of said plurality of test genes. In some embodiments, said plurality of test genes comprises at least 4 or 5 or 6 CCP genes, and the combined weight given to said at least 4 or 5 or 6 CCP genes is at least 40% of the total weight given to the expression of all of said plurality of test genes. In some embodiments the combined weight given to said cell-cycle genes is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the total weight given to the expression of all of said plurality of test genes. The meaning of these combined and total weights is explained further below.

In some embodiments, said plurality of test genes comprises one or more CCP genes constituting from 1% to about 95% of said plurality of test genes, and the combined weight given to said one or more CCP genes is at least at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the total weight given to the expression of all of said plurality of test genes. In some embodiments, said plurality of test genes includes at least 2, at least 4, at least 5 CCP genes, or at least 6 CCP genes.

The sample used in the method may be a sample derived from prostate, lung, bladder, brain or breast, e.g., by way of biopsy or surgery. The sample may also be cells naturally shedded by prostate, lung, bladder, brain or breast, e.g., into blood, urine, sputum, etc. Samples from an individual who has not been diagnosed of cancer may be used for the diagnosis of cancer as described below in Section II. Samples from an individual diagnosed of cancer may be used for the cancer prognosis in accordance with the present invention.

For example, the method may be performed on a tumor sample from a patient identified as having prostate cancer, lung cancer, bladder cancer or brain cancer. Such a method includes at least the following steps: (1) obtaining a tumor sample from a patient identified as having prostate cancer, lung cancer, bladder cancer or brain cancer; (2) determining the expression of a panel of genes in the tumor sample including at least 2, 4, 6, 8 or 10 cell-cycle progression genes; and (3) providing a test value by (a) weighting the determined expression of each of a plurality of test genes selected from said panel of genes with a predefined coefficient, and (b) combining the weighted expression to provide said test value, wherein at least 20%, 50%, at least 75% or at least 90% of said plurality of test genes are cell-cycle progression genes.

The method also may be performed on a sample from a patient who has not been diagnosed of (but may be suspected of) cancer (e.g., prostate cancer, lung cancer, bladder cancer, breast or brain cancer). The sample may be a tissue biopsy or surgical sample directly from the organ (e.g., prostate, lung, bladder, breast or brain), or cells in a bodily fluid (e.g., blood or urine) shedded from such an organ. Such a method includes at least the following steps: (1) obtaining a sample that is a tissue or cell from prostate, lung, bladder, breast or brain, from an individual who have not been diagnosed of cancer; (2) determining the expression of a panel of genes in the sample including at least 2, 4, 6, 8 or 10 cell-cycle progression genes; and (3) providing a test value by (a) weighting the determined expression of each of a plurality of test genes selected from said panel of genes with a predefined coefficient, and (b) combining the weighted expression to provide said test value, wherein at least 20%, 50%, at least 75% or at least 90% of said plurality of test genes are cell-cycle progression genes.

In some embodiments of the method in accordance with this aspect of the invention, said plurality of test genes includes at least 2 CCP genes which constitute at least 50% or at least 60% of said plurality of test genes. In some embodiments, said plurality of test genes includes at least 4 CCP genes which constitute at least 20% or 30% or 50% or 60% of said plurality of test genes.

In some embodiments, the sample is from prostate, lung, bladder or brain, but not from breast, and said plurality of test genes includes the CCP genes Survivin (BIRC5), KI67, MYBL2, CCNB1 and STK15. In some embodiments, the sample is from prostate, lung, bladder or brain, but not from breast, and said panel of genes in the method described above comprises the genes in Table 24, and said plurality of test genes includes the test genes in Table 24, and optionally the weighting of the expression of the test gens is according to that in Paik et al., *N Engl J Med.*, 2817-2826 (2004), which is incorporated herein by reference.

In the various embodiments described above, the weight coefficient given to each CCP gene in said plurality of test genes is greater than 1/N where N is the total number of test genes in the plurality of test genes.

In another aspect of the present invention, a method is provided for analyzing gene expression in a sample. Generally, the method includes at least the following steps: (1) obtaining expression level data from a sample for a panel of genes including at least 2, 4, 6, 8 or 10 cell-cycle progression genes; and (2) providing a test value by (a) weighting the determined expression of each of a plurality of test genes selected from said panel of genes with a predefined coefficient, and (b) combining the weighted expression to provide said test value, wherein at least 20%, 50%, at least 75% or at least 90% of said plurality of test genes are cell-cycle progression genes. In some embodiments, the plurality of test genes includes at least 6 CCP genes, which constitute at least 35%, 50% or 75% of said plurality of test genes. In some embodiments, the plurality of test genes includes at least 8 CCP genes, which constitute at least 20%, 35%, 50% or 75% of said plurality of test genes. In some embodiments the expression level data comes from a tumor sample from a patient identified as having prostate cancer, lung cancer, bladder cancer or brain cancer.

Gene expression can be determined either at the RNA level (i.e., noncoding RNA (ncRNA), mRNA, miRNA, tRNA, rRNA, snoRNA, siRNA and piRNA) or at the protein level. Levels of proteins in a tumor sample can be determined by any known techniques in the art, e.g., HPLC, mass spectrometry, or using antibodies specific to selected proteins (e.g., IHC, ELISA, etc.).

In some embodiments, the amount of RNA transcribed from the panel of genes including test genes is measured in the tumor sample. In addition, the amount of RNA of one or more housekeeping genes in the tumor sample is also measured, and used to normalize or calibrate the expression of the test genes. The terms "normalizing genes" and "housekeeping genes" are defined herein below.

In some embodiments, the plurality of test genes includes at least 2, 3 or 4 cell-cycle progression genes, which constitute at least 50%, 75% or 80% of the plurality of test genes, and in some embodiments 100% of the plurality of test genes. In some embodiments, the plurality of test genes includes at least 5, 6 or 7, or at least 8 cell-cycle progression genes, which constitute at least 20%, 25%, 30%, 40%, 50%, 60%, 70%, 75%, 80% or 90% of the plurality of test genes, and in some embodiments 100% of the plurality of test genes.

In some other embodiments, the plurality of test genes includes at least 8, 10, 12, 15, 20, 25 or 30 cell-cycle progression genes, which constitute at least 20%, 25%, 30%, 40%, 50%, 60%, 70%, 75%, 80% or 90% of the plurality of test genes, and in some embodiments 100% of the plurality of test genes.

As will be apparent to a skilled artisan apprised of the present invention and the disclosure herein, "sample" means any biological sample from a patient (including apparently healthy patients). Examples include fluids (e.g., blood, urine, sputum, pleural fluid, semen, saliva, etc.), tissues (e.g., skin, bone, soft tissue from any particular organ or organ system, etc.), waste products (e.g., stool), etc. In this context, "sample" includes any material extracted, purified, amplified, or derived from the preceding. Examples include nucleic acids, proteins, metabolites, etc.

As will be apparent to a skilled artisan apprised of the present invention and the disclosure herein, "tumor sample" means any "sample" containing one or more tumor cells, or one or more tumor-derived RNA or protein, and obtained from a patient. For example, a tissue sample obtained from a tumor tissue of a cancer patient is a useful tumor sample in the present invention. The tissue sample can be an FFPE sample, or fresh frozen sample, and in some embodiments contain largely tumor cells. A single malignant cell from a cancer patient's tumor is also a useful tumor sample. Such a malignant cell can be obtained directly from the patient's tumor, or purified from the patient's bodily fluid such as blood and urine. In addition, a bodily fluid such as blood, urine, sputum and saliva containing one or tumor cells, or tumor-derived RNA or proteins, can also be useful as a tumor sample for purposes of practicing the present invention.

Those skilled in the art are familiar with various techniques for determining the status of a gene or protein in a tissue or cell sample including, but not limited to, microarray analysis (e.g., for assaying mRNA or microRNA expression, copy number, etc.), quantitative real-time PCR™ ("qRT-PCR™", e.g., TaqMan™), immunoanalysis (e.g., ELISA, immunohistochemistry), etc. The activity level of a polypeptide encoded by a gene may be used in much the same way as the expression level of the gene or polypeptide. Often higher activity levels indicate higher expression levels and while lower activity levels indicate lower expression levels. Thus, in some embodiments, the invention provides any of the methods discussed above, wherein the activity level of a polypeptide encoded by the CCP is determined rather than or in adition to the expression level of the CCP. Those skilled in the art are familiar with techniques for measuring the activity of various such proteins, including those encoded by the genes listed in any of Table 1, 2, 3, 9, 11, 16, 25, 26, 28, 29 or 30 or any of Panel A, B, C, D, E, F, or G. The methods of the invention may be practiced independent of the particular technique used.

In some embodiments, the expression of one or more normalizing genes is also obtained for use in normalizing the expression of test genes. As used herein, "normalizing genes" referred to the genes whose expression is used to calibrate or normalize the measured expression of the gene of interest (e.g., test genes). Importantly, the expression of normalizing genes should be independent of cancer outcome/prognosis, and the expression of the normalizing genes is very similar among all the tumor samples. The normalization ensures accurate comparison of expression of a test gene between different samples. For this purpose, housekeeping genes known in the art can be used. Housekeeping genes are well known in the art, with examples including, but are not limited to, GUSB (glucuronidase, beta), HMBS (hydroxymethylbilane synthase), SDHA (succinate dehydrogenase complex, subunit A, flavoprotein), UBC (ubiquitin C) and YWHAZ (tyrosine 3-monooxygenase/tryptophan 5-monooxygenase activation protein, zeta polypeptide). One or more housekeeping genes can be used. In some embodiments, at least 2, 5, 10 or 15 housekeeping genes are used to provide a combined normalizing gene set. In some embodiments the top 1, 2, 3, 4, 5, 6, 7, 8, 9, 10, 11, 12, 13, 14, or 15 genes in Table 27 are used to provide a combined normalizing gene set. The amount of gene expression of such normalizing genes can be averaged, combined together by straight additions or by a defined algorithm. Some examples of particularly useful housekeeping genes for use in the methods and compositions of the invention include those listed in Table A below.

TABLE A

| Gene Symbol | Entrez GeneID | Applied Biosystems Assay ID | RefSeq Accession Nos. |
|---|---|---|---|
| CLTC* | 1213 | Hs00191535_m1 | NM_004859.3 |
| GUSB | 2990 | Hs99999908_m1 | NM_000181.2 |
| HMBS | 3145 | Hs00609297_m1 | NM_000190.3 |
| MMADHC* | 27249 | Hs00739517_g1 | NM_015702.2 |
| MRFAP1* | 93621 | Hs00738144_g1 | NM_033296.1 |
| PPP2CA* | 5515 | Hs00427259_m1 | NM_002715.2 |
| PSMA1* | 5682 | Hs00267631_m1 | |
| PSMC1* | 5700 | Hs02386942_g1 | NM_002802.2 |
| RPL13A* | 23521 | Hs03043885_g1 | NM_012423.2 |
| RPL37* | 6167 | Hs02340038_g1 | NM_000997.4 |
| RPL38* | 6169 | Hs00605263_g1 | NM_000999.3 |
| RPL4* | 6124 | Hs03044647_g1 | NM_000968.2 |
| RPL8* | 6132 | Hs00361285_g1 | NM_033301.1; NM_000973.3 |
| RPS29* | 6235 | Hs03004310_g1 | NM_001030001.1; NM_001032.3 |
| SDHA | 6389 | Hs00188166_m1 | NM_004168.2 |
| SLC25A3* | 6515 | Hs00358082_m1 | NM_213611.1; NM_002635.2; NM_005888.2 |
| TXNL1* | 9352 | Hs00355488_m1 | NR_024546.1; NM_004786.2 |
| UBA52* | 7311 | Hs03004332_g1 | NM_001033930.1; NM_003333.3 |
| UBC | 7316 | Hs00824723_m1 | NM_021009.4 |
| YWHAZ | 7534 | Hs00237047_m1 | NM_003406.3 |

*Subset of housekeeping genes used in, e.g., Example 5.

In the case of measuring RNA levels for the genes, one convenient and sensitive approach is real-time quantitative PCR (qPCR) assay, following a reverse transcription reaction. Typically, a cycle threshold ($C_t$) is determined for each test gene and each normalizing gene, i.e., the number of cycle at which the fluorescence from a qPCR reaction above background is detectable.

The overall expression of the one or more normalizing genes can be represented by a "normalizing value" which can be generated by combining the expression of all normalizing genes, either weighted equally (straight addition or averaging) or by different predefined coefficients. For example, in a simplest manner, the normalizing value $C_{tH}$ can be the cycle threshold ($C_t$) of one single normalizing gene, or an average of the $C_t$ values of 2 or more, 5 or more, 10 or more, or 15 or more normalizing genes, in which case, the predefined coefficient is 1/N, where N is the total number of normalizing genes used. Thus, $C_{tH}=(C_{tH1}+C_{tH2}+ \ldots C_{tHn})/N$. As will be apparent to skilled artisans, depending on the normalizing genes used, and the weight desired to be given to each normalizing gene, any coefficients (from 0/N to N/N) can be given to the normalizing genes in weighting the expression of such normalizing genes. That is, $C_{tH}=xC_{tH1}+yC_{tH2}+ \ldots zC_{tHn}$, wherein $x+y+ \ldots +z=1$.

As discussed above, the methods of the invention generally involve determining the level of expression of a panel of CCP genes. With modern high-throughput techniques, it is often possible to determine the expression level of tens, hundreds or thousands of genes. Indeed, it is possible to determine the level of expression of the entire transcriptome (i.e., each transcribed gene in the genome). Once such a global assay has been performed, one may then informatically analyze one or more subsets (i.e., panels) of genes. After measuring the expression of hundreds or thousands of genes in a sample, for example, one may analyze (e.g., informatically) the expression of a panel comprising primarily CCP genes according to the present invention by combining the expression level values of the individual test genes to obtain a test value.

As will be apparent to a skilled artisan, the test value provided in the present invention represents the overall expression level of the plurality of test genes composed of substantially cell-cycle progression genes. In one embodiment, to provide a test value in the methods of the invention, the normalized expression for a test gene can be obtained by normalizing the measured $C_t$ for the test gene against the $C_{tH}$, i.e., $\Delta C_{t1}=(C_{t1}-C_{tH})$. Thus, the test value representing the overall expression of the plurality of test genes can be provided by combining the normalized expression of all test genes, either by straight addition or averaging (i.e., weighted equally) or by a different predefined coefficient. For example, the simplest approach is averaging the normalized expression of all test genes: test value=$(\Delta C_{t1}+\Delta C_{t2}+ \ldots \Delta C_{tn})/n$. As will be apparent to skilled artisans, depending on the test genes used, different weight can also be given to different test genes in the present invention. For example, in some embodiments described above, the plurality of test genes comprises at least 2 CCP genes, and the combined weight given to the at least 2 CCP genes is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the total weight given to all of said plurality of test genes. That is, test value=$xΔC_{t1}+yΔC_{t2}+ \ldots zΔC_{tn}$, wherein $ΔC_{t1}$ and $ΔC_{t2}$ represent the gene expression of the 2 CCP genes, respectively, and $(x+y)/(x+y+ \ldots +z)$ is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100%.

As discussed in more detail below, panels of CCGs may be assessed according to the methods of the invention. Thus in some embodiments the plurality of gene evaluated comprises the genes listed in any of Table 1, 2, 3, 9, 11, 16, 25, 26, 28, 29 or 30 or any of Panel A, B, C, D, E, F, or G.

When choosing specific CCGs for inclusion in any embodiment of the invention, the individual predictive power of each gene may also be used to rank them in importance. The inventors have determined that the CCGs in Panel C can be ranked as shown in Table 29 according to the predictive power of each individual gene. The CCGs in Panel F can be similarly ranked as shown in Table 30.

Thus, in some embodiments of each of the various aspects of the invention the plurality of test genes comprises the top 2, 3, 4, 5, 6, 7, 8, 9, 10, 11, 12, 13, 14, 15, 20, 25, 30, 35, 40 or more CCGs listed in Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9, 10, 15, or of the following genes: ASPM, BIRC5, BUB1B, CCNB2, CDC2, CDC20, CDCA8, CDKN3, CENPF, DLGAP 5, FOXM1, KIAA 0101, KIF11, KIF2C, KIF4A, MCM10, NUSAP1, PRC1, RACGAP1, and TPX2. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9, 10, 15, or 20 of the following genes: TPX2, CCNB2, KIF4A, KIF2C, BIRC5, RACGAP1, CDC2, PRC1, DLGAP5/DLG7, CEP 55, CCNB1, TOP2A, CDC20, KIF20A, BUB1B, CDKN3, NUSAP1, CCNA2, KIF11, and CDCA8. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, or ten or all of gene numbers 1 & 2, 1 to 3, 1 to 4, 1 to 5, 1 to 6, 1 to 7, 1 to 8, 1 to 9, or 1 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, or nine or all of gene numbers 2 & 3, 2 to 4, 2 to 5, 2 to 6, 2 to 7, 2 to 8, 2 to 9, or 2 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, or eight or all of gene numbers 3 & 4, 3 to 5, 3 to 6, 3 to 7, 3 to 8, 3 to 9, or 3 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, or seven or all of gene numbers 4 & 5, 4 to 6, 4 to 7, 4 to 8, 4 to 9, or 4 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, 10, 11, 12, 13, 14, or 15 or all of gene numbers 1 & 2, 1 to 3, 1 to 4, 1 to 5, 1 to 6, 1 to 7, 1 to 8, 1 to 9, 1 to 10, 1 to 11, 1 to 12, 1 to 13, 1 to 14, or 1 to 15 of any of Table 25, 26, 28, 29, or 30.

II. Cancer Diagnosis and Prognosis

1. Diagnosis

As stated above, it has been surprisingly discovered the expression of cell-cycle progression genes can accurately detect cancer in patient samples. Thus, the above-described method of determining cell-cycle gene expression can be applied in the diagnosis of cancer. For this purpose, the description above about the method of determining CCP gene expression is incorporated herein.

Generally, a method is provided for diagnosing cancer in a patient comprising determining CCP gene expression as described above, wherein overexpression of cell-cycle progression genes indicates the patient has cancer. That is, the method of diagnosing cancer generally comprises (1) obtaining a sample from a patient; (2) determining the expression of a panel of genes in the sample including at least 2, 4, 6, 8 or 10 cell-cycle progression genes; and (3) providing a test value by (a) weighting the determined expression of each of a plurality of test genes selected from said panel of genes with a predefined coefficient, and (b) combining the weighted expression to provide said test value, wherein at least 20%, 50%, at least 75% or at least 90% of said plurality of test genes are cell-cycle progression genes, wherein overexpression of said cell-cycle progression genes (e.g., as represented by a higher test value as compared to a reference value) indicates the patient has cancer.

In some embodiments, the diagnosis method further includes a step of comparing the test value provided in step (2) above to one or more reference values, and correlating the test value to the presence or absence of cancer. Optionally cancer is indicated if the test value is greater than the reference value.

In some embodiments, the diagnosis method is used for diagnosing prostate cancer, breast cancer, lung cancer, bladder cancer or brain cancer, e.g., in biopsy or surgical samples, or in cells from prostate, lung, breast, bladder or brain in a bodily fluid such as blood or urine. In some embodiments the sample is a tissue sample for which a diagnosis is ambiguous (e.g., not clear whether cancerous). In some embodiments, the sample is a tissue sample that upon pathological or other preliminary analysis indicated a diagnosis of no cancer, for which the methods, kits, systems, etc. of the present invention may be used to either confirm the diagnosis of no cancer or to indicate the patient has cancer or has an increased likelihood of cancer. In some embodiments, the sample is a bodily fluid or waste sample for which the methods, kits, systems, etc. of the present invention may be as a screen to indicate the patient (e.g., apparently healthy patient, patient suspected of having cancer, patient at increased risk of cancer) has cancer or has an increased likelihood of cancer.

As shown in Example 7, CCP scores generated from matched pairs of tumor and adjacent benign tissue had a positive correlation, showing that a CCP score from an apparently negative biopsy could be used to diagnose aggressive cancer. Thus, in some embodiments, the method of diagnosing cancer further comprises a step of analyzing a biopsy tissue sample based on pathology examination of the biopsy sample and determining the presence or absence of cancer cells in the biopsy sample. If the pathology examination is negative, it could be because the biopsy procedure missed the cancerous tissue and only retrieved the benign tissue adjacent the cancer cells. However, the CCP gene expression analysis described herein can be useful in diagnosing cancer based on benign tissues adjacent to cancer cells. Therefore, the method of diagnosing cancer based on determination of CCP gene expression can be used in conjunction with pathology examination to avoid misdiagnosis due to inaccurate biopsy. On the other hand, if the pathology examination is positive, the determination of CCP gene expression as disclosed herein may still be used in conjunction to confirm the diagnosis of cancer.

In one embodiment, the diagnosis method comprises (1) determining in a sample the expression of a panel of genes including at least 4, 5, 6, or at least 8 cell-cycle progression genes; and (2) providing a test value by (a) weighting the determined expression of each of a plurality of test genes selected from the panel of genes with a predefined coefficient, and (b) combining the weighted expression to provide the test value, wherein at least 25%, at least 50%, at least 75% or at least 85% of the plurality of test genes are cell-cycle progression genes, and wherein an increased level (e.g., overall) of expression of the plurality of test genes indicates the patient has cancer.

Some embodiments provide a method for diagnosing cancer comprising: (1) obtaining expression level data from a sample for a panel of genes including at least 2, 4, 6, 8 or 10 cell-cycle progression genes; and (2) providing a test value by (a) weighting the determined expression of each of a plurality of test genes selected from said panel of genes with a predefined coefficient, and (b) combining the weighted expression to provide said test value, wherein at least 20%, 50%, at least 75% or at least 90% of said plurality of test genes are cell-cycle progression genes.

In some embodiments, said plurality of test genes includes at least 2 CCP genes which constitute at least 50% or at least 60% of said plurality of test genes. In some embodiments, said plurality of test genes includes at least 4 CCP genes which constitute at least 20% or 30% or 50% or 60% of said plurality of test genes.

In some embodiments, said plurality of test genes comprises at least 2 CCP genes, and the combined weight given to said at least 2 CCP genes is at least 40% of the total weight given to the expression of all of said plurality of test genes. In some embodiments, said plurality of test genes comprises at least 4 or 5 or 6 CCP genes, and the combined weight given to said at least 4 or 5 or 6 CCP genes is at least 40% of the total weight given to the expression of all of said plurality of test genes. In some embodiments the combined weight given to said cell-cycle genes is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the total weight given to the expression of all of said plurality of test genes. The meaning of these combined and total weights is as described above.

In some embodiments, said plurality of test genes comprises one or more CCP genes constituting from 1% to about 95% of said plurality of test genes, and the combined weight given to said one or more CCP genes is at least 40% or 50% or 100% of the total weight given to the expression of all of said plurality of test genes. In some embodiments, said plurality of test genes includes at least 2, at least 4, at least 5 CCP genes, or at least 6 CCP genes.

In some embodiments, said plurality of test genes includes the CCP genes Survivin (BIRC5), KI67, MYBL2, CCNB1 and STK15. In some embodiments, said panel of genes in the method described above comprises the genes in Table 24, and said plurality of test genes includes the test genes in Table 24, and optionally the weighting of the expression of the test gens is according to that in Paik et al., N Engl J Med., 2817-2826 (2004), which is incorporated herein by reference.

In the various embodiments described above, the weight coefficient given to each CCP gene in said plurality of test genes is greater than 1/N where N is the total number of test genes in the plurality of test genes.

In another aspect of the present invention, a method is provided for determining gene expression in a patient sample, in some embodiments from a patient suspected of prostate cancer, breast cancer, lung cancer, bladder cancer or brain cancer. Such a method includes at least the following steps: (1) obtaining a tumor sample from a patient identified as having prostate cancer, lung cancer, bladder cancer or brain cancer; (2) determining the expression of a panel of genes in the tumor sample including at least 2, 4, 6, 8 or 10 cell-cycle progression genes; and (3) providing a test value by (a) weighting the determined expression of each of a plurality of test genes selected from said panel of genes with a predefined coefficient, and (b) combining the weighted expression to provide said test value, wherein said plurality of test genes comprises at least 2 CCP genes, and the combined weight given to said at least 2 CCP genes is at least 40% of the total weight given to the expression of all of said plurality of test genes. In some embodiments, said plurality of test genes comprises at least 4 or 5 or 6 CCP genes, and the combined weight given to said at least 4 or 5 or 6 CCP genes is at least 40% of the total weight given to the expression of all of said plurality of test genes.

In some embodiments the method further comprises a confirmatory test (e.g., imaging, biopsy, etc.) that is recommended, prescribed, and/or performed if there is an increased level of expression of the plurality of test genes. In some embodiments, no increased expression of the test genes indicates the patient does not have cancer. In some embodiments, no increased expression of the test genes indicates any cancer that may be present in the sample (or in the patient) is indolent (e.g., not aggressive).

2. Prognosis

It has further been surprisingly discovered that in selected cancers such as prostate cancer, lung cancer, bladder cancer and brain cancer, but not certain other cancers such as colon cancer, the expression of cell-cycle progression genes in tumor cells can accurately predict the degree of aggression of the cancer and risk of recurrence after treatment (e.g., surgical removal of cancer tissue, chemotherapy and radiation therapy, etc.). Thus, the above-described method of determining cell-cycle gene expression can be applied in the prognosis and treatment of these cancers. For this purpose, the description above about the method of determining CCP gene expression is incorporated herein.

Generally, a method is further provided for prognosing cancer selected from prostate cancer, lung cancer, bladder cancer or brain cancer, which comprises determining in a tumor sample from a patient diagnosed of prostate cancer, lung cancer, bladder cancer or brain cancer, the expression of at least 2, 4, 5, 6, 7 or at least 8, 9, 10 or 12 cell-cycle progression genes, wherein overexpression of the at least 4 cell-cycle progression genes indicates a poor prognosis or an increased likelihood of recurrence of cancer in the patient. The expression can be determined in accordance with the method described above.

In some embodiments, the diagnosis method further includes a step of comparing the test value provided in step (2) above to one or more reference values, and correlating the test value to the prognosis of cancer. Optionally poor prognosis of the cancer is indicated if the test value is greater than the reference value.

In one embodiment, the prognosis method comprises (1) determining in a sample the expression of a panel of genes including at least 4, 5, 6, or at least 8 cell-cycle progression genes; and (2) providing a test value by (a) weighting the determined expression of each of a plurality of test genes selected from the panel of genes with a predefined coefficient, and (b) combining the weighted expression to provide the test value, wherein at least 25%, at least 50%, at least 75% or at least 85% of the plurality of test genes are cell-cycle progression genes, and wherein an increased level (e.g., overall) of expression of the plurality of test genes indicates the patient has a poor prognosis or an increased likelihood that the patient's cancer will progress aggresively.

In some embodiments, said plurality of test genes includes at least 2 CCP genes which constitute at least 50% or at least 60% of said plurality of test genes. In some embodiments, said plurality of test genes includes at least 4 CCP genes which constitute at least 20% or 30% or 50% or 60% of said plurality of test genes.

In some embodiments, said plurality of test genes comprises at least 2 CCP genes, and the combined weight given to said at least 2 CCP genes is at least 40% of the total weight given to the expression of all of said plurality of test genes. In some embodiments, said plurality of test genes comprises at least 4 or 5 or 6 CCP genes, and the combined weight given to said at least 4 or 5 or 6 CCP genes is at least 40% of the total weight given to the expression of all of said plurality of test genes. In some embodiments the combined weight given to said cell-cycle genes is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the total weight given to the expression of all of said plurality of test genes.

In some embodiments, said plurality of test genes comprises one or more CCP genes constituting from 1% to about 95% of said plurality of test genes, and the combined weight given to said one or more CCP genes is at least 40% or 50% or 100% of the total weight given to the expression of all of said plurality of test genes. In some embodiments, said plurality of test genes includes at least 2, at least 4, at least 5 CCP genes, or at least 6 CCP genes.

In some embodiments, said plurality of test genes includes the CCP genes Survivin (BIRC5), KI67, MYBL2, CCNB1 and STK15. In some embodiments, said panel of genes in the method described above comprises the genes in Table 24, and said plurality of test genes includes the test genes in Table 24, and optionally the weighting of the expression of the test gens is according to that in Paik et al., *N Engl J Med.*, 2817-2826 (2004), which is incorporated herein by reference.

In the various embodiments described above, the weight coefficient given to each CCP gene in said plurality of test genes is greater than 1/N where N is the total number of test genes in the plurality of test genes.

In some embodiments, the prognosis method includes (1) obtaining a tumor sample from a patient identified as having prostate cancer, lung cancer, bladder cancer or brain cancer; (2) determining the expression of a panel of genes in the tumor sample including at least 2, 4, 6, 8 or 10 cell-cycle progression genes; and (3) providing a test value by (a) weighting the determined expression of each of a plurality of test genes selected from the panel of genes with a predefined coefficient, and (b) combining the weighted expression to provide said test value, wherein at least 20%, 50%, at least 75% or at least 90% of said plurality of test genes are cell-cycle progression genes, and wherein an increased level of expression of the plurality of test genes indicates a poor prognosis or an increased likelihood of cancer recurrence.

Some embodiments provide a method for prognosing cancer comprising: (1) obtaining expression level data, from a sample (e.g., tumor sample) from a patient identified as having prostate cancer, lung cancer, bladder cancer or brain cancer, for a panel of genes including at least 2, 4, 6, 8 or 10 cell-cycle progression genes; and (2) providing a test value by (a) weighting the determined expression of each of a plurality of test genes selected from said panel of genes with a predefined coefficient, and (b) combining the weighted expression to provide said test value, wherein at least 20%, 50%, at least 75% or at least 90% of said plurality of test genes are cell-cycle progression genes.

In some embodiments, the test value representing the expression (e.g., overall) of the plurality of test genes is compared to one or more reference values (or index values), and optionally correlated to a risk of cancer progression or risk of cancer recurrence. Optionally an increased likelihood of poor prognosis is indicated if the test value is greater than the reference value.

III. Other Aspects of the Invention and Additional Embodiments of All Aspects of the Invention Those skilled in the art are familiar with various ways of deriving and using index values in each aspect of the invention (including but not limited to the gene expression, diagnosis, and prognosis aspects discussed above and the kit, method of treatment, and system aspects discussed below). For example, the index value may represent the gene expression levels found in a normal sample obtained from the patient of interest, in which case an expression level in the test sample significantly higher than this index value would indicate, e.g., cancer, a poor prognosis, increased likelihood of cancer recurrence, or a need for aggressive treatment.

Alternatively, the index value may represent the average expression level for a set of individuals from a diverse population or a subset of the population. For example, one may determine the average expression level of a gene or gene panel in a random sampling of patients (either cancer-free controls or patients with cancer, e.g., prostate, bladder, brain, breast, or lung cancer). This average expression level may be termed the "threshold index value," with patients having CCP expression higher than this value expected to have, depending on context, cancer, a higher probability of having cancer than patients having expression lower than this value, a poorer prognosis than patients having expression lower than this value, etc.

Alternatively the index value may represent the average expression level of a particular gene marker in a plurality of training patients (e.g., healthy controls, prostate cancer patients) with similar clinical features (e.g., similar outcomes whose clinical and follow-up data are available and sufficient to define and categorize the patients by disease outcome, e.g., recurrence or prognosis. See, e.g., Examples, infra. For example, a "good prognosis index value" can be generated from a plurality of training cancer patients characterized as having "good outcome", e.g., those who have not had cancer recurrence five years (or ten years or more) after initial treatment, or who have not had progression in their cancer five years (or ten years or more) after initial diagnosis. A "poor prognosis index value" can be generated from a plurality of training cancer patients defined as having "poor outcome", e.g., those who have had cancer recurrence within five years (or ten years, etc.) after initial treatment, or who have had progression in their cancer within five years (or ten years, etc.) after initial diagnosis. Thus, a good prognosis index value of a particular gene may represent the average level of expression of the particular gene in patients having a "good outcome," whereas a poor prognosis index value of a particular gene represents the average level of expression of the particular gene in patients having a "poor outcome." Similar index values ("cancer index value," "cancer-free index value," etc.) can be established for and used in the diagnostic methods of the invention.

Thus one aspect of the invention provides a method of diagnosing cancer comprising determining the status of a panel of genes comprising at least two CCP genes, in a sample, particularly a tumor sample, from a patient, wherein an abnormal status indicates the patient has cancer. A related aspect of the invention provides a method of classifying cancer comprising determining the status of a panel of genes comprising at least two CCP genes, in tissue or cell sample, particularly a tumor sample, from a patient, wherein an abnormal status indicates a negative cancer classification. As used herein, "determining the status" of a gene refers to determining the presence, absence, or extent/level of some physical, chemical, or genetic characteristic of the gene or its expression product(s). Such characteristics include, but are not limited to, expression levels, activity levels, mutations, copy number, methylation status, etc.

In the context of CCP genes as used to diagnose cancer, determine risk of cancer recurrence or progression, or determine the need for aggressive treatment, particularly useful characteristics include expression levels (e.g., mRNA or protein levels) and activity levels. Characteristics may be assayed directly (e.g., by assaying a CCP's expression level) or determined indirectly (e.g., assaying the level of a gene or genes whose expression level is correlated to the expression level of the CCP). Thus some embodiments of the invention provide a method of classifying cancer comprising determining the expression level, particularly mRNA (alternatively cDNA) level of a panel of genes comprising at least two CCP genes, in a tumor sample, wherein elevated expression indicates (a) the patient has cancer, (b) a negative cancer classification, (c) an increased risk of cancer recurrence or progression, or (d) a need for aggressive treatment.

"Abnormal status" means a marker's status in a particular sample differs from the status generally found in average samples (e.g., healthy samples or average diseased samples). Examples include mutated, elevated, decreased, present, absent, etc. An "elevated status" means that one or more of the above characteristics (e.g., expression or mRNA level) is higher than normal levels. Generally this means an increase in the characteristic (e.g., expression or mRNA level) as compared to an index value. Conversely a "low status" means that one or more of the above characteristics (e.g., gene expression or mRNA level) is lower than normal levels. Generally this means a decrease in the characteristic (e.g., expression) as compared to an index value. In this context, a "negative status" generally means the characteristic is absent or undetectable. For example, PTEN status is negative if PTEN nucleic acid and/or protein is absent or undetectable in a sample. However, negative PTEN status also includes a mutation or copy number reduction in PTEN.

In some embodiments of the invention the methods comprise determining the expression of one or more CCP genes and, if this expression is "increased," the patient has cancer, a poor prognosis, etc. In the context of the invention, "increased" expression of a CCP means the patient's expression level is either elevated over a normal index value or a threshold index (e.g., by at least some threshold amount) or closer to the one index value (e.g., "cancer index value," "poor prognosis index value," etc.) than to another index value (e.g., "cancer-free index value," "good prognosis index value," etc.).

Thus, when the determined level of expression of a relevant gene marker is closer to the cancer index value of the gene than to the cancer-free index value of the gene, then it can be concluded that the patient has cancer. On the other hand, if the determined level of expression of a relevant gene marker is closer to the cancer-free index value of the gene than to the cancer index value of the gene, then it can be concluded that the patient does not have cancer. Likewise, when the determined level of expression of a relevant gene marker is closer to the good prognosis index value of the gene than to the poor prognosis index value of the gene, then it can be concluded that the patient is more likely to have a good prognosis, i.e., a low (or no increased) likelihood of cancer recurrence. On the other hand, if the determined level of expression of a relevant gene marker is closer to the poor prognosis index value of the gene than to the good prognosis index value of the gene, then it can be concluded that the patient is more likely to have a poor prognosis, i.e., an increased likelihood of cancer recurrence.

Alternatively index values may be determined thusly: In order to assign patients to risk groups (e.g., high likelihood of having cancer, high likelihood of recurrence/progression), a threshold value will be set for the cell cycle mean. The optimal threshold value is selected based on the receiver operating characteristic (ROC) curve, which plots sensitivity vs (1-specificity). For each increment of the cell cycle mean, the sensitivity and specificity of the test is calculated using that value as a threshold. The actual threshold will be the value that optimizes these metrics according to the artisan's requirements (e.g., what degree of sensitivity or specificity is desired, etc.). Example 5 demonstrates determination of a threshold value determined and validated experimentally.

Panels of CCP genes (e.g., 2, 3, 4, 5, 6, 7, 8, 9, or 10 or more CCP genes) can diagnose cancer (Example 7) and predict prognosis (Example 3). Those skilled in the art are familiar with various ways of determining the expression of a panel (i.e., a plurality) of genes. Sometimes herein this is called determining the "overall expression" of a panel or plurality of genes. One may determine the expression of a panel of genes by determining the average expression level (normalized or absolute) of all panel genes in a sample obtained from a particular patient (either throughout the sample or in a subset of cells from the sample or in a single cell). Increased expression in this context will mean the average expression is higher than the average expression level of these genes in normal patients (or higher than some index value that has been determined to represent the average expression level in a reference population such as healthy patients or patients with a particular cancer). Alternatively, one may determine the expression of a panel of genes by determining the average expression level (normalized or absolute) of at least a certain number (e.g., 1, 2, 3, 4, 5, 6, 7, 8, 9, 10, 15, 20, 25, 30 or more) or at least a certain proportion (e.g., 10%, 20%, 30%, 40%, 50%, 60%, 70%, 80%, 90%, 95%, 99%, 100%) of the genes in the panel. Alternatively, one may determine the expression of a panel of genes by determining the absolute copy number of the mRNA (or protein) of all the genes in the panel and either total or average these across the genes.

As used herein, "classifying a cancer" and "cancer classification" refer to determining one or more clinically-relevant features of a cancer and/or determining a particular prognosis of a patient having said cancer. Thus "classifying a cancer" includes, but is not limited to: (i) evaluating metastatic potential, potential to metastasize to specific organs, risk of recurrence, and/or course of the tumor; (ii) evaluating tumor stage; (iii) determining patient prognosis in the absence of treatment of the cancer; (iv) determining prognosis of patient response (e.g., tumor shrinkage or progression-free survival) to treatment (e.g., chemotherapy, radiation therapy, surgery to excise tumor, etc.); (v) diagnosis of actual patient response to current and/or past treatment; (vi) determining a preferred course of treatment for the patient; (vii) prognosis for patient relapse after treatment (either treatment in general or some particular treatment); (viii) prognosis of patient life expectancy (e.g., prognosis for overall survival), etc.

Thus, a "negative classification" means an unfavorable clinical feature of the cancer (e.g., a poor prognosis). Examples include (i) an increased metastatic potential, potential to metastasize to specific organs, and/or risk of recurrence; (ii) an advanced tumor stage; (iii) a poor patient prognosis in the absence of treatment of the cancer; (iv) a poor prognosis of patient response (e.g., tumor shrinkage or progression-free survival) to a particular treatment (e.g., chemotherapy, radiation therapy, surgery to excise tumor, etc.); (v) a poor prognosis for patient relapse after treatment (either treatment in general or some particular treatment); (vi) a poor prognosis of patient life expectancy (e.g., prognosis for overall survival), etc. In some embodiments a recurrence-associated clinical parameter (or a high nomogram score) and increased expression of a CCP indicate a negative classification in cancer (e.g., increased likelihood of recurrence or progression).

As discussed above, it is thought that elevated CCP expression accompanies rapidly proliferating (and thus more aggressive) cancer cells. The inventors have found this to be true in both cancer cells themselves and in adjacent non-cancer cells. Elevated CCP expression in non-cancer cells in a sample has been found to be indicative of the presence of cancer cells somewhere in the patient (Example 7). This so-called field effect on non-cancerous cells can be used to diagnose cancer. In some embodiments elevated CCP expression indicates cancer in adjacent solid tissue (e.g., lung and prostate tissues as shown in Example 7). The CCP signature of cancer cells can also be detected in blood, urine and other body fluids. This is generally thought to be due to shedding of nucleic acids and proteins by dying cancer cells (e.g., apoptosis) and live cancer cells (e.g., in extracellular microvesicles). Thus in some methods of the invention the level of CCP expression is determined in a blood sample, urine sample, or some other body fluid sample.

If a patient's cancer has elevated CCP expression, this will often mean the patient has an increased likelihood of recurrence after treatment (e.g., the cancer cells not killed or removed by the treatment will quickly grow back). Such a cancer can also mean the patient has an increased likelihood of cancer progression or more rapid progression (e.g., the rapidly proliferating cells will cause any tumor to grow quickly, gain in virulence, and/or metastasize). Such a cancer can also mean the patient may require a relatively more aggressive treatment. Thus, in some embodiments the invention provides a method of classifying cancer comprising determining the status of a panel of genes comprising at least two CCP genes, wherein an abnormal status indicates an increased likelihood of recurrence or progression. As discussed above, in some embodiments the status to be determined is gene expression levels. Thus in some embodiments the invention provides a method of determining the prognosis of a patient's cancer comprising determining the expression level of a panel of genes comprising at least two CCP genes, wherein elevated expression indicates an increased likelihood of recurrence or progression of the cancer.

"Recurrence" and "progression" are terms well-known in the art and are used herein according to their known meanings. As an example, the meaning of "progression" may be cancer-type dependent, with progression in lung cancer meaning something different from progression in prostate cancer. However, within each cancer-type and subtype "progression" is clearly understood to those skilled in the art. As used herein, a patient has an "increased likelihood" of some clinical feature or outcome (e.g., recurrence or progression) if the probability of the patient having the feature or outcome exceeds some reference probability or value. The reference probability may be the probability of the feature or outcome across the general relevant patient population. For example, if the probability of recurrence in the general prostate cancer population is X % and a particular patient has been determined by the methods of the present invention to have a probability of recurrence of Y %, and if Y>X, then the patient has an "increased likelihood" of recurrence. Alternatively, as discussed above, a threshold or reference value may be determined and a particular patient's probability of recurrence may be compared to that threshold or reference. Because predicting recurrence and predicting progression are prognostic endeavors, "predicting prognosis" will often be used herein to refer to either or both. In these cases, a "poor prognosis" will generally refer to an increased likelihood of recurrence, progression, or both.

As shown in Example 3, individual CCP genes can predict prognosis quite well. As shown in Example 7, individual CCP gene expression is correlated between cancer cells and adjacent non-cancer cells. Thus the invention provides methods of diagnosing cancer and methods of predicting prognosis comprising determining the expression of at least one CCP listed in any of Table 1, 2, 3, 9, 11, 16, 25, 26, 28, 29 or 30 or any of Panel A, B, C, D, E, F, or G.

Example 3 also shows that panels of CCP genes (e.g., 2, 3, 4, 5, or 6 CCP genes) can accurately predict prognosis. Thus in some embodiments the methods of the invention comprise determining the status of a panel (i.e., a plurality) of test genes comprising a plurality of CCP genes (e.g., to provide a test value representing the average expression of the test genes). For example, increased expression in a panel of test genes may refer to the average expression level of all panel genes in a particular patient being higher than the average expression level of these genes in normal patients (or higher than some index value that has been determined to represent the normal average expression level). Alternatively, increased expression in a panel of test genes may refer to increased expression in at least a certain number (e.g., 1, 2, 3, 4, 5, 6, 7, 8, 9, 10, 15, 20, 25, 30 or more) or at least a certain proportion (e.g., 10%, 20%, 30%, 40%, 50%, 60%, 70%, 80%, 90%, 95%, 99%, 100%) of the genes in the panel as compared to the average normal expression level.

In some embodiments of each aspect of the invention (including but not limited to the gene expression, diagnosis, and prognosis aspects discussed above and the kit, method of treatment, and system aspects discussed below), the test panel (which may itself be a sub-panel analyzed informatically) comprises at least 3, 4, 5, 6, 7, 8, 9, 10, 15, 20, 25, 30, 35, 40, 45, 50, 70, 80, 90, 100, 200, or more CCP genes. In some embodiments the test panel comprises at least 10, 15, 20, or more CCP genes. In some embodiments the test panel comprises between 5 and 100 CCP genes, between 7 and 40 CCP genes, between 5 and 25 CCP genes, between 10 and 20 CCP genes, or between 10 and 15 CCP genes. In some embodiments CCP genes comprise at least a certain proportion of the test panel used to provide a test value. Thus in some embodiments the test panel comprises at least 25%, 30%, 40%, 50%, 60%, 70%, 75%, 80%, 85%, 90%, 95%, 96%, 97%, 98%, or 99% CCP genes. In some embodiments the test panel comprises at least 10, 15, 20, 25, 30, 35, 40, 45, 50, 70, 80, 90, 100, 200, or more CCP genes, and such CCP genes constitute at least 50%, 60%, 70%, in some embodiments at least 75%, 80%, 85%, in some embodiments at least 90%, 95%, 96%, 97%, 98%, or 99% or more of the total number of genes in the test panel. In some embodiments the CCP genes are chosen from the group consisting of the genes in any of Table 1, 2, 3, 9, 11, 16, 25, 26, 28, 29 or 30 or any of Panel A, B, C, D, E, F, or G. In some embodiments the test panel comprises at least 2, 3, 4, 5, 6, 7, 8, 9, 10, 11, 12, 13, 14, 15, 20, 25, 30, or more of the genes in any of Table 1, 2, 3, 9, 11, 16, 25, 26, 28, 29 or 30 or any of Panel A, B, C, D, E, F, or G. In some embodiments the invention provides a method of diagnosing cancer comprising determining (e.g., in a sample) the status of the CCP genes in any of Table 1, 2, 3, 9, 11, 16, 25, 26, 28, 29 or 30 or any of Panel A, B, C, D, E, F, or G, wherein abnormal status indicates cancer. In some embodiments the invention provides a method of predicting prognosis comprising determining (e.g., in a sample) the status of the CCP genes in any of Table 1, 2, 3, 9, 11, 16, 25, 26, 28, 29 or 30 or any of Panel A, B, C, D, E, F, or G, wherein abnormal status indicates a poor prognosis.

In some of these embodiments elevated expression indicates the presence of cancer and/or an increased likelihood of recurrence or progression. Thus in some embodiments the invention provides a method of predicting risk of cancer recurrence or progression in a patient comprising determining the status of a panel of genes, wherein the panel comprises between about 10 and about 15 CCP genes, the CCP genes constitute at least 90% of the panel, and an elevated status for the CCP genes indicates an increased likelihood or recurrence or progression.

Several panels of CCP genes (Table 2, supra, and Tables 3 & 4, infra) have been evaluated for their ability to predict prognosis in several different cancers and for the correlation between cancer cells and adjacent non-cancer cells. The results of these studies are described in Examples 1 through 7 below.

TABLE 3

"Panel C" Evaluated in Examples 1 through 4

| Gene Symbol | Entrez GeneID |
|---|---|
| AURKA | 6790 |
| BUB1* | 699 |
| CCNB1* | 891 |
| CCNB2* | 9133 |
| CDC2* | 983 |
| CDC20* | 991 |
| CDC45L* | 8318 |
| CDCA8* | 55143 |
| CENPA | 1058 |
| CKS2* | 1164 |
| DLG7* | 9787 |
| DTL* | 51514 |
| FOXM1* | 2305 |
| HMMR* | 3161 |
| KIF23* | 9493 |
| KPNA2 | 3838 |
| MAD2L1* | 4085 |
| MELK | 9833 |
| MYBL2* | 4605 |
| NUSAP1* | 51203 |
| PBK* | 55872 |
| PRC1* | 9055 |
| PTTG1* | 9232 |
| RRM2* | 6241 |
| TIMELESS* | 8914 |
| TPX2* | 22974 |
| TRIP13* | 9319 |
| TTK* | 7272 |
| UBE2C | 11065 |
| UBE2S* | 27338 |
| ZWINT* | 11130 |

*These genes were used as a 26-gene subset panel ("Panel D") in the validation arm of the experiment described in Example 2.

TABLE 4

"Panel E"

| Name | GeneID |
|---|---|
| ASF1B* | 55723 |
| ASPM* | 259266 |
| BIRC5* | 332 |
| BUB1B* | 701 |
| C18orf24* | 220134 |
| CDC2* | 983 |
| CDC20* | 991 |
| CDCA3* | 83461 |
| CDCA8* | 55143 |
| CDKN3* | 1033 |
| CENPF* | 1063 |
| CENPM* | 79019 |
| CEP55* | 55165 |
| DLGAP5* | 9787 |
| DTL* | 51514 |
| FOXM1* | 2305 |
| KIAA0101* | 9768 |
| KIF11* | 3832 |
| KIF20A* | 10112 |
| KIF4A | 24137 |
| MCM10* | 55388 |
| NUSAP1* | 51203 |
| ORC6L* | 23594 |
| PBK* | 55872 |
| PLK1* | 5347 |
| PRC1* | 9055 |
| PTTG1* | 9232 |
| RAD51* | 5888 |
| RAD54L* | 8438 |
| RRM2* | 6241 |
| TK1* | 7083 |
| TOP2A* | 7153 |

*These genes were used as a 31-gene subset panel ("Panel F") in the experiment described in Example 5.

It has been determined that the choice of individual CCP genes for a test panel can in some embodiments be relatively arbitrary. In other words, many CCP genes have been found to be very good surrogates for each other. One way of assessing whether particular CCP genes will serve well in the methods and compositions of the invention is by assessing their correlation with the mean expression of CCP genes (e.g., all known CCP genes, a specific set of CCP genes, etc.). Those CCP genes that correlate particularly well with the mean are expected to perform well in assays of the invention, e.g., because these will reduce noise in the assay. A ranking of select CCP genes according to their correlation with the mean CCP expression is given in Tables 25, 26 & 28.

When choosing specific CCGs for inclusion in any embodiment of the invention, the individual predictive power of each gene may also be used to rank them in importance. The inventors have determined that the CCGs in Panel C can be ranked as shown in Table 29 according to the predictive power of each individual gene. The CCGs in Panel F can be similarly ranked as shown in Table 30.

Thus, in some embodiments of each of the various aspects of the invention the plurality of test genes comprises the top 2, 3, 4, 5, 6, 7, 8, 9, 10, 11, 12, 13, 14, 15, 20, 25, 30, 35, 40 or more CCGs listed in Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9, 10, 15, or 20 of the following genes: ASPM, BIRC5, BUB1B, CCNB2, CDC2, CDC20, CDCA8, CDKN3, CENPF, DL GAP 5, FOXM1, KIAA 0101, KIF11, KIF2C, KIF4A, MCM10, NUSAP1, PRC1, RACGAP1, and TPX2. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9, 10, 15, or 20 of the following genes: TPX2, CCNB2, KIF4A, KIF2C, BIRC5, RACGAP1, CDC2, PRC1, DLGAP5/DLG7, CEP55, CCNB1, TOP2A, CDC20, KIF20A, BUB1B, CDKN3, NUSAP1, CCNA2, KIF11, and CDCA8. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, or ten or all of gene numbers 1 & 2, 1 to 3, 1 to 4, 1 to 5, 1 to 6, 1 to 7, 1 to 8, 1 to 9, or 1 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, or nine or all of gene numbers 2 & 3, 2 to 4, 2 to 5, 2 to 6, 2 to 7, 2 to 8, 2 to 9, or 2 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, or eight or all of gene numbers 3 & 4, 3 to 5, 3 to 6, 3 to 7, 3 to 8, 3 to 9, or 3 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, or seven or all of gene numbers 4 & 5, 4 to 6, 4 to 7, 4 to 8, 4 to 9, or 4 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, 10, 11, 12, 13, 14, or 15 or all of gene numbers 1 & 2, 1 to 3, 1 to 4, 1 to 5, 1 to 6, 1 to 7, 1 to 8, 1 to 9, 1 to 10, 1 to 11, 1 to 12, 1 to 13, 1 to 14, or 1 to 15 of any of Table 25, 26, 28, 29, or 30.

In CCP signatures the particular CCP genes analyzed is often not as important as the total number of CCP genes. The number of CCP genes analyzed can vary depending on many factors, e.g., technical constraints, cost considerations, the classification being made, the cancer being tested, the desired level of predictive power, etc. Increasing the number of CCP genes analyzed in a panel according to the invention is, as a general matter, advantageous because, e.g., a larger pool of genes to be analyzed means less "noise" caused by outliers and less chance of an error in measurement or analysis throwing off the overall predictive power of the test. However, cost and other considerations will sometimes limit this number and finding the optimal number of CCP genes for a signature is desirable.

It has been discovered that the predictive power of a CCP signature often ceases to increase significantly beyond a certain number of CCP genes (see FIG. 1; Example 1). More specifically, the optimal number of CCP genes in a signature ($n_O$) can be found wherever the following is true $$(P_{n+1} - P_n) < C_O,$$

wherein P is the predictive power (i.e., $P_n$ is the predictive power of a signature with n genes and $P_{n+1}$ is the predictive power of a signature with n genes plus one) and $C_O$ is some optimization constant. Predictive power can be defined in many ways known to those skilled in the art including, but not limited to, the signature's p-value. $C_O$ can be chosen by the artisan based on his or her specific constraints. For example, if cost is not a critical factor and extremely high levels of sensitivity and specificity are desired, $C_O$ can be set very low such that only trivial increases in predictive power are disregarded. On the other hand, if cost is decisive and moderate levels of sensitivity and specificity are acceptable, $C_O$ can be set higher such that only significant increases in predictive power warrant increasing the number of genes in the signature.

Alternatively, a graph of predictive power as a function of gene number may be plotted (as in FIG. 1) and the second derivative of this plot taken. The point at which the second derivative decreases to some predetermined value ($C_O'$) may be the optimal number of genes in the signature.

Examples 1 & 3 and FIG. 1 illustrate the empirical determination of optimal numbers of CCP genes in CCP panels of the invention. Randomly selected subsets of the 31 CCP genes listed in Table 3 were tested as distinct CCP signatures and predictive power (i.e., p-value) was determined for each. As FIG. 1 shows, p-values ceased to improve significantly beyond about 10 or 15 CCP genes, thus indicating that, in some embodiments, a preferred number of CCP genes in a diagnostic or prognostic panel is from about 10 to about 15. Thus some embodiments of the invention provide a method of diagnosing cancer comprising determining the status of a panel of genes, wherein the panel comprises between about 10 and about 15 CCP genes and an elevated status (e.g., increased expression) for the CCP genes indicates cancer. Other embodiments of the invention provide a method of predicting prognosis in a cancer patient (e.g., having prostate cancer) comprising determining the status of a panel of genes, wherein the panel comprises between about 10 and about 15 CCP genes and an elevated status for the CCP genes indicates a poor prognosis. In some embodiments the panel comprises between about 10 and about 15 CCP genes and the CCP genes constitute at least 90% of the panel. In other embodiments the panel comprises CCP genes plus one or more additional markers that significantly increase the predictive power of the panel (i.e., make the predictive power significantly better than if the panel consisted of only the CCP genes). Any other combination of CCGs (including any of those listed in any of Table 1, 2, 3, 9, 11, 16, 25, 26, 28, 29 or 30 or any of Panel A, B, C, D, E, F, or G) can be used to practice the invention.

In some embodiments the panel comprises at least 3, 4, 5, 6, 7, 8, 9, 10, 15, 20, 25, 30, 35, 40, 45, 50 or more CCGs. In some embodiments the panel comprises between 5 and 100 CCGs, between 7 and 40 CCGs, between 5 and 25 CCGs, between 10 and 20 CCGs, or between 10 and 15 CCGs. In some embodiments CCGs comprise at least a certain proportion of the panel. Thus in some embodiments the panel comprises at least 25%, 30%, 40%, 50%, 60%, 70%, 75%, 80%, 85%, 90%, 95%, 96%, 97%, 98%, or 99% CCGs. In some embodiments the CCGs are any of the genes listed in any of Table 1, 2, 3, 9, 11, 16, 25, 26, 28, 29 or 30 or any of Panel A, B, C, D, E, F, or G. In some embodiments the panel comprises at least 2, 3, 4, 5, 6, 7, 8, 9, 10, 15, 20, 25, 30, 35, 40, 45, 50 or more genes in any of Table 1, 2, 3, 9, 11, 16, 25, 26, 28, 29 or 30 or any of Panel A, B, C, D, E, F, or G. In some embodiments the panel comprises all of the genes in any of Table 1, 2, 3, 9, 11, 16, 25, 26, 28, 29 or 30 or any of Panel A, B, C, D, E, F, or G.

As mentioned above, many of the CCGs of the invention have been analyzed to determine their correlation to the CCG mean and also, for the genes, to determine their relative predictive value within a panel (see Table 1, 2, 3, 9, 11, 16, 25, 26, 28, 29 or 30 or Panel A, B, C, D, E, F, or G). Thus in some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises the top 2, 3, 4, 5, 6, 7, 8, 9, 10, 11, 12, 13, 14, 15, 20, 25, 30, 35, 40 or more CCGs listed in any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9, 10, 15, or 20 of the following genes: ASPM, BIRC5, BUB1B, CCNB2, CDC2, CDC20, CDCA8, CDKN3, CENPF, DLGAP5, FOXM1, KIAA0101, KIF11, KIF2C, KIF4A, MCM10, NUSAP1, PRO, RACGAP1, and TPX2. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, or ten or all of gene numbers 1 & 2, 1 to 3, 1 to 4, 1 to 5, 1 to 6, 1 to 7, 1 to 8, 1 to 9, or 1 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, or nine or all of gene numbers 2 & 3, 2 to 4, 2 to 5, 2 to 6, 2 to 7, 2 to 8, 2 to 9, or 2 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, or eight or all of gene numbers 3 & 4, 3 to 5, 3 to 6, 3 to 7, 3 to 8, 3 to 9, or 3 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, or seven or all of gene numbers 4 & 5, 4 to 6, 4 to 7, 4 to 8, 4 to 9, or 4 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, 10, 11, 12, 13, 14, or 15 or all of gene numbers 1 & 2, 1 to 3, 1 to 4, 1 to 5, 1 to 6, 1 to 7, 1 to 8, 1 to 9, 1 to 10, 1 to 11, 1 to 12, 1 to 13, 1 to 14, or 1 to 15 of any of Table 25, 26, 28, 29, or 30.

It has been discovered that CCP genes are particularly predictive in certain cancers. For example, panels of CCP genes have been determined to be accurate in predicting recurrence in prostate cancer (Examples 1 through 5). Further, CCP genes can determine prognosis in bladder, brain, breast and lung cancers, as summarized in Example 6 and Tables 21 and 22 below.

Thus the invention provides a method comprising determining the status of a panel of genes comprising at least two CCP genes, wherein an abnormal status indicates a poor prognosis. In some embodiments the panel comprises at least 2 genes chosen from the group of genes in at least one of Panels A through G. In some embodiments the panel comprises at least 10 genes chosen from the group of genes in at least one of Panels A through G. In some embodiments the panel comprises at least 15 genes chosen from the group of genes in at least one of Panels A through G. In some embodiments the panel comprises all of the genes in at least one of Panels A through G. The invention also provides a method of determining the prognosis of bladder cancer, comprising determining the status of a panel of genes comprising at least two CCP genes (e.g., at least two of the genes in any of Panels B, C, & F), wherein an abnormal status indicates a poor prognosis. The invention also provides a method of determining the prognosis of brain cancer, comprising determining the status of a panel of genes comprising at least two CCP genes (e.g., at least two of the genes in any of Panels B, C, & F), wherein an abnormal status indicates a poor prognosis. The invention further provides a method of determining the prognosis of breast cancer, comprising determining the status of a panel of genes comprising at least two CCP genes (e.g., at least two of the genes in any of Panels B, C, & F), wherein an abnormal status indicates a poor prognosis. The invention also provides a method of determining the prognosis of lung cancer, comprising determining the status of a panel of genes comprising at least two CCP genes (e.g., at least two of the genes in any of Panels B, C, & F), wherein an abnormal status indicates a poor prognosis.

In some embodiments the panel comprises at least 3, 4, 5, 6, 7, 8, 9, 10, 15, 20, 25, 30, 35, 40, 45, 50 or more CCP genes. In some embodiments the panel comprises between 5 and 100 CCP genes, between 7 and 40 CCP genes, between 5 and 25 CCP genes, between 10 and 20 CCP genes, or between 10 and 15 CCP genes. In some embodiments CCP genes comprise at least a certain proportion of the panel. Thus in some embodiments the panel comprises at least 25%, 30%, 40%, 50%, 60%, 70%, 75%, 80%, 85%, 90%, 95%, 96%, 97%, 98%, or 99% CCP genes. In some embodiments the CCP genes are chosen from the group consisting of the genes listed in any of Table 1, 2, 3, 9, 11, 16, 25, 26, 28, 29 or 30 or any of Panel A, B, C, D, E, F, or G. In some embodiments the panel comprises at least 2 genes chosen from the group of genes in any of Panels A through G. In some embodiments the panel comprises at least 10 genes chosen from the group of genes in any of Panels A through G. In some embodiments the panel comprises at least 15 genes chosen from the group of genes in any of Panels A through G. In some embodiments the panel comprises all of the genes in any of Panels A through G.

It has further been discovered that CCP status synergistically adds to clinical parameters in prognosing cancer. In the case of prostate cancer, for example, it has been discovered that a high level of gene expression of any one of the genes in Panels C through F is associated with an increased risk of prostate cancer recurrence or progression in patients whose clinical nomogram score indicates a relatively low risk of recurrence or progression. Because evaluating CCP expression levels can thus detect increased risk not detected using clinical parameters alone, the invention generally provides methods combining evaluating at least one clinical parameter with evaluating the status of at least one CCP.

As Example 3 shows, even individual CCP genes add to clinical parameters in predicting cancer recurrence. Thus one aspect of the invention provides an in vitro diagnostic method comprising determining at least one clinical parameter for a cancer patient and determining the status of at least one CCP in a sample obtained from the patient. However, assessing the status of multiple CCP genes improves predictive power even more (also shown in Example 1). Thus in some embodiments the status of a plurality of CCP genes (e.g., 2, 3, 4, 5, 6, 7, 8, 9, 10, 15, 20, 25, 30, 40, 50 or more) is determined. In some embodiments abnormal status indicates an increased likelihood of recurrence or progression. In some embodiments the patient has prostate cancer. In some embodiments the patient has lung cancer. Often the clinical parameter is at least somewhat independently predictive of recurrence or progression and the addition of CCP status improves the predictive power. As used herein, "clinical parameter" and "clinical measure" refer to disease or patient characteristics that are typically applied to assess disease course and/or predict outcome. Examples in cancer generally include tumor stage, tumor grade, lymph node status, histology, performance status, type of surgery, surgical margins, type of treatment, and age of onset. In prostate cancer clinicians often use pre-sugery blood PSA levels, stage (defined by size of tumor and evidence of metastasis), and Gleason score (similar to concept of grade). After surgical intervention, important clinical parameters in prostate cancer include margin and lymph node status. In breast cancer clinicians often use size of index lesion in cm, invasion, number of nodes involved, and grade.

Often certain clinical parameters are correlated with a particular disease character. For example, in cancer generally as well as in specific cancers, certain clinical parameters are correlated with, e.g., likelihood of recurrence or metastasis, prognosis for survival for a certain amount of time, likelihood of response to treatment generally or to a specific treatment, etc. In prostate cancer some clinical parameters are such that their status (presence, absence, level, etc.) is associated with increased likelihood of recurrence. Examples of such recurrence-associated parameters (some but not all of which are specific to prostate cancer) include high PSA levels (e.g., greater than 4 ng/ml), high Gleason score, large tumor size, evidence of metastasis, advanced tumor stage, nuclear grade, lymph node involvement, early age of onset. Other types of cancer may have different parameters correlated to likelihood of recurrence or progression, and CCP status, as a measure of proliferative activity, adds to these parameters in predicting prognosis in these cancers. As used herein, "recurrence-associated clinical parameter" has its conventional meaning for each specific cancer, with which those skilled in the art are quite familiar. In fact, those skilled in the art are familiar with various recurrence-associated clinical parameters beyond those listed here.

Often a physician will assess more than one clinical parameter in a patient and make a more comprehensive evaluation for the disease characters of interest. Example 5 shows how CCP status can add to one particular grouping of clinical parameters used to determine risk of recurrence in prostate cancer. Clinical parameters in Example 5 include binary variables for organ-confined disease and Gleason score less than or equal to 6, and a continuous variable for logarithmic PSA (Table 14). This model includes all of the clinical parameters incorporated in the post-RP nomogram (i.e., Kattan-Stephenson nomogram) except for Year of RP and the two components of the Gleason score. Thus in some embodiments at least two clinical parameters (e.g., two of the above listed parameters) are assessed along with the expression level of at least one CCP.

One way in which single, but more often multiple, clinical parameters are utilized by physicians is with the help of nomograms. In the clinical setting, nomograms are representations (often visual) of a correlation between one or more parameters and one or more patient or disease characters. An example of a prevalent clinical nomogram used in determining a prostate cancer patient's likelihood of recurrence is described in Kattan et al., J. CLIN. ONCOL. (1999) 17:1499-1507, and updated in Stephenson et al., J. CLIN. ONCOL. (2005) 23:7005-7012 ("Kattan-Stephenson nomogram"). This nomogram evaluates a patient by assigning a point value to each of several clinical parameters (year of RP, surgical margins, extracapsular extension, seminal vesicle invasion, lymph node involvement, primary Gleason score, secondary Gleason score, and preoperative PSA level), totalling the points for a patient into a nomogram score, and then predicting the patient's likelihood of being recurrence-free at varying time intervals (up to 10 years) based on this nomogram score. An example of a prevalent clinical nomogram used in determining a breast cancer patient's prognosis for survival is the Nottingham Prognostic Index (NPI). See, e.g., Galea et al., BREAST CANCER RES. & TREAT. (1992) 22:207-19.

It has been discovered that determining the status of a CCP in a sample obtained from a prostate cancer patient, along with the patient's Kattan-Stephenson nomogram score, is a better predictor of 10-year recurrence-free survival than the nomogram score alone. See, e.g., Examples 2 & 5, infra. Specifically, adding CCP status to the Kattan-Stephenson nomogram detects patients at significantly increased risk of recurrence that the nomogram alone does not. Table 3 above provides an exemplary panel of 31 CCP genes (Panel C) and a subset panel of 26 CCP genes (Panel D, shown with *) determined in Example 2 to show predictive synergy with the Kattan-Stephenson nomogram in prostate cancer prognosis. It has also been discovered that determining the status of a CCP in a sample obtained from a breast cancer patient, along with the patient's NPI score, is a better prognostic predictor than NPI score alone. See, e.g., Example 6, infra. Specifically, adding CCP status to the NPI nomogram detects patients at significantly increased risk of recurrence that the nomogram alone does not. Panels B, C and D were determined in Example 2 to show predictive synergy with the NPI nomogram in breast cancer prognosis.

Thus another aspect of the invention provides an in vitro method comprising determining a clinical nomogram score (e.g., Kattan-Stephenson or NPI nomogram score) for a cancer patient and determining the status of at least one CCP in a sample obtained from the patient. Example 3 illustrates the empirical determination of the predictive power of individual CCP genes and of several CCP panels of varying size over the Kattan-Stephenson nomogram. Randomly selected subsets of the 31 CCP genes listed in Table 3 were tested as distinct CCP signatures and predictive power (i.e., p-value) was determined for each. As FIG. 1 shows, CCP signatures of 2, 3, 4, 5, 6, 10, 15, 20, 25, and 26 genes each add predictive power to the nomogram. Thus the invention provides a method of determining whether a prostate cancer patient has an increased likelihood of recurrence comprising determining the status of a panel of genes comprising at least 2, 3, 4, 5, 6, 10, 15, 20, 25, 26, 27, 28, 29, 30, 31, 32, 33, 34, 35, 40, 45, 50, 60, 70, 80, 90, or 100 or more CCP genes, wherein an elevated status (e.g., increased expression) for the CCP genes indicates an increased likelihood of recurrence. In some embodiments the method further comprises determining a clinical nomogram score of the patient. The invention further provides a method of determining whether a breast cancer patient has an increased likelihood of recurrence comprising determining the status of a panel of genes comprising at least 2, 3, 4, 5, 6, 10, 15, 20, 25, 26, 27, 28, 29, 30, 31, 32, 33, 34, 35, 40, 45, 50, 60, 70, 80, 90, or 100 or more CCP genes, wherein an elevated status (e.g., increased expression) for the CCP genes indicates an increased likelihood of recurrence. In some embodiments the method further comprises determining a clinical nomogram score of the patient.

Often clinical nomograms for cancer are designed such that a particular value (e.g., high score) correlates with an increased risk of recurrence. Elevated CCP status (e.g., increased expression or activity) is also correlated with increased risk. Thus, in some embodiments the invention provides a method of determining whether a cancer patient has an increased likelihood of recurrence or progression comprising determining a clinical nomogram score for the patient and determining the status of at least one CCP in a sample obtained from the patient, wherein a high nomogram score and/or an elevated CCP status indicate the patient has an increased likelihood of recurrence or progression. In some embodiments the cancer is prostate cancer. In some embodiments the cancer is lung cancer.

In some embodiments this assessment is made before radical prostatectomy (e.g., using a prostate biopsy sample) while in some embodiments it is made after (e.g., using the resected prostate sample). In some embodiments, a sample of one or more cells are obtained from a prostate cancer patient before or after treatment for analysis according to the present invention. Prostate cancer treatment currently applied in the art includes, e.g., prostatectomy, radiotherapy, hormonal therapy (e.g., using GnRH antagonists, GnRH agonists, antiandrogens), chemotherapy, and high intensity focused ultrasound. In some embodiments, one or more prostate tumor cells from prostate cancer tissue are obtained from a prostate cancer patient during biopsy or prostatectomy and are used for analysis in the method of the present invention.

The present invention is also based on the discovery that PTEN status predicts aggressive prostate cancer. PTEN status adds to both clinical parameters (e.g., Kattan-Stephenson nomogram) and CCP genes (e.g., the genes in Table 1, 2, 3, 9, 11, 16, 25, 26, 28, 29 or 30 or any of Panel A, B, C, D, E, F, or G). As described in more detail in Example 4 below, PTEN status was determined in 191 prostate cancer patient samples with accompanying clinical history data and CCP signature data. Negative PTEN status was found to be a significant predictor for risk of recurrence (p-value 0.031). PTEN remained a significant predictor of recurrence after adjusting for post-surgery clinical parameters and the CCP signature shown in Table 3 (p-value 0.026). In addition, and importantly, the combination of PTEN and the CCP signature seems to be a better predictor of recurrence than post-surgery clinical parameters (p-value 0.0002).

Because PTEN is an independent predictor of prostate cancer recurrence, one aspect of the invention provides a method of predicting a patient's likelihood of prostate cancer recurrence comprising determining PTEN status in a sample from the patient, wherein a low or negative PTEN status indicates the patient has a high likelihood of recurrence. PTEN status can be determined by any technique known in the art, including but not limited to those discussed herein.

Because PTEN adds to CCP status in predicting prostate cancer recurrence, another aspect of the invention provides an in vitro method comprising determining PTEN status and determining the status of a plurality of CCP genes in a sample obtained from a patient. Different combinations of techniques can be used to determine the status the various markers. For example, in one embodiment PTEN status is determined by immunohistochemistry (IHC) while the status of the plurality of CCP genes is determined by quantitative polymerase chain reaction (qPCR™), e.g., TaqMan™. Some embodiments of the invention provide a method of determining a prostate cancer patient's likelihood of recurrence comprising determining PTEN status in a sample obtained from the patient, determining the status of a plurality of CCP genes in a sample obtained from the patient, wherein low or negative PTEN status and/or elevated CCP status indicate the patient has an increased likelihood of recurrence.

Because PTEN status adds predictive value to clinical parameters in predicting prostate recurrence, yet another aspect of the invention provides an in vitro method comprising determining PTEN status and determining at least one clinical parameter for a cancer patient. Often the clinical parameter is at least somewhat independently predictive of recurrence and the addition of PTEN status improves the predictive power. In some embodiments the invention provides a method of determining whether a cancer patient has an increased likelihood of recurrence comprising determining the status of PTEN in a sample obtained from the patient and determining a clinical nomogram score for the patient, wherein low or negative PTEN status and/or a high nomogram score indicate the patient has an increased likelihood of recurrence.

Because all three of the above markers are additive, some embodiments of the invention provide a method of determining whether a cancer patient has an increased likelihood of recurrence comprising determining the status of PTEN in a sample obtained from the patient, determining a clinical nomogram score for the patient and determining the status of at least one CCP in a sample obtained from the patient, wherein low or negative PTEN status, a high nomogram score and an elevated CCP status indicate the patient has an increased likelihood of recurrence.

The results of any analyses according to the invention will often be communicated to physicians, genetic counselors and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. For example, graphs showing expression or activity level or sequence variation information for various genes can be used in explaining the results. Diagrams showing such information for additional target gene(s) are also useful in indicating some testing results. The statements and visual forms can be recorded on a tangible medium such as papers, computer readable media such as floppy disks, compact disks, etc., or on an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an expression level, activity level, or sequencing (or genotyping) assay is conducted outside the United States, the information and data on a test result may be generated, cast in a transmittable form as described above, and then imported into the United States. Accordingly, the present invention also encompasses a method for producing a transmittable form of information on at least one of (a) expression level or (b) activity level for at least one patient sample. The method comprises the steps of (1) determining at least one of (a) or (b) above according to methods of the present invention; and (2) embodying the result of the determining step in a transmittable form. The transmittable form is the product of such a method.

Techniques for analyzing such expression, activity, and/or sequence data (indeed any data obtained according to the invention) will often be implemented using hardware, software or a combination thereof in one or more computer systems or other processing systems capable of effectuating such analysis.

Thus one aspect of the present invention provides systems related to the above methods of the invention. In one embodiment the invention provides a system for determining gene expression in a tumor sample, comprising: (1) a sample analyzer for determining the expression levels of a panel of genes in a sample including at least 4 cell-cycle progression genes, wherein the sample analyzer contains the sample, mRNA from the sample and expressed from the panel of genes, or cDNA synthesized from said mRNA; (2) a first computer program means for (a) receiving gene expression data on at least 4 test genes selected from the panel of genes, (b) weighting the determined expression of each of the test genes with a predefined coefficient, and (c) combining the weighted expression to provide a test value, wherein at least 50%, at least at least 75% of at least 4 test genes are cell-cycle progression genes; and optionally (3) a second computer program means for comparing the test value to one or more reference values each associated with a predetermined degree of risk of cancer.

In another embodiment the invention provides a system for determining gene expression in a sample, comprising: (1) a sample analyzer for determining the expression levels of a panel of genes in a tumor sample including at least 4 cell-cycle progression genes, wherein the sample analyzer contains the tumor sample which is from a patient identified as having prostate cancer, lung cancer, bladder cancer or brain cancer, or cDNA molecules from mRNA expressed from the panel of genes; (2) a first computer program for (a) receiving gene expression data on at least 4 test genes selected from the panel of genes, (b) weighting the determined expression of each of the test genes with a predefined coefficient, and (c) combining the weighted expression to provide a test value, wherein at least 50%, at least at least 75% of at least 4 test genes are cell-cycle progression genes; and optionally (3) a second computer program for comparing the test value to one or more reference values each associated with a predetermined degree of risk of cancer recurrence or progression of the prostate cancer, lung cancer, bladder cancer or brain cancer.

In some embodiments, the system further comprises a display module displaying the comparison between the test value and the one or more reference values, or displaying a result of the comparing step. In some embodiments the system displays a conclusion as to the patient's diagnosis (e.g., the patient has cancer, has an increased likelihood of having cancer, has a specific percent probability of having cancer, etc.) or prognosis (e.g., the patient has a poor prognosis, has an increased likelihood of recurrence or progression, has a specific percent probability of cancer-specific death within 5 or 10 years, etc.).

In some embodiments, said plurality of test genes comprises at least 2 CCP genes, and the combined weight given to said at least 2 CCP genes is at least 40% of the total weight given to the expression of all of said plurality of test genes. In some embodiments, said plurality of test genes comprises at least 4 or 5 or 6 CCP genes, and the combined weight given to said at least 4 or 5 or 6 CCP genes is at least 40% of the total weight given to the expression of all of said plurality of test genes. In some embodiments the combined weight given to said cell-cycle genes is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% or 100% of the total weight given to the expression of all of said plurality of test genes.

In some embodiments, the amount of RNA transcribed from the panel of genes including test genes is measured in the sample. In addition, the amount of RNA of one or more housekeeping genes in the sample is also measured, and used to normalize or calibrate the expression of the test genes, as described above.

In some embodiments, the plurality of test genes includes at least 2, 3 or 4 cell-cycle progression genes, which constitute at least 50%, 75% or 80% of the plurality of test genes, and in some embodiments 100% of the plurality of test genes. In some embodiments, the plurality of test genes includes at least 5, 6 or 7, or at least 8 cell-cycle progression genes, which constitute at least 20%, 25%, 30%, 40%, 50%, 60%, 70%, 75%, 80% or 90% of the plurality of test genes, and in some embodiments 100% of the plurality of test genes.

In some embodiments, the plurality of test genes includes at least 2, 3 or 4 CCGs, which constitute at least 50%, 75% or 80% of the plurality of test genes, and in some embodiments 100% of the plurality of test genes. In some embodiments, the plurality of test genes includes at least 5, 6 or 7, or at least 8 CCGs, which constitute at least 20%, 25%, 30%, 40%, 50%, 60%, 70%, 75%, 80% or 90% of the plurality of test genes, and in some embodiments 100% of the plurality of test genes. Thus in some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises the top 2, 3, 4, 5, 6, 7, 8, 9, 10, 11, 12, 13, 14, 15, 20, 25, 30, 35, 40 or more CCGs listed in any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9, 10, 15, or 20 of the following genes: ASPM, BIRC5, BUB1B, CCNB2, CDC2, CDC20, CDCA8, CDKN3, CENPF, DLGAP5, FOXM1, KIAA0101, KIF11, KIF2C, KIF4A, MCM10, NUSAP1, PRO, RACGAP1, and TPX2. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, or ten or all of gene numbers 1 & 2, 1 to 3, 1 to 4, 1 to 5, 1 to 6, 1 to 7, 1 to 8, 1 to 9, or 1 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, or nine or all of gene numbers 2 & 3, 2 to 4, 2 to 5, 2 to 6, 2 to 7, 2 to 8, 2 to 9, or 2 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, or eight or all of gene numbers 3 & 4, 3 to 5, 3 to 6, 3 to 7, 3 to 8, 3 to 9, or 3 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, or seven or all of gene numbers 4 & 5, 4 to 6, 4 to 7, 4 to 8, 4 to 9, or 4 to 10 of any of Table 25, 26, 28, 29, or 30. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, nine, 10, 11, 12, 13, 14, or 15 or all of gene numbers 1 & 2, 1 to 3, 1 to 4, 1 to 5, 1 to 6, 1 to 7, 1 to 8, 1 to 9, 1 to 10, 1 to 11, 1 to 12, 1 to 13, 1 to 14, or 1 to 15 of any of Table 25, 26, 28, 29, or 30.

In some other embodiments, the plurality of test genes includes at least 8, 10, 12, 15, 20, 25 or 30 cell-cycle progression genes, which constitute at least 20%, 25%, 30%, 40%, 50%, 60%, 70%, 75%, 80% or 90% of the plurality of test genes, and in some embodiments 100% of the plurality of test genes.

The sample analyzer can be any instrument useful in determining gene expression, including, e.g., a sequencing machine, a real-time PCR machine, a microarray instrument, etc.

The computer-based analysis function can be implemented in any suitable language and/or browsers. For example, it may be implemented with C language and in some embodiments using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out gene status analysis. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

Some embodiments of the present invention provide a system for determining whether a patient has increased likelihood of recurrence. Generally speaking, the system comprises (1) computer program means for receiving, storing, and/or retrieving a patient's gene status data (e.g., expression level, activity level, variants) and optionally clinical parameter data (e.g., Gleason score, nomogram score); (2) computer program means for querying this patient data; (3) computer program means for concluding whether there is an increased likelihood of recurrence based on this patient data; and optionally (4) computer program means for outputting/displaying this conclusion. In some embodiments this means for outputting the conclusion may comprise a computer program means for informing a health care professional of the conclusion.

Figure 6:
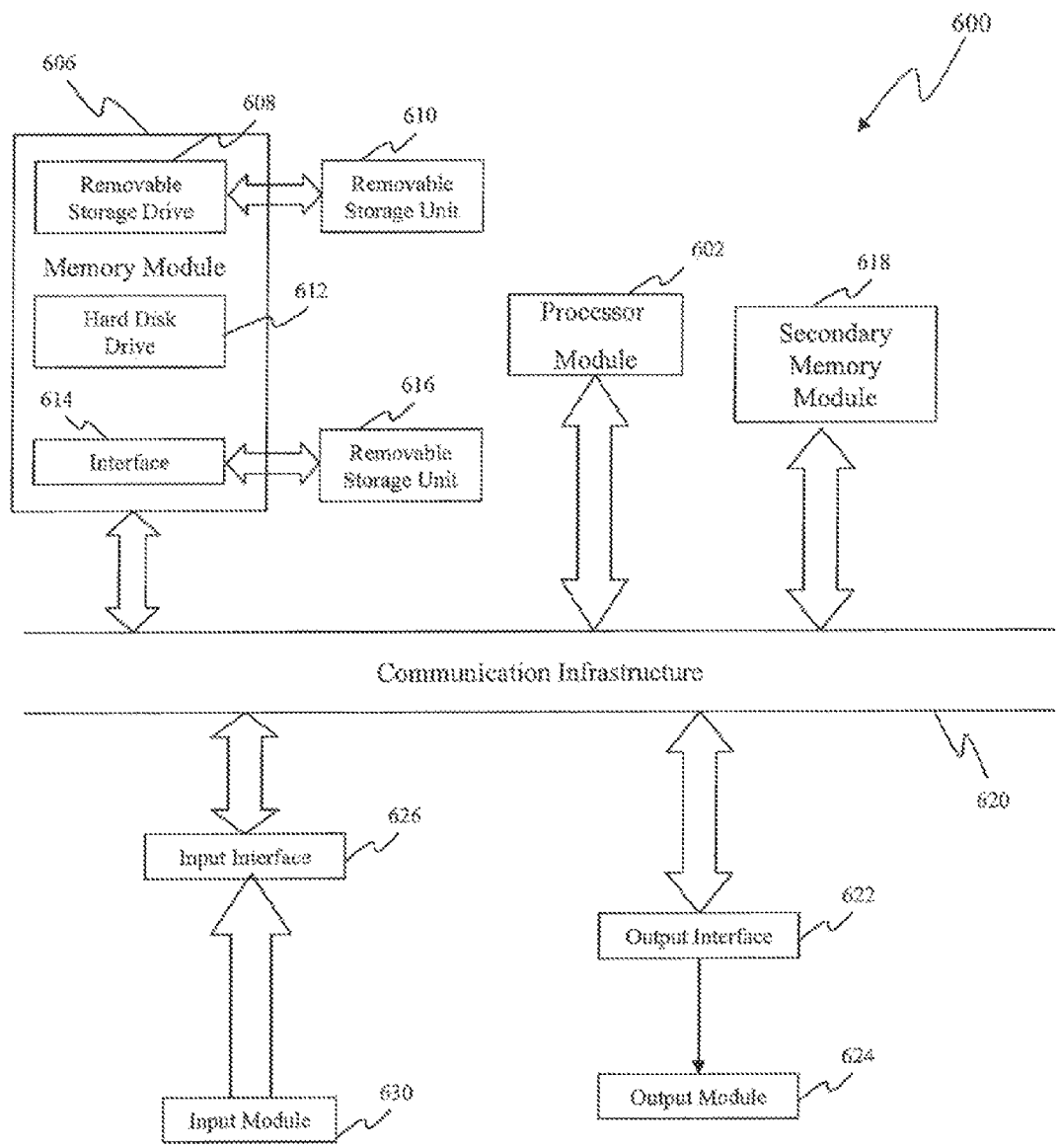
FIG. 6 is an illustration of an example of a system useful in certain aspects and embodiments of the invention.

One example of such a computer system is the computer system [600] illustrated in FIG. 6. Computer system [600] may include at least one input module [630] for entering patient data into the computer system [600]. The computer system [600] may include at least one output module [624] for indicating whether a patient has an increased or decreased likelihood of response and/or indicating suggested treatments determined by the computer system [600]. Computer system [600] may include at least one memory module [606] in communication with the at least one input module [630] and the at least one output module [624].

The at least one memory module [606] may include, e.g., a removable storage drive [608], which can be in various forms, including but not limited to, a magnetic tape drive, a floppy disk drive, a VCD drive, a DVD drive, an optical disk drive, etc. The removable storage drive [608] may be compatible with a removable storage unit [610] such that it can read from and/or write to the removable storage unit [610]. Removable storage unit [610] may include a computer usable storage medium having stored therein computer-readable program codes or instructions and/or computer readable data. For example, removable storage unit [610] may store patient data. Example of removable storage unit [610] are well known in the art, including, but not limited to, floppy disks, magnetic tapes, optical disks, and the like. The at least one memory module [606] may also include a hard disk drive [612], which can be used to store computer readable program codes or instructions, and/or computer readable data.

In addition, as shown in FIG. 1, the at least one memory module [606] may further include an interface [614] and a removable storage unit [616] that is compatible with interface [614] such that software, computer readable codes or instructions can be transferred from the removable storage unit [616] into computer system [600]. Examples of interface [614] and removable storage unit [616] pairs include, e.g., removable memory chips (e.g., EPROMs or PROMs) and sockets associated therewith, program cartridges and cartridge interface, and the like. Computer system [600] may also include a secondary memory module [618], such as random access memory (RAM).

Computer system [600] may include at least one processor module [602]. It should be understood that the at least one processor module [602] may consist of any number of devices. The at least one processor module [602] may include a data processing device, such as a microprocessor or microcontroller or a central processing unit. The at least one processor module may include another logic device such as a DMA (Direct Memory Access) processor, an integrated communication processor device, a custom VLSI (Very Large Scale Integration) device or an ASIC (Application Specific Integrated Circuit) device. In addition, the at least one processor module [602] may include any other type of analog or digital circuitry that is designed to perform the processing functions described herein.

As shown in FIG. 6, in computer system [600], the at least one memory module [606], the at least one processor module [602], and secondary memory module [618] are all operably linked together through communication infrastructure [620], which may be a communications bus, system board, cross-bar, etc.). Through the communication infrastructure [620], computer program codes or instructions or computer readable data can be transferred and exchanged. Input interface [626] may operably connect the at least one input module [626] to the communication infrastructure [620]. Likewise, output interface [622] may operably connect the at least one output module [624] to the communication infrastructure [620].

The at least one input module [630] may include, for example, a keyboard, mouse, touch screen, scanner, and other input devices known in the art. The at least one output module [624] may include, for example, a display screen, such as a computer monitor, TV monitor, or the touch screen of the at least one input module [630]; a printer; and audio speakers. Computer system [600] may also include, modems, communication ports, network cards such as Ethernet cards, and newly developed devices for accessing intranets or the internet.

The at least one memory module [606] may be configured for storing patient data entered via the at least one input module [630] and processed via the at least one processor module [602]. Patient data relevant to the present invention may include expression level, activity level, copy number and/or sequence information for a CCP and optionally PTEN. Patient data relevant to the present invention may also include clinical parameters relevant to the patient's disease. Any other patient data a physician might find useful in making treatment decisions/recommendations may also be entered into the system, including but not limited to age, gender, and race/ethnicity and lifestyle data such as diet information. Other possible types of patient data include symptoms currently or previously experienced, patient's history of illnesses, medications, and medical procedures.

The at least one memory module [606] may include a computer-implemented method stored therein. The at least one processor module [602] may be used to execute software or computer-readable instruction codes of the computer-implemented method. The computer-implemented method may be configured to, based upon the patient data, indicate whether the patient has an increased likelihood of recurrence, progression or response to any particular treatment, generate a list of possible treatments, etc.

In certain embodiments, the computer-implemented method may be configured to identify a patient as having or not having cancer (or an increased likelihood of having cancer) or as having or not having an increased likelihood of recurrence or progression. For example, the computer-implemented method may be configured to inform a physician that a particular patient has cancer, has a quantified probability of having cancer, has an increased likelihood of recurrence, etc. Alternatively or additionally, the computer-implemented method may be configured to actually suggest a particular course of treatment based on the answers to/results for various queries.

Figure 7:
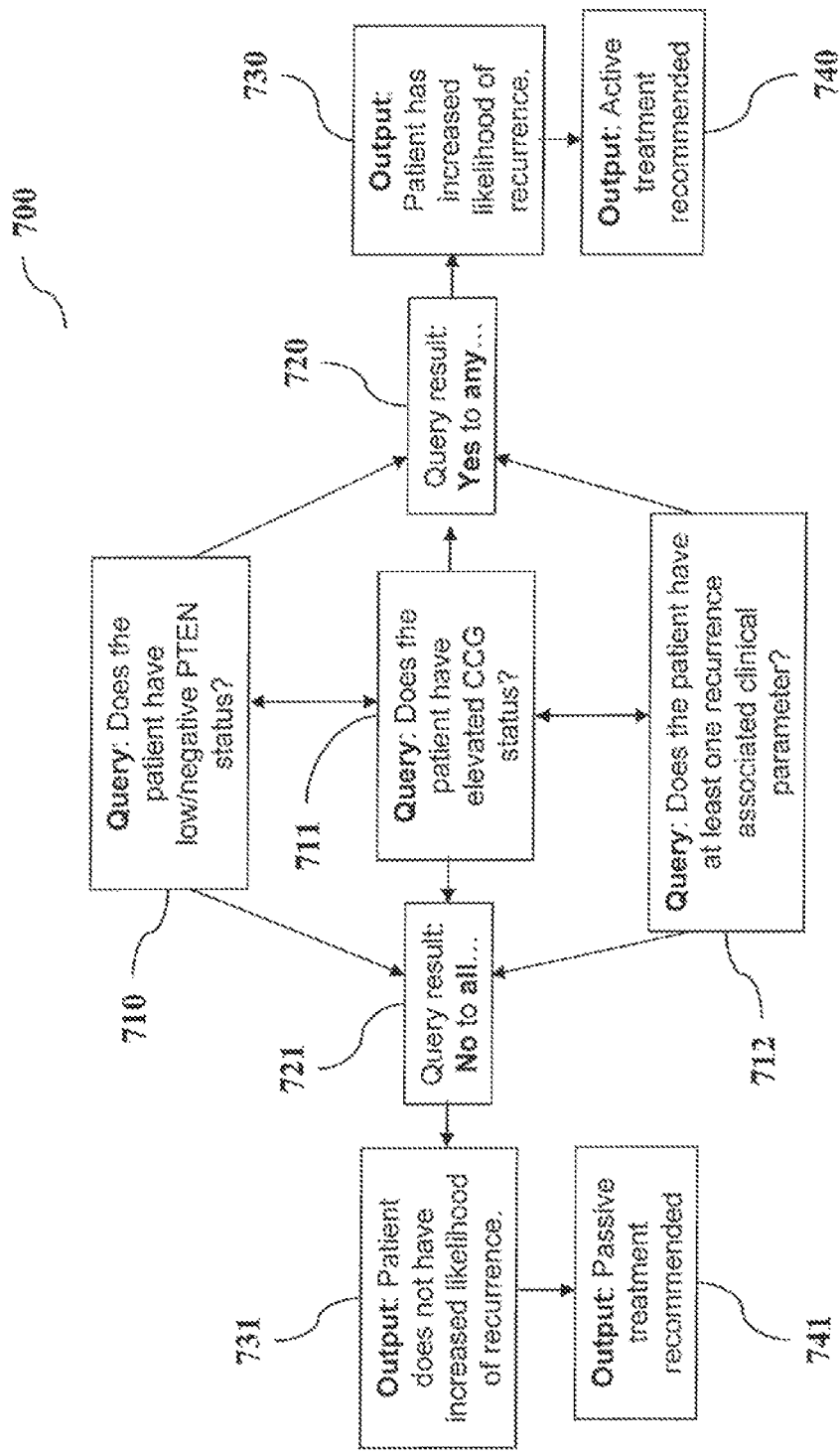
FIG. 7 is a flowchart illustrating an example of a computer-implemented method of the invention.

FIG. 7 illustrates one embodiment of a computer-implemented method [700] of the invention that may be implemented with the computer system [600] of the invention. The method [700] begins with one of three queries ([710], [711], [712]), either sequentially or substantially simultaneously. If the answer to/result for any of these queries is "Yes" [720], the method concludes [730] that the patient has an increased likelihood of recurrence (or has cancer or an increased likelihood of having cancer). If the answer to/result for all of these queries is "No" [721], the method concludes [731] that the patient does not have an increased likelihood of recurrence (or does not have cancer or an increased likelihood of having cancer). The method [700] may then proceed with more queries, make a particular treatment recommendation ([740], [741]), or simply end.

When the queries are performed sequentially, they may be made in the order suggested by FIG. 7 or in any other order. Whether subsequent queries are made can also be dependent on the results/answers for preceding queries. In some embodiments of the method illustrated in FIG. 7, for example, the method asks about clinical parameters [712] first and, if the patient has one or more clinical parameters identifying the patient as at increased risk for recurrence then the method concludes such [730] or optionally confirms by querying CCP status, while if the patient has no such clinical parameters then the method proceeds to ask about CCP status [711]. Optionally, if CCP status is not elevated, then the method may continue to ask about PTEN status [710]. As mentioned above, the preceding order of queries may be modified. In some embodiments an answer of "yes" to one query (e.g., [712]) prompts one or more of the remaining queries to confirm that the patient has increased risk of recurrence.

In some embodiments, the computer-implemented method of the invention is open-ended. In other words, the apparent first step [710, 711, and/or 712] in FIG. 7 may actually form part of a larger process and, within this larger process, need not be the first step/query. Additional steps may also be added onto the core methods discussed above. These additional steps include, but are not limited to, informing a health care professional (or the patient itself) of the conclusion reached; combining the conclusion reached by the illustrated method [700] with other facts or conclusions to reach some additional or refined conclusion regarding the patient's diagnosis, prognosis, treatment, etc.; making a recommendation for treatment (e.g., "patient should/should not undergo radical prostatectomy"); additional queries about additional biomarkers, clinical parameters, or other useful patient information (e.g., age at diagnosis, general patient health, etc.).

Regarding the above computer-implemented method [700], the answers to the queries may be determined by the method instituting a search of patient data for the answer. For example, to answer the respective queries [710, 711, 712], patient data may be searched for PTEN status (e.g., PTEN IHC or mutation screening), CCP status (e.g., CCP expression level data), or clinical parameters (e.g., Gleason score, nomogram score, etc.). If such a comparison has not already been performed, the method may compare these data to some reference in order to determine if the patient has an abnormal (e.g., elevated, low, negative) status. Additionally or alternatively, the method may present one or more of the queries [710, 711, 712] to a user (e.g., a physician) of the computer system [100]. For example, the questions [710, 711, 712] may be presented via an output module [624]. The user may then answer "Yes" or "No" via an input module [630]. The method may then proceed based upon the answer received. Likewise, the conclusions [730, 731] may be presented to a user of the computer-implemented method via an output module [624].

Thus in some embodiments the invention provides a method comprising: accessing information on a patient's CCP status, clinical parameters and/or PTEN status stored in a computer-readable medium; querying this information to determine at least one of whether a sample obtained from the patient shows increased expression of at least one CCP, whether the patient has a recurrence-associated clinical parameter, and/or whether the patient has a low/negative PTEN status; outputting [or displaying] the sample's CCP expression status, the patient's recurrence-associated clinical parameter status, and/or the sample's PTEN status. As used herein in the context of computer-implemented embodiments of the invention, "displaying" means communicating any information by any sensory means. Examples include, but are not limited to, visual displays, e.g., on a computer screen or on a sheet of paper printed at the command of the computer, and auditory displays, e.g., computer generated or recorded auditory expression of a patient's genotype.

As discussed at length above, recurrence-associated clinical parameters or PTEN status combined with elevated CCP status indicate a significantly increased likelihood of recurrence. Thus some embodiments provide a computer-implemented method of determining whether a patient has an increased likelihood of recurrence comprising accessing information on a patient's PTEN status (e.g., from a tumor sample obtained from the patient) or clinical parameters and CCP status (e.g., from a tumor sample obtained from the patient) stored in a computer-readable medium; querying this information to determine at least one of whether the patient has a low/negative PTEN status or whether the patient has a recurrence-associated clinical parameter; querying this information to determine whether a sample obtained from the patient shows increased expression of at least one CCP; outputting (or displaying) an indication that the patient has an increased likelihood of recurrence if the patient has a low/negative PTEN status or a recurrence-associated clinical parameter and the sample shows increased expression of at least one CCP. Some embodiments further comprise displaying PTEN, clinical parameters (or their values) and/or the CCP genes and their status (including, e.g., expression levels), optionally together with an indication of whether the PTEN or CCP status and/or clinical parameter indicates increased likelihood of risk.

The practice of the present invention may also employ conventional biology methods, software and systems. Computer software products of the invention typically include computer readable media having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. Basic computational biology methods are described in, for example, Setubal et al., INTRODUCTION TO COMPUTATIONAL BIOLOGY METHODS (PWS Publishing Company, Boston, 1997); Salzberg et al. (Ed.), COMPUTATIONAL METHODS IN MOLECULAR BIOLOGY, (Elsevier, Amsterdam, 1998); Rashidi & Buehler, BIOINFORMATICS BASICS: APPLICATION IN BIOLOGICAL SCIENCE AND MEDICINE (CRC Press, London, 2000); and Ouelette & Bzevanis, BIOINFORMATICS: A PRACTICAL GUIDE FOR ANALYSIS OF GENE AND PROTEINS (Wiley & Sons, Inc., $2^{nd}$ ed., 2001); see also, U.S. Pat. No. 6,420,108.

The present invention may also make use of various computer program products and software for a variety of purposes, such as probe design, management of data, analysis, and instrument operation. See U.S. Pat. Nos. 5,593,839; 5,795,716; 5,733,729; 5,974,164; 6,066,454; 6,090,555; 6,185,561; 6,188,783; 6,223,127; 6,229,911 and 6,308,170. Additionally, the present invention may have embodiments that include methods for providing genetic information over networks such as the Internet as shown in U.S. Ser. No. 10/197,621 (U.S. Pub. No. 20030097222); Ser. No. 10/063, 559 (U.S. Pub. No. 20020183936), Ser. No. 10/065,856 (U.S. Pub. No. 20030100995); Ser. No. 10/065,868 (U.S. Pub. No. 20030120432); Ser. No. 10/423,403 (U.S. Pub. No. 20040049354).

In one aspect, the present invention provides methods of treating a cancer patient comprising obtaining CCP status information (e.g., the CCP genes in Table 1, 2, 3, 9, 11, 16, 25, 26, 28, 29 or 30 or any of Panel A, B, C, D, E, F, or G), and recommending, prescribing or administering a treatment for the cancer patient based on the CCP status. In some embodiments, the method further includes obtaining clinical parameter information, and/or obtaining PTEN status information from a sample from the patient and treating the patient with a particular treatment based on the CCP status, clinical parameter and/or PTEN status information. For example, the invention provides a method of treating a patient (including a patient diagnosed with cancer) comprising:

(1) determining the status of at least one CCP;
(2) determining the status of at least on clinical parameter;
(3) determining the status of PTEN in a sample obtained from the patient; and
(4) recommending, prescribing or administering either
    (a) an active (including aggressive) treatment if the patient has at least one of increased expression of the CCP, recurrence-associated clinical parameter, or low/negative PTEN status, or
    (b) a passive (or less aggressive) treatment if the patient has none of increased expression of the CCP, recurrence-associated clinical parameter, or low/negative PTEN status.

Whether a treatment is aggressive or not will generally depend on the cancer-type, the age of the patient, etc. For example, in breast cancer adjuvant chemotherapy is a common aggressive treatment given to complement the less aggressive standards of surgery and hormonal therapy. Those skilled in the art are familiar with various other aggressive and less aggressive treatments for each type of cancer. "Active treatment" in prostate cancer is well-understood by those skilled in the art and, as used herein, has the conventional meaning in the art. Generally speaking, active treatment in prostate cancer is anything other than "watchful waiting." Active treatment currently applied in the art of prostate cancer treatment includes, e.g., prostatectomy, radiotherapy, hormonal therapy (e.g., GnRH antagonists, GnRH agonists, antiandrogens), chemotherapy, high intensity focused ultrasound ("HIFU"), etc. Each treatment option carries with it certain risks as well as side-effects of varying severity, e.g., impotence, urinary incontinence, etc. Thus it is common for doctors, depending on the age and general health of the man diagnosed with prostate cancer, to recommend a regime of "watchful-waiting."

"Watchful-waiting," also called "active surveillance," also has its conventional meaning in the art. This generally means observation and regular monitoring without invasive treatment. Watchful-waiting is sometimes used, e.g., when an early stage, slow-growing prostate cancer is found in an older man. Watchful-waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.).

Although men who choose watchful-waiting avoid the risks of surgery and radiation, watchful-waiting carries its own risks, e.g., increased risk of metastasis. For younger men, a trial of active surveillance may not mean avoiding treatment altogether, but may reasonably allow a delay of a few years or more, during which time the quality of life impact of active treatment can be avoided. Published data to date suggest that carefully selected men will not miss a window for cure with this approach. Additional health problems that develop with advancing age during the observation period can also make it harder to undergo surgery and radiation therapy. Thus it is clinically important to carefully determine which prostate cancer patients are good candidates for watchful-waiting and which patients should receive active treatment.

Thus, the invention provides a method of treating a prostate cancer patient or providing guidance to the treatment of a patient. In this method, the status of at least one CCP (e.g., those in Table 1, 2, 3, 9, 11, 16, 25, 26, 28, 29 or 30 or any of Panel A, B, C, D, E, F, or G), at least one recurrence-associated clinical parameter, and/or the status of PTEN is determined, and (a) active treatment is recommended, initiated or continued if a sample from the patient has an elevated status for at least one CCP, the patient has at least one recurrence-associated clinical parameter, and/or low/negative PTEN status, or (b) watchful-waiting is recommended/initiated/continued if the patient has neither an elevated status for at least one CCP, a recurrence-associated clinical parameter, nor low/negative PTEN status. In certain embodiments, CCP status, the clinical parameter(s) and PTEN status may indicate not just that active treatment is recommended, but that a particular active treatment is preferable for the patient (including relatively aggressive treatments such as, e.g., RP and/or adjuvant therapy).

In general, adjuvant therapy (e.g., chemotherapy, radiotherapy, HIFU, hormonal therapy, etc. after prostatectomy or radiotherapy) is not the standard of care in prostate cancer. According to the present invention, however, physicians may be able to determine which prostate cancer patients have particularly aggressive disease and thus should receive adjuvant therapy. Thus in one embodiment, the invention provides a method of treating a patient (e.g., a prostate cancer patient) comprising determining the status of at least one CCP (e.g., those in Table 1, 2, 3, 9, 11, 16, 25, 26, 28, 29 or 30 or any of Panel A, B, C, D, E, F, or G), the status of at least one recurrence-associated clinical parameter, and/or the status of PTEN and initiating adjuvant therapy after prostatectomy or radiotherapy if a sample from the patient has an elevated status for at least one CCP, the patient has at least one recurrence-associated clinical parameter and/or the patient has low/negative PTEN status.

In one aspect, the invention provides compositions useful in the above methods. Such compositions include, but are not limited to, nucleic acid probes hybridizing to PTEN or a CCP (or to any nucleic acids encoded thereby or complementary thereto); nucleic acid primers and primer pairs suitable for amplifying all or a portion of PTEN or a CCP or any nucleic acids encoded thereby; antibodies binding immunologically to a polypeptide encoded by PTEN or a CCP; probe sets comprising a plurality of said nucleic acid probes, nucleic acid primers, antibodies, and/or polypeptides; microarrays comprising any of these; kits comprising any of these; etc. In some aspects, the invention provides computer methods, systems, software and/or modules for use in the above methods.

In some embodiments the invention provides a probe comprising an isolated oligonucleotide capable of selectively hybridizing to PTEN or at least one of the genes in Table 1, 2, 3, 9, 11, 16, 25, 26, 28, 29 or 30 or any of Panel A, B, C, D, E, F, or G. The terms "probe" and "oligonucleotide" (also "oligo"), when used in the context of nucleic acids, interchangeably refer to a relatively short nucleic acid fragment or sequence. The invention also provides primers useful in the methods of the invention. "Primers" are probes capable, under the right conditions and with the right companion reagents, of selectively amplifying a target nucleic acid (e.g., a target gene). In the context of nucleic acids, "probe" is used herein to encompass "primer" since primers can generally also serve as probes.

The probe can generally be of any suitable size/length. In some embodiments the probe has a length from about 8 to 200, 15 to 150, 15 to 100, 15 to 75, 15 to 60, or 20 to 55 bases in length. They can be labeled with detectable markers with any suitable detection marker including but not limited to, radioactive isotopes, fluorophores, biotin, enzymes (e.g., alkaline phosphatase), enzyme substrates, ligands and antibodies, etc. See Jablonski et al., NUCLEIC ACIDS RES. (1986) 14:6115-6128; Nguyen et al., BIOTECHNIQUES (1992) 13:116-123; Rigby et al., J. MOL. BIOL. (1977) 113:237-251. Indeed, probes may be modified in any conventional manner for various molecular biological applications. Techniques for producing and using such oligonucleotide probes are conventional in the art.

Probes according to the invention can be used in the hybridization/amplification/detection techniques discussed above. Thus, some embodiments of the invention comprise probe sets suitable for use in a microarray in detecting, amplifying and/or quantitating PTEN and/or a plurality of CCP genes. In some embodiments the probe sets have a certain proportion of their probes directed to CCP genes—e.g., a probe set consisting of 10%, 20%, 30%, 40%, 50%, 55%, 60%, 65%, 70%, 75%, 80%, 85%, 90%, 95%, 96%, 97%, 98%, 99%, or 100% probes specific for CCP genes. In some embodiments the probe set comprises probes directed to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 60, 70, 80, 90, 100, 125, 150, 175, 200, 250, 300, 350, 400, 450, 500, 600, 700, or 800 or more, or all, of the genes in Table 1, 2, 3, 9, 11, 16, 25, 26, 28, 29 or 30 or any of Panel A, B, C, D, E, F, or G. Such probe sets can be incorporated into high-density arrays comprising 5,000, 10,000, 20,000, 50,000, 100,000, 200,000, 300,000, 400,000, 500,000, 600,000, 700,000, 800,000, 900,000, or 1,000,000 or more different probes. In other embodiments the probe sets comprise primers (e.g., primer pairs) for amplifying nucleic acids comprising at least a portion of PTEN or of one or more of the CCP genes in Table 1, 2, 3, 9, 11, 16, 25, 26, 28, 29 or 30 or any of Panel A, B, C, D, E, F, or G.

In another aspect of the present invention, a kit is provided for practicing the prognosis of the present invention. The kit may include a carrier for the various components of the kit. The carrier can be a container or support, in the form of, e.g., bag, box, tube, rack, and is optionally compartmentalized. The carrier may define an enclosed confinement for safety purposes during shipment and storage. The kit includes various components useful in determining the status of one or more CCP genes and one or more housekeeping gene markers, using the above-discussed detection techniques. For example, the kit many include oligonucleotides specifically hybridizing under high stringency to mRNA or cDNA of the genes in any of Table 1, 2, 3, 9, 11, 16, 25, 26, 28, 29 or 30 or any of Panel A, B, C, D, E, F, or G. Such oligonucleotides can be used as PCR primers in RT-PCR reactions, or hybridization probes. In some embodiments the kit comprises reagents (e.g., probes, primers, and or antibodies) for determining the expression level of a panel of genes, where said panel comprises at least 25%, 30%, 40%, 50%, 60%, 75%, 80%, 90%, 95%, 99%, or 100% CCP genes (e.g., CCP genes in any of Table 1, 2, 3, 9, 11, 16, 25, 26, 28, 29 or 30 or any of Panel A, B, C, D, E, F, or G). In some embodiments the kit consists of reagents (e.g., probes, primers, and or antibodies) for determining the expression level of no more than 2500 genes, wherein at least 5, 10, 15, 20, 30, 40, 50, 60, 70, 80, 90, 100, 120, 150, 200, 250, or more of these genes are CCP genes (e.g., CCP genes in Any of Table 1, 2, 3, 9, 11, 16, 25, 26, 28, 29 or 30 or any of Panel A, B, C, D, E, F, or G).

The oligonucleotides in the detection kit can be labeled with any suitable detection marker including but not limited to, radioactive isotopes, fluorephores, biotin, enzymes (e.g., alkaline phosphatase), enzyme substrates, ligands and antibodies, etc. See Jablonski et al., *Nucleic Acids Res.*, 14:6115-6128 (1986); Nguyen et al., *Biotechniques*, 13:116-123 (1992); Rigby et al., *J. Mol. Biol.*, 113:237-251 (1977). Alternatively, the oligonucleotides included in the kit are not labeled, and instead, one or more markers are provided in the kit so that users may label the oligonucleotides at the time of use.

In another embodiment of the invention, the detection kit contains one or more antibodies selectively immunoreactive with one or more proteins encoded by PTEN or one or more CCP genes or optionally any additional markers. Examples include antibodies that bind immunologically to PTEN or a protein encoded by a gene in Table 1 or Panels A through G. Methods for producing and using such antibodies have been described above in detail.

Various other components useful in the detection techniques may also be included in the detection kit of this invention. Examples of such components include, but are not limited to, Taq polymerase, deoxyribonucleotides, dideoxyribonucleotides, other primers suitable for the amplification of a target DNA sequence, RNase A, and the like. In addition, the detection kit in some embodiments includes instructions on using the kit for practice the prognosis method of the present invention using human samples.

EXAMPLE 1

The following cell cycle gene (CCP) signature was tested for predicting time to chemical recurrence after radical prostatectomy.

| 31-CCP Gene Cancer Recurrence Signature |
| --- |
| AURKA |
| BUB1 |
| CCNB1 |
| CCNB2 |
| CDC2 |
| CDC20 |
| CDC45L |
| CDCA8 |
| CENPA |
| CKS2 |
| DLG7 |
| DTL |
| FOXM1 |
| HMMR |
| KIF23 |
| KPNA2 |
| MAD2L1 |
| MELK |
| MYBL2 |
| NUSAP1 |
| PBK |
| PRC1 |
| PTTG1 |
| RRM2 |
| TIMELESS |
| TPX2 |
| TRIP13 |
| TTK |
| UBE2C |
| UBE2S |
| ZWINT |

Mean mRNA expression for the above 31 CCP genes was tested on 440 prostate tumor FFPE samples using a Cox Proportional Hazard model in Splus 7.1 (Insightful, Inc., Seattle Wash.). The p-value for the likelihood ratio test was $3.98 \times 10^{-5}$.

The mean of CCP expression is robust to measurement error and individual variation between genes. In order to determine the optimal number of cell cycle genes for the signature, the predictive power of the mean was tested for randomly selected sets of from 1 to 30 of the CCP genes listed above. This simulation showed that there is a threshold number of CCP genes in a panel that provides significantly improved predictive power.

EXAMPLE 2

In a univariate analysis a set of 31 CCP genes (Table 3) was found to be a significant predictor of biochemical recurrence (p-value=$1.8 \times 10^{-9}$) after RP in prostate cancer patients. This signature was further evaluated to determine whether it added to an established clinical nomogram for prostate cancer recurrence (the Kattan-Stephenson nomogram). In summary, the nomogram was a highly significant predictor of recurrence (p-value $1.6 \times 10^{-10}$) and, after adjusting for the nomogram, the CCP signature was a significant predictor of biochemical recurrence (p-value $4.8 \times 10^{-5}$, Table 6).

Patients and Methods

Eight hundred four consecutive RP patients were followed for a median of 9.5 years. The patient characteristics and the treatment outcomes of the entire cohort have been previously reported (Swanson et al., UROL ONCOL. (2007) 25:110-114). Tissue blocks and/or slides from the final pathological evaluation with enough tissue for analysis were available for 430 patients. The cohort was divided randomly into 212 patients utilized for a training and 199 patient samples as a validation set.

Gene Expression (Statistical methods): Association between biochemical recurrence and CCP expression was evaluated using Cox PH models for time to recurrence. All of the p-values reported in this study were derived from a likelihood ratio test comparing the null model to the model containing the test variable. A set of 31 CCP genes (Table 3, supra) was randomly selected. The assays were used to generate expression data from 212 patients in the training set. All of the expression data were generated in triplicate. The expression data were combined into a signature by calculating the mean expression level for 26 CCP genes.

Association between biochemical recurrence and CCP expression was evaluated using Cox PH models for time to recurrence.

Sample Preparation and Study Design: RNA was isolated from FFPE tumor sections derived from 411 prostate cancer patients treated with RP. Representative 10 µm thick tumor sections were used to isolate RNA. When necessary, a pathologist guided macro- or micro-dissection of the sample was used to enrich for tumor tissue before RNA isolation. None of the samples in the validation cohort were micro-dissected. Prior to any analysis, the cohort was split into 212 patients for initial characterization of the signature ("training set") and 199 patients for validation. The clinical characteristics of the training and validation cohort are listed on Table 5.

TABLE 5

|  | Training | Validation | p-value | Statistic |
|---|---|---|---|---|
| Age in years at RP, mean (sd) | 67.3 (5.9) | 66.8 (5.8) | 0.355 | t-test |
| Ethnicity (% non-white) | 2.80% | 7.60% | 0.042 | Fisher's exact |
| Dissection method (% lcm) | 24% | 0% | NA | NA |
| Recurrence (%) | 71/212 (33.5%) | 72/199 (36.2%) | 0.605 | Fisher's exact |
| Days to recurrence, median | 910 | 822 | 0.463 | t-test |
| Days to follow-up, median | 3373 | 3387 | 0.173 | t-test |
| Pre-surgery PSA (median) | 7.3 | 6.8 | 0.163 | t-test of log |
| Seminal vesicle | 23/212 (10.8%) | 28/199 (14.1%) | 0.37 | Fisher's exact |
| Bladder | 12/212 (5.7%) | 17/199 (8.5%) | 0.335 | Fisher's exact |
| Lymph node | 8/212 (3.8%) | 10/199 (5.0%) | 0.632 | Fisher's exact |
| Capsular | 100/212 (47.2%) | 101/199 (50.8%) | 0.49 | Fisher's exact |
| Through capsule | 59/212 (27.8%) | 66/199 (33.2%) | 0.283 | Fisher's exact |
| Positive margins | 43/212 (20.3%) | 57/199 (28.6%) | 0.051 | Fisher's exact |
| Post-RP Gleason score >6 | 80/212 (37.7%) | 66/199 (33.2%) | 0.354 | Fisher's exact |
| Post-RP nomogram, mean (sd) | 137 (19.5) | 138 (23.0) | 0.424 | t-test |

Results

Figure 2:
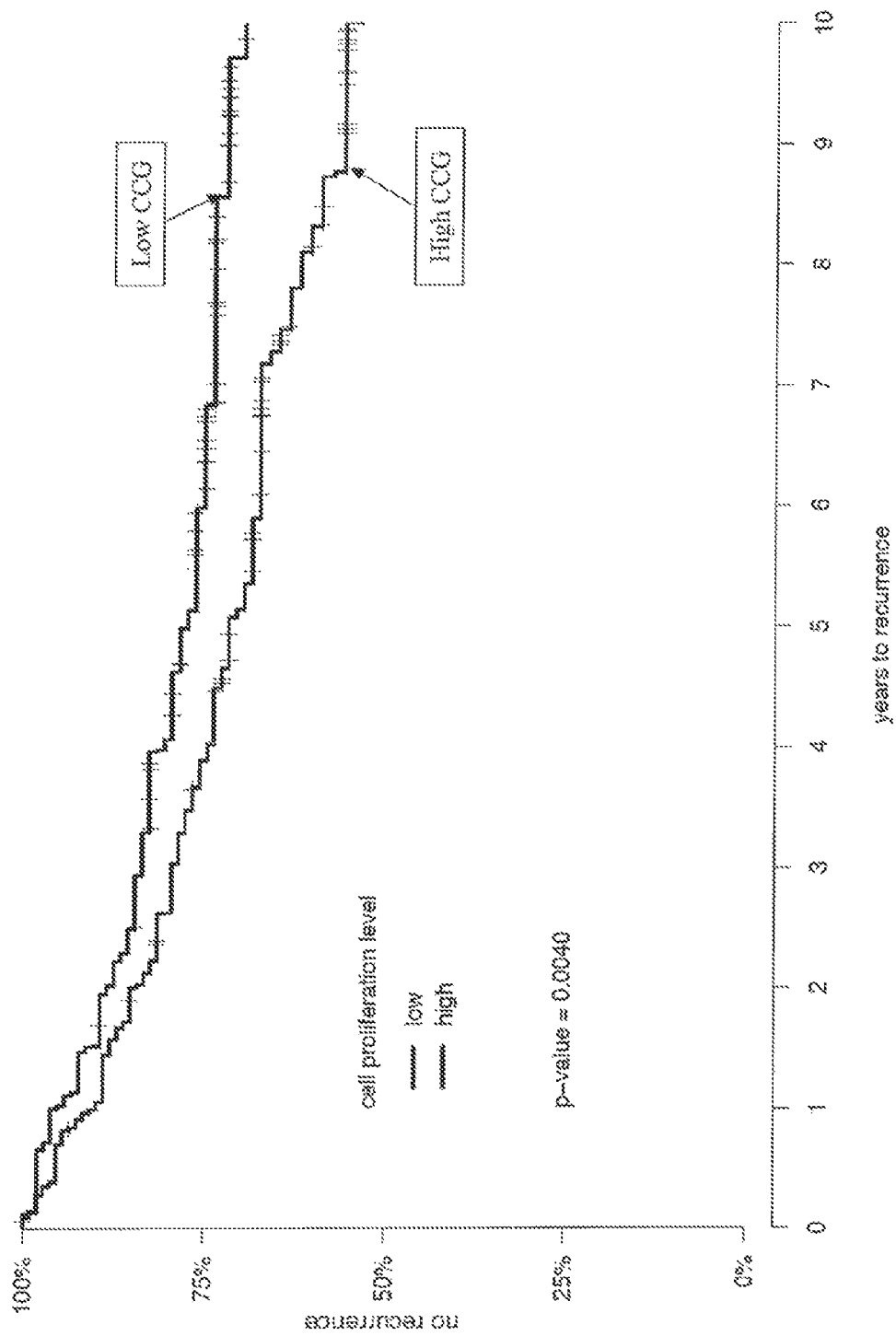
FIG. 2 is an illustration of CCP genes predicting time to recurrence.

The CCP expression signature (Table 3, supra) was predictive of disease recurrence in a univariate analysis (p-value=$1.8 \times 10^{-9}$, Table 6). The distribution of the signature score was skewed toward higher values (lower expression). The median value of signature score was used to divide the training cohort into two groups containing samples with either high or low CCP expression. The survival versus time for both groups is shown in FIG. 2.

Figure 3:
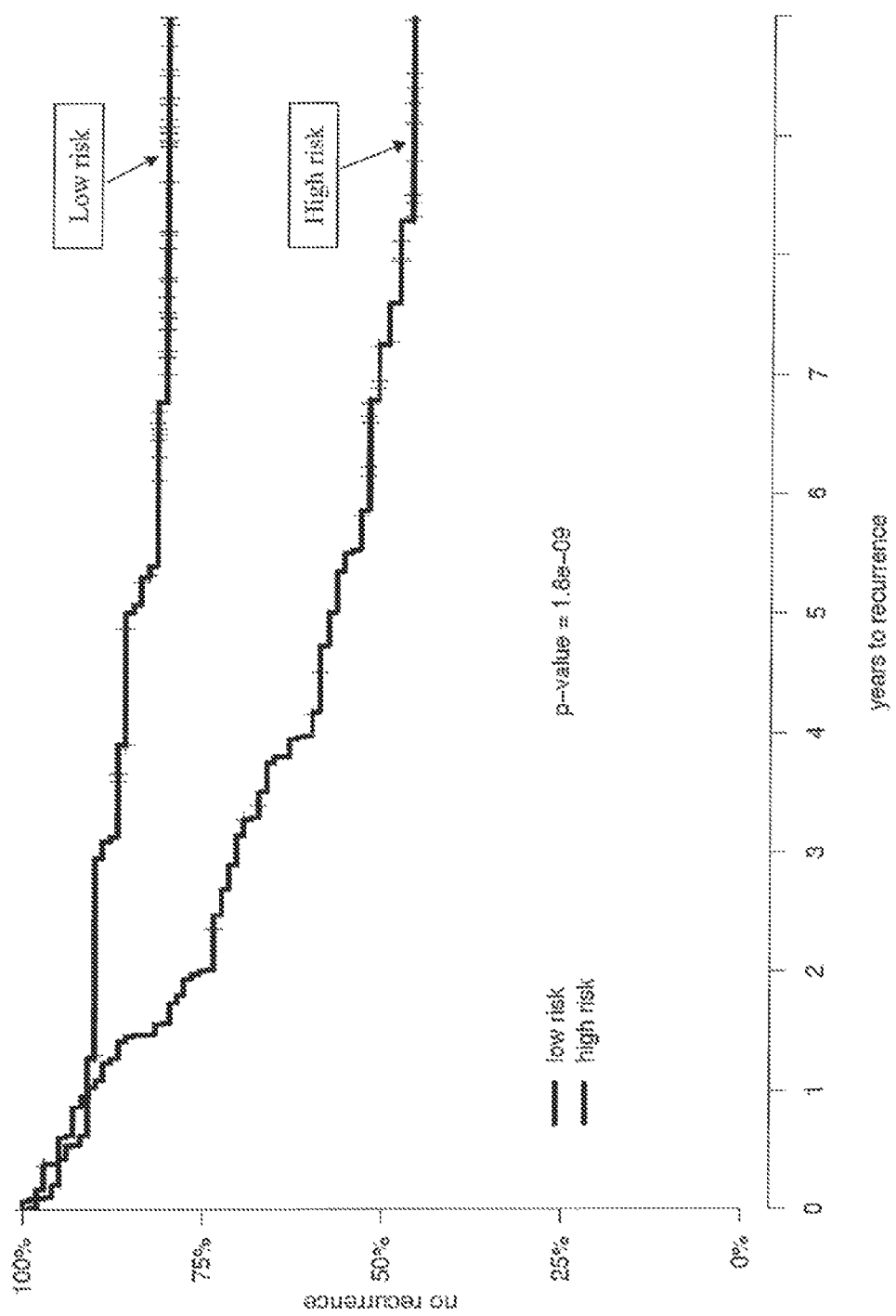
FIG. 3 is an illustration of nomogram predicting time to recurrence.

Predictive power of the CCP signature after accounting for clinical variables typically included in a post-surgical nomogram (the Kattan-Stephenson nomogram) was also evaluated. The nomogram was a highly significant predictor of recurrence (p-value $1.6 \times 10^{-10}$). After adjusting for the nomogram, the CCP signature was a significant predictor of biochemical recurrence (FIG. 3) in the discovery cohort (p-value 0.03) and in the clinical validation cohort (p-value $4.8 \times 10^{-5}$).

TABLE 6

|  | N | Co-variates | CCP mean p-value* | Recurrence Hazard Ratio |
|---|---|---|---|---|
| TRAINING | 212 | none | 0.00404 | 1.24 |
| (31 CCP genes) | 204 | post-surgery nomogram | 0.03320 | 1.16 |
| VALIDATION | 199 | none | $1.8 \times 10^{-9}$ | 2.68 |
| (26-CCP subset) | 197 | post-surgery nomogram | $4.8 \times 10^{-5}$ | 1.94 |

*Mean of cell cycle gene expression with imputation of missing values, likelihood ratio test for Cox proportional hazards model.

To help understand the interaction between the nomogram and the CCP expression signature, a scatter plot comparing these predictors (FIG. 4) was generated (light gray stars represent patients whose cancer recurred while black stars represent patients whose cancer did not). Analysis of the scatter plot by KM means divided the samples into three clusters based on nomogram score only. Subsequently, it was discovered that the clusters were based on well-understood clinical parameters. The patients in the lowest scoring cluster (116/117) had organ-confined disease. Patients in the middle scoring cluster (48/60) had at least one post-surgical parameter known to be associated with poor outcome (i.e., disease through the capsule, disease positive lymph nodes, and/or disease positive seminal vesicles) and low pre-surgical PSA (<10 ng/ml). Patients in the highest scoring cluster had at least one unfavorable post-surgical parameter and high pre-surgery PSA. Next, the patients in the low and medium scoring clusters were divided by the mean of the CCP score. Outcomes for patients in the highest scoring cluster are adequately predicted by the nomogram and, therefore, were not divided further. As a result, the scatter plot defines five patient groups with disease recurrence rates of 2%, 40% (for two groups), 65%, and 80% (Table 7). The recurrence rate of all five groups versus time is shown in FIG. 5.

TABLE 7

|  | Post-RP nomogram | | |
|---|---|---|---|
| CCP score | Low | Medium | High |
| Low | 1/62 (1.6%) | 13/31 (41.9%) | 16/20 (80%) |
| High | 21/55 (38.2%) | 19/29 (65.5%) |  |

Figure 4:
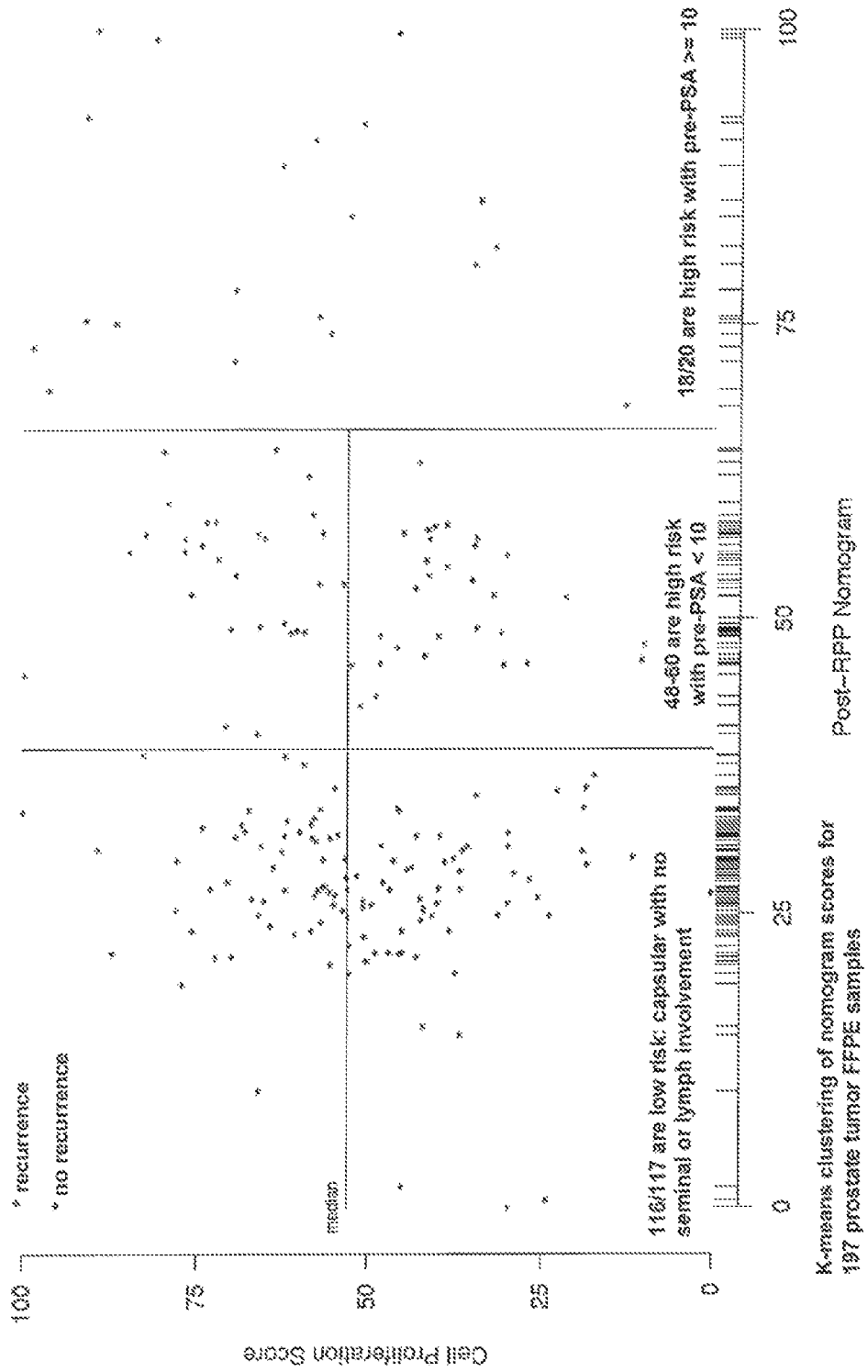
FIG. 4 is an illustration of the non-overlapping recurrence predicted by nomogram and a CCP signature.
Figure 5:
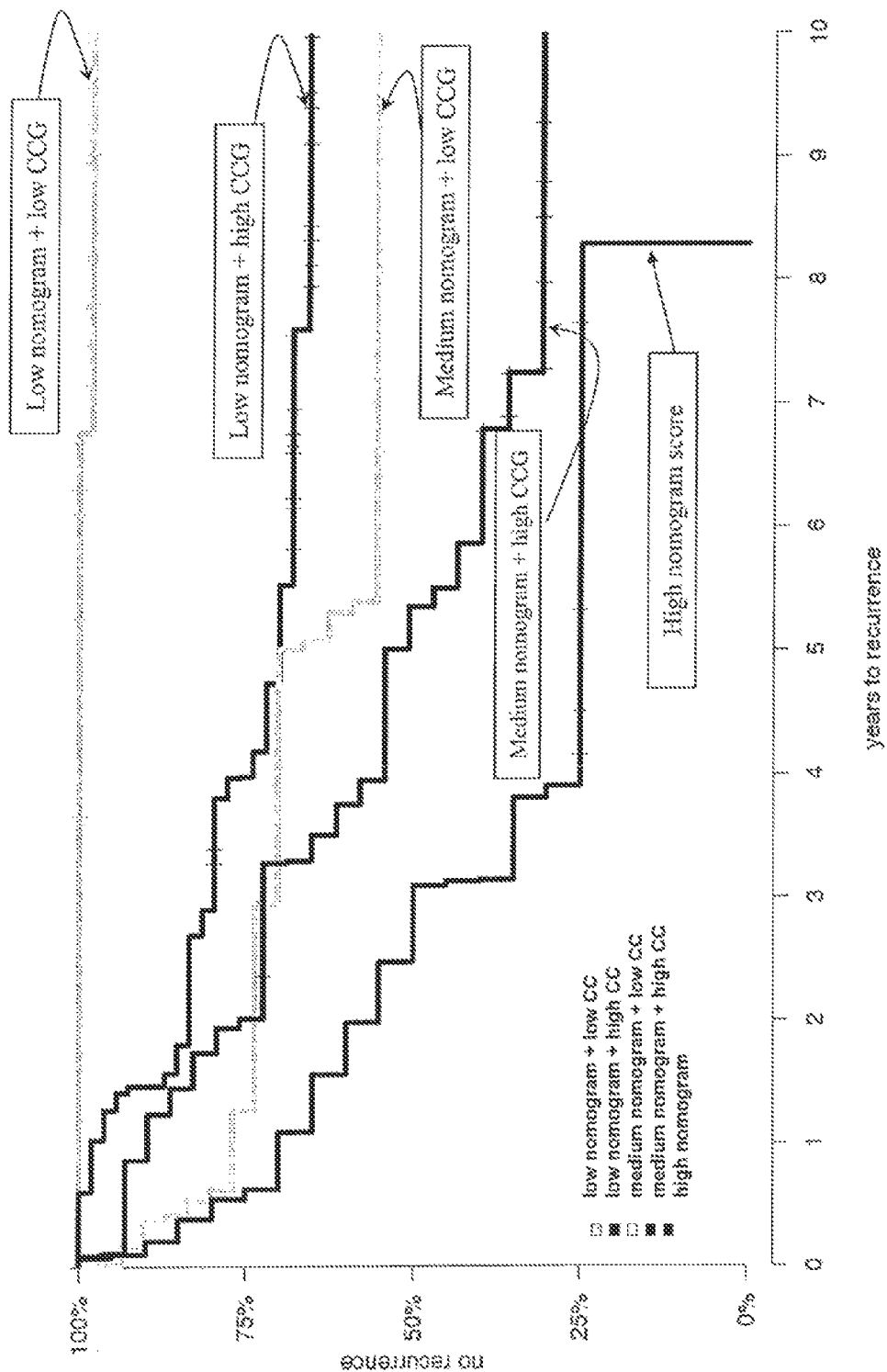
FIG. 5 is an illustration of time to recurrence for several patient populations defined by nomogram and/or CCP status.

The scatter plot shown in FIG. 4 suggests that there is a non-linear interaction between the CCP signature and the post-surgical nomogram. That is, the CCP signature is a better predictor in patients with low nomogram scores. Therefore, the study tested for statistical evidence of an interaction between these variables in a multivariate model for predicting disease recurrence (Table 8). There was significant evidence for a favorable interaction in both training and validation studies. Including the interaction term in the model dramatically improved the prognostic significance of the CCP signature after adjusting for the nomogram (p-values of 0.0015 in training and $1.2 \times 10^{-8}$ in validation cohort).

TABLE 8

Statistical Summary

| Cohort | N | Independent variables | Co-variates | Interaction p-value | Variable p-value | Recurrence Hazard ratio |
|---|---|---|---|---|---|---|
| Training | 204 | nomogram | none | NA | $1.6 \times 10^{-10}$ | |
| | 212 | CCP signature | none | NA | 0.004 | 1.24 |
| | 204 | CCP signature | nomogram | 0.021 | 0.0015 | |
| Validation | 197 | nomogram | none | NA | $7.7 \times 10^{-13}$ | |
| | 199 | CCP signature | none | NA | $1.8 \times 10^{-9}$ | 2.68 |
| | 197 | CCP signature | nomogram | 0.0001 | $1.28 \times 10^{-8}$ | |

EXAMPLE 3

The following study aimed at determining the optimal number of CCP genes to include in the signature. As mentioned above, CCP expression levels are correlated to each other so it was possible that measuring a small number of genes would be sufficient to predict disease outcome. In fact, single CCP genes from the 31-gene set in Table 3 (Panel C) add significantly to the Kattan-Stephenson nomogram, as shown in Table 9 below (after adjustment for the nomogram and an interaction term between the nomogram and CCP expression):

TABLE 9

| Gene | p-value* | Gene | p-value* | Gene | p-value* |
|---|---|---|---|---|---|
| NUSAP1 | $2.8 \times 10^{-7}$ | BUB1 | $8.3 \times 10^{-5}$ | KPNA2 | $2.0 \times 10^{-2}$ |
| DLG7 | $5.9 \times 10^{-7}$ | PBK | $1.2 \times 10^{-4}$ | UBE2C | $2.2 \times 10^{-2}$ |
| CDC2 | $6.0 \times 10^{-7}$ | TTK | $3.2 \times 10^{-4}$ | MELK | $2.5 \times 10^{-2}$ |
| FOXM1 | $1.1 \times 10^{-6}$ | CDC45L | $7.7 \times 10^{-4}$ | CENPA | $2.9 \times 10^{-2}$ |
| MYBL2 | $1.1 \times 10^{-6}$ | PRC1 | $1.2 \times 10^{-3}$ | CKS2 | $5.7 \times 10^{-2}$ |
| CDCA8 | $3.3 \times 10^{-6}$ | DTL | $1.4 \times 10^{-3}$ | MAD2L1 | $1.7 \times 10^{-1}$ |
| CDC20 | $3.8 \times 10^{-6}$ | CCNB1 | $1.5 \times 10^{-3}$ | UBE2S | $2.0 \times 10^{-1}$ |
| RRM2 | $7.2 \times 10^{-6}$ | TPX2 | $1.9 \times 10^{-3}$ | AURKA | $4.8 \times 10^{-1}$ |
| PTTG1 | $1.8 \times 10^{-5}$ | ZWINT | $9.3 \times 10^{-3}$ | TIMELESS | $4.8 \times 10^{-1}$ |
| CCNB2 | $5.2 \times 10^{-5}$ | KIF23 | $1.1 \times 10^{-2}$ | | |
| HMMR | $5.2 \times 10^{-5}$ | TRIP13 | $1.7 \times 10^{-2}$ | | |

*p-value for likelihood ratio test of full (post-RP nomogram score + cell cycle expression + nomogram:cell cycle) vs reduced (post-RP nomogram score only) CoxPH model of time-to-recurrence.

To evaluate how smaller subsets of the larger CCP set (i.e., smaller CCP panels) performed, the study also compared how well the signature predicted outcome as a function of the number of CCP genes included in the signature (FIG. 1). Time to chemical recurrence after prostate surgery was regressed on the CCP mean adjusted by the post-RP nomogram score. Data consist of TLDA assays expressed as deltaCT for 199 FFPE prostate tumor samples and 26 CCP genes and were analyzed by a CoxPH multivariate model. P-values are for the likelihood ratio test of the full model (nomogram+cell cycle mean including interaction) vs the reduced model (nomogram only). As shown in Table 10 below and FIG. 1, small CCP signatures (e.g., 2, 3, 4, 5, 6 CCP GENES, etc.) add significantly to the Kattan-Stephenson nomogram:

TABLE 10

| # of CCP genes | Mean of log10(p-value)* |
|---|---|
| 1 | −3.579 |
| 2 | −4.279 |
| 3 | −5.049 |
| 4 | −5.473 |
| 5 | −5.877 |
| 6 | −6.228 |

*For 1000 randomly drawn subsets, size 1 through 6, of cell cycle genes.

EXAMPLE 4

The aim of this experiment was to evaluate the association between PTEN mutations and biochemical recurrence in prostate cancer patients after radical prostatectomy. Somatic mutations in PTEN were found to be significantly associated with recurrence, and importantly, it added prognostic information beyond both the established clinical nomogram for prostate cancer recurrence (the Kattan-Stephenson nomogram) and the CCP signature score (described in Examples 1 & 2, supra).

Patients and Methods

Eight hundred four consecutive RP patients were followed for a median of 9.5 years. The patient characteristics and the treatment outcomes of the entire cohort have been previously reported (Swanson et al., UROL. ONCOL. (2007) 25:110-114). Tissue blocks and/or slides from the final pathological evaluation with enough tissue for analysis were available for 430 patients. Of these, 191 were selected for PTEN mutation screening based on the amount of available tumor.

Genomic DNA was isolated from the FFPE tumor samples for mutation screening of PTEN using the QIAamp DNA FFPE Tissue kit (Qiagen, Valencia, Calif.) according to the kit protocol. The FFPE slides were first stained with hematoxylin and eosin and examined by a pathologist to identify the tumor region. After deparaffinization, tumor tissue was cut out from the slides by a razor blade. For a few samples dissection was aided by laser capture microscopy (LCM), owing to the dispersion of the tumor cells Mutations were detected by designing sequencing primers to interrogate the PTEN genomic sequence. The primers contained M13 forward and reverse tails to facilitate sequencing. After amplification, DNA sequence was determined on a Mega BASE 4500 (GE healthcare) using dye-primer chemistry as described in Frank et al., J. CLIN. ONCOL. (2002) 20:1480-1490. Due to the technical difficulties associated with sequencing DNA derived from FFPE material, each mutation was detected by at least two independent amplification and sequencing reactions.

Statistical methods: Unless otherwise specified, the association between biochemical recurrence and PTEN mutations was evaluated using Cox PH models for time to recurrence. The resultant p-values were derived from a likelihood ratio test comparing the null model to the model containing the test variable. In this example (Example 4), the CCP signature was derived from 26 CCP genes (Panel D in Table 2, supra). All of the expression data were generated in triplicate. The expression data were combined into a signature by calculating the mean expression level for 26 CCP genes. The clinical data were the variables included in the Kattan-Stephenson nomogram.

Results

PTEN mutations were found in 13 individuals (13/191). In this subset of 191 patients, PTEN was a significant predictor of biochemical recurrence (p-value=0.031). The recurrence rate in mutation carriers was 69% (9/13) compared to 36% (64/178) in non-mutant patients. The difference in recurrence rate is also significant using a Fisher's exact test (p-value=0.034). In the subset of patients with clinical parameter data, CCP signature score, and PTEN mutations, PTEN status was a significant predictor of biochemical recurrence after adjusting for both clinical parameters and CCP signature (p-value 0.024). Finally, the combination of PTEN mutation with CCP signature was a better predictor of outcome after adjusting for clinical parameters than using the CCP signature after adjusting for clinical parameters (p-value=0.0002 for the combination compared to 0.0028 for CCP only). These results show that PTEN mutations provide information about the likelihood of recurrence that is uncorrelated with either clinical parameters or CCP signature, and that using all three parameters to evaluate recurrence risk provides a more accurate estimate of recurrence probability than previously possible.

EXAMPLE 5

This Example describes further studies to validate and refine some embodiments of the CCP signatures of the invention.

Patients and Methods

Eight hundred four consecutive radical prostatectomy patients were followed for a median of 9.5 years. The median age was 67 years. The clinical stage was T1 34%, T2 66% and T3<1%. The median preoperative PSA was 6.6 ng/ml with 72%<10 ng/ml and 28%>10 ng/ml. The specimens were inked and clinical parameters were recorded as to positive bladder neck or urethral margin, invasion into the capsule, extension through the capsule, positive margins and the involvement of the seminal vesicles. Biochemical recurrence was defined as a PSA>0.3 ng/ml. For this study we had access to clinical data on 690 patients. Tissue blocks and/or slides from the final pathological evaluation with enough tissue for analysis were available for 442 patients. The cohort was divided into 195 patients for a training cohort, and 247 patients for validation.

Selection of Genes

Assays of 126 CCP genes and 47 HK (housekeeping) genes were run against 96 commercially obtained, anonymous prostate tumor FFPE samples without outcome or other clinical data. The working hypothesis was that the assays would measure with varying degrees of accuracy the same underlying phenomenon (cell cycle proliferation within the tumor for the CCP genes, and sample concentration for the HK genes). Assays were ranked by the Pearson's correlation coefficient between the individual gene and the mean of all the candidate genes, that being the best available estimate of biological activity. Results for the correlation of each of the 126 CCP genes to the mean are reported in Table 23. Not including CCP genes with low average expression, or assays that produced sample failures, approximately half the CCP genes had correlations less than 0.58, and a quarter of the HK genes had correlations less than 0.95. These assays were interpreted as not reflecting the underlying phenomenon and were eliminated, leaving a subset of 56 CCP genes (Panel G) and 36 HK candidate genes (Tables 11 and 12). Correlation coefficients were recalculated on this subset, and the final selection was made from the ranked list.

TABLE 11

Complete list of evaluated CCP genes ("Panel G")

| Gene Symbol | Correlation with CCP mean |
|---|---|
| FOXM1 | 0.908 |
| CDC20 | 0.907 |
| CDKN3 | 0.9 |
| CDC2 | 0.899 |
| KIF11 | 0.898 |
| KIAA0101 | 0.89 |
| NUSAP1 | 0.887 |
| CENPF | 0.882 |
| ASPM | 0.879 |
| BUB1B | 0.879 |
| RRM2 | 0.876 |
| DLGAP5 | 0.875 |
| BIRC5 | 0.864 |
| KIF20A | 0.86 |
| PLK1 | 0.86 |
| TOP2A | 0.851 |
| TK1 | 0.837 |
| PBK | 0.831 |
| ASF1B | 0.827 |
| C18orf24 | 0.817 |
| RAD54L | 0.816 |
| PTTG1 | 0.814 |
| KIF4A | 0.814 |
| CDCA3 | 0.811 |
| MCM10 | 0.802 |
| PRC1 | 0.79 |
| DTL | 0.788 |
| CEP55 | 0.787 |
| RAD51 | 0.783 |
| CENPM | 0.781 |
| CDCA8 | 0.774 |
| OIP5 | 0.773 |
| SHCBP1 | 0.762 |
| ORC6L | 0.736 |
| CCNB1 | 0.727 |
| CHEK1 | 0.723 |
| TACC3 | 0.722 |
| MCM4 | 0.703 |
| FANCI | 0.702 |
| KIF15 | 0.701 |
| PLK4 | 0.688 |
| APOBEC3B | 0.67 |
| NCAPG | 0.667 |
| TRIP13 | 0.653 |
| KIF23 | 0.652 |
| NCAPH | 0.649 |
| TYMS | 0.648 |
| GINS1 | 0.639 |
| STMN1 | 0.63 |
| ZWINT | 0.621 |
| BLM | 0.62 |
| TTK | 0.62 |
| CDC6 | 0.619 |
| KIF2C | 0.596 |
| RAD51AP1 | 0.567 |
| NCAPG2 | 0.535 |

TABLE 12

List of 15 housekeeping (HK) genes

| Gene Symbol | Correaltion with HK Mean |
|---|---|
| RPL38 | 0.989 |
| UBA52 | 0.986 |
| PSMC1 | 0.985 |
| RPL4 | 0.984 |
| RPL37 | 0.983 |
| RPS29 | 0.983 |
| SLC25A3 | 0.982 |
| CLTC | 0.981 |
| TXNL1 | 0.98 |
| PSMA1 | 0.98 |
| RPL8 | 0.98 |
| MMADHC | 0.979 |
| RPL13A; LOC728658 | 0.979 |
| PPP2CA | 0.978 |
| MRFAP1 | 0.978 |

Gene Expression

Total RNA was extracted from representative 5 μM thick FFPE tumor sections. The samples were de-paraffinized using a xylene bath and subsequently hydrated in graded series of ethanol baths. Afterward, the tumor region was dissected from the slide using a razor blade according to the pathologist instructions. Alternatively, the tumor region was dissected directly into an eppendorf tube and the paraffin was removed using xylene and washed with ethanol. After, samples were treated overnight with proteinase K digestion at 55° C. Total RNA was extracted using either RNeasy FFPE or miRNeasy (Qiagen) as described by the manufacturer (with the only exception being the extended proteinase K digestion described above). Isolated total RNA was treated with DNase I (Sigma) prior to cDNA synthesis. Subsequently, we employed the High-capacity cDNA Archive Kit (Applied Biosystems) to convert total RNA into single strand cDNA as described by the manufacturer. A minimum of 200 ng RNA was required for the RT reaction.

Prior to measuring expression levels, the cDNA was pre-amplified with a pooled reaction containing TaqMan™ assays. Pre-amplification reaction conditions were: 14 cycles of 95° C. for 15 sec and 60° C. for 4 minutes. The first cycle was modified to include a 10 minute incubation at 95° C. The amplification reaction was diluted 1:20 using the 1×TE buffer prior to loading on TaqMan™ Low Density Arrays (TLDA, Applied Biosystems) to measure gene expression.

CCP Score

The CCP score is calculated from RNA expression of 31 CCP genes (Panel F) normalized by 15 housekeeper genes (HK). The relative numbers of CCP genes (31) and HK genes (15) were optimized in order to minimize the variance of the CCP score. The CCP score is the unweighted mean of CT values for CCP expression, normalized by the unweighted mean of the HK genes so that higher values indicate higher expression. One unit is equivalent to a two-fold change in expression. Missing values were imputed using the mean expression for each gene determined in the training set using only good quality samples. The CCP scores were centered by the mean value, again determined in the training set.

A dilution experiment was performed on four of the commercial prostate samples to estimate the measurement error of the CCP score (se=0.10) and the effect of missing values. It was found that the CCP score remained stable as concentration decreased to the point of 5 failures out of the total 31 CCP genes. Based on this result, samples with more than 4 missing values were not assigned a CCP score.

The CCP score threshold for determining low-risk was based on the lowest CCP score of recurrences in the training set. The threshold was then adjusted downward by 1 standard deviation in order to optimize the negative predictive value of the test.

Model of Clinical Risk

A Cox proportional hazards model was used to summarize the available clinical parameter data and estimate the prior clinical risk of biochemical recurrence for each patient. The data set consisted of 195 cases from the training set and 248 other cases with clinical parameter information but insufficient sample to measure RNA expression. Univariate tests were performed on clinical parameters known to be associated with outcome (see Table 13 below). Non-significant parameters were excluded from the model. A composite variable was created for organ-confined disease, with invasion defined as surgical margins, extracapsular extension, or involvement of any of seminal vesicles, bladder neck/urethral margins, or lymph nodes. The composite variable for organ-confined disease proved more significant in the model than any of its five components, some of which were inter-correlated or not prevalent. Model fitting was performed using the AIC criteria for post-operative covariates.

TABLE 13

Univariate analysis of clinical parameters and association with biochemical recurrence

| Cinical Variable | p-value* | # occurrences | Total | Frequency |
|---|---|---|---|---|
| BLADDER | 0.0002 | 36 | 443 | 0.081 |
| CAPSULAR | $1.1 \times 10^{-9}$ | 194 | 443 | 0.438 |
| ETHNICITY (WHITE) | 0.6741 | 416 | 439 | 0.948 |
| LYMPHNOD | 0.0009 | 33 | 443 | 0.074 |
| MARG.POS | $6.1 \times 10^{-11}$ | 83 | 443 | 0.187 |
| PATHGLEA | $6.7 \times 10^{-16}$ | NA | 443 | NA |
| PATHGRAD | $2.4 \times 10^{-11}$ | NA | 443 | NA |
| PATHSTAG | $3.1 \times 10^{-15}$ | NA | 443 | NA |
| PRE.PSA.LOG10 | $6.2 \times 10^{-12}$ | NA | 443 | NA |
| SEM.VES | $3.0 \times 10^{-8}$ | 56 | 443 | 0.126 |
| SURGERY.YEAR | 0.0803 | NA | 443 | NA |
| THRU.CAP | $1.3 \times 10^{-10}$ | 114 | 443 | 0.257 |

*Cox PH p-value for likelihood ratio test

Figure 8:
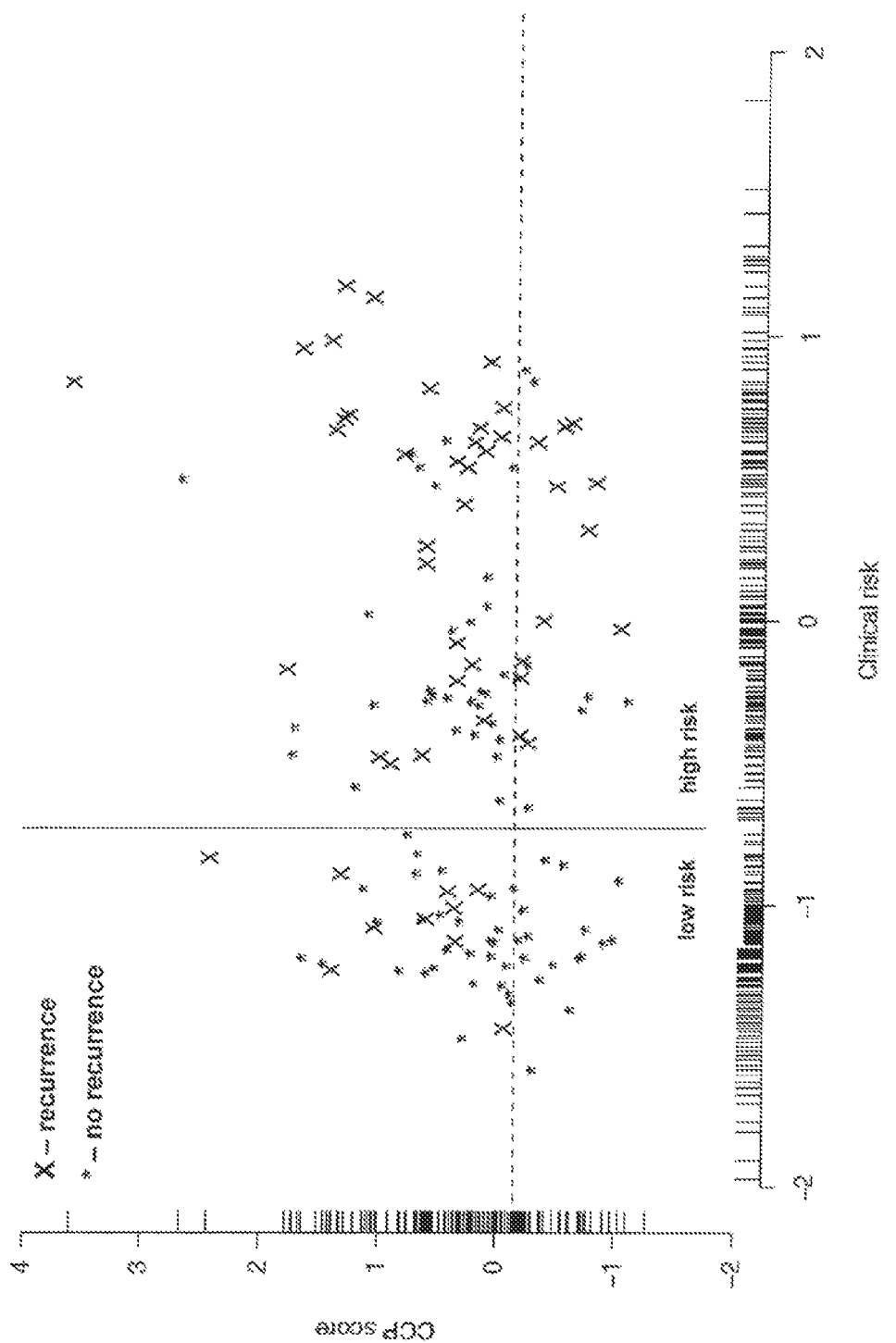
FIG. 8 a scatter plot comparing clinical parameters and CCP score as predictors of recurrence from Example 5.

The final model (i.e., nomogram) has binary variables for organ-confined disease and Gleason score less than or equal to 6, and a continuous variable for logarithmic PSA (Table 14). This model includes all of the clinical parameters incorporated in the post-RP nomogram (i.e., Kattan-Stephenson nomogram) except for Year of RP and the two components of the Gleason score. The distribution of prior clinical risk shows three distinct nodes (FIG. 8). K-means clustering with 3 centers was used to set the threshold for the low-risk cluster, which comprises approximately 50% of the sample.

TABLE 14

Clinical Model

| Clinical Parameter | Coefficient | HR | p-value* |
|---|---|---|---|
| organ-confined disease | −0.827 | 0.44 | $3.4 \times 10^{-6}$ |
| Gleason score ≤6 | −0.8734 | 0.42 | $4.2 \times 10^{-7}$ |
| log PSA | 0.6678 | 1.95 | $2.0 \times 10^{-4}$ |

*Cox PH p-value for likelihood ratio test

Statistical Analysis

Clinical parameters were compared between the training and validation sets using the Student's t-test for continuous parameters and Fisher's exact test for categorical parameters. The prior clinical risk of patients for biochemical recurrence after surgery was estimated by a post-RP nomogram score summarizing 7 covariates. K-means clustering of the nomogram score was used to categorize patients as low or high prior clinical risk. Expression data were expressed as the CT (the PCR cycle at which the fluorescence intensity exceeds a predetermined threshold) of each CCP normalized by the mean of the 15 housekeeper genes (Table 12 above).

Poor quality samples were excluded from analysis to eliminate poor quality samples or dubious readings without compromising the integrity of the signature by inadvertently excluding samples with low CCP expression. Accordingly, the thresholds for cleaning or filtering the data were set conservatively. Mean expression levels of the HK genes for each sample, which were higher than those of the CCP genes, were used to identify poor quality samples. Technical metrics for the amplification efficiency and excessively high standard deviations of replicates were used to identify unreliable CT measurements. No failures of HK genes, and no more than 1 failure out of 3 replicates for CCP genes, were allowed.

The association between biochemical recurrence and CCP expression after adjusting for clinical risk predicted by clinical parameters was evaluated using a Cox proportional hazards model for time-to-recurrence. The proportional hazards assumption of no time-dependence was tested for the full model of the CCP signature plus the binary clinical parameter score with an interaction term, and for the CCP signature only in the clinical risk subsets. It was not significant in either training or validation, indicating that there is no evidence for time-dependence. All of the p-values reported are from a likelihood ratio test comparing the reduced or null model to the model containing the test variable. Kaplan-Meier plots are used to show estimated survival probabilities for subsets of patients; however, p-values are from the Cox likelihood ratio test for the continuous values of the variable. All statistical analyses were performed in S+ Version 8.1.1 for Linux (TIBCO Spotfire) or R 2.9.0 (www.r-project.org).

Results

We isolated RNA from FFPE tumor sections derived from 442 prostate cancer patients treated with RP. The cohort was split into 195 patients for initial characterization of the signature ("training set") and 247 patients for validation. The clinical parameters of the training and validation cohort are listed in Table 15. There were no significant differences after adjusting for multiple comparisons.

TABLE 15

Clinical parameters of training and validation patient cohorts

| Clinical Parameter | Training | Validation | p-value | Statistical Analysis |
|---|---|---|---|---|
| Age in years at RP, mean (sd) | 67.5 (6.2) | 66.8 (5.6) | 0.204 | t-test |
| Ethnicity (% non-white) | 3.10% (2 Black, 3 Hispanic, 1 other) | 7.30% (10 Black, 7 Hispanic, 1 other) | 0.058 | Fisher's exact |
| Recurrence | 73/195 (37.4%) | 90/247 (36.4%) | 0.843 | Fisher's exact |
| Days to recurrence, median | 839 | 736 | 0.308 | t-test |

TABLE 15-continued

Clinical parameters of training and validation patient cohorts

| Clinical Parameter | Training | Validation | p-value | Statistical Analysis |
|---|---|---|---|---|
| Days to follow-up, median | 3300 | 3332 | 0.556 | t-test |
| Pre-RP surgery PSA, median | 7.4 | 6.4 | 0.022 | t-test of log |
| Seminal vesicles | 23/195 (11.8%) | 33/247 (13.4%) | 0.668 | Fisher's exact |
| Bladder neck/urethral margin | 12/195 (6.2%) | 16/247 (6.5%) | 1 | Fisher's exact |
| Lymph nodes | 8/195 (4.1%) | 12/247 (4.9%) | 0.819 | Fisher's exact |
| Capsular penetration | 104/195 (53.3%) | 115/247 (46.6%) | 0.18 | Fisher's exact |
| Through the capsule | 66/195 (33.8%) | 73/247 (29.6%) | 0.354 | Fisher's exact |
| Positive margins | 51/195 (26.2%) | 61/247 (24.7%) | 0.742 | Fisher's exact |
| Post-RP Gleason score <7 | 114/195 (58.5%) | 166/247 (67.2%) | 0.06 | Fisher's exact |
| Organ-confined disease | 108/195 (55.4%) | 156/247 (63.2%) | 0.118 | Fisher's exact |
| 10-year PFP (95% CI) | 61% (52%, 69%) | 67% (60%, 73%) | 0.905 | Log-rank test |

To analyze the CCP signature for this study, we tested 126 CCP genes on RNA derived from 96 prostate tumors (Table 11). The tumor samples were anonymous and not associated with clinical data. From this set of genes, we selected 31 genes (Panel F) for inclusion in our signature (Table 16). The genes were selected based on their technical performance, and by how well each gene correlated with the mean expression level of the entire CCP set, in the 96 anonymous samples.

TABLE 16

CCP Signature from Training Set (Panel F)

| Symbol | GeneID |
|---|---|
| ASF1B | 55723 |
| ASPM | 259266 |
| BIRC5 | 332 |
| BUB1B | 701 |
| C18orf24 | 220134 |
| CDC2 | 983 |
| CDC20 | 991 |
| CDCA3 | 83461 |
| CDCA8 | 55143 |
| CDKN3 | 1033 |
| CENPF | 1063 |
| CENPM | 79019 |
| CEP55 | 55165 |
| DLGAP5 | 9787 |
| DTL | 51514 |
| FOXM1 | 2305 |
| KIAA0101 | 9768 |
| KIF11 | 3832 |
| KIF20A | 10112 |
| MCM10 | 55388 |
| NUSAP1 | 51203 |
| ORC6L | 23594 |
| PBK | 55872 |
| PLK1 | 5347 |
| PRC1 | 9055 |
| PTTG1 | 9232 |
| RAD51 | 5888 |
| RAD54L | 8438 |
| RRM2 | 6241 |
| TK1 | 7083 |
| TOP2A | 7153 |

To evaluate the prognostic utility of the CCP signature, we generated expression data on 195 patients in the training set. Since the individual gene expression levels were correlated, we combined them into a signature score by calculating the mean expression for the entire set of 31 genes (Panel F), normalized by 15 housekeepers (Table 12). The CCP score distribution was centered at zero, and each score unit corresponds to a 2-fold change in expression level. Poor quality samples were identified by observing either low expression of housekeeping genes or an unacceptable number of CCP failures, and excluded from the analysis. After applying our exclusion rules, there were 140 samples available for analysis. Association between biochemical recurrence and CCP expression was evaluated using Cox PH models for time to recurrence. A high CCP expression value was predictive of disease recurrence in a univariate analysis (p-value=0.01, Table 17).

Next, we evaluated the prognostic utility of the CCP signature after accounting for clinical parameters known to be associated with recurrence after RP. To account for clinical measures in our analysis, we created a model/nomogram that included preoperative PSA, Gleason score, and evidence of disease outside the prostate (i.e., any of either extracapsular extension, or positive post-surgical pathology on lymph nodes, margins, bladder neck, urethral margin or seminal vesicles). The model was optimized in 443 patients (Tables 13 & 14), including all patients for whom we had clinical data but were not in the validation set, and was a highly significant predictor of recurrence in the training cohort (p-value=$2.5 \times 10^{-11}$). The distribution of the scores from the clinical model contained several modes (FIG. 8), separating high- and low-risk patient groups. Therefore, the score was used subsequently as a binary variable (high or low risk). The low-risk cluster correlated with a consistent set of clinical parameters. Specifically, the vast majority (215/218) had organ-confined disease and Gleason score <7. In addition, 80% had low pre-surgical PSA (<10 ng/ml). Patients in the high-risk cluster (N=225) were more heterogeneous, but tended to have clinical characteristics known to be associated with poor outcome (e.g., Gleason >6 and/or disease through the capsule).

Multivariate analysis of the training set incorporating our binary clinical model, showed evidence for a non-linear interaction between the expression signature and clinical parameters (Table 17). To help us understand the nature of this interaction, we generated a scatter plot comparing these predictors (FIG. 8). As evident from the figure, the CCP score proved useful for evaluating recurrence risk in patients defined as low risk by clinical parameters. In fact, even after adjusting for the clinical model within the low risk patients, the CCP signature was a strong predictor of biochemical recurrence (p-value=0.0071).

TABLE 17

Statistical Summary

| | | 31-gene training N = 195 | | | 31-gene validation N = 247 | | |
|---|---|---|---|---|---|---|---|
| | Subset based on clin. model | Main effect p-value | Interaction p-value | n | Main effect p-value | Interaction p-value | n |
| CCP score | | 0.01 | | 140 | $5.8 \times 10^{-8}$ | | 218 |
| Binary clin. risk (low vs high) | | $5.1 \times 10^{-6}$ | | 133 | $1.1 \times 10^{-10}$ | | 215 |
| CCP score adjusted for binary clin. risk + interaction | | 0.018 | 0.032 | 133 | $8.3 \times 10^{-7}$ | 0.026 | 215 |
| CCP score only | low-risk | 0.0038 | | 54 | $7.5 \times 10^{-5}$ | | 112 |
| Clin. risk score | low-risk | 0.22 | | 54 | 0.044 | | 112 |
| CCP score adjusted for clin. risk (clin. risk vs clin. risk + CCP) | low-risk | 0.0071 | | 54 | 0.00019 | | 112 |
| CCP score | high-risk | 0.48 | | 79 | $5.8 \times 10^{-4}$ | | 103 |
| Clin. risk score | high-risk | $2.8 \times 10^{-6}$ | | 79 | 0.0076 | | 103 |
| CCP score adjusted for clin. risk (clin. risk vs clin. risk + CCP) | high-risk | 0.51 | | 79 | 0.0026 | | 103 |

Figure 12:
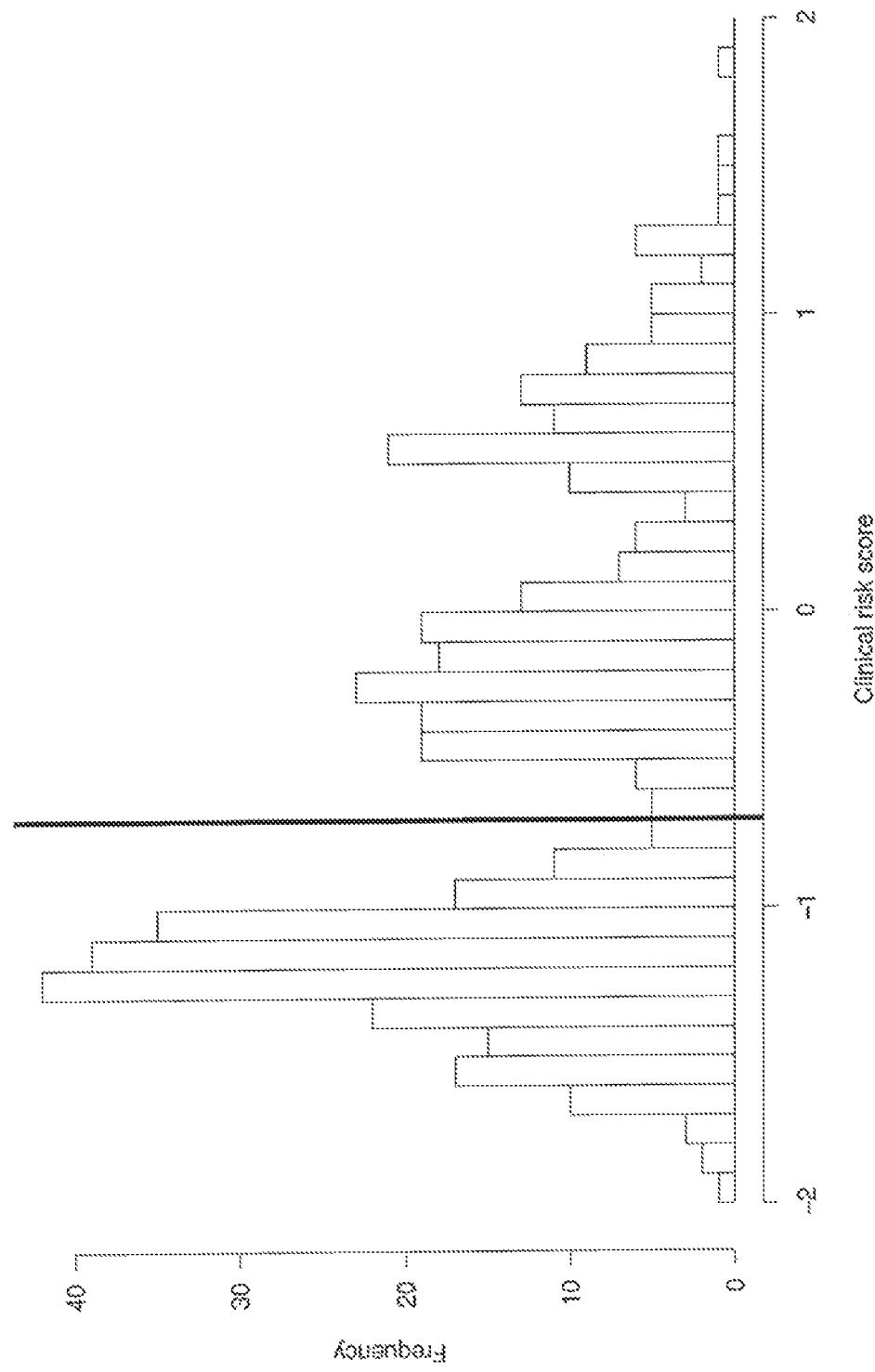
FIG. 12 illustrates the distribution of clinical risk score in 443 patients studied in Example 5. The dark vertical line represents the threshold chosen by KM means to divide low- and high-risk patients and used throughout this study.
Figure 13:
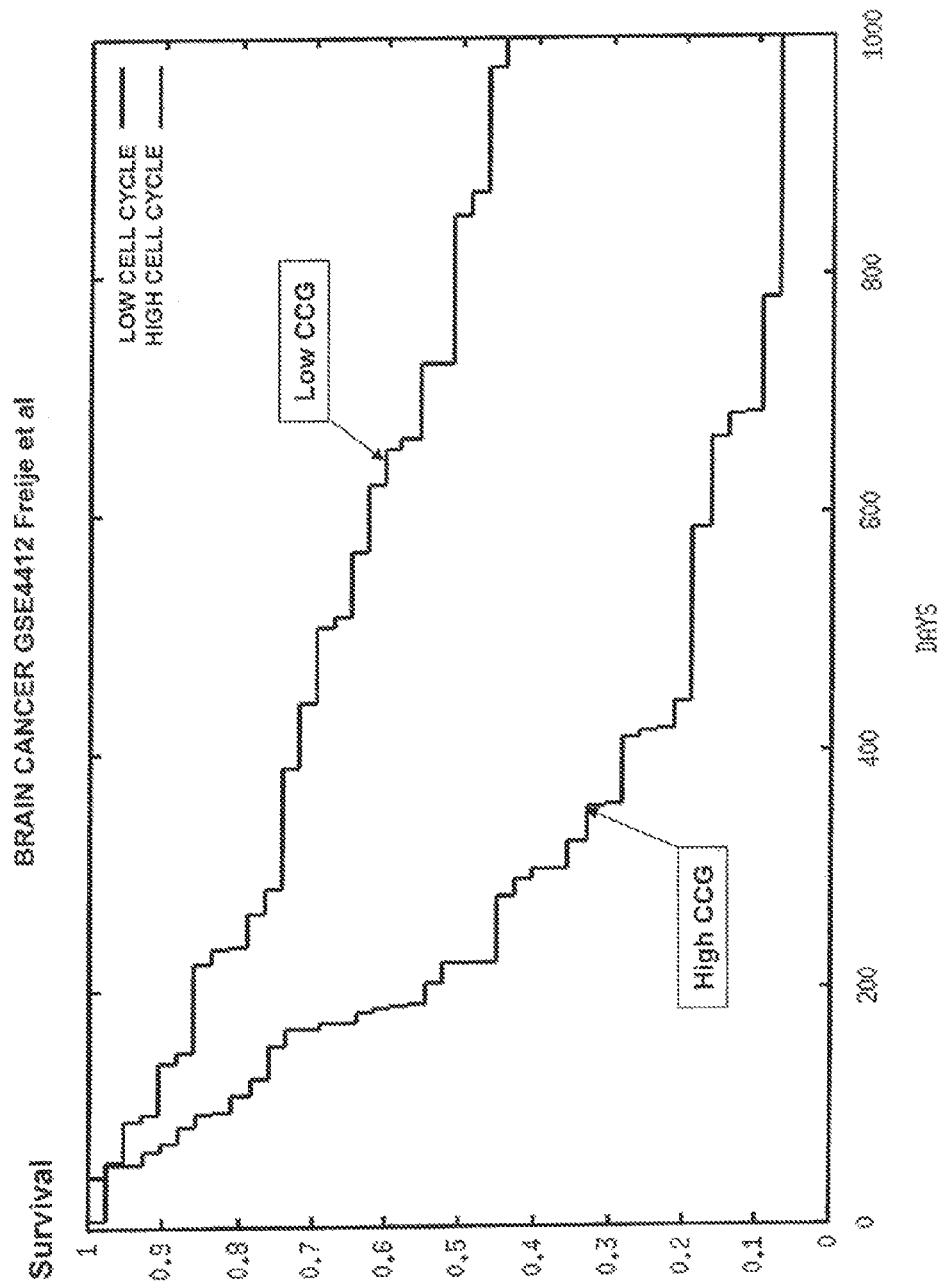
FIG. 13 illustrates the correlation between CCP score and survival in brain cancer.
Figure 14:
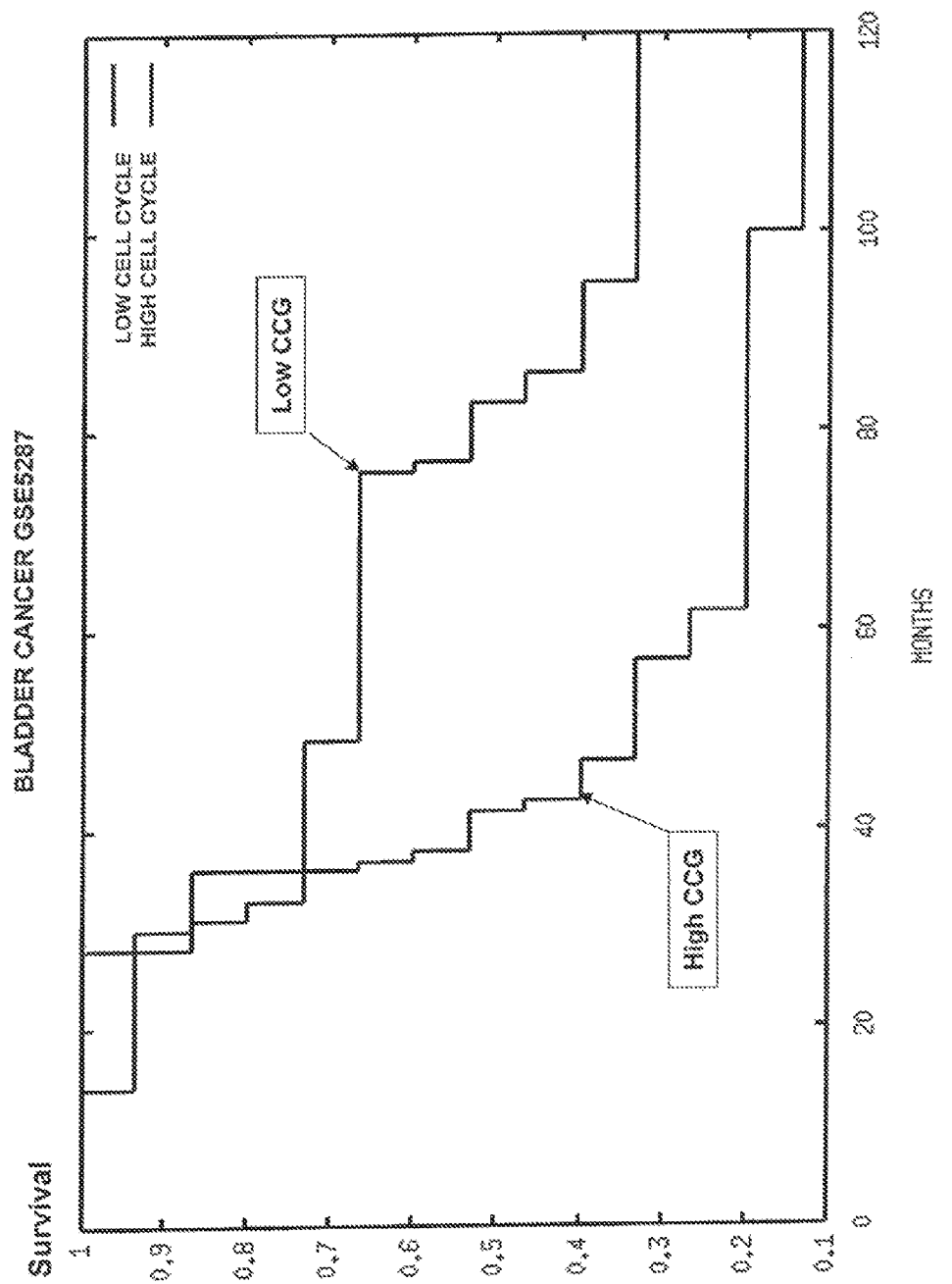
FIG. 14 illustrates illustrates the correlation between CCP score and survival in bladder cancer.
Figure 15:
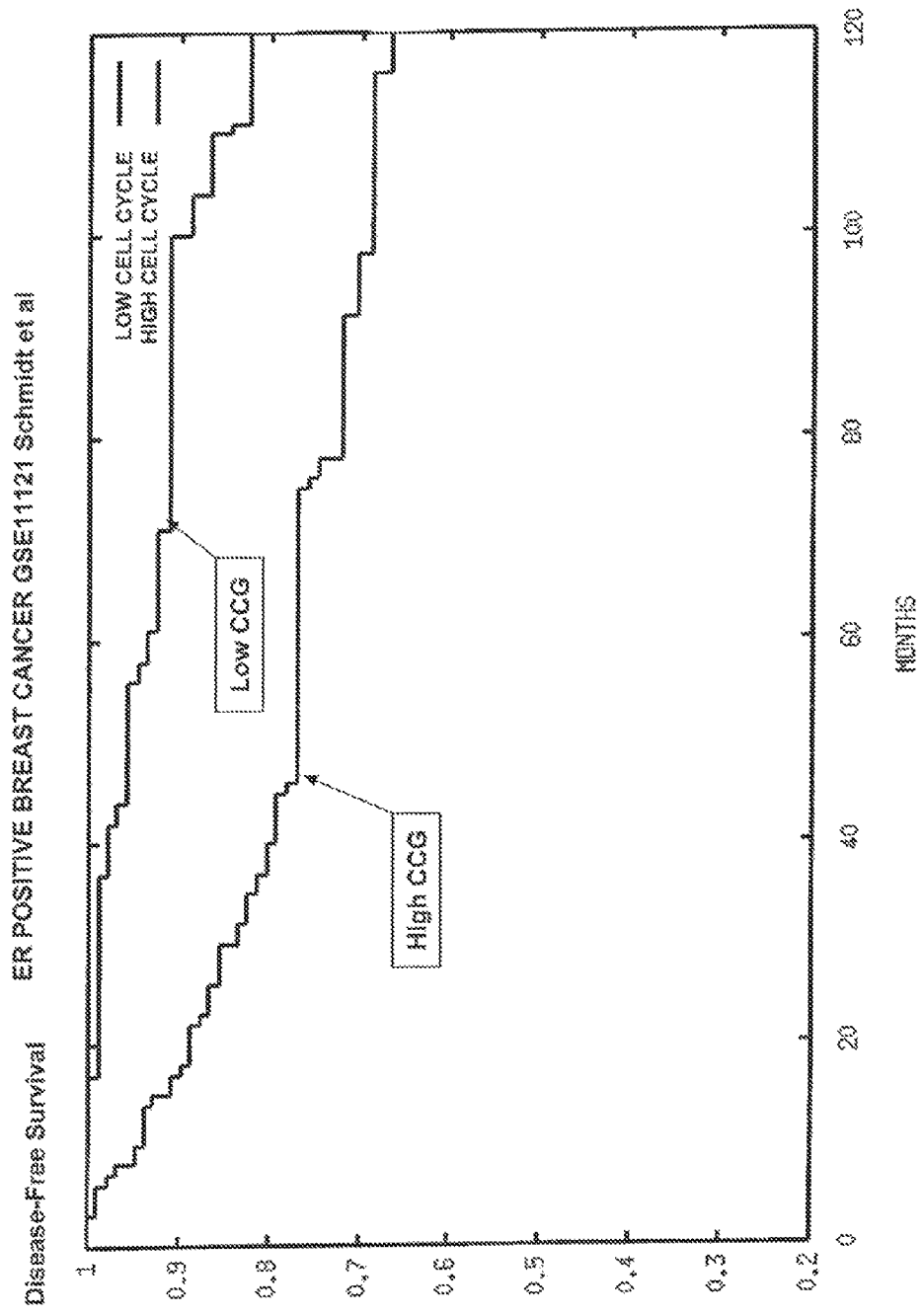
FIG. 15 illustrates illustrates the correlation between CCP score and survival in breast cancer.
Figure 16:
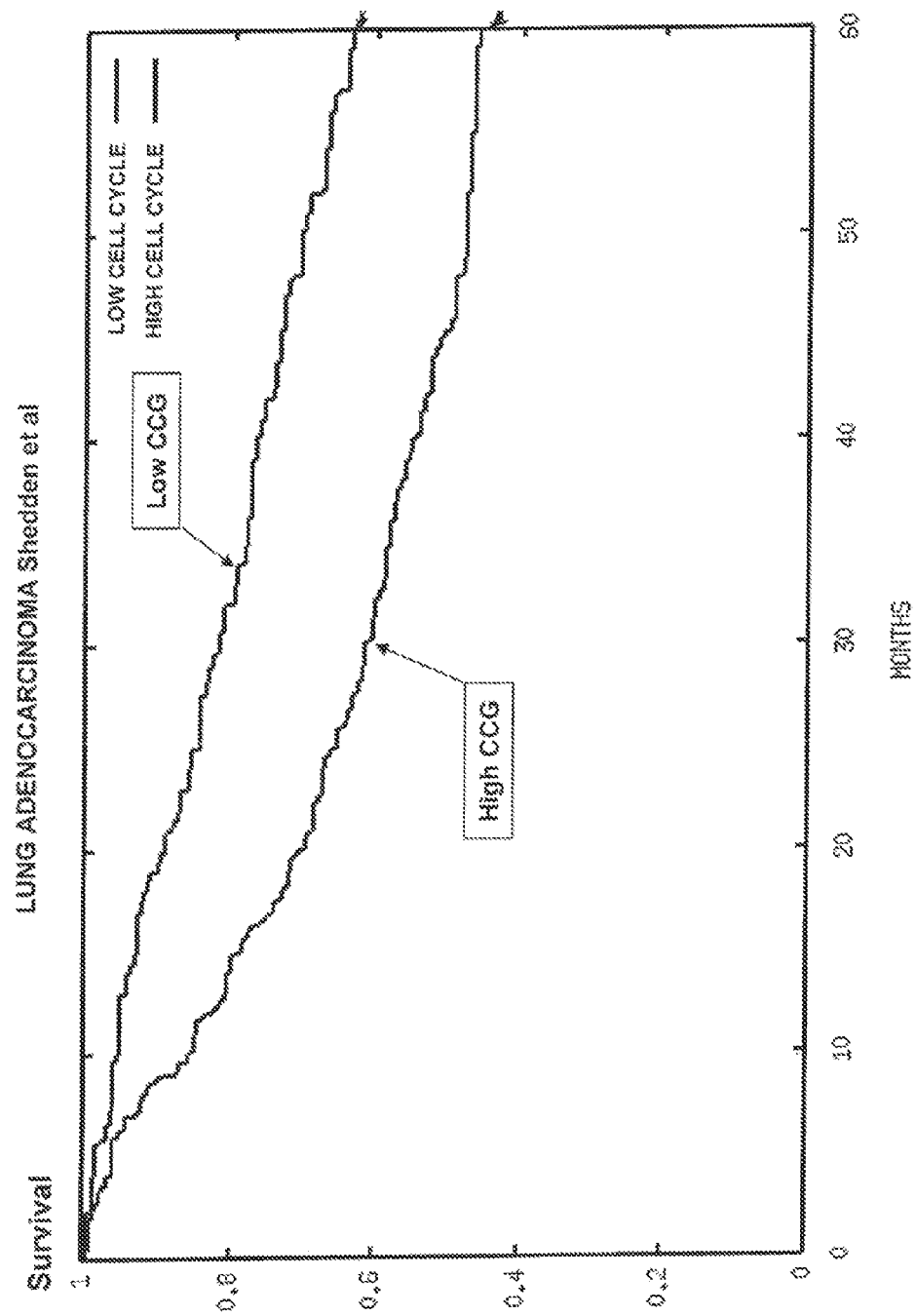
FIG. 16 illustrates the correlation between CCP score and survival in lung cancer.

We used our training data in the scatter plot to establish an optimized threshold score of −0.16 for the CCP signature (the mean CCP score is zero). FIG. 12 shows this threshold applied to the 443 patients studied in this example. Forty percent of low-risk patients fall below this threshold, and it was selected so that there were no recurrences 10-years after RP (i.e., negative predictive value (NPV) of 100%). As a result of establishing threshold values for both the clinical model and CCP score, the scatter plot was divided into four sections with recurrence rates of 0% (low CCP) and 26% (high CCP) for low-risk patients; and 60% (low CCP) and 50% for high-risk patients.

Next, we generated CCP expression data on 247 patients in our validation cohort. Thirty-two samples were eliminated from further analysis according to the exclusion rules developed on the training cohort. Panel F was a significant predictor of biochemical recurrence in a univariate analysis (p-value=$5.8 \times 10^{-8}$, Table 17). After adjusting for the binary clinical model, the CCP signature was highly predictive of recurrence in the validation cohort (p-value $8.3 \times 10^{-7}$), and as in the training set, there was significant evidence for a non-linear interaction between variables. The CCP signature was informative across the entire spectrum of clinically defined risk (Table 17). In terms of validating the training results, the p-value for association between recurrence and CCP signature in low-risk patients was $1.9 \times 10^{-4}$.

Figure 9:
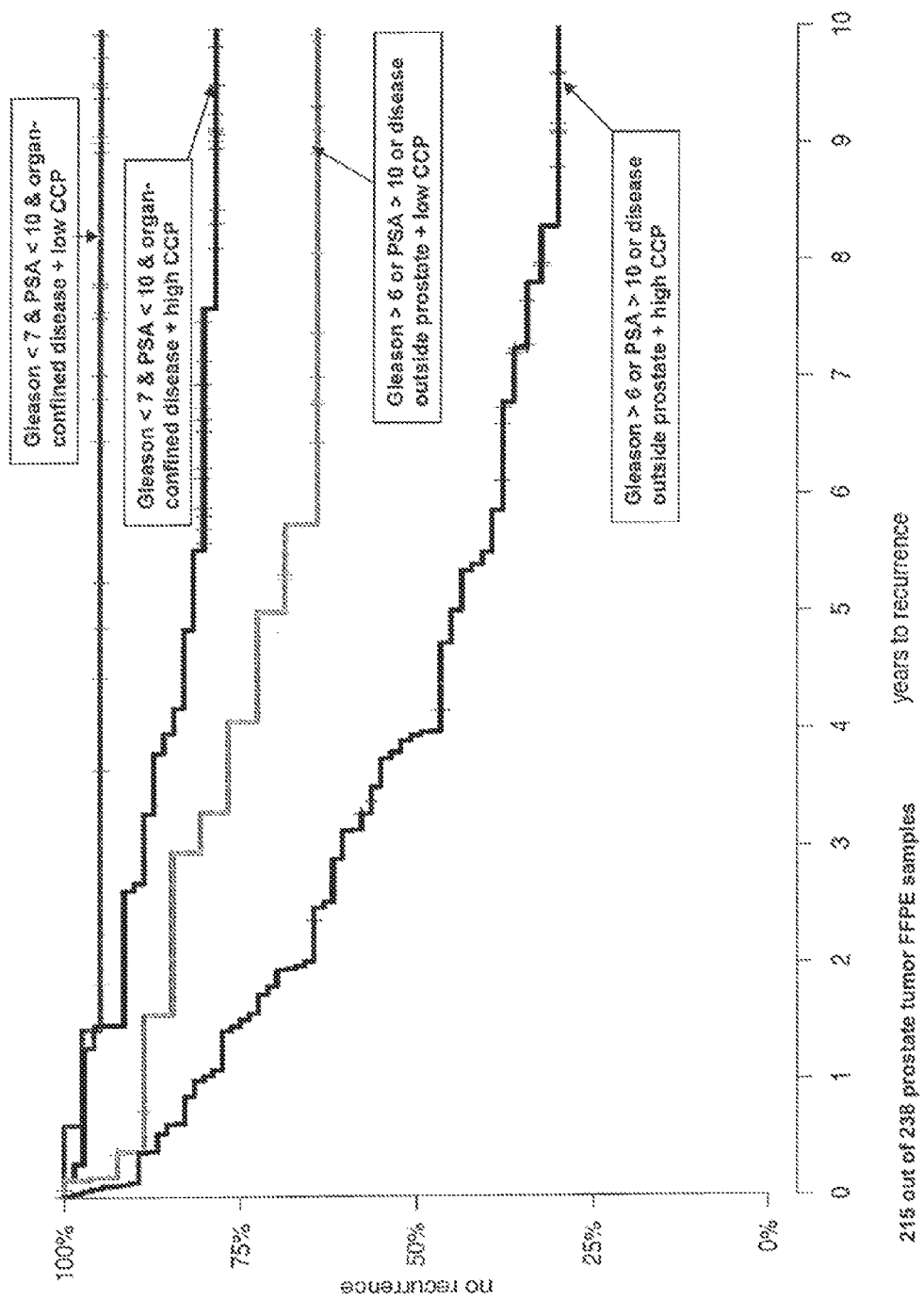
FIG. 9 illustrates, from Example 5, the CCP threshold derived from analysis of the training cohort to the validation data set, with the CCP signature score effectively subdividing patients identified as low-risk using clinical parameters into patients with very low recurrence rates and a higher risk of recurrence.
Figure 10:
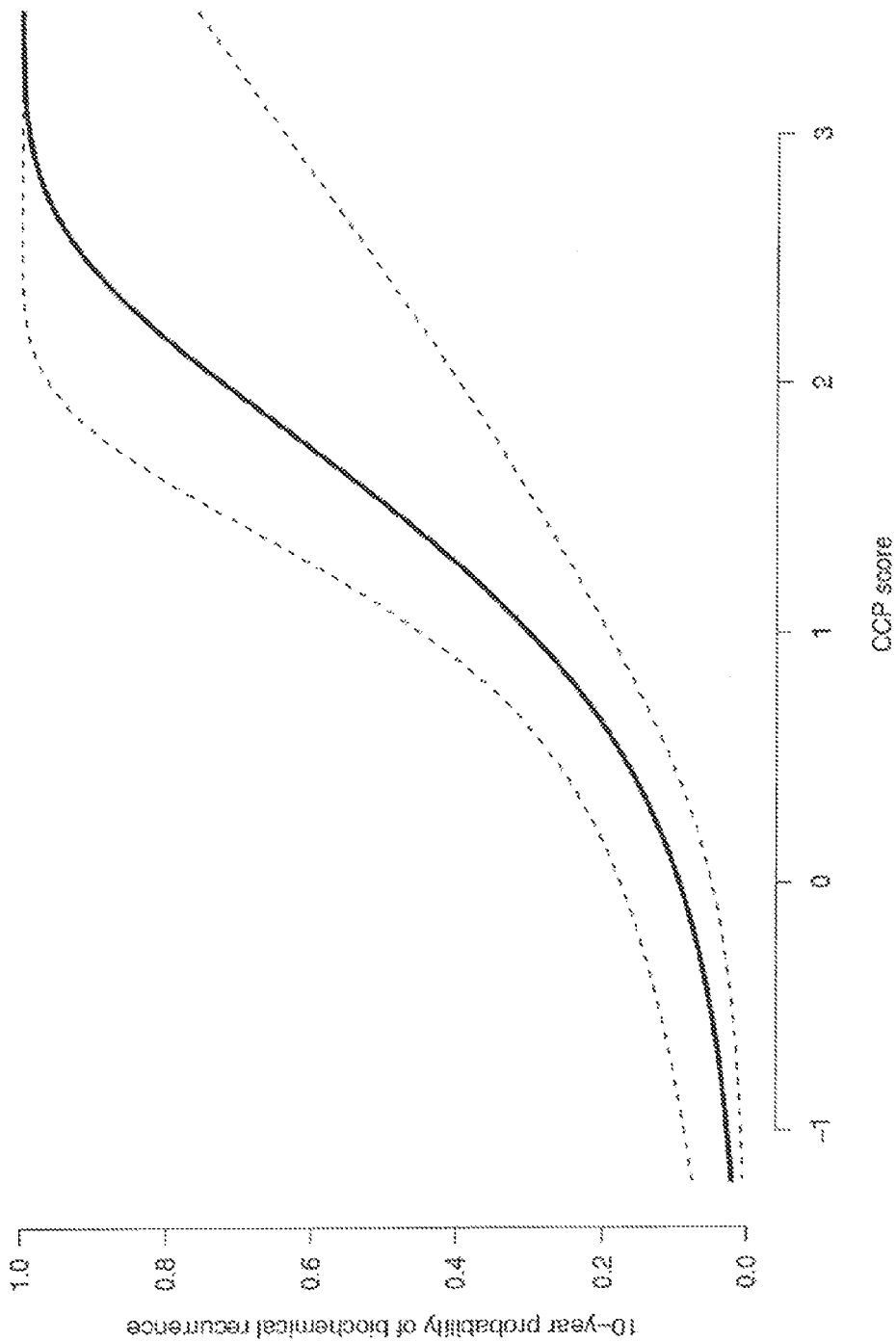
FIG. 10 illustrates the predicted recurrence rate versus CCP score for patients in the validation cohort of Example 5.
Figure 11:
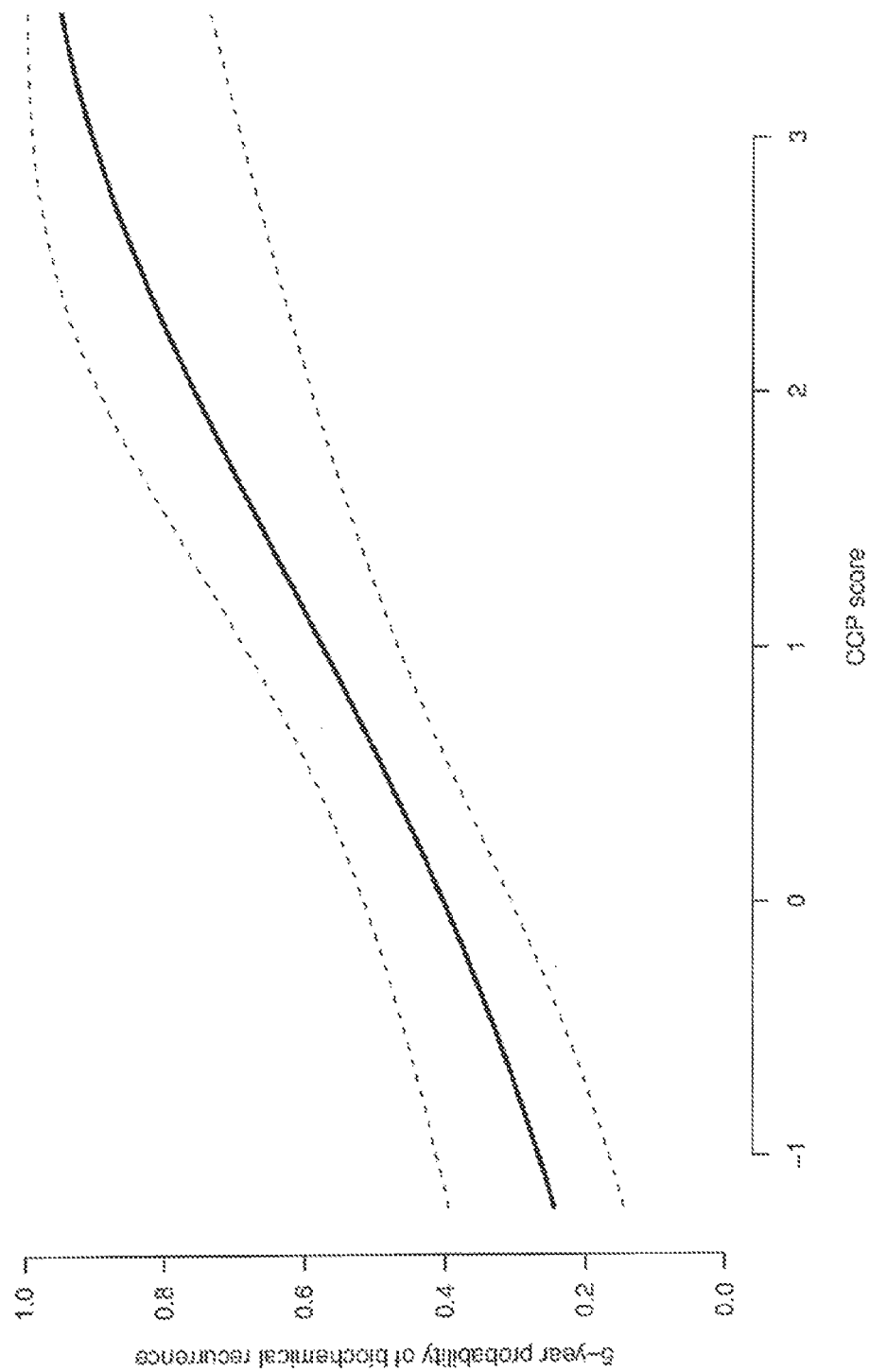
FIG. 11 illustrates the predicted recurrence rate versus CCP score for patients in the validation cohort of Example 5.

We applied the CCP threshold derived from our analysis of the training cohort to our validation data set (FIG. 9). Low risk patients with CCP scores below the threshold had a 10-year predicted recurrence rate of 5% (equivalent to validated NPV of 0.95). Overall, the combination of CCP score and clinical parameters divided the cohort into four groups with 10 year predicted recurrence rates of 5%, 22%, 36% and 70% (Table 18). The predicted recurrence rate versus CCP score for patients in the validation cohort is shown in FIGS. 10 & 11.

TABLE 18

Summary of recurrence rates in validation cohort defined by clinical risk and CCP score

| Clinical risk | CCP score | 10-year recurrence rate Kaplan-Meier estimate | n |
|---|---|---|---|
| low | low | 0.05 | 39 |
| low | high | 0.22 | 73 |
| high | low | 0.36 | 27 |
| high | high | 0.7 | 76 |

We tested our validated threshold versus various definitions of low-risk patients (Table 19). The signature score was a significant prognostic indicator in a variety of low-risk clinical definitions, and depending on definition, generated a 10-year predicted recurrence rate of 0.05 to 0.10.

TABLE 19

NPV of CCP signature in other definitions of low-risk patients

| | low CCP* | | |
|---|---|---|---|
| Clinical definition of low risk | 10-yr predicted recurrence** | n | p-value*** |
| Organ-confined disease and Gleason score <7 & PSA <10 | 0.05 | 39 | $9.4 \times 10^{-4}$ |
| Organ-confined disease and Gleason score <7 | 0.08 | 40 | $5.8 \times 10^{-3}$ |
| Organ-confined disease and Gleason score <8 & PSA <10 | 0.07 | 42 | $8.7 \times 10^{-4}$ |
| Organ-confined disease and Gleason score <8 | 0.1 | 43 | $4.1 \times 10^{-3}$ |
| Organ-confined disease only | 0.1 | 44 | $2.4 \times 10^{-3}$ |

*defined by validated threshold
**Kaplan-Meier estimates
***for difference between KM estimates for low and high risk adjusted by Greenwood variance.

Comment

We have developed and validated a prognostic molecular signature for prostate cancer. The signature is based on measuring mRNA expression levels of cell cycle genes (CCP genes). By definition, expression of CCP genes is regulated as a function of cell cycle stage. That is, they are turned on at specific cell cycle stages, so that actively growing cells have higher expression levels of CCP than quiescent cells. Presumably this fact underlies the signature's ability to predict cancer progression. Without wishing to be bound by theory, it is thought that by measuring the expression levels of CCP we are indirectly measuring the growth rate and inherent aggressiveness of the tumor, which ultimately impacts on the likelihood of prostate cancer recurrence after prostatectomy.

There is an important distinction between this study and many others that have attempted to generate prognostic molecular signatures. Often, similar studies begin with a very large number of candidate biomarkers (sometimes exceeding 1000's of genes) that are then evaluated for association with a clinical phenotype of interest. This approach may at times suffer from inherent multiple testing which can make the significance of the derived signature uncertain. Here we have tested a single hypothesis: CCP would be prognostic in prostate cancer (in fact we selected genes based on their correlation with CCP expression, not based on association with recurrence). And since CCP expression is correlated, we combined the expression data into a predictive signature by determining the mean expression value of all the genes in the signature. The simplicity of this approach, biologically and computationally, supports the view that the central claim of this study is likely to be highly robust, and replicated in subsequent studies.

The CCP signature (Panel F) is independently predictive and adds significantly to the predictive power of the clinical parameters typically employed to predict disease recurrence after surgery. This is true in both our training and validation cohorts.

The signature is immediately useful for defining the risk of patients who present with low-risk clinical parameters. Here, we essentially defined low-risk as Gleason <7, PSA<10 and organ-confined disease. The CCP signature score effectively subdivides the low-risk group into patients with very low recurrence rates (5%), and a higher risk of recurrence (22%) (FIG. 9 & Table 18). This is the most dramatic effect of the molecular signature—accurately redefining the risk of patients previously defined as low-risk based on clinical parameters. It is noteworthy that within this patient subpopulation (i.e., patients defined as low-risk based on clinical parameters) clinical parameters are not particularly prognostic (see Table 17). Therefore as a diagnostic test, the signature could be useful for a large number of patients. In this study, nearly 60% of the cohort was characterized as low-risk and 40% of those are expected to have low CCP scores. Therefore, the CCP signature can predict indolent disease in a quarter of the patients who have previously been identified as high-risk (and therefore identified as candidates for radical prostatectomy). Finally, the validation data in particular suggests that the CCP signature may be useful for defining risk in all patients. Specifically, it helped to divide patients defined as high-risk according to clinical parameters into those with 30% and 70% recurrence rates (Table 18).

The combination of clinical parameters and CCP signature enables physicians to more accurately predict risk of surgical failure, and therefore, identify the appropriate course of therapeutic intervention. As we have shown, the signature dramatically improves the recurrence prediction for patients who present with general clinical parameters of non-aggressive disease (Table 19). Within this clinical subgroup, patients with low CCP scores would benefit from the absolute reassurance that no further treatment is indicated.

Conversely, the high CCP group may warrant immediate intervention. Patients with unfavorable post-surgical clinical parameters benefit from adjuvant radiation therapy. Therefore the CCP signature should predict the efficacy of adjuvant radiation for patients with low-risk clinical characteristics and high CCP scores. In the validation cohort, patients with high CCP scores and disease beyond the prostate have a recurrence rate of 70%, which should clearly identify patients who are good candidates for adjuvant radiation. Thus the combination of clinical parameters and CCP signature clearly leads to more accurately defined patient risk, which should enable a more intelligent assessment of the need for further treatment.

EXAMPLE 6

Some of the CCP genes panels described herein were further evaluated for their ability to prognose additional cancers. Panels C, D, and F were found to be prognostic to varying degrees in bladder, brain, breast, and lung cancer.

Methods

Gene expression and patient data was obtained from the following publicly available datasets: GSE7390 (Desmedt et al., CLIN. CANCER RES. (2007) 13:3207-14; PMID 17545524); GSE11121 (Schmidt et al., CANCER RES. (2008) 68:5405-13; PMID 18593943); GSE8894 (Son et al.; no publication); Shedden (Shedden et al., NATURE MED. (2008) 14:822; PMID 18641660); GSE4412 (Freije et al., CANCER RES. (2004) 64:6503-10; PMID 15374961); GSE4271 (Phillips et al., CANCER CELL (2006) 9:157-73; PMID 16530701); GSE5287 (Als et al., CLIN. CANCER RES. (2007) 13:4407-14; PMID 17671123). Each of these datasets has an associated detailed description of the experimental procedures used in gathering expression and patient data. The expression microarrays used to generate each dataset are summarized below in Table 20.

TABLE 20

| Dataset | Array |
| --- | --- |
| GSE7390 | Affymetrix U133 A |
| GSE11121 | Affymetrix U133 A |
| GSE8894 | Affymetrix U133 plus 2.0 |
| Shedden | Affymetrix U133 A |
| GSE4412 | Affymetrix U133 A and B |
| GSE4271 | Affymetrix U133 A and B |
| GSE5287 | Affymetrix U133 A |

Expression data for each of the genes in Panels C, D and F was gathered from these datasets and the mean expression level for each Panel was determined for each patient, whose clinical outcome was known (e.g., recurrence, progression, progression-free survival, overall survival, etc.). If a gene is represented by more than one probe set on the array, the gene expression is an average expression of all the probe sets representing the gene. Since the arrays generally measured expression of thousands of genes, our analysis in this Example 6 is one example of using a subset of genes to create a test value and using that test value to determine, e.g., recurrence likelihood. CCP score is an average expression of the genes in a panel. The association between CCP score and survival or disease recurrence was tested using univariate and multivariate Cox proportional hazard model. Multivariate analysis was performed when relevant clinical parameters (grade in brain cancer, stage in lung cancer, NPI in breast cancer) were available.

Results

As shown in Table 21 below, each Panel, in univariate analysis, was a prognostic factor in each of the cancers analyzed.

TABLE 21

| | | p-value | | |
| --- | --- | --- | --- | --- |
| Cancer Type | Dataset | Panel C | Panel F | Panel B |
| ER positive breast cancer | GSE7390 | $2.4 \times 10^{-3}$ | $2.3 \times 10^{-3}$ | $4.3 \times 10^{-3}$ |
| ER positive breast cancer | GSE11121 | $1.2 \times 10^{-5}$ | $8.7 \times 10^{-6}$ | $1.5 \times 10^{-5}$ |
| Lung adenocarcinoma | GSE8894 | $2.0 \times 10^{-3}$ | $2.5 \times 10^{-3}$ | $5.6 \times 10^{-3}$ |
| Lung adenocarcinoma | Shedden | $1.3 \times 10^{-7}$ | $2.6 \times 10^{-7}$ | $2.2 \times 10^{-7}$ |
| Brain cancer | GSE4412 | $3.2 \times 10^{-5}$ | $2.2 \times 10^{-5}$ | $9.0 \times 10^{-5}$ |
| Brain cancer | GSE4271 | $1.3 \times 10^{-3}$ | $1.0 \times 10^{-3}$ | $2.8 \times 10^{-4}$ |
| Bladder cancer | GSE5287 | $6.4 \times 10^{-2}$ | $5.0 \times 10^{-2}$ | $8.6 \times 10^{-2}$ |

As shown in Table 22 below, each Panel was also prognostic in multivariate analysis when combined with at least one clinical parameter (or nomogram).

TABLE 22

| Cancer Type | Dataset | p-value | | | Additional Clinical Variable/ Nomogram |
| --- | --- | --- | --- | --- | --- |
| | | Panel C | Panel F | Panel B | |
| Brain cancer | GSE4271 | 0.022 | 0.017 | 0.0065 | grade |
| Lung adeno-carcinoma | Shedden | $1 \times 10^{-6}$ | $2.1 \times 10^{-6}$ | $1.4 \times 10^{-6}$ | stage |
| ER positive breast cancer | GSE7390 | 0.0077 | 0.0064 | 0.011 | Nottingham Prognostic Index (NPI) |
| ER positive breast cancer | GSE11121 | 0.0041 | 0.0027 | 0.0045 | NPI |

EXAMPLE 7

The aim of this experiment was to evaluate the relationship between CCP scores generated from tumor tissue and CCP scores generated from benign tissue adjacent to the tumor. We found that CCP scores generated from matched pairs of tumor and adjacent benign tissue had a positive correlation, suggesting that a CCP score from an apparently negative biopsy could be used to diagnose aggressive prostate cancer.

Patients and Methods

For lung cancer samples, normal tissue was re-dissected from 53 of the 137 Stage I and II NSCLC adeno-carcinoma slides from the Wistuba MDA cohort. The slides had been stored for approximately 9 months at 4° C. Normal tissue was isolated by macro-dissection according to a pathologist's instructions. The normal samples were run in duplicate on TLDA using ProsAssay4.

For prostate cancer samples, a total of 7 unidentified prostate slides were selected for comparing tumor to adjacent begin tissue. Tissue was taken from the area circled by the pathologist (tumor). Tissue was also taken from the surrounding area of relatively benign tissue (normal). In addition, two of the 7 samples were also prepared by scraping the entire slide for a mixture of tumor and normal tissue (both). The resulting 16 samples were run on two cards without replication on TLDA ProsAssay4.

RNA was isolated from the FFPE samples (tumor or normal) using our standard protocol. CCP scores were calculated as described in earlier Examples.

Statistics and Results

Figure 17:
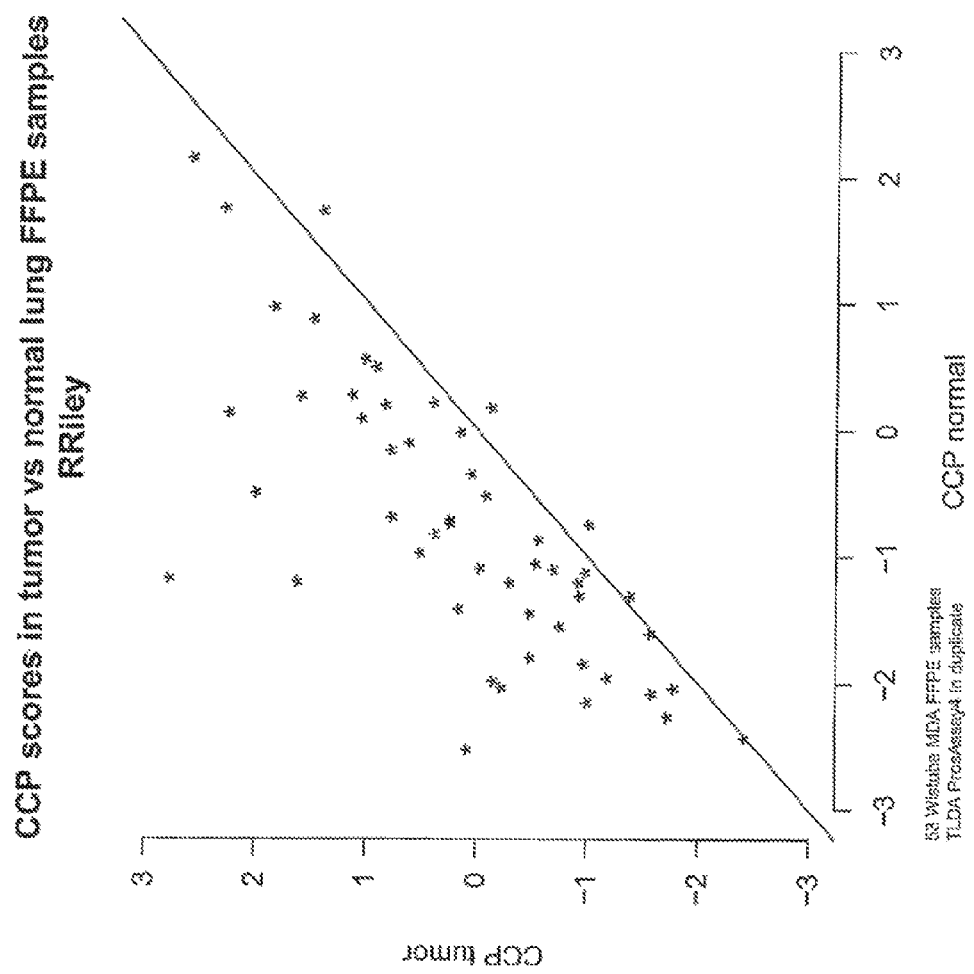
FIG. 17 illustrates the correlation between CCP expression in tumor cells and CCP expression in adjacent non-cancer cells in lung cancer.
Figure 18:
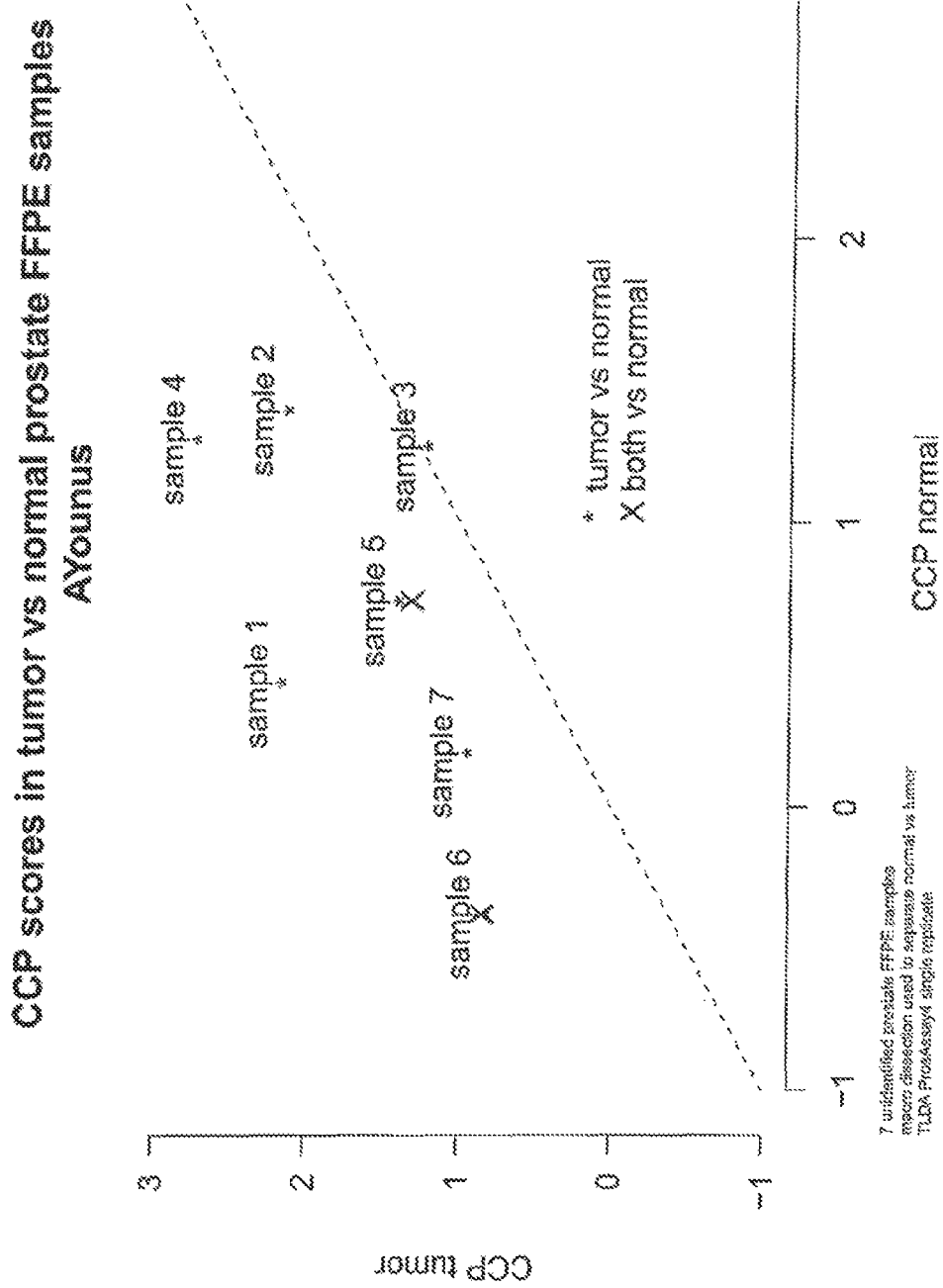
FIG. 18 illustrates the correlation between CCP expression in tumor cells and CCP expression in adjacent non-cancer cells in prostate cancer.

The correlation between the CCP scores in tumor vs. normal tissue was tested by means of the Pearson's product-moment correlation coefficient. As shown in FIG. 17, the correlation was highly significant for lung (n=48; correlation coefficient (95% CI)=0.75 (0.60, 0.85); p-value=$1.7 \times 10^{-10}$). Despite the limited prostate sample, the correlation was positive as shown in FIG. 18.

EXAMPLE 8

The OncotypeDx gene signature commercial available for the breast cancer prognosis includes 16 test genes and 5 housekeeping genes. See Paik et al., *N Engl J Med.*, 2817-2826 (2004), which is incorporated herein by reference. These genes are provided in Table 23 below. Five of the genes: Survivin, KI67, MYBL2, CCNB1 and STK15 are CCP genes.

TABLE 23

| Test genes | GRB7, HER2, ER, PGR, BCL2, SCUBE2, Survivin, KI67, MYBL2, CCNB1, STK15, CTSL2, MMP11, CD68, GSTM1, BAG1 |
|---|---|
| Reference genes | ACTB, GAPDH, RPLPO, GUS, TFRC |

The average expression of the 5 CCP genes (KI67, STK15, BIRC5, CCNB1, and MYBL2) and the average expression of the genes in Panel F in Table 16 above were both calculated from the publicly available datasets as indicated in Table 24 below. The two different average expression values from the same dataset were compared, and the correlation coefficient was obtained. Table 24 below shows that the 5-gene signature is statistically significantly correlated with the 31-gene signature in Panel F in the cancers analyzed. The 31-gene signature in Panel F has been shown to be particularly useful in prognosising the disease progression and cancer recurrence in cancers including prostate cancer, breast cancer, brain cancer, bladder cancer and lung cancer, and in diagnosing prostate cancer. Thus, like the gene signature in Panel F, the 5-gene signature, as well as the 16-gene signature of OncotypeDx (breast cancer) should also be predictive for the prognosis and diagnosis of prostate cancer, lung cancer, bladder cancer, and brain cancer.

TABLE 24

| Cancer Tissue | Corr. Coeff. | Public Dataset |
|---|---|---|
| Prostate | 0.95 | NCBI GEO Database GSE17951 |
| Brain | 0.98 | NCBI GEO Database GSE4412 |
| Bladder | 0.97 | NCBI GEO Database GSE13507 |
| Colon | 0.91 | NCBI GEO Database GSE17538 |
| Breast | 0.94 | NCBI GEO Database GSE12093 |
| Lung | 0.95 | NCI caArray Database, Identifier: Jacob-00182 |

EXAMPLE 9

The average expression of the 31-gene signature of Panel F was analyzed in the publicly available GSE17538 dataset (n=187) for the predictive power of the expression signature in predicting colon cancer recurrence. Cox proportional hazard analysis produced a p-value of 0.46. Therefore, the gene expression of such cell-cycle progression genes is not prognostic for colon cancer.

EXAMPLE 10

126 CCGs and 47 housekeeping genes had their expression compared to the CCG and housekeeping mean in order to determine preferred genes for use in some embodiments of the invention. Rankings of select CCGs according to their correlation with the mean CCG expression as well as their ranking according to predictive value are given in Tables 25, 26, 28, 29, & 30.

Assays of 126 CCGs and 47 HK (housekeeping) genes were run against 96 commercially obtained, anonymous prostate tumor FFPE samples without outcome or other clinical data. The working hypothesis was that the assays would measure with varying degrees of accuracy the same underlying phenomenon (cell cycle proliferation within the tumor for the CCGs, and sample concentration for the HK genes). Assays were ranked by the Pearson's correlation coefficient between the individual gene and the mean of all the candidate genes, that being the best available estimate of biological activity. Rankings for these 126 CCGs according to their correlation to the overall CCG mean are reported in Table 2.

TABLE 25

| Gene # | Gene Symbol | Correl. w/ Mean |
|---|---|---|
| 1 | TPX2 | 0.931 |
| 2 | CCNB2 | 0.9287 |
| 3 | KIF4A | 0.9163 |
| 4 | KIF2C | 0.9147 |
| 5 | BIRC5 | 0.9077 |
| 6 | BIRC5 | 0.9077 |
| 7 | RACGAP1 | 0.9073 |
| 8 | CDC2 | 0.906 |
| 9 | PRC1 | 0.9053 |
| 10 | DLGAP5/DLG7 | 0.9033 |
| 11 | CEP55 | 0.903 |
| 12 | CCNB1 | 0.9 |
| 13 | TOP2A | 0.8967 |
| 14 | CDC20 | 0.8953 |
| 15 | KIF20A | 0.8927 |
| 16 | BUB1B | 0.8927 |
| 17 | CDKN3 | 0.8887 |
| 18 | NUSAP1 | 0.8873 |
| 19 | CCNA2 | 0.8853 |
| 20 | KIF11 | 0.8723 |
| 21 | CDCA8 | 0.8713 |
| 22 | NCAPG | 0.8707 |
| 23 | ASPM | 0.8703 |
| 24 | FOXM1 | 0.87 |
| 25 | NEK2 | 0.869 |
| 26 | ZWINT | 0.8683 |
| 27 | PTTG1 | 0.8647 |
| 28 | RRM2 | 0.8557 |
| 29 | TTK | 0.8483 |
| 30 | TRIP13 | 0.841 |
| 31 | GINS1 | 0.841 |
| 32 | CENPF | 0.8397 |
| 33 | HMMR | 0.8367 |
| 34 | NCAPH | 0.8353 |
| 35 | NDC80 | 0.8313 |
| 36 | KIF15 | 0.8307 |
| 37 | CENPE | 0.8287 |
| 38 | TYMS | 0.8283 |
| 39 | KIAA0101 | 0.8203 |
| 40 | FANCI | 0.813 |

TABLE 25-continued

| Gene # | Gene Symbol | Correl. w/ Mean |
|---|---|---|
| 41 | RAD51AP1 | 0.8107 |
| 42 | CKS2 | 0.81 |
| 43 | MCM2 | 0.8063 |
| 44 | PBK | 0.805 |
| 45 | ESPL1 | 0.805 |
| 46 | MKI67 | 0.7993 |
| 47 | SPAG5 | 0.7993 |
| 48 | MCM10 | 0.7963 |
| 49 | MCM6 | 0.7957 |
| 50 | OIP5 | 0.7943 |
| 51 | CDC45L | 0.7937 |
| 52 | KIF23 | 0.7927 |
| 53 | EZH2 | 0.789 |
| 54 | SPC25 | 0.7887 |
| 55 | STIL | 0.7843 |
| 56 | CENPN | 0.783 |
| 57 | GTSE1 | 0.7793 |
| 58 | RAD51 | 0.779 |
| 59 | CDCA3 | 0.7783 |
| 60 | TACC3 | 0.778 |
| 61 | PLK4 | 0.7753 |
| 62 | ASF1B | 0.7733 |
| 63 | DTL | 0.769 |
| 64 | CHEK1 | 0.7673 |
| 65 | NCAPG2 | 0.7667 |
| 66 | PLK1 | 0.7657 |
| 67 | TIMELESS | 0.762 |
| 68 | E2F8 | 0.7587 |
| 69 | EXO1 | 0.758 |
| 70 | ECT2 | 0.744 |
| 71 | STMN1 | 0.737 |
| 72 | STMN1 | 0.737 |
| 73 | RFC4 | 0.737 |
| 74 | CDC6 | 0.7363 |
| 75 | CENPM | 0.7267 |
| 76 | MYBL2 | 0.725 |
| 77 | SHCBP1 | 0.723 |
| 78 | ATA2D2 | 0.723 |
| 79 | KIFC1 | 0.7183 |
| 80 | DBF4 | 0.718 |
| 81 | CKS1B | 0.712 |
| 82 | PCNA | 0.7103 |
| 83 | FBXO5 | 0.7053 |
| 84 | C12orf48 | 0.7027 |
| 85 | TK1 | 0.7017 |
| 86 | BLM | 0.701 |
| 87 | KIF18A | 0.6987 |
| 88 | DONSON | 0.688 |
| 89 | MCM4 | 0.686 |
| 90 | RAD54B | 0.679 |
| 91 | RNASEH2A | 0.6733 |
| 92 | TUBA1C | 0.6697 |
| 93 | C18orf24 | 0.6697 |
| 94 | SMC2 | 0.6697 |
| 95 | CENPI | 0.6697 |
| 96 | GMPS | 0.6683 |
| 97 | DDX39 | 0.6673 |
| 98 | POLE2 | 0.6583 |
| 99 | APOBEC3B | 0.6513 |
| 100 | RFC2 | 0.648 |
| 101 | PSMA7 | 0.6473 |
| 102 | MPHOSPH1/kif20b | 0.6457 |
| 103 | CDT1 | 0.645 |
| 104 | H2AFX | 0.6387 |
| 105 | ORC6L | 0.634 |
| 106 | C1orf135 | 0.6333 |
| 107 | PSRC1 | 0.633 |
| 108 | VRK1 | 0.6323 |
| 109 | CKAP2 | 0.6307 |
| 110 | CCDC99 | 0.6303 |
| 111 | CCNE1 | 0.6283 |
| 112 | LMNB2 | 0.625 |
| 113 | GPSM2 | 0.625 |
| 114 | PAICS | 0.6243 |
| 115 | MCAM | 0.6227 |
| 116 | DSN1 | 0.622 |
| 117 | NCAPD2 | 0.6213 |
| 118 | RAD54L | 0.6213 |
| 119 | PDSS1 | 0.6203 |
| 120 | HN1 | 0.62 |
| 121 | C21orf45 | 0.6193 |
| 122 | CTSL2 | 0.619 |
| 123 | CTPS | 0.6183 |
| 124 | MCM7 | 0.618 |
| 125 | ZWILCH | 0.618 |
| 126 | RFC5 | 0.6177 |

After excluding CCGs with low average expression, assays that produced sample failures, CCGs with correlations less than 0.58, and HK genes with correlations less than 0.95, a subset of 56 CCGs (Panel G) and 36 HK candidate genes were left. Correlation coefficients were recalculated on these subsets, with the rankings shown in Tables 3 and 4, respectively.

TABLE 26

("Panel G")

| Gene # | Gene Symbol | Correl. w/CCG mean |
|---|---|---|
| 1 | FOXM1 | 0.908 |
| 2 | CDC20 | 0.907 |
| 3 | CDKN3 | 0.9 |
| 4 | CDC2 | 0.899 |
| 5 | KIF11 | 0.898 |
| 6 | KIAA0101 | 0.89 |
| 7 | NUSAP1 | 0.887 |
| 8 | CENPF | 0.882 |
| 9 | ASPM | 0.879 |
| 10 | BUB1B | 0.879 |
| 11 | RRM2 | 0.876 |
| 12 | DLGAP5 | 0.875 |
| 13 | BIRC5 | 0.864 |
| 14 | KIF20A | 0.86 |
| 15 | PLK1 | 0.86 |
| 16 | TOP2A | 0.851 |
| 17 | TK1 | 0.837 |
| 18 | PBK | 0.831 |
| 19 | ASF1B | 0.827 |
| 20 | C18orf24 | 0.817 |
| 21 | RAD54L | 0.816 |
| 22 | PTTG1 | 0.814 |
| 23 | KIF4A | 0.814 |
| 24 | CDCA3 | 0.811 |
| 25 | MCM10 | 0.802 |
| 26 | PRC1 | 0.79 |
| 27 | DTL | 0.788 |
| 28 | CEP55 | 0.787 |
| 29 | RAD51 | 0.783 |
| 30 | CENPM | 0.781 |
| 31 | CDCA8 | 0.774 |
| 32 | OIP5 | 0.773 |
| 33 | SHCBP1 | 0.762 |
| 34 | ORC6L | 0.736 |
| 35 | CCNB1 | 0.727 |
| 36 | CHEK1 | 0.723 |
| 37 | TACC3 | 0.722 |
| 38 | MCM4 | 0.703 |
| 39 | FANCI | 0.702 |
| 40 | KIF15 | 0.701 |
| 41 | PLK4 | 0.688 |
| 42 | APOBEC3B | 0.67 |
| 43 | NCAPG | 0.667 |
| 44 | TRIP13 | 0.653 |
| 45 | KIF23 | 0.652 |
| 46 | NCAPH | 0.649 |
| 47 | TYMS | 0.648 |

TABLE 26-continued ("Panel G")

| Gene # | Gene Symbol | Correl. w/CCG mean |
|---|---|---|
| 48 | GINS1 | 0.639 |
| 49 | STMN1 | 0.63 |
| 50 | ZWINT | 0.621 |
| 51 | BLM | 0.62 |
| 52 | TTK | 0.62 |
| 53 | CDC6 | 0.619 |
| 54 | KIF2C | 0.596 |
| 55 | RAD51AP1 | 0.567 |
| 56 | NCAPG2 | 0.535 |

TABLE 27

| Gene # | Gene Symbol | Correlation with HK Mean |
|---|---|---|
| 1 | RPL38 | 0.989 |
| 2 | UBA52 | 0.986 |
| 3 | PSMC1 | 0.985 |
| 4 | RPL4 | 0.984 |
| 5 | RPL37 | 0.983 |
| 6 | RPS29 | 0.983 |
| 7 | SLC25A3 | 0.982 |
| 8 | CLTC | 0.981 |
| 9 | TXNL1 | 0.98 |
| 10 | PSMA1 | 0.98 |
| 11 | RPL8 | 0.98 |
| 12 | MMADHC | 0.979 |
| 13 | RPL13A; LOC728658 | 0.979 |
| 14 | PPP2CA | 0.978 |
| 15 | MRFAP1 | 0.978 |

The CCGs in Panel F were likewise ranked according to correlation to the CCG mean as shown in Table 5 below.

TABLE 28

| Gene # | Gene Symbol | Correl. w/CCG mean |
|---|---|---|
| 1 | DLGAP5 | 0.931 |
| 2 | ASPM | 0.931 |
| 3 | KIF11 | 0.926 |
| 4 | BIRC5 | 0.916 |
| 5 | CDCA8 | 0.902 |
| 6 | CDC20 | 0.9 |
| 7 | MCM10 | 0.899 |
| 8 | PRC1 | 0.895 |
| 9 | BUB1B | 0.892 |
| 10 | FOXM1 | 0.889 |
| 11 | NUSAP1 | 0.888 |
| 12 | C18orf24 | 0.885 |
| 13 | PLK1 | 0.879 |
| 14 | CDKN3 | 0.874 |
| 15 | RRM2 | 0.871 |
| 16 | RAD51 | 0.864 |
| 17 | CEP55 | 0.862 |
| 18 | ORC6L | 0.86 |
| 19 | RAD54L | 0.86 |
| 20 | CDC2 | 0.858 |
| 21 | CENPF | 0.855 |
| 22 | TOP2A | 0.852 |
| 23 | KIF20A | 0.851 |
| 24 | KIAA0101 | 0.839 |
| 25 | CDCA3 | 0.835 |
| 26 | ASF1B | 0.797 |
| 27 | CENPM | 0.786 |
| 28 | TK1 | 0.783 |
| 29 | PBK | 0.775 |

TABLE 28-continued

| Gene # | Gene Symbol | Correl. w/CCG mean |
|---|---|---|
| 30 | PTTG1 | 0.751 |
| 31 | DTL | 0.737 |

The inventors have determined that the CCGs in Panel C can be ranked as shown in Table 6 below according to the predictive power of each individual gene. The CCGs in Panel F can be similarly ranked as shown in Table 7 below.

TABLE 29

| Gene # | Gene | p-value |
|---|---|---|
| 1 | NUSAP1 | 2.8E−07 |
| 2 | DLG7 | 5.9E−07 |
| 3 | CDC2 | 6.0E−07 |
| 4 | FOXM1 | 1.1E−06 |
| 5 | MYBL2 | 1.1E−06 |
| 6 | CDCA8 | 3.3E−06 |
| 7 | CDC20 | 3.8E−06 |
| 8 | RRM2 | 7.2E−06 |
| 9 | PTTG1 | 1.8E−05 |
| 10 | CCNB2 | 5.2E−05 |
| 11 | HMMR | 5.2E−05 |
| 12 | BUB1 | 8.3E−05 |
| 13 | PBK | 1.2E−04 |
| 14 | TTK | 3.2E−04 |
| 15 | CDC45L | 7.7E−04 |
| 16 | PRC1 | 1.2E−03 |
| 17 | DTL | 1.4E−03 |
| 18 | CCNB1 | 1.5E−03 |
| 19 | TPX2 | 1.9E−03 |
| 20 | ZWINT | 9.3E−03 |
| 21 | KIF23 | 1.1E−02 |
| 22 | TRIP13 | 1.7E−02 |
| 23 | KPNA2 | 2.0E−02 |
| 24 | UBE2C | 2.2E−02 |
| 25 | MELK | 2.5E−02 |
| 26 | CENPA | 2.9E−02 |
| 27 | CKS2 | 5.7E−02 |
| 28 | MAD2L1 | 1.7E−01 |
| 29 | UBE2S | 2.0E−01 |
| 30 | AURKA | 4.8E−01 |
| 31 | TIMELESS | 4.8E−01 |

TABLE 30

| Gene # | Gene Symbol | p-value |
|---|---|---|
| 1 | MCM10 | 8.60E−10 |
| 2 | ASPM | 2.30E−09 |
| 3 | DLGAP5 | 1.20E−08 |
| 4 | CENPF | 1.40E−08 |
| 5 | CDC20 | 2.10E−08 |
| 6 | FOXM1 | 3.40E−07 |
| 7 | TOP2A | 4.30E−07 |
| 8 | NUSAP1 | 4.70E−07 |
| 9 | CDKN3 | 5.50E−07 |
| 10 | KIF11 | 6.30E−06 |
| 11 | KIF20A | 6.50E−06 |
| 12 | BUB1B | 1.10E−05 |
| 13 | RAD54L | 1.40E−05 |
| 14 | CEP55 | 2.60E−05 |
| 15 | CDCA8 | 3.10E−05 |
| 16 | TK1 | 3.30E−05 |
| 17 | DTL | 3.60E−05 |
| 18 | PRC1 | 3.90E−05 |
| 19 | PTTG1 | 4.10E−05 |
| 20 | CDC2 | 0.00013 |
| 21 | ORC6L | 0.00017 |

TABLE 30-continued

| Gene # | Gene Symbol | p-value |
|---|---|---|
| 22 | PLK1 | 0.0005 |
| 23 | C18orf24 | 0.0011 |
| 24 | BIRC5 | 0.00118 |
| 25 | RRM2 | 0.00255 |
| 26 | CENPM | 0.0027 |
| 27 | RAD51 | 0.0028 |
| 28 | KIAA0101 | 0.00348 |
| 29 | CDCA3 | 0.00863 |
| 30 | PBK | 0.00923 |
| 31 | ASF1B | 0.00936 |

Table 1 below provides a large, but not exhaustive, list of CCGs.

TABLE 1

Gene (Name and/or Symbol) or Number (EST, cDNA clone, or Accession)

1  STK15: serine/threonine kinase 15 Hs.48915 R11407
2  PLK: polo (*Drosophia*)-like kinase Hs.77597 AA629262
3  UBCH10: ubiquitin carrier protein E2-C Hs.93002 AA430504
4  MAPK13: mitogen-activated protein kinase 13 Hs.178695 AA157499 p38delta mRNA = stress-activated protein kinase 4
5  CDC2: cell division cycle 2, G1 to S and G2 to M Hs.184572 AA598974
6  TOP2A: topoisomerase (DNA) II alpha (170 kD) Hs.156346 AA504348
7  CENPE: centromere protein E (312 kD) Hs.75573 AA402431 CENP-E = putative kinetochore motor that accumulates just befo
8  TOP2A: topoisomerase (DNA) II alpha (170 kD) Hs.156346 AA026682
9  KPNA2: karyopherin alpha 2 (RAG cohort 1, importin alpha 1) Hs.159557 AA676460
10 FLJ10468: hypothetical protein FLJ10468 Hs.48855 N63744
11 CCNF: cyclin F Hs.1973 AA676797
12 DKFZp762E1312: hypothetical protein DKFZp762E1312 Hs.104859 T66935
13 CKS2: CDC2-Associated Protein CKS2 Hs.83758 AA292964
14 C20ORF1: chromosome 20 open reading frame 1 Hs.9329 H73329
15 BUB1: budding uninhibited by benzimidazoles 1 (yeast homolog) Hs.98658 AA430092 BUB1 = putative mitotic checkpoint protein ser/thr kinase
16 TOP2A: **topoisomerase (DNA) II alpha (170 kD) Hs.156346 AI734240
17 CKS2: CDC2-Associated Protein CKS1 Hs.83758 AA010065 ckshs2 = homolog of Cks1 = p34Cdc28/Cdc2-associated protein
18 ARL6IP: ADP-ribosylation factor-like 6 interacting protein Hs.75249 H20558
19 L2DTL: L2DTL protein Hs.126774 R06900
20 STK15: **serine/threonine kinase 15 Hs.48915 H63492 aurora/IPL1-related kinase
21 E2-EPF: ubiquitin carrier protein Hs.174070 AA464019
22 UBCH10: ubiquitin carrier protein E2-C Hs.93002 R80790
23 KNSL5: kinesin-like 5 (mitotic kinesin-like protein 1) Hs.270845 AA452513 Mitotic kinesin-like protein-1
24 CENPF: centromere protein F (350/400 kD, mitosin) Hs.77204 AA701455
25 CCNA2: cyclin A2 Hs.85137 AA608568 Cyclin A
26 CDC2: cell division cycle 2, G1 to S and G2 to M Hs.184572 AA278152 CDC2 = Cell division control protein 2 homolog = P34 protein kin
27 HMMR: **hyaluronan-mediated motility receptor (RHAMM) Hs.72550 AA171715
28 KIAA0008: KIAA0008 gene product Hs.77695 AA262211
29 HSPC145: HSPC145 protein Hs.18349 R22949
30 FLJ20510: hypothetical protein FLJ20510 Hs.6844 N53214
31 *Homo sapiens* NUF2R mRNA, complete cds Hs.234545 AA421171:
32 HSPC216: hypothetical protein Hs.13525 T87341
33 P37NB: 37 kDa leucine-rich repeat (LRR) protein Hs.155545 AA423870
34 CDC20:
35 CCNE1: cyclin E1 Hs.9700 T54121
36 ESTs: Hs.221754 R84407
37 FLJ11252: hypothetical protein FLJ11252 Hs.23495 N30185
38 LOC51203: clone HQ0310 PRO0310p1 Hs.279905 AA620485
39 FLJ10491: hypothetical protein FLJ10491 Hs.274283 AA425404
40 KNSL1: kinesin-like 1 Hs.8878 AA504625
41 CENPA: centromere protein A (17 kD) Hs.1594 AI369629
42 *Homo sapiens*, clone IMAGE: 2823731, mRNA, partial cds Hs.70704 R96941:
43 CDC6: CDC6 (cell division cycle 6, *S. cerevisiae*) homolog Hs.69563 H59203
44 *Homo sapiens* DNA helicase homolog (PIF1) mRNA, partial cds Hs.112160 AA464521:
45 ESTs: Hs.48480 AA135809
46 TSN: translin Hs.75066 AA460927
47 KPNA2: karyopherin alpha 2 (RAG cohort 1, importin alpha 1) Hs.159557 AA489087
48 RRM2: ribonucleotide reductase M2 polypeptide Hs.75319 AA187351
49 ESTs: Hs.14119 AA204830
50 CCNB1: cyclin B1 Hs.23960 R25788
51 GTSE1: G-2 and S-phase expressed 1 Hs.122552 AI369284
52 C20ORF1: chromosome 20 open reading frame 1 Hs.9329 AA936183
53 TACC3: transforming, acidic coiled-coil containing protein 3 Hs.104019 AA279990 JkR1 mRNA downregulated upon T-cell activation
54 E2F1: E2F transcription factor 1 Hs.96055 H61303

TABLE 1-continued

| | Gene (Name and/or Symbol) or Number (EST, cDNA clone, or Accession) |
|---|---|
| 55 | BUB1B: budding uninhibited by benzimidazoles 1 (yeast homolog), beta Hs.36708 AA488324 |
| 56 | ESTs,: Weakly similar to CGHU7L collagen alpha 1(III) chain precursor [*H. sapiens*] Hs.19322 AA088457 |
| 57 | KIAA0074: KIAA0074 protein Hs.1192 N54344 |
| 58 | MPHOSPH1: M-phase phosphoprotein 1 Hs.240 AA282935 |
| 59 | ANLN: anillin (*Drosophila* Scraps homolog), actin binding protein Hs.62180 R12261 |
| 60 | BIRC5: baculoviral IAP repeat-containing 5 (survivin) Hs.1578 AA460685 Survivin = apoptosis inhibitor = effector cell protease EPR-1 |
| 61 | PTTG1: pituitary tumor-transforming 1 Hs.252587 AA430032 |
| 62 | KIAA0159: chromosome condensation-related SMC-associated protein 1 Hs.5719 AA668256 |
| 63 | ESTs,: Weakly similar to OS-4 protein [*H. sapiens*] Hs.18714 W93120 |
| 64 | HMMR: hyaluronan-mediated motility receptor (RHAMM) Hs.72550 R10284 |
| 65 | DKFZp762E1312: hypothetical protein DKFZp762E1312 Hs.104859 AA936181 |
| 66 | CKAP2: cytoskeleton associated protein 2 Hs.24641 T52152 |
| 67 | RAMP: RA-regulated nuclear matrix-associated protein |
| 68 | SMAP: thyroid hormone receptor coactivating protein Hs.5464 AA481555 |
| 69 | FLJ22624: hypothetical protein FLJ22624 Hs.166425 AA488791 |
| 70 | CKS1: CDC2-Associated Protein CKS1 Hs.77550 N48162 |
| 71 | NEK2: NIMA (never in mitosis gene a)-related kinase 2 Hs.153704 W93379 |
| 72 | MKI67: antigen identified by monoclonal antibody Ki-67 |
| 73 | TTK: TTK protein kinase Hs.169840 AI337292 |
| 74 | VEGFC: vascular endothelial growth factor C Hs.79141 H07899 vascular endothelial growth factor related protein VRP |
| 75 | CDKN3: cyclin-dependent kinase inhibitor 3 (CDK2-associated dual specificity phosphatase) Hs.84113 AA284072 CIP2 = Cdi1 = KAP1 phosphatase = G1/S cell cycle gene |
| 76 | *Homo sapiens* NUF2R mRNA, complete cds Hs.234545 R92435: |
| 77 | *Homo sapiens* cDNA FLJ10325 fis, clone NT2RM2000569 Hs.245342 AA235662: |
| 78 | HSPC145: HSPC145 protein Hs.18349 AA628867 |
| 79 | HSU54999: LGN protein Hs.278338 W92010 |
| 80 | FLJ20333: hypothetical protein FLJ20333 Hs.79828 R27552 |
| 81 | KNSL2: kinesin-like 2 Hs.20830 N69491 |
| 82 | ESTs: Hs.133294 AI053446 |
| 83 | **ESTs: Hs.41294 H95819 |
| 84 | SMTN: smoothelin Hs.149098 AA449234 |
| 85 | FLJ23311: hypothetical protein FLJ23311 Hs.94292 N73916 |
| 86 | USF1: upstream transcription factor 1 Hs.247842 AA719022 |
| 87 | LOC51203: clone HQ0310 PRO0310p1 Hs.279905 AA779949 |
| 88 | ADH4: alcohol dehydrogenase 4 (class II), pi polypeptide Hs.1219 AA007395 |
| 89 | ESTs: Hs.186579 AA960844 |
| 90 | CCNB2: cyclin B2 Hs.194698 AA774665 |
| 91 | *Homo sapiens*, Similar to gene rich cluster, C8 gene, clone MGC: 2577, mRNA, complete cds Hs.30114 AA634371: |
| 92 | ESTs: Hs.99480 AA485454 |
| 93 | *Homo sapiens* IRE1b mRNA for protein kinase/ribonuclease IRE1 beta, complete cds Hs.114905 AA088442: |
| 94 | PCNA: proliferating cell nuclear antigen Hs.78996 AA450264 PCNA = proliferating cell nuclear antigen |
| 95 | AA075920: |
| 96 | GTSE1: G-2 and S-phase expressed 1 Hs.122552 AA449474 |
| 97 | CKS1: CDC2-Associated Protein CKS1 Hs.77550 AA278629 |
| 98 | CDC25B: cell division cycle 25B Hs.153752 AA448659 cdc25B = M-phase inducer phosphatase 2 |
| 99 | ESTs,: Weakly similar to unnamed protein product [*H. sapiens*] Hs.99807 AA489023 Unknown UG Hs.99807 ESTs sc_id384 |
| 100 | PCNA: proliferating cell nuclear antigen Hs.78996 H05891 |
| 101 | LTBP3: **latent transforming growth factor beta binding protein 3 Hs.289019 R60197 |
| 102 | *Homo sapiens* mRNA; cDNA DKFZp434D0818 (from clone DKFZp434D0818) Hs.5855 N95578: |
| 103 | ESTs: Hs.126714 AA919126 |
| 104 | CIT: citron (rho-interacting, serine/threonine kinase 21) Hs.15767 H10788 |
| 105 | LBR: lamin B receptor Hs.152931 AA099136 |
| 106 | E2F1: E2F transcription factor 1 Hs.96055 AA424949 |
| 107 | AA699928: |
| 108 | CDKN2C: cyclin-dependent kinase inhibitor 2C (p18, inhibits CDK4) Hs.4854 N72115 p18-INK6 = Cyclin-dependent kinase 6 inhibitor |
| 109 | STK12: serine/threonine kinase 12 Hs.180655 H81023 ARK2 = aurora-related kinase 2 |
| 110 | ESTs: Hs.111471 AA682533 |
| 111 | ESTs: Hs.44269 AA465090 |
| 112 | MCM4: minichromosome maintenance deficient (*S. cerevisiae*) 4 Hs.154443 AA485983 |
| 113 | PMSCL1: **polymyositis/scleroderma autoantigen 1 (75 kD) Hs.91728 AA458994 Cyclin A |
| 114 | MKI67: antigen identified by monoclonal antibody Ki-67 Hs.80976 AA425973 Ki67 (long type) |
| 115 | ESTs: Hs.133294 AI144063 |

TABLE 1-continued

| | Gene (Name and/or Symbol) or Number (EST, cDNA clone, or Accession) |
|---|---|
| 116 | CDC25B: cell division cycle 25B Hs.153752 H14343 cdc25B = M-phase inducer phosphatase 2 |
| 117 | FOXM1: forkhead box M1 Hs.239 AA129552 MPP2 = putative M phase phosphoprotein 2 |
| 118 | FLJ11029: hypothetical protein FLJ11029 Hs.274448 AI124082 |
| 119 | H2AFX: H2A histone family, member X Hs.147097 H95392 |
| 120 | FLJ20333: hypothetical protein FLJ20333 Hs.79828 AA147792 |
| 121 | SLC17A2: solute carrier family 17 (sodium phosphate), member 2 Hs.19710 H60423 |
| 122 | Homo sapiens IRE1b mRNA for protein kinase/ribonuclease IRE1 beta, complete cds Hs.114905 AA102368: |
| 123 | ESTs: Hs.163921 AA573689 |
| 124 | MCM5: minichromosome maintenance deficient (S. cerevisiae) 5 (cell division cycle 46) Hs.77171 AA283961 |
| 125 | CDKN1B: cyclin-dependent kinase inhibitor 1B (p27, Kip1) Hs.238990 AA630082 |
| 126 | AA779865: |
| 127 | PTTG1: pituitary tumor-transforming 1 Hs.252587 AI362866 |
| 128 | RAD21: RAD21 (S. pombe) homolog Hs.81848 AA683102 |
| 129 | Homo sapiens cDNA FLJ10325 fis, clone NT2RM2000569 Hs.245342 AA430511: |
| 130 | NEK2: NIMA (never in mitosis gene a)-related kinase 2 Hs.153704 AA682321 |
| 131 | FLJ20101: LIS1-interacting protein NUDE1, rat homolog Hs.263925 N79612 |
| 132 | FZR1: Fzr1 protein Hs.268384 AA621026 |
| 133 | ESTs: Hs.120605 AI220472 |
| 134 | KIAA0855: golgin-67 Hs.182982 AA098902 |
| 135 | SRD5A1: steroid-5-alpha-reductase, alpha polypeptide 1 (3-oxo-5 alpha-steroid delta 4-dehydrogenase alpha 1) Hs.552 H16833 |
| 136 | RAD51: RAD51 (S. cerevisiae) homolog (E coli RecA homolog) Hs.23044 N70010 |
| 137 | KNSL2: kinesin-like 2 Hs.20830 R11542 |
| 138 | KIAA0097: KIAA0097 gene product Hs.76989 AA598942 |
| 139 | TUBB: tubulin, beta polypeptide Hs.179661 AA427899 |
| 140 | HEC: highly expressed in cancer, rich in leucine heptad repeats Hs.58169 W72679 |
| 141 | TROAP: trophinin associated protein (tastin) Hs.171955 H94949 |
| 142 | ESTs: Hs.49047 N64737 |
| 143 | ESTs: Hs.15091 AA678348 |
| 144 | ESTs: Hs.133431 AI061169 |
| 145 | KIAA0042: KIAA0042 gene product Hs.3104 AA477501 |
| 146 | FZR1: Fzr1 protein Hs.268384 AA862886 |
| 147 | FEN1: flap structure-specific endonuclease 1 Hs.4756 AA620553 |
| 148 | CKS1: CDC2-Associated Protein CKS1 Hs.77550 AA459292 ckshs1 = homolog of Cks1 = p34Cdc28/Cdc2-associated protein |
| 149 | ESTs: Hs.193379 N57936 |
| 150 | CASP8AP2: CASP8 associated protein 2 Hs.122843 H50582 |
| 151 | BIRC2: baculoviral IAP repeat-containing 2 Hs.289107 R19628 c-IAP1 = MIHB = IAP homolog B |
| 152 | CKAP2: cytoskeleton associated protein 2 Hs.24641 AA504130 |
| 153 | HLA-DRA: major histocompatibility complex, class II, DR alpha Hs.76807 R47979 |
| 154 | HBP: Hairpin binding protein, histone Hs.75257 AA629558 |
| 155 | FLJ10483: hypothetical protein FLJ10483 Hs.6877 H12254 |
| 156 | CASP3: caspase 3, apoptosis-related cysteine protease Hs.74552 R14760 CASPASE-3 = CPP32 isoform alpha = yama = cysteine protease |
| 157 | **ESTs,: Weakly similar to protein that is immuno-reactive with anti-PTH polyclonal antibodies [H. sapiens] Hs.301486 AA088258 |
| 158 | HMG2: high-mobility group (nonhistone chromosomal) protein 2 Hs.80684 AA019203 |
| 159 | PRO2000: PRO2000 protein Hs.46677 H58234 |
| 160 | FLJ20333: hypothetical protein FLJ20333 Hs.79828 T48760 |
| 161 | T56726: |
| 162 | TIMP1: tissue inhibitor of metalloproteinase 1 (erythroid potentiating activity, collagenase inhibitor) Hs.5831 H80214 |
| 163 | ESTs: Hs.102004 R94281 |
| 164 | FLJ10858: hypothetical protein FLJ10858 Hs.134403 AA677552 |
| 165 | Homo sapiens cDNA FLJ11883 fis, clone HEMBA1007178 Hs.157148 N62451: |
| 166 | RFC4: replication factor C (activator 1) 4 (37 kD) Hs.35120 N93924 replication factor C |
| 167 | PRO2000: PRO2000 protein Hs.46677 N47113 |
| 168 | ECT2: epithelial cell transforming sequence 2 oncogene Hs.132808 AI031571 |
| 169 | ESTs: Hs.165909 AA629538 |
| 170 | PCF11: PCF11p homolog Hs.123654 AA053411 |
| 171 | BIRC3: baculoviral IAP repeat-containing 3 Hs.127799 H48533 c-IAP2 = MIHC = IAP homolog C = TNFR2-TRAF signalling complex prot |
| 172 | EST,: Weakly similar to dJ45P21.2 [H. sapiens] Hs.326451 AA931528 |
| 173 | KIAA0952: KIAA0952 protein Hs.7935 AA454989 |
| 174 | KIF5B: kinesin family member 5B Hs.149436 AA608707 |
| 175 | DKFZP566C134: DKFZP566C134 protein Hs.20237 N39306 |
| 176 | ANLN: anillin (Drosophila Scraps homolog), actin binding protein Hs.62180 R17092 |
| 177 | ORC1L: origin recognition complex, subunit 1 (yeast homolog)-like Hs.17908 H51719 |
| 178 | ESTs: Hs.14139 T77757 |
| 179 | IFIT1: interferon-induced protein with tetratricopeptide repeats 1 Hs.20315 AA074989 |
| 180 | MGC5338: hypothetical protein MGC5338 Hs.99598 AA463627 |
| 181 | COPEB: core promoter element binding protein Hs.285313 AA013481 |

TABLE 1-continued

| | Gene (Name and/or Symbol) or Number (EST, cDNA clone, or Accession) |
|---|---|
| 182 | UK114: translational inhibitor protein p14.5 Hs.18426 N72715 |
| 183 | ESTs: Hs.265592 H67282 |
| 184 | HMG4: high-mobility group (nonhistone chromosomal) protein 4 Hs.19114 AA670197 |
| 185 | MDS025: hypothetical protein MDS025 Hs.154938 AI225067 |
| 186 | DKFZP564A122: DKFZP564A122 protein Hs.187991 N53236 |
| 187 | TSC22: transforming growth factor beta-stimulated protein TSC-22 Hs.114360 AA664389 |
| 188 | AAAS: aladin Hs.125262 AA916726 |
| 189 | PLAG1: **pleiomorphic adenoma gene 1 Hs.14968 AA418251 |
| 190 | FLJ23293: **hypothetical protein FLJ23293 similar to ARL-6 interacting protein-2 Hs.31236 R91583 |
| 191 | H11: protein kinase H11; small stress protein-like protein HSP22 Hs.111676 AA010110 |
| 192 | POLD3: polymerase (DNA directed), delta 3 Hs.82502 AA504204 |
| 193 | SERPINB3: serine (or cysteine) proteinase inhibitor, clade B (ovalbumin), member 3 Hs.227948 AA292860 |
| 194 | DNAJB1: DnaJ (Hsp40) homolog, subfamily B, member 1 Hs.82646 AA435948 |
| 195 | ESTs: Hs.99480 AA458886 |
| 196 | BUB3: BUB3 (budding uninhibited by benzimidazoles 3, yeast) homolog Hs.40323 AA405690 |
| 197 | TUBB2: tubulin, beta, 2 Hs.251653 AI000256 |
| 198 | *Homo sapiens* SNC73 protein (SNC73) mRNA, complete cds Hs.293441 H28469: |
| 199 | BUB3: BUB3 (budding uninhibited by benzimidazoles 3, yeast) homolog Hs.40323 H38804 |
| 200 | FLJ20699: hypothetical protein FLJ20699 Hs.15125 AA459420 |
| 201 | KIAA0013: KIAA0013 gene product Hs.172652 N63575 |
| 202 | ESTs: Hs.20575 N20305 |
| 203 | CDC25C: cell division cycle 25C Hs.656 W95000 cdc25C = M-phase inducer phosphatase 3 |
| 204 | FLJ11186: hypothetical protein FLJ11186 Hs.89278 AA394225 |
| 205 | TOPK: PDZ-binding kinase; T-cell originated protein kinase Hs.104741 AA448898 |
| 206 | KIAA0165: extra spindle poles, *S. cerevisiae*, homolog of Hs.153479 AA948058 |
| 207 | LOC51659: HSPC037 protein Hs.108196 AA961752 |
| 208 | ESTs: Hs.10338 AA436456 |
| 209 | SUCLG2: succinate-CoA ligase, GDP-forming, beta subunit Hs.247309 AA465233 |
| 210 | ZNF265: zinc finger protein 265 Hs.194718 AA452256 |
| 211 | SKP2: S-phase kinase-associated protein 2 (p45) Hs.23348 R22188 |
| 212 | NS1-BP: NS1-binding protein Hs.197298 AA486796 |
| 213 | C21ORF50: chromosome 21 open reading frame 50 Hs.4055 AA416628 |
| 214 | BIRC2: baculoviral IAP repeat-containing 2 Hs.289107 AA702174 |
| 215 | BIRC3: baculoviral IAP repeat-containing 3 Hs.127799 AA002125 c-IAP2 = MIHC = IAP homolog C = TNFR2-TRAF signalling complex prot |
| 216 | INDO: indoleamine-pyrrole 2,3 dioxygenase Hs.840 AA478279 |
| 217 | DEEPEST: mitotic spindle coiled-coil related protein Hs.16244 T97349 |
| 218 | ESTs: Hs.105826 AA534321 |
| 219 | C20ORF1: chromosome 20 open reading frame 1 Hs.9329 AI654707 |
| 220 | *Homo sapiens* cDNA: FLJ21869 fis, clone HEP02442 Hs.28465 R63929: |
| 221 | RGS3: regulator of G-protein signalling 3 Hs.82294 AI369623 |
| 222 | *Homo sapiens* DC29 mRNA, complete cds Hs.85573 AA186460: |
| 223 | MCM6: minichromosome maintenance deficient (mis5, *S. pombe*) 6 Hs.155462 AA663995 |
| 224 | NPAT: nuclear protein, ataxia-telangiectasia locus Hs.89385 AA284172 NPAT = E14 = gene in ATM locus |
| 225 | KNSL6: kinesin-like 6 (mitotic centromere-associated kinesin) Hs.69360 AA400450 |
| 226 | HN1: hematological and neurological expressed 1 Hs.109706 AA459865 |
| 227 | TUBA3: Tubulin, alpha, brain-specific Hs.272897 AA865469 |
| 228 | ESTs: Hs.221197 N55457 |
| 229 | KIAA0175: KIAA0175 gene product Hs.184339 AA903137 |
| 230 | CLASPIN: homolog of *Xenopus* Claspin Hs.175613 AA857804 |
| 231 | CTNNA1: **catenin (cadherin-associated protein), alpha 1 (102 kD) Hs.178452 AA026631 |
| 232 | ESTs: Hs.221962 AA229644 |
| 233 | SMC4L1: SMC4 (structural maintenance of chromosomes 4, yeast)-like 1 Hs.50758 AA452095 |
| 234 | ICBP90: transcription factor Hs.108106 AA026356 |
| 235 | EXO1: exonuclease 1 Hs.47504 AA703000 |
| 236 | *Homo sapiens* TRAF4 associated factor 1 mRNA, partial cds Hs.181466 T84975: |
| 237 | ESTs: Hs.186814 AA700879 |
| 238 | FLJ11269: hypothetical protein FLJ11269 Hs.25245 R37817 |
| 239 | SFPQ: splicing factor proline/glutamine rich (polypyrimidine tract-binding protein-associated) Hs.180610 AA425258 |
| 240 | ZF: HCF-binding transcription factor Zhangfei Hs.29417 AA164474 |
| 241 | TUBA2: tubulin, alpha 2 Hs.98102 AA626698 |
| 242 | *Homo sapiens* mRNA; cDNA DKFZp434M0435 (from clone DKFZp434M0435) Hs.25700 N94435: |
| 243 | FLJ20530: **hypothetical protein FLJ20530 Hs.279521 AA425442 |
| 244 | BTEB1: basic transcription element binding protein 1 Hs.150557 N80235 |

TABLE 1-continued

| | Gene (Name and/or Symbol) or Number (EST, cDNA clone, or Accession) |
|---|---|
| 245 | LOC51053: geminin Hs.234896 H51100 |
| 246 | D21S2056E: DNA segment on chromosome 21 (unique) 2056 expressed sequence Hs.110757 AI362799 |
| 247 | HDAC3: histone deacetylase 3 Hs.279789 H88540 |
| 248 | USP1: ubiquitin specific protease 1 Hs.35086 AA099033 |
| 249 | C21ORF50: chromosome 21 open reading frame 50 Hs.4055 AA135912 |
| 250 | FLJ13046: **hypothetical protein FLJ13046 similar to exportin 4 Hs.117102 T95333 |
| 251 | ESTs: Hs.181059 AA912032 |
| 252 | FLJ22009: hypothetical protein FLJ22009 Hs.123253 AA401234 |
| 253 | ESTs: Hs.62711 AA056377 |
| 254 | RAD51C: RAD51 (*S. cerevisiae*) homolog C Hs.11393 R37145 RAD51C = Recombination/repair Rad51-related protein |
| 255 | ESTs: Hs.268919 H53508 |
| 256 | *Homo sapiens* cDNA FLJ11381 fis, clone HEMBA1000501 Hs.127797 AA885096: |
| 257 | SAP30: sin3-associated polypeptide, 30 kD Hs.20985 AA126982 |
| 258 | H4FG: H4 histone family, member G Hs.46423 AA868008 |
| 259 | TUBA1: tubulin, alpha 1 (testis specific) Hs.75318 AA180742 tubulin-alpha-4 |
| 260 | DHFR: dihydrofolate reductase Hs.83765 R00884 DHFR = Dihydrofolate reductase |
| 261 | DHFR: dihydrofolate reductase Hs.83765 N52980 |
| 262 | MGC5528: hypothetical protein MGC5528 Hs.315167 AA934904 |
| 263 | NNMT: nicotinamide N-methyltransferase Hs.76669 T72089 |
| 264 | TUBB: tubulin, beta polypeptide Hs.179661 AI672565 |
| 265 | HSPA1L: heat shock 70 kD protein-like 1 Hs.80288 H17513 HSP70-HOM = Heat shock 70 KD protein 1 |
| 266 | TUBA1: **tubulin, alpha 1 (testis specific) Hs.75318 R36063 |
| 267 | PRO1073: **PRO1073 protein Hs.6975 AA176999 CIP4 = Cdc42-interacting protein 4 |
| 268 | POLD3: polymerase (DNA directed), delta 3 Hs.82502 AI017254 |
| 269 | ESTs,: Moderately similar to T50635 hypothetical protein DKFZp762L0311.1 [*H. sapiens*] Hs.47378 N38809 |
| 270 | DKFZP564A122: DKFZP564A122 protein Hs.187991 N57723 |
| 271 | LRRFIP1: **leucine rich repeat (in FLII) interacting protein 1 Hs.326159 T84633 |
| 272 | ESTs: Hs.55468 AA165312 |
| 273 | ESTs: Hs.31444 H16772 |
| 274 | AFAP: actin filament associated protein Hs.80306 R69355 |
| 275 | CXCR4: chemokine (C—X—C motif), receptor 4 (fusin) Hs.89414 T62491 CXC chemokine receptor 4 = fusin = neuropeptide Y receptor = L3 |
| 276 | MSH2: **mutS (*E. coli*) homolog 2 (colon cancer, nonpolyposis type 1) Hs.78934 AA679697 |
| 277 | ESTs: Hs.48474 N62074 |
| 278 | AA677337: |
| 279 | ESTs,: Moderately similar to TBB2_HUMAN TUBULIN BETA-2 CHAIN [*H. sapiens*] Hs.23189 AA629908 |
| 280 | HP1-BP74: HP1-BP74 Hs.142442 H79795 |
| 281 | FLJ20101: LIS1-interacting protein NUDE1, rat homolog Hs.263925 AA459394 |
| 282 | *Homo sapiens* mRNA; cDNA DKFZp434D1428 (from clone DKFZp434D1428); complete cds Hs.321775 AA431268: |
| 283 | ESTs: Hs.265592 AA992658 |
| 284 | ESTs: |
| 285 | DDX11: DEAD/H (Asp-Glu-Ala-Asp/His) box polypeptide 11 (*S. cerevisiae* CHL1-like helicase) Hs.27424 AA402879 |
| 286 | CDC27: cell division cycle 27 Hs.172405 T81764 |
| 287 | ARGBP2: Arg/Abl-interacting protein ArgBP2 Hs.278626 N89738 |
| 288 | DKFZP564A122: DKFZP564A122 protein Hs.187991 AA025807 |
| 289 | OPN3: opsin 3 (encephalopsin) Hs.279926 AA150060 |
| 290 | DKFZP566C134: DKFZP566C134 protein Hs.20237 AA456319 |
| 291 | KIAA0855: golgin-67 Hs.182982 H15101 |
| 292 | PIN: dynein, cytoplasmic, light polypeptide Hs.5120 AA644679 |
| 293 | ESTs,: Weakly similar to LIP1_HUMAN PANCREATIC LIPASE RELATED PROTEIN 1 PRECURSO [*H. sapiens*] Hs.68864 AA088857 |
| 294 | HDAC3: histone deacetylase 3 Hs.279789 AA973283 |
| 295 | DONSON: downstream neighbor of SON Hs.17834 AA417895 |
| 296 | LOC51053: geminin Hs.234896 AA447662 |
| 297 | FLJ10545: hypothetical protein FLJ10545 Hs.88663 AA460110 |
| 298 | MAD2L1: MAD2 (mitotic arrest deficient, yeast, homolog)-like 1 Hs.79078 AA481076 mitotic feedback control protein Madp2 homolog |
| 299 | TASR2: TLS-associated serine-arginine protein 2 Hs.3530 H11042 |
| 300 | MCM6: minichromosome maintenance deficient (mis5, *S. pombe*) 6 Hs.155462 N57722 |
| 301 | CIT: citron (rho-interacting, serine/threonine kinase 21) Hs.15767 W69425 |
| 302 | **ESTs: Hs.205066 AA284803 |
| 303 | ICAM1: intercellular adhesion molecule 1 (CD54), human rhinovirus receptor Hs.168383 R77293 CD54 = ICAM-1 |
| 304 | KIAA0855: golgin-67 Hs.182982 AA456818 |
| 305 | ESTs,: Weakly similar to putative p150 [*H. sapiens*] Hs.300070 R10422 |
| 306 | DEEPEST: mitotic spindle coiled-coil related protein Hs.16244 AI652290 |
| 307 | MCM2: minichromosome maintenance deficient (*S. cerevisiae*) 2 (mitotin) Hs.57101 AA454572 |
| 308 | *Homo sapiens* cDNA: FLJ22272 fis, clone HRC03192 Hs.50740 AA495943: |

TABLE 1-continued

| | Gene (Name and/or Symbol) or Number (EST, cDNA clone, or Accession) |
|---|---|
| 309 | WISP1: **WNT1 inducible signaling pathway protein 1 Hs.194680 T54850 |
| 310 | KIAA0855: golgin-67 Hs.182982 AA280248 |
| 311 | TEM8: tumor endothelial marker 8 Hs.8966 H58644 |
| 312 | BITE: p10-binding protein Hs.42315 H96392 |
| 313 | RAN: RAN, member RAS oncogene family Hs.10842 AA456636 |
| 314 | EZH2: enhancer of zeste (*Drosophila*) homolog 2 Hs.77256 AA428252 |
| 315 | MCM4: minichromosome maintenance deficient (*S. cerevisiae*) 4 Hs.154443 W74071 |
| 316 | DKFZp434J0310: hypothetical protein Hs.278408 AA279657 Unknown UG Hs.23595 ESTs sc_id6950 |
| 317 | PPP1R10: protein phosphatase 1, regulatory subunit 10 Hs.106019 AA071526 |
| 318 | H11: protein kinase H11; small stress protein-like protein HSP22 Hs.111676 H57493 |
| 319 | ESTs,: Weakly similar to KIAA1074 protein [*H. sapiens*] Hs.200483 AA463220 |
| 320 | ESTs,: Weakly similar to ALU8_HUMAN ALU SUBFAMILY SX SEQUENCE CONTAMINATION WARNING ENTRY [*H. sapiens*] Hs.226414 N72576 |
| 321 | AA775033: |
| 322 | LOC51004: CGI-10 protein Hs.12239 AA677920 |
| 323 | ESTs: Hs.150028 AI292036 |
| 324 | MCM6: minichromosome maintenance deficient (mis5, *S. pombe*) 6 Hs.155462 AA976533 |
| 325 | ESTs,: Moderately similar to T50635 hypothetical protein DKFZp762L0311.1 [*H. sapiens*] Hs.47378 AA406348 |
| 326 | UCP4: uncoupling protein 4 Hs.40510 H60279 |
| 327 | MSH5: mutS (*E. coli*) homolog 5 Hs.112193 AA621155 |
| 328 | ROCK1: Rho-associated, coiled-coil containing protein kinase 1 Hs.17820 AA872143 |
| 329 | KIAA0855: golgin-67 Hs.182982 AA694481 |
| 330 | AA705332: |
| 331 | CDC27: cell division cycle 27 Hs.172405 N47994 |
| 332 | DONSON: downstream neighbor of SON Hs.17834 AI732249 |
| 333 | SH3GL2: SH3-domain GRB2-like 2 Hs.75149 R12817 |
| 334 | PRC1: protein regulator of cytokinesis 1 Hs.5101 AA449336 |
| 335 | ESTs,: Weakly similar to unnamed protein product [*H. sapiens*] Hs.99807 AA417744 Unknown UG Hs.119424 ESTs sc_id2235 |
| 336 | Human: clone 23719 mRNA sequence Hs.80305 AA425722 |
| 337 | *Homo sapiens* mRNA; cDNA DKFZp564O2364 (from clone DKFZp564O2364) Hs.28893 W90240: |
| 338 | ESTs,: Weakly similar to LIP1_HUMAN PANCREATIC LIPASE RELATED PROTEIN 1 PRECURSO [*H. sapiens*] Hs.68864 AA132858 |
| 339 | TUBA3: Tubulin, alpha, brain-specific Hs.272897 AA864642 |
| 340 | AI283530: |
| 341 | ESTs: Hs.302878 R92512 |
| 342 | PPP1R10: protein phosphatase 1, regulatory subunit 10 Hs.106019 T75485 |
| 343 | SFRS5: splicing factor, arginine/serine-rich 5 Hs.166975 R73672 |
| 344 | SFRS3: splicing factor, arginine/serine-rich 3 Hs.167460 AA598400 |
| 345 | PRIM1: primase, polypeptide 1 (49 kD) Hs.82741 AA025937 DNA primase (subunit p48) |
| 346 | FLJ20333: hypothetical protein FLJ20333 Hs.79828 H66982 |
| 347 | HSPA8: heat shock 70 kD protein 8 Hs.180414 AA620511 |
| 348 | C4A: complement component 4A Hs.170250 AA664406 |
| 349 | DKC1: dyskeratosis congenita 1, dyskerin Hs.4747 AA052960 |
| 350 | HP1-BP74: HP1-BP74 Hs.142442 T84669 |
| 351 | ETV4: ets variant gene 4 (E1A enhancer-binding protein, E1AF) Hs.77711 AA010400 E1A-F = E1A enhancer binding protein = ETS translocation variant |
| 352 | *Homo sapiens* cDNA: FLJ23037 fis, clone LNG02036, highly similar to HSU68019 *Homo sapiens* mad protein homolog (hMAD-3) mRNA Hs.288261 W42414 Smad3 = hMAD-3 = Homologue of Mothers Against Decapentaplegic (M: |
| 353 | KIAA0952: KIAA0952 protein Hs.7935 AA679150 |
| 354 | STK9: serine/threonine kinase 9 Hs.50905 N80713 |
| 355 | NXF1: **nuclear RNA export factor 1 Hs.323502 R01238 |
| 356 | FLJ12892: hypothetical protein FLJ12892 Hs.17731 AA449357 |
| 357 | UNG: uracil-DNA glycosylase Hs.78853 H15111 |
| 358 | STK17B: **serine/threonine kinase 17b (apoptosis-inducing) Hs.120996 AA419485 |
| 359 | YWHAH: tyrosine 3-monooxygenase/tryptophan 5-monooxygenase activation protein, eta polypeptide Hs.75544 N69107 |
| 360 | FLJ13154: hypothetical protein FLJ13154 Hs.25303 AA923560 |
| 361 | LOC51116: CGI-91 protein Hs.20776 AA459419 |
| 362 | SSXT: synovial sarcoma, translocated to X chromosome Hs.153221 N59206 |
| 363 | KIAA0978: KIAA0978 protein Hs.3686 AA485878 |
| 364 | EST: Hs.147907 AI223432 |
| 365 | FLJ23468: hypothetical protein FLJ23468 Hs.38178 AA431741 |
| 366 | FLJ10339: **hypothetical protein FLJ10339 Hs.203963 N95450 |
| 367 | BMP2: bone morphogenetic protein 2 Hs.73853 AA011061 |
| 368 | PIR51: RAD51-interacting protein Hs.24596 AI214426 |
| 369 | FLJ20364: hypothetical protein FLJ20364 Hs.32471 AA676296 |
| 370 | EIF4A2: **eukaryotic translation initiation factor 4A, isoform 2 Hs.173912 H54751 |
| 371 | ESTs,: Weakly similar to MCAT_HUMAN MITOCHONDRIAL CARNITINE/ACYLCARNITINE CARRIER PROTEIN [*H. sapiens*] Hs.27769 AA469975 |
| 372 | FLJ11323: hypothetical protein FLJ11323 Hs.25625 AA775600 |

TABLE 1-continued

| | Gene (Name and/or Symbol) or Number (EST, cDNA clone, or Accession) |
|---|---|
| 373 | DKFZP564D0764: DKFZP564D0764 protein Hs.26799 AA460732 |
| 374 | CTL2: CTL2 gene Hs.105509 AA454710 |
| 375 | ESTs: Hs.293419 AA775845 |
| 376 | IFIT1: interferon-induced protein with tetratricopeptide repeats 1 Hs.20315 AA489640 Interferon-induced 56-KDa protein |
| 377 | RBBP8: retinoblastoma-binding protein 8 Hs.29287 H23021 |
| 378 | ***Homo sapiens* clone 25061 mRNA sequence Hs.183475 R38944: |
| 379 | Human: DNA sequence from clone RP3-383J4 on chromosome 1q24.1-24.3 Contains part of a gene encoding a kelch motif containing protein, part of a novel gene encoding a protein similar to Aspartyl-TRNA sy Hs.117305 N29457 |
| 380 | FLJ12888: hypothetical protein FLJ12888 Hs.284137 N68390 |
| 381 | ESTs,: Weakly similar to IF38_HUMAN EUKARYOTIC TRANSLATION INITIATION FACTOR 3 SUBUNIT 8 [*H. sapiens*] Hs.222088 AI139629 |
| 382 | ESTs: Hs.241101 AA133590 |
| 383 | H4FI: H4 histone family, member I Hs.143080 AI218900 |
| 384 | SP38: *zona pellucida* binding protein Hs.99875 AA400474 |
| 385 | GABPB1: GA-binding protein transcription factor, beta subunit 1 (53 kD) Hs.78915 H91651 |
| 386 | LCHN: LCHN protein Hs.12461 AA029330 |
| 387 | DKFZP564D0462: hypothetical protein DKFZp564D0462 Hs.44197 N32904 |
| 388 | LENG8: leukocyte receptor cluster (LRC) encoded novel gene 8 Hs.306121 AA464698 |
| 389 | HIF1A: hypoxia-inducible factor 1, alpha subunit (basic helix-loop-helix transcription factor) Hs.197540 AA598526 |
| 390 | ESTs: Hs.93714 R09201 |
| 391 | FLJ23468: hypothetical protein FLJ23468 Hs.38178 AA454949 |
| 392 | DKFZP566C134: DKFZP566C134 protein Hs.20237 AA448164 |
| 393 | PPP3CA: protein phosphatase 3 (formerly 2B), catalytic subunit, alpha isoform (calcineurin A alpha) Hs.272458 W60310 |
| 394 | HMGE: GrpE-like protein cochaperone Hs.151903 H55907 |
| 395 | CDK7: cyclin-dependent kinase 7 (homolog of *Xenopus* MO15 cdk-activating kinase) Hs.184298 R22624 CAK = cdk7 = NRTALRE = sdk = CDK activating kinase |
| 396 | ABCC5: **ATP-binding cassette, sub-family C (CFTR/MRP), member 5 Hs.108660 AA186613 |
| 397 | AA477707: |
| 398 | **ESTs: Hs.15607 R92899 |
| 399 | LOC57209: Kruppel-type zinc finger protein Hs.25275 N50827 |
| 400 | FLJ20101: LIS1-interacting protein NUDE1, rat homolog Hs.263925 R87716 |
| 401 | KNSL4: kinesin-like 4 Hs.119324 AA430503 |
| 402 | E2F5: E2F transcription factor 5, p130-binding Hs.2331 AA455521 E2F-5 = pRB-binding transcription factor |
| 403 | TMPO: thymopoietin Hs.11355 T63980 |
| 404 | POLQ: polymerase (DNA directed), theta Hs.241517 AI057325 |
| 405 | TGIF: TG-interacting factor (TALE family homeobox) Hs.90077 H51705 |
| 406 | TRIP13: thyroid hormone receptor interactor 13 Hs.6566 AA630784 |
| 407 | GAS6: growth arrest-specific 6 Hs.78501 AA461110 |
| 408 | HN1: hematological and neurological expressed 1 Hs.109706 AA035429 |
| 409 | BARD1: BRCA1 associated RING domain 1 Hs.54089 AA558464 |
| 410 | DHFR: dihydrofolate reductase Hs.83765 AA424790 |
| 411 | AA490946: |
| 412 | ESTs: Hs.130435 AA167114 |
| 413 | HSPA8: heat shock 70 kD protein 8 Hs.180414 AA629567 |
| 414 | RRM2: ribonucleotide reductase M2 polypeptide Hs.75319 AA826373 |
| 415 | FLJ20036: hypothetical protein FLJ20036 Hs.32922 H59114 |
| 416 | COPEB: core promoter element binding protein Hs.285313 AA055584 CPBP = CBA1 = DNA-binding protein |
| 417 | FLJ10604: hypothetical protein FLJ10604 Hs.26516 N72697 |
| 418 | ESTs,: Weakly similar to cDNA EST yk415c12.5 comes from this gene [*C. elegans*] Hs.108824 H97880 |
| 419 | UBE2D3: **ubiquitin-conjugating enzyme E2D 3 (homologous to yeast UBC4/5) Hs.118797 AA017199 |
| 420 | FLJ10890: **hypothetical protein FLJ10890 Hs.17283 AA004210 |
| 421 | ESTs: Hs.214410 AA579336 |
| 422 | OLR1: oxidised low density lipoprotein (lectin-like) receptor 1 Hs.77729 AA682386 |
| 423 | FLJ13231: hypothetical protein FLJ13231 Hs.156148 W92787 |
| 424 | EST: Hs.323101 W40398 |
| 425 | ESTs,: Weakly similar to R06F6.5b [*C. elegans*] Hs.180591 N59330 |
| 426 | *Homo sapiens* cDNA: FLJ23285 fis, clone HEP09071 Hs.90424 N26163: |
| 427 | *Homo sapiens* mRNA full length insert cDNA clone EUROIMAGE 42408 Hs.284123 AA211446: |
| 428 | NFKB1: nuclear factor of kappa light polypeptide gene enhancer in B-cells 1 (p105) Hs.83428 AA451716 NFkB1 = NF-kappaB p105 = p50 |
| 429 | LOC58486: transposon-derived Buster1 transposase-like protein Hs.25726 AA630256 |
| 430 | *Homo sapiens* cDNA FLJ10976 fis, clone PLACE1001399 Hs.296323 AA424756: |
| 431 | KIAA0182: KIAA0182 protein Hs.75909 AI023801 |
| 432 | RANGAP1: Ran GTPase activating protein 1 Hs.183800 AA991855 |
| 433 | PKMYT1: membrane-associated tyrosine- and threonine-specific cdc2-inhibitory kinase Hs.77783 AA478066 Myt1 kinase |

TABLE 1-continued

| | Gene (Name and/or Symbol) or Number (EST, cDNA clone, or Accession) |
|---|---|
| 434 | HSPA8: heat shock 70 kD protein 8 Hs.180414 H64096 |
| 435 | LUC7A: cisplatin resistance-associated overexpressed protein Hs.3688 AA411969 |
| 436 | RRM1: ribonucleotide reductase M1 polypeptide Hs.2934 AA633549 |
| 437 | SET07: PR/SET domain containing protein 7 Hs.111988 AA421470 |
| 438 | **ESTs,: Weakly similar to ALU1_HUMAN ALU SUBFAMILY J SEQUENCE CONTAMINATION WARNING ENTRY [*H. sapiens*] Hs.193452 W96179 |
| 439 | *Homo sapiens* clone 25058 mRNA sequence Hs.179397 R38894: |
| 440 | ESTs,: Weakly similar to KIAA0973 protein [*H. sapiens*] Hs.14014 AA780791 |
| 441 | EST: Hs.105298 AA489813 |
| 442 | CTCF: CCCTC-binding factor (zinc finger protein) Hs.57419 H89996 |
| 443 | HRB: HIV-1 Rev binding protein Hs.171545 AA485958 |
| 444 | **ESTs: Hs.294083 AA447679 |
| 445 | KIAA0878: KIAA0878 protein Hs.188006 AA599094 |
| 446 | ESTs,: Weakly similar to ALUB_HUMAN !!!! ALU CLASS B WARNING ENTRY !!! [*H. sapiens*] Hs.180552 AA481283 |
| 447 | OGT: O-linked N-acetylglucosamine (GlcNAc) transferase (UDP-N-acetylglucosamine:polypeptide-N-acetylglucosaminyl transferase) Hs.100293 AA425229 |
| 448 | *Homo sapiens* mRNA for KIAA1700 protein, partial cds Hs.20281 N40952: |
| 449 | Human: DNA sequence from clone RP1-187J11 on chromosome 6q11.1-22.33. Contains the gene for a novel protein similar to *S. pombe* and *S. cerevisiae* predicted proteins, the gene for a novel protein simila Hs.72325 AA159962 |
| 450 | KIAA1265: KIAA1265 protein Hs.24936 AA479302 |
| 451 | H1F0: H1 histone family, member 0 Hs.226117 H57830 |
| 452 | ARGBP2: Arg/Abl-interacting protein ArgBP2 Hs.278626 H02525 |
| 453 | ODF2: outer dense fibre of sperm tails 2 Hs.129055 AA149882 |
| 454 | CD97: CD97 antigen Hs.3107 AI651871 |
| 455 | BMI1: **murine leukemia viral (bmi-1) oncogene homolog Hs.431 AA193573 |
| 456 | POLG: polymerase (DNA directed), gamma Hs.80961 AA188629 |
| 457 | XPR1: xenotropic and polytropic retrovirus receptor Hs.227656 AA453474 |
| 458 | ESTs: Hs.128096 AA971179 |
| 459 | DNAJB1: DnaJ (Hsp40) homolog, subfamily B, member 1 Hs.82646 AA481022 |
| 460 | ARL4: ADP-ribosylation factor-like 4 Hs.201672 AI142552 |
| 461 | SFRS5: splicing factor, arginine/serine-rich 5 Hs.166975 AA598965 |
| 462 | ESTs: Hs.25933 R11605 |
| 463 | RIG-I: RNA helicase Hs.145612 AA126958 |
| 464 | FLJ10339: hypothetical protein FLJ10339 Hs.203963 AA628231 |
| 465 | DR1: down-regulator of transcription 1, TBP-binding (negative cofactor 2) Hs.16697 AA043503 |
| 466 | *Homo sapiens*, Similar to hypothetical protein FLJ20093, clone MGC: 1076, mRNA, complete cds Hs.298998 AA703249: |
| 467 | HSPC163: HSPC163 protein Hs.108854 H98963 |
| 468 | DKFZP564A122: DKFZP564A122 protein Hs.187991 R27345 |
| 469 | FLJ10128: uveal autoantigen with coiled coil domains and ankyrin repeats Hs.49753 T47624 |
| 470 | DSCR1: Down syndrome critical region gene 1 Hs.184222 AA629707 |
| 471 | FLJ10342: hypothetical protein FLJ10342 Hs.101514 AA490935 |
| 472 | *Homo sapiens* mRNA; cDNA DKFZp586N1323 (from clone DKFZp586N1323) Hs.24064 R26176: |
| 473 | ESTs: Hs.4983 H59921 |
| 474 | ESTs,: Weakly similar to ALUB_HUMAN !!!! ALU CLASS B WARNING ENTRY !!! [*H. sapiens*] Hs.117949 H91167 |
| 475 | CDC45L: CDC45 (cell division cycle 45, *S. cerevisiae*, homolog)-like Hs.114311 AA700904 |
| 476 | STAT5B: signal transducer and activator of transcription 5B Hs.244613 AA280647 STAT5A/5B |
| 477 | *Homo sapiens* cDNA FLJ14028 fis, clone HEMBA1003838 Hs.281434 AA454682: |
| 478 | KIAA1524: KIAA1524 protein Hs.151343 AI248987 |
| 479 | CTSD: cathepsin D (lysosomal aspartyl protease) Hs.79572 AA485373 |
| 480 | *Homo sapiens*, Similar to hypothetical protein FLJ20093, clone MGC: 1076, mRNA, complete cds Hs.298998 AA682274: |
| 481 | GTPBP2: GTP binding protein 2 Hs.13011 T67069 |
| 482 | LOC51003: CGI-125 protein Hs.27289 AA485945 |
| 483 | VCL: vinculin Hs.75350 AA486727 |
| 484 | KIF5B: kinesin family member 5B Hs.149436 AA046613 |
| 485 | CDC25A: cell division cycle 25A Hs.1634 AA071514 |
| 486 | LOC51141: insulin induced protein 2 Hs.7089 AA045308 |
| 487 | **ESTs,: Moderately similar to CALD_HUMAN CALDESMON [*H. sapiens*] Hs.117774 H48508 |
| 488 | TBX3-iso: TBX3-iso protein Hs.267182 T48941 |
| 489 | KIAA0176: KIAA0176 protein Hs.4935 R44371 |
| 490 | PRKAR1A: protein kinase, cAMP-dependent, regulatory, type I, alpha (tissue specific extinguisher 1) Hs.183037 N25969 PKA-R1 alpha = cAMP-dependent protein kinase type I-alpha-cata |
| 491 | ESTs: Hs.268991 H77818 |
| 492 | ESTs,: Weakly similar to A53028 isopentenyl-diphosphate Delta-isomerase [*H. sapiens*] Hs.9270 R17362 |
| 493 | ESTs,: Weakly similar to B34087 hypothetical protein [*H. sapiens*] Hs.120946 H50656 |

TABLE 1-continued

| | Gene (Name and/or Symbol) or Number (EST, cDNA clone, or Accession) |
|---|---|
| 494 | TRN2: karyopherin beta 2b, transportin Hs.278378 R08897 |
| 495 | LMNA: lamin A/C Hs.77886 AA489582 |
| 496 | NFE2L2: nuclear factor (erythroid-derived 2)-like 2 Hs.155396 AA629687 |
| 497 | DKFZp762L0311: hypothetical protein DKFZp762L0311 Hs.16520 AA486418 |
| 498 | ESTs,: Weakly similar to S71752 giant protein p619 [*H. sapiens*] Hs.14870 T96829 |
| 499 | *Homo sapiens* mRNA; cDNA DKFZp434A1315 (from clone DKFZp434A1315); complete cds Hs.298312 AA991355: |
| 500 | E2IG4: hypothetical protein, estradiol-induced Hs.8361 R13844 |
| 501 | RANGAP1: Ran GTPase activating protein 1 Hs.183800 AA485734 |
| 502 | H1F0: H1 histone family, member 0 Hs.226117 W69399 |
| 503 | KIAA0239: KIAA0239 protein Hs.9729 AA454740 |
| 504 | ESTs,: Weakly similar to ALU7_HUMAN ALU SUBFAMILY SQ SEQUENCE CONTAMINATION WARNING ENTRY [*H. sapiens*] Hs.68647 R96804 |
| 505 | PRO0650: PRO0650 protein Hs.177258 N54333 |
| 506 | DNAJB9: DnaJ (Hsp40) homolog, subfamily B, member 9 Hs.6790 AA045792 |
| 507 | *Homo sapiens* cDNA: FLJ21971 fis, clone HEP05790 Hs.71331 AA774678: |
| 508 | LOC56996: **cation-chloride cotransporter-interacting protein Hs.119178 AA037466 |
| 509 | AP3D1: adaptor-related protein complex 3, delta 1 subunit Hs.75056 AA630776 |
| 510 | SGK: serum/glucocorticoid regulated kinase Hs.159640 AA486082 sgk = putative serine/threonine protein kinase transcriptional |
| 511 | HSPC148: hypothetical protein Hs.42743 R23666 |
| 512 | MRPL19: mitochondrial ribosomal protein L19 Hs.75574 AA521243 KIAA0104 |
| 513 | AA455102: |
| 514 | ESTs: Hs.150325 AI278813 |
| 515 | **ESTs: Hs.40527 AA029844 |
| 516 | HSPC145: HSPC145 protein Hs.18349 AI271431 |
| 517 | KIAA0170: KIAA0170 gene product Hs.277585 H68789 |
| 518 | FLJ11127: hypothetical protein Hs.91165 T98200 |
| 519 | KIAA0182: KIAA0182 protein Hs.75909 H05099 |
| 520 | FLJ23151: hypothetical protein FLJ23151 Hs.137260 AA284259 |
| 521 | AMD1: S-adenosylmethionine decarboxylase 1 Hs.262476 AA425692 |
| 522 | FLJ10342: **hypothetical protein FLJ10342 Hs.101514 AA934516 |
| 523 | SPS: SELENOPHOSPHATE SYNTHETASE; Human selenium donor protein Hs.124027 AA486372 |
| 524 | KIAA1586: KIAA1586 protein Hs.180663 AA779733 |
| 525 | ICBP90: transcription factor Hs.108106 AA908902 |
| 526 | Homo sapiens cDNA: FLJ21971 fis, clone HEP05790 Hs.71331 AI002036: |
| 527 | ABCC2: ATP-binding cassette, sub-family C (CFTR/MRP), member 2 Hs.193852 R91502 |
| 528 | ARHGDIB: Rho GDP dissociation inhibitor (GDI) beta Hs.83656 AA487426 LyGDI = Rho GDP-dissociation inhibitor 2 = RHO GDI 2 |
| 529 | RAD53: protein kinase Chk2 Hs.146329 AI653182 |
| 530 | R96880: |
| 531 | TNFAIP3: tumor necrosis factor, alpha-induced protein 3 Hs.211600 AA433807 |
| 532 | ESTs: Hs.26979 H23469 |
| 533 | AOC2: amine oxidase, copper containing 2 (retina-specific) Hs.143102 N50959 |
| 534 | *Homo sapiens* mRNA; cDNA DKFZp586N1323 (from clone DKFZp586N1323) Hs.24064 R30941: |
| 535 | AA452872: |
| 536 | ESTs: Hs.124169 R58970 |
| 537 | ACYP1: acylphosphatase 1, erythrocyte (common) type Hs.18573 W78754 |
| 538 | SIL: TAL1 (SCL) interrupting locus Hs.323032 AA704809 |
| 539 | AA016234: |
| 540 | *Homo sapiens* mRNA; cDNA DKFZp566P1124 (from clone DKFZp566P1124) Hs.321022 N50895: |
| 541 | KIAA1067: KIAA1067 protein Hs.325530 AA099138 |
| 542 | SMC4L1: SMC4 (structural maintenance of chromosomes 4, yeast)-like 1 Hs.50758 AA283006 |
| 543 | ESTs: Hs.29074 R70174 |
| 544 | SNK: serum-inducible kinase Hs.3838 AA460152 |
| 545 | FANCG: Fanconi anemia, complementation group G Hs.8047 AA427484 |
| 546 | *Homo sapiens* cDNA: FLJ21531 fis, clone COL06036 Hs.102941 N95440: |
| 547 | *Homo sapiens* mRNA; cDNA DKFZp547B086 (from clone DKFZp547B086) Hs.36606 N48700: |
| 548 | C1ORF2: chromosome 1 open reading frame 2 Hs.19554 H11464 cote1 = ORF in glucocerebrosidase locus |
| 549 | HTF9C: HpaII tiny fragments locus 9C Hs.63609 H17888 |
| 550 | ATF4: activating transcription factor 4 (tax-responsive enhancer element B67) Hs.181243 AA600217 |
| 551 | ESTs: Hs.101014 AA194941 |
| 552 | CDC25A: cell division cycle 25A Hs.1634 AA913262 |
| 553 | TOPK: PDZ-binding kinase; T-cell originated protein kinase Hs.104741 AI002631 |
| 554 | ASIP: agouti (mouse)-signaling protein Hs.37006 AI220203 |
| 555 | DKFZP564F013: **hypothetical protein DKFZp564F013 Hs.128653 R14908 |
| 556 | ZNF265: zinc finger protein 265 Hs.194718 N66014 |
| 557 | SLC30A1: solute carrier family 30 (zinc transporter), member 1 Hs.55610 AA195463 |
| 558 | ESTs: Hs.28462 R63922 |
| 559 | ESTs: Hs.114055 R27431 |

TABLE 1-continued

| | Gene (Name and/or Symbol) or Number (EST, cDNA clone, or Accession) |
|---|---|
| 560 | IL6: interleukin 6 (interferon, beta 2) Hs.93913 N98591 IL-6 |
| 561 | H3F3B: H3 histone, family 3B (H3.3B) Hs.180877 AA608514 |
| 562 | ESTs: Hs.81263 W81524 |
| 563 | *Homo sapiens* cDNA: FLJ23538 fis, clone LNG08010, highly similar to BETA2 Human MEN1 region clone epsilon/beta mRNA Hs.240443 AA400234: |
| 564 | AMD1: S-adenosylmethionine decarboxylase 1 Hs.262476 R82299 |
| 565 | MAP3K2: mitogen-activated protein kinase kinase kinase 2 Hs.28827 AA447971 |
| 566 | NET1: neuroepithelial cell transforming gene 1 Hs.25155 R24543 |
| 567 | CHAF1A: chromatin assembly factor 1, subunit A (p150) Hs.79018 AA704459 |
| 568 | MGC5585: hypothetical protein MGC5585 Hs.5152 H50655 |
| 569 | KIAA1598: KIAA1598 protein Hs.23740 H17868 |
| 570 | PNN: pinin, desmosome associated protein Hs.44499 W86139 |
| 571 | ESTs: Hs.238797 N70848 |
| 572 | ESTs,: Weakly similar to ALUB_HUMAN !!!! ALU CLASS B WARNING ENTRY !!! [*H. sapiens*] Hs.180552 AA600192 |
| 573 | PDGFA: platelet-derived growth factor alpha polypeptide Hs.37040 AA701502 |
| 574 | *Homo sapiens* clone FLC0675 PRO2870 mRNA, complete cds Hs.306117 AA443127: |
| 575 | ESTs: Hs.143375 AA001841 |
| 576 | TUBB: tubulin, beta polypeptide Hs.179661 H37989 |
| 577 | MSH2: mutS (*E. coli*) homolog 2 (colon cancer, nonpolyposis type 1) Hs.78934 AA219060 MSH2 = DNA mismatch repair mutS homologue |
| 578 | TOPBP1: topoisomerase (DNA) II binding protein Hs.91417 R97785 |
| 579 | KIAA0869: KIAA0869 protein Hs.21543 R43798 |
| 580 | H4FH: H4 histone family, member H Hs.93758 AA702781 |
| 581 | FLJ23293: hypothetical protein FLJ23293 similar to ARL-6 interacting protein-2 Hs.31236 AA629027 |
| 582 | **Homo sapiens* cDNA: FLJ23538 fis, clone LNG08010, highly similar to BETA2 Human MEN1 region clone epsilon/beta mRNA Hs.240443 AA053165: |
| 583 | KIAA0978: KIAA0978 protein Hs.3686 N64780 |
| 584 | KIAA1547: KIAA1547 protein Hs.31305 AA057737 |
| 585 | DKFZP761C169: hypothetical protein DKFZp761C169 Hs.71252 AA608709 |
| 586 | WS-3: novel RGD-containing protein Hs.39913 AA449975 |
| 587 | FRZB: frizzled-related protein Hs.153684 H87275 |
| 588 | BRCA1: breast cancer 1, early onset Hs.194143 H90415 BRCA1 = Mutated in breast and ovarian cancer |
| 589 | ESTs: Hs.4983 H22936 |
| 590 | HSPC150: HSPC150 protein similar to ubiquitin-conjugating enzyme Hs.5199 AA460431 |
| 591 | *Homo sapiens* mRNA for KIAA1712 protein, partial cds Hs.29798 H54592: |
| 592 | FLJ11186: hypothetical protein FLJ11186 Hs.89278 AA504111 Unknown UG Hs.89278 ESTs |
| 593 | ESTs,: Weakly similar to unnamed protein product [*H. sapiens*] Hs.118338 R25481 |
| 594 | APEXL2: apurinic/apyrimidinic endonuclease(APEX nuclease)-like 2 protein Hs.154149 AI674393 |
| 595 | CDR2: cerebellar degeneration-related protein (62 kD) Hs.75124 AA074613 |
| 596 | ESTs: Hs.69662 AA459724 |
| 597 | PSCD2L: pleckstrin homology, Sec7 and coiled/coil domains 2-like Hs.8517 AA464957 |
| 598 | CRK: v-crk avian sarcoma virus CT10 oncogene homolog Hs.306088 H75530 |
| 599 | CCNE2: cyclin E2 Hs.30464 AA520999 Unknown UG Hs.30464 cyclin E2 |
| 600 | LOC51240: hypothetical protein Hs.7870 AA988037 |
| 601 | FLJ11259: hypothetical protein FLJ11259 Hs.184465 AA485877 |
| 602 | PTP4A1: protein tyrosine phosphatase type IVA, member 1 Hs.227777 AA482193 |
| 603 | *Homo sapiens* cDNA: FLJ22355 fis, clone HRC06344 Hs.288283 AA026375: |
| 604 | Human: clone 23719 mRNA sequence Hs.80305 H43437 |
| 605 | *Homo sapiens* clone FLC0675 PRO2870 mRNA, complete cds Hs.306117 AA485453: |
| 606 | MSE55: serum constituent protein Hs.148101 H73234 |
| 607 | CFLAR: CASP8 and FADD-like apoptosis regulator Hs.195175 AA453766 |
| 608 | *Homo sapiens* cDNA: FLJ22844 fis, clone KAIA5181 Hs.296322 AA975103: |
| 609 | Human: DNA sequence from clone RP11-371L19 on chromosome 20 Contains two novel genes, the gene for a novel protein similar to 40S ribosomal protein S10 (RPS10), ESTs, STSs, GSSs and five CpG islands Hs.19002 R00846 |
| 610 | ESTs: Hs.60054 R26390 |
| 611 | ESTs,: Weakly similar to ALU7_HUMAN ALU SUBFAMILY SQ SEQUENCE CONTAMINATION WARNING ENTRY [*H. sapiens*] Hs.325158 AA032084 |
| 612 | FLJ10980: hypothetical protein FLJ10980 Hs.29716 N45467 |
| 613 | IFIT1: **interferon-induced protein with tetratricopeptide repeats 1 Hs.20315 AA157787 |
| 614 | ESTs: Hs.21734 AA429809 |
| 615 | DKFZP434C245: DKFZP434C245 protein Hs.59461 AA705518 |
| 616 | RNPS1: RNA-binding protein S1, serine-rich domain Hs.75104 AA496837 |
| 617 | FLJ13639: hypothetical protein FLJ13639 Hs.101821 AA131681 |
| 618 | PCF11: PCF11p homolog Hs.123654 W73749 |
| 619 | EIF4G3: eukaryotic translation initiation factor 4 gamma, 3 Hs.25732 N92469 |
| 620 | *Homo sapiens* cDNA: FLJ21971 fis, clone HEP05790 Hs.71331 AA130595: |
| 621 | STAT1: signal transducer and activator of transcription 1, 91 kD Hs.21486 AA079495 |
| 622 | BIRC3: baculoviral IAP repeat-containing 3 Hs.127799 R07870 |
| 623 | HP1-BP74: HP1-BP74 Hs.142442 N20589 |

TABLE 1-continued

| | Gene (Name and/or Symbol) or Number (EST, cDNA clone, or Accession) |
|---|---|
| 624 | HSPC228: hypothetical protein Hs.267288 AI734268 |
| 625 | KIAA0675: KIAA0675 gene product Hs.165662 AA454867 |
| 626 | AMD1: S-adenosylmethionine decarboxylase 1 Hs.262476 AA504772 |
| 627 | EST: Hs.149338 AI249089 |
| 628 | PWP1: nuclear phosphoprotein similar to *S. cerevisiae* PWP1 Hs.172589 AA485992 |
| 629 | AI336973: |
| 630 | DUSP4: dual specificity phosphatase 4 Hs.2359 AA444049 |
| 631 | FLJ12788: hypothetical protein FLJ12788 Hs.20242 AA497041 |
| 632 | HSPC150: HSPC150 protein similar to ubiquitin-conjugating enzyme Hs.5199 AA985450 |
| 633 | FLJ11729: hypothetical protein FLJ11729 Hs.286212 W15533 |
| 634 | KLF4: Kruppel-like factor 4 (gut) Hs.7934 H45668 |
| 635 | FLJ11058: hypothetical protein FLJ11058 Hs.180817 N63911 |
| 636 | FLJ23468: hypothetical protein FLJ23468 Hs.38178 AA460299 |
| 637 | ESTs: Hs.115315 AI278336 |
| 638 | EBI3: Epstein-Barr virus induced gene 3 Hs.185705 AA425028 EBI3 = cytokine receptor |
| 639 | ESTs: Hs.293797 N63988 |
| 640 | MGAT2: mannosyl (alpha-1,6-)-glycoprotein beta-1,2-N-acetylglucosaminyltransferase Hs.172195 AA485653 |
| 641 | H2BFQ: H2B histone family, member Q Hs.2178 AA456298 |
| 642 | NMB: neuromedin B Hs.83321 AI650675 |
| 643 | SSR3: signal sequence receptor, gamma (translocon-associated protein gamma) Hs.28707 AA453486 |
| 644 | HSPC196: hypothetical protein Hs.239938 R78498 |
| 645 | EST: Hs.44522 N33610 |
| 646 | BRF1: butyrate response factor 1 (EGF-response factor 1) Hs.85155 AA723035 |
| 647 | MAN1A2: mannosidase, alpha, class 1A, member 2 Hs.239114 H97940 |
| 648 | KIAA1201: KIAA1201 protein Hs.251278 AA427719 |
| 649 | NUCKS: similar to rat nuclear ubiquitous casein kinase 2 Hs.118064 AA158345 |
| 650 | MAGEF1: MAGEF1 protein Hs.306123 AA425302 |
| 651 | Human: Chromosome 16 BAC clone CIT987SK-A-362G6 Hs.6349 N75498 |
| 652 | R40377: |
| 653 | AP3M2: adaptor-related protein complex 3, mu 2 subunit Hs.77770 R14443 |
| 654 | ESTs,: Weakly similar to 1207289A reverse transcriptase related protein [*H. sapiens*] Hs.272135 AA705010 |
| 655 | *Homo sapiens* mRNA for FLJ00116 protein, partial cds Hs.72363 AA159893: |
| 656 | EIF4E: eukaryotic translation initiation factor 4E Hs.79306 AA193254 |
| 657 | *Homo sapiens* mRNA for hypothetical protein (TR2/D15 gene) Hs.180545 N47285: |
| 658 | ESTs: Hs.99542 AA461474 |
| 659 | CTNND1: catenin (cadherin-associated protein), delta 1 Hs.166011 AA024656 |
| 660 | ESTs: Hs.188554 R75884 |
| 661 | ZNF217: zinc finger protein 217 Hs.155040 R81830 |
| 662 | FLJ12892: hypothetical protein FLJ12892 Hs.17731 AI243595 |
| 663 | ETV5: ets variant gene 5 (ets-related molecule) Hs.43697 AA460265 |
| 664 | EST: Hs.251574 T54821 |
| 665 | RPS25: ribosomal protein S25 Hs.113029 T98662 |
| 666 | CNN2: calponin 2 Hs.169718 AA284568 |
| 667 | ESTs,: Weakly similar to plakophilin 2b [*H. sapiens*] Hs.12705 AA485365 |
| 668 | PAPPA: pregnancy-associated plasma protein A Hs.75874 AA609463 |
| 669 | TFF3: trefoil factor 3 (intestinal) Hs.82961 N74131 |
| 670 | AI204264: |
| 671 | DJ328E19.C1.1: hypothetical protein Hs.218329 AA486041 |
| 672 | ME3: malic enzyme 3, NADP(+)-dependent, mitochondrial Hs.2838 AA779401 |
| 673 | ESTs,: Weakly similar to IEFS_HUMAN TRANSFORMATION-SENSITIVE PROTEIN IEF SSP 3521 [*H. sapiens*] Hs.43213 AA490554 |
| 674 | FLJ13181: hypothetical protein FLJ13181 Hs.301526 AA057266 |
| 675 | KIAA1547: KIAA1547 protein Hs.31305 AA136692 |
| 676 | ZNF281: zinc finger protein 281 Hs.59757 N47468 |
| 677 | *Homo sapiens* cDNA: FLJ23260 fis, clone COL05804, highly similar to HSU90911 Human clone 23652 mRNA sequence Hs.13996 AA463961: |
| 678 | ESTs: Hs.25933 AA411392 |
| 679 | NCBP1: nuclear cap binding protein subunit 1, 80 kD Hs.89563 AA278749 nuclear cap binding protein |
| 680 | H2BFL: H2B histone family, member L Hs.239884 H70774 |
| 681 | DKFZP564A122: DKFZP564A122 protein Hs.187991 H66150 |
| 682 | NASP: nuclear autoantigenic sperm protein (histone-binding) Hs.243886 AA644128 |
| 683 | **ESTs,: Weakly similar to KIAA0822 protein [*H. sapiens*] Hs.98368 AA422008 |
| 684 | MAP2K6: mitogen-activated protein kinase kinase 6 Hs.118825 H07920 |
| 685 | ESTs: Hs.158357 AA865842 |
| 686 | GADD45A: growth arrest and DNA-damage-inducible, alpha Hs.80409 AA147214 GADD45 alpha = growth arrest and DNA-damage-inducible protein |
| 687 | DHFR: dihydrofolate reductase Hs.83765 AA488803 |
| 688 | AA151930: |
| 689 | *Homo sapiens* mRNA; cDNA DKFZp434P116 (from clone DKFZp434P116); complete cds Hs.103378 AA431133: |
| 690 | *Homo sapiens* mRNA; cDNA DKFZp564D156 (from clone DKFZp564D156) Hs.9927 T55704: |

TABLE 1-continued

| | Gene (Name and/or Symbol) or Number (EST, cDNA clone, or Accession) |
|---|---|
| 691 | ESTs: Hs.32204 R93719 |
| 692 | PRPSAP1: phosphoribosyl pyrophosphate synthetase-associated protein 1 Hs.77498 R20005 |
| 693 | ZNF42: zinc finger protein 42 (myeloid-specific retinoic acid-responsive) Hs.169832 AA987906 |
| 694 | **ESTs: Hs.43712 N25936 |
| 695 | RUNX1: runt-related transcription factor 1 (acute myeloid leukemia 1; aml1 oncogene) Hs.129914 AA146826 |
| 696 | *Homo sapiens* mRNA; cDNA DKFZp547C244 (from clone DKFZp547C244) Hs.9460 T64452: |
| 697 | TYMS: thymidylate synthetase Hs.82962 AA663310 |
| 698 | MGC5528: hypothetical protein MGC5528 Hs.315167 AA843451 |
| 699 | ESTs: Hs.268685 R22952 |
| 700 | SFPQ: splicing factor proline/glutamine rich (polypyrimidine tract-binding protein-associated) Hs.180610 AA418910 |
| 701 | ESTs: Hs.155105 AI221390 |
| 702 | FLJ10624: hypothetical protein FLJ10624 Hs.306000 AA489592 |
| 703 | TRIP8: thyroid hormone receptor interactor 8 Hs.6685 AA425205 |
| 704 | DNAJB6: DnaJ (Hsp40) homolog, subfamily B, member 6 Hs.181195 AA496105 |
| 705 | ESTs: Hs.18331 T98244 |
| 706 | RBM14: RNA binding motif protein 14 Hs.11170 AA421233 |
| 707 | SCYA2: small inducible cytokine A2 (monocyte chemotactic protein 1, homologous to mouse Sig-je) Hs.303649 AA425102 MCP-1 = MCAF = small inducible cytokine A2 = JE = chemokine |
| 708 | MGC4161: hypothetical protein MGC4161 Hs.177688 AI224867 |
| 709 | TUBB2: tubulin, beta, 2 Hs.251653 AA888148 |
| 710 | FLJ20280: hypothetical protein FLJ20280 Hs.270134 N74086 |
| 711 | TERA: TERA protein Hs.180780 AA465096 |
| 712 | CPS1: **carbamoyl-phosphate synthetase 1, mitochondrial Hs.50966 N68399 |
| 713 | KIAA0802: KIAA0802 protein Hs.27657 W55875 |
| 714 | FYN: FYN oncogene related to SRC, FGR, YES Hs.169370 N22980 |
| 715 | *Homo sapiens* PRO2751 mRNA, complete cds Hs.283978 H12784: |
| 716 | CLTH: Clathrin assembly lymphoid-myeloid leukemia gene Hs.7885 AA441930 |
| 717 | CHMP1.5: CHMP1.5 protein Hs.42733 W85875 |
| 718 | SMARCB1: SWI/SNF related, matrix associated, actin dependent regulator of chromatin, subfamily b, member 1 Hs.159971 AA446018 |
| 719 | AA487823: SRF = c-fos serum response element-binding transcription facto |
| 720 | **ESTs: Hs.130741 AA608725 |
| 721 | *Homo sapiens* cDNA FLJ10976 fis, clone PLACE1001399 Hs.296323 R36085: |
| 722 | FLJ20036: hypothetical protein FLJ20036 Hs.32922 N91145 |
| 723 | C11ORF5: chromosome 11 open reading frame 5 Hs.121025 AA776702 |
| 724 | AF3P21: SH3 protein Hs.102929 N94372 |
| 725 | LOC54104: hypothetical protein Hs.12871 H05934 |
| 726 | DF: D component of complement (adipsin) Hs.155597 AA233549 |
| 727 | CEP4: Cdc42 effector protein 4; binder of Rho GTPases 4 Hs.3903 AA449061 |
| 728 | KIF5B: kinesin family member 5B Hs.149436 AA644218 |
| 729 | MGC5627: hypothetical protein MGC5627 Hs.237971 H02336 |
| 730 | G3BP: Ras-GTPase-activating protein SH3-domain-binding protein Hs.220689 AA449834 |
| 731 | ESTs: Hs.293987 AA229758 |
| 732 | ESTs: Hs.36828 AA194796 |
| 733 | *Homo sapiens* mRNA for FLJ00101 protein, partial cds Hs.221600 W92262: |
| 734 | *Homo sapiens* cDNA: FLJ21288 fis, clone COL01927 Hs.6019 R07184: |
| 735 | ESTs,: Weakly similar to 1207289A reverse transcriptase related protein [*H. sapiens*] Hs.250594 H86813 |
| 736 | *Homo sapiens* cDNA FLJ11941 fis, clone HEMBB1000649 Hs.124106 AI301573: |
| 737 | ESTs: Hs.24908 H77726 |
| 738 | TOB2: transducer of ERBB2, 2 Hs.4994 AA486088 |
| 739 | ESTs: Hs.143900 AI193212 |
| 740 | *Homo sapiens* clone FLC0675 PRO2870 mRNA, complete cds Hs.306117 H16589: |
| 741 | ESTs,: Weakly similar to KIAA0638 protein [*H. sapiens*] Hs.296288 T83657 |
| 742 | FLJ20039: hypothetical protein FLJ20039 Hs.267448 AA448268 |
| 743 | RPA2: replication protein A2 (32 kD) Hs.79411 R13557 |
| 744 | GAS1: growth arrest-specific 1 Hs.65029 AA025819 |
| 745 | Human: DNA sequence from clone 967N21 on chromosome 20p12.3-13. Contains the CHGB gene for chromogranin B (secretogranin 1, SCG1), a pseudogene similar to part of KIAA0172, the gene for a novel protein Hs.88959 R56678 |
| 746 | ESTs: Hs.21175 AI341642 |
| 747 | LBC: lymphoid blast crisis oncogene Hs.301946 AA135716 |
| 748 | ESTs: Hs.194595 R06761 |
| 749 | MGC4707: hypothetical protein MGC4707 Hs.291003 R14653 |
| 750 | ZNF183: zinc finger protein 183 (RING finger, C3HC4 type) Hs.64794 AA132766 |
| 751 | RAD18: postreplication repair protein hRAD18p Hs.21320 R59197 |
| 752 | EIF4EBP2: **eukaryotic translation initiation factor 4E binding protein 2 Hs.278712 H15159 |
| 753 | ***Homo sapiens* mRNA; cDNA DKFZp586M0723 (from clone DKFZp586M0723) Hs.27860 AA446650: |
| 754 | ORC3L: origin recognition complex, subunit 3 (yeast homolog)-like Hs.74420 H99257 |

TABLE 1-continued

| | Gene (Name and/or Symbol) or Number (EST, cDNA clone, or Accession) |
|---|---|
| 755 | CDK7: cyclin-dependent kinase 7 (homolog of *Xenopus* MO15 cdk-activating kinase) Hs.184298 AI311067 |
| 756 | USP10: ubiquitin specific protease 10 Hs.78829 AA455233 |
| 757 | KIAA0733: TAK1-binding protein 2; KIAA0733 protein Hs.109727 AA931658 |
| 758 | R89286: |
| 759 | ALDH4: aldehyde dehydrogenase 4 (glutamate gamma-semialdehyde dehydrogenase; pyrroline-5-carboxylate dehydrogenase) Hs.77448 AA181378 |
| 760 | IDN3: IDN3 protein Hs.225767 N62911 |
| 761 | ESTs: Hs.50180 H48143 |
| 762 | MIG2: mitogen inducible 2 Hs.75260 H29252 |
| 763 | KIAA0856: KIAA0856 protein Hs.13264 R12847 |
| 764 | EST: Hs.47763 N54162 |
| 765 | *Homo sapiens* mRNA; cDNA DKFZp547C244 (from clone DKFZp547C244) Hs.9460 AA447553: |
| 766 | KIAA0855: golgin-67 Hs.182982 AA775625 |
| 767 | ESTs,: Weakly similar to JH0148 nucleolin - rat [*R. norvegicus*] Hs.30120 R54659 |
| 768 | FLJ22313: hypothetical protein FLJ22313 Hs.30211 H52061 |
| 769 | ESTs: Hs.71818 AI028074 |
| 770 | KIAA0618: KIAA0618 gene product Hs.295112 AA455506 |
| 771 | ESTs: Hs.59413 W93056 |
| 772 | ESTs: Hs.165607 AA992090 |
| 773 | UBAP: ubiquitin associated protein Hs.75425 AA446016 |
| 774 | HAN11: WD-repeat protein Hs.176600 AA725641 |
| 775 | USP16: ubiquitin specific protease 16 Hs.99819 AA489619 |
| 776 | ESTs: Hs.67776 AA464963 |
| 777 | SM-20: similar to rat smooth muscle protein SM-20 Hs.6523 H56028 |
| 778 | CCNG2: cyclin G2 Hs.79069 AA489647 |
| 779 | *Homo sapiens* mRNA; cDNA DKFZp566P1124 (from clone DKFZp566P1124) Hs.321022 N62953: |
| 780 | FLJ20094: hypothetical protein FLJ20094 Hs.29700 N95490 |
| 781 | LOC51174: delta-tubulin Hs.270847 W33133 |
| 782 | *Homo sapiens* mRNA; cDNA DKFZp434I1820 (from clone DKFZp434I1820); partial cds Hs.14235 N52394: |
| 783 | FANCA: Fanconi anemia, complementation group A Hs.284153 AA644129 |
| 784 | P5-1: MHC class I region ORF Hs.1845 T58146 |
| 785 | DNA2L: DNA2 (DNA replication helicase, yeast, homolog)-like Hs.194665 AA974495 KIAA0083 |
| 786 | LOC51578: **adrenal gland protein AD-004 Hs.279586 AA150301 |
| 787 | ESTs: Hs.326417 AA913304 |
| 788 | CDKN2D: cyclin-dependent kinase inhibitor 2D (p19, inhibits CDK4) Hs.29656 R77517 p19-INK4D = Cyclin-dependent kinase 4 inhibitor D |
| 789 | FABP1: fatty acid binding protein 1, liver Hs.5241 AA682392 |
| 790 | TERA: TERA protein Hs.180780 AA906997 |
| 791 | ESTs: Hs.145383 AI253072 |
| 792 | SLC7A5: solute carrier family 7 (cationic amino acid transporter, y+ system), member 5 Hs.184601 AA419176 |
| 793 | AXL: AXL receptor tyrosine kinase Hs.83341 H15336 axl = ufo = tyrosine kinase receptor |
| 794 | LOC57190: selenoprotein N Hs.8518 AA284276 |
| 795 | ESTs: Hs.99037 AA443948 |
| 796 | STCH: stress 70 protein chaperone, microsome-associated, 60 kD Hs.288799 H85311 |
| 797 | ESTs: Hs.88523 AA278591 Unknown UG Hs.88523 ESTs |
| 798 | ESD: **esterase D/formylglutathione hydrolase Hs.82193 AA250931 |
| 799 | ESTs: Hs.122444 R31021 |
| 800 | ESTs: Hs.283127 AI291262 |
| 801 | KIAA0480: **KIAA0480 gene product Hs.92200 H91332 |
| 802 | HP1-BP74: HP1-BP74 Hs.142442 AA598791 |
| 803 | **ESTs,: Moderately similar to ALU1_HUMAN ALU SUBFAMILY J SEQUENCE CONTAMINATION WARNING ENTRY [*H. sapiens*] Hs.144662 AA987667 |
| 804 | TTF2: transcription termination factor, RNA polymerase II Hs.142157 AI023603 |
| 805 | ESTs: Hs.13740 T70541 |
| 806 | DJ37E16.5: hypothetical protein dJ37E16.5 Hs.5790 AA400021 |
| 807 | CDH24: cadherin-like 24 Hs.155912 AI732266 |
| 808 | DJ465N24.2.1: **hypothetical protein dJ465N24.2.1 Hs.8084 AA932375 |
| 809 | ESTs,: Weakly similar to S57447 HPBRII-7 protein [*H. sapiens*] Hs.16346 AA410490 |
| 810 | *Homo sapiens* cDNA: FLJ23285 fis, clone HEP09071 Hs.90424 AI005038: |
| 811 | KRAS2: v-Ki-ras2 Kirsten rat sarcoma 2 viral oncogene homolog Hs.184050 N95249 |
| 812 | FLJ20038: hypothetical protein FLJ20038 Hs.72071 H96090 |
| 813 | ESTs,: Weakly similar to ALU4_HUMAN ALU SUBFAMILY SB2 SEQUENCE CONTAMINATION WARNING ENTRY [*H. sapiens*] Hs.28848 AA486607 |
| 814 | H2AFN: H2A histone family, member N Hs.134999 AI095013 |
| 815 | RERE: arginine-glutamic acid dipeptide (RE) repeats Hs.194369 AA490249 |
| 816 | USP1: ubiquitin specific protease 1 Hs.35086 T55607 |
| 817 | TIP47: cargo selection protein (mannose 6 phosphate receptor binding protein) Hs.140452 AA416787 |
| 818 | KIAA0135: KIAA0135 protein Hs.79337 AA427740 KIAA0135 = related to pim-1 kinase. |
| 819 | ESTs: Hs.214410 T95273 |

TABLE 1-continued

| | Gene (Name and/or Symbol) or Number (EST, cDNA clone, or Accession) |
|---|---|
| 820 | PPP1R2: protein phosphatase 1, regulatory (inhibitor) subunit 2 Hs.267819 N52605 |
| 821 | Homo sapiens cDNA: FLJ21210 fis, clone COL00479 Hs.325093 AA978323: |
| 822 | CSNK2A2: casein kinase 2, alpha prime polypeptide Hs.82201 AA054996 |
| 823 | HSRTSBETA: rTS beta protein Hs.180433 N66132 |
| 824 | FLJ13110: hypothetical protein FLJ13110 Hs.7358 AA431233 |
| 825 | ESTs: Hs.238797 N30704 |
| 826 | FYN: FYN oncogene related to SRC, FGR, YES Hs.169370 N35086 |
| 827 | RBM8A: RNA binding motif protein 8A Hs.65648 AA448402 |
| 828 | ESTs: Hs.21906 AA608546 |
| 829 | ESTs: Hs.128081 AA971042 |
| 830 | PP591: hypothetical protein PP591 Hs.118666 AA626336 |
| 831 | N63866: |
| 832 | HM74: putative chemokine receptor; GTP-binding protein Hs.137555 R02739 |
| 833 | MID1: midline 1 (Opitz/BBB syndrome) Hs.27695 AA598640 |
| 834 | KIAA1586: KIAA1586 protein Hs.180663 AA938639 |
| 835 | Homo sapiens clone CDABP0014 mRNA sequence Hs.92679 AA443139: |
| 836 | HSU79274: protein predicted by clone 23733 Hs.150555 AA451900 |
| 837 | AOC3: amine oxidase, copper containing 3 (vascular adhesion protein 1) Hs.198241 AA036974 |
| 838 | AA548037: |
| 839 | FLJ10154: hypothetical protein FLJ10154 Hs.179972 AA457133 |
| 840 | THBS1: thrombospondin 1 Hs.87409 AA464532 |
| 841 | DNAJB6: DnaJ (Hsp40) homolog, subfamily B, member 6 Hs.181195 AA431203 |
| 842 | KIAA1547: KIAA1547 protein Hs.31305 AI216623 |
| 843 | GATA2: GATA-binding protein 2 Hs.760 R32405 |
| 844 | ESTs: Hs.176950 R82522 |
| 845 | KIAA1018: KIAA1018 protein Hs.5400 AA156859 |
| 846 | B4GALT1: **UDP-Gal:betaGlcNAc beta 1,4-galactosyltransferase, polypeptide 1 Hs.198248 AA043795 |
| 847 | HMGCR: 3-hydroxy-3-methylglutaryl-Coenzyme A reductase Hs.11899 AA779417 |
| 848 | ESTs,: Weakly similar to 1819485A CENP-E protein [H. sapiens] Hs.167652 H94466 |
| 849 | ESTs: Hs.294088 AA971073 |
| 850 | KIAA1637: coactivator independent of AF-2 (CIA); KIAA1637 protein Hs.288140 AA918007 |
| 851 | HSPC196: hypothetical protein Hs.239938 H66023 |
| 852 | DR1: down-regulator of transcription 1, TBP-binding (negative cofactor 2) Hs.16697 AA132007 |
| 853 | CG1I: putative cyclin G1 interacting protein Hs.10028 AA486444 |
| 854 | IGSF4: immunoglobulin superfamily, member 4 Hs.70337 AA487505 |
| 855 | ESTs: Hs.179309 AA664350 |
| 856 | HSPC163: HSPC163 protein Hs.108854 AA053139 |
| 857 | FLJ12788: hypothetical protein FLJ12788 Hs.20242 AI061317 |
| 858 | FEM1B: FEM-1 (C. elegans) homolog b Hs.6048 H82273 |
| 859 | FXR1: fragile X mental retardation, autosomal homolog 1 Hs.82712 N62761 |
| 860 | NCOA3: nuclear receptor coactivator 3 Hs.225977 AA156793 |
| 861 | H2BFB: H2B histone family, member B Hs.180779 N33927 |
| 862 | ESTs: Hs.23830 AA460601 |
| 863 | CDK7: cyclin-dependent kinase 7 (homolog of Xenopus MO15 cdk-activating kinase) Hs.184298 AA031961 CAK = cdk7 = NRTALRE = sdk = CDK activating kinase |
| 864 | FLJ20259: hypothetical protein FLJ20259 Hs.9956 T55949 |
| 865 | Homo sapiens cDNA FLJ20678 fis, clone KAIA4163 Hs.143601 T95823: |
| 866 | RPS19: ribosomal protein S19 Hs.298262 T72208 |
| 867 | Homo sapiens mRNA; cDNA DKFZp434M0420 (from clone DKFZp434M0420) Hs.326048 AA443976: |
| 868 | TP53: tumor protein p53 (Li-Fraumeni syndrome) Hs.1846 R39356 p53 |
| 869 | FBI1: HIV-1 inducer of short transcripts binding protein Hs.104640 R06252 |
| 870 | GOT1: glutamic-oxaloacetic transaminase 1, soluble (aspartate aminotransferase 1) Hs.597 H22855 |
| 871 | FLJ21434: hypothetical protein FLJ21434 Hs.298503 AA680129 |
| 872 | DNMT2: DNA (cytosine-5-)-methyltransferase 2 Hs.97681 R95731 |
| 873 | ESTs: Hs.55272 W02785 |
| 874 | H2BFQ: H2B histone family, member Q Hs.2178 AA010223 |
| 875 | NFIC: nuclear factor I/C (CCAAT-binding transcription factor) Hs.184771 N20996 |
| 876 | NPTX1: neuronal pentraxin I Hs.84154 H22445 |
| 877 | TLOC1: translocation protein 1 Hs.8146 AA450205 |
| 878 | MGC5302: endoplasmic reticulum resident protein 58; hypothetical protein MGC5302 Hs.44970 N39195 |
| 879 | ACTR2: ARP2 (actin-related protein 2, yeast) homolog Hs.42915 AA032090 |
| 880 | AI287555: |
| 881 | ABCA7: ATP-binding cassette, sub-family A (ABC1), member 7 Hs.134514 AI668632 |
| 882 | COL7A1: collagen, type VII, alpha 1 (epidermolysis bullosa, dystrophic, dominant and recessive) Hs.1640 AA598507 |
| 883 | RFC2: replication factor C (activator 1) 2 (40 kD) Hs.139226 AA663472 |
| 884 | FLJ22583: hypothetical protein FLJ22583 Hs.287700 AA135836 |
| 885 | **ESTs,: Weakly similar to ORF2 [M. musculus] Hs.172208 AI820570 |
| 886 | ESTs: Hs.21667 R15709 |
| 887 | RBBP4: retinoblastoma-binding protein 4 Hs.16003 AA705035 |

TABLE 1-continued

| | Gene (Name and/or Symbol) or Number (EST, cDNA clone, or Accession) |
|---|---|
| 888 | *Homo sapiens* mRNA; cDNA DKFZp434J1027 (from clone DKFZp434J1027); partial cds Hs.22908 R20166: |
| 889 | ESTs: Hs.166539 AI080987 |
| 890 | NKTR: natural killer-tumor recognition sequence Hs.241493 AA279666 NK-tumor recognition protein = cyclophilin-related protein |
| 891 | MUC1: mucin 1, transmembrane Hs.89603 AA486365 |
| 892 | AP4B1: adaptor-related protein complex 4, beta 1 subunit Hs.28298 AA481045 |
| 893 | ESTs: Hs.94943 AA452165 |
| 894 | MITF: microphthalmia-associated transcription factor Hs.166017 N66177 |
| 895 | ESTs: Hs.183299 AA286914 Unknown UG Hs.183299 ESTs sc_id2032 |
| 896 | BAG3: BCL2-associated athanogene 3 Hs.15259 AI269958 |
| 897 | INSR: insulin receptor Hs.89695 AA001106 |
| 898 | TRIP: TRAF interacting protein Hs.21254 AA186426 |
| 899 | EST: Hs.307975 R22182 |
| 900 | **Homo sapiens* cDNA: FLJ23037 fis, clone LNG02036, highly similar to HSU68019 *Homo sapiens* mad protein homolog (hMAD-3) mRNA Hs.288261 W72201: |
| 901 | HLA-DNA: major histocompatibility complex, class II, DN alpha Hs.11135 AA702254 Major histocompatibility complex, class II, DN alpha |
| 902 | FLJ10392: **hypothetical protein FLJ10392 Hs.20887 AI261305 |
| 903 | MPHOSPH1: **M-phase phosphoprotein 1 Hs.240 N63752 |
| 904 | STAG1: stromal antigen 1 Hs.286148 R36160 |
| 905 | USP1: ubiquitin specific protease 1 Hs.35086 AA970066 |
| 906 | ESTs,: Moderately similar to ALU4_HUMAN ALU SUBFAMILY SB2 SEQUENCE CONTAMINATION WARNING ENTRY [*H. sapiens*] Hs.181315 AA448251 |
| 907 | PA26: p53 regulated PA26 nuclear protein Hs.14125 AA447661 |
| 908 | ESTs,: Weakly similar to zinc finger protein [*H. sapiens*] Hs.71243 N92478 |
| 909 | SH3PX1: SH3 and PX domain-containing protein SH3PX1 Hs.7905 R69163 |
| 910 | **Homo sapiens* cDNA: FLJ22554 fis, clone HSI01092 Hs.93842 H58317: |
| 911 | RPS25: ribosomal protein S25 Hs.113029 AA779404 |
| 912 | ESTs,: Weakly similar to A49134 Ig kappa chain V-I region [*H. sapiens*] Hs.5890 N34799 fra-2 = fos-related antigen 2 |
| 913 | TXNRD1: thioredoxin reductase 1 Hs.13046 AA453335 Thioredoxin reductase |
| 914 | **ESTs: Hs.184378 N77828 |
| 915 | GCSH: glycine cleavage system protein H (aminomethyl carrier) Hs.77631 R71327 |
| 916 | *Homo sapiens* cDNA FLJ11904 fis, clone HEMBB1000048 Hs.285519 AA447098: |
| 917 | NCOA3: nuclear receptor coactivator 3 Hs.225977 H51990 AIB1 = Amplified in Breast Cancer = TRAM-1 = RAC3 = ACTR = CAGH16 = nucl |
| 918 | FLJ20159: hypothetical protein FLJ20159 Hs.288809 R33122 |
| 919 | IL7R: interleukin 7 receptor Hs.237868 AA487121 |
| 920 | RAB23: RAB23, member RAS oncogene family Hs.94769 AA134569 |
| 921 | ESTs: Hs.132493 AA923168 |
| 922 | ESTs: Hs.87507 AA236015 |
| 923 | SHC1: SHC (Src homology 2 domain-containing) transforming protein 1 Hs.81972 R52960 |
| 924 | KIAA1321: KIAA1321 protein Hs.24336 W37999 |
| 925 | GLI: glioma-associated oncogene homolog (zinc finger protein) Hs.2693 AI373071 |
| 926 | ESTs: Hs.183299 AA291137 Unknown UG Hs.183299 ESTs sc_id2032 |
| 927 | GPRK6: G protein-coupled receptor kinase 6 Hs.76297 AA291284 |
| 928 | ESTs: Hs.93704 AA702684 |
| 929 | CAPS: calcyphosine Hs.26685 AA858390 |
| 930 | *Homo sapiens* cDNA FLJ10976 fis, clone PLACE1001399 Hs.296323 R27711: |
| 931 | C6: complement component 6 Hs.1282 N59396 |
| 932 | UBE2D3: ubiquitin-conjugating enzyme E2D 3 (homologous to yeast UBC4/5) Hs.118797 AA465196 |
| 933 | DDX8: DEAD/H (Asp-Glu-Ala-Asp/His) box polypeptide 8 (RNA helicase) Hs.171872 AA465387 RNA helicase (HRH1) |
| 934 | DKFZP434B168: DKFZP434B168 protein Hs.48604 N62684 |
| 935 | FLJ10512: hypothetical protein FLJ10512 Hs.93581 T39933 |
| 936 | *Homo sapiens* mRNA; cDNA DKFZp564F093 (from clone DKFZp564F093) Hs.18724 W87709: |
| 937 | F8A: coagulation factor VIII-associated (intronic transcript) Hs.83363 AA463924 |
| 938 | HSU53209: transformer-2 alpha (htra-2 alpha) Hs.24937 AA465172 |
| 939 | UBQLN2: ubiquilin 2 Hs.4552 R43580 |
| 940 | EIF2C2: eukaryotic translation initiation factor 2C, 2 Hs.193053 N93082 |
| 941 | *Homo sapiens* mRNA for FLJ00012 protein, partial cds Hs.21051 H17645: |
| 942 | KIAA0841: KIAA0841 protein Hs.7426 R20299 |
| 943 | KCNAB2: potassium voltage-gated channel, shaker-related subfamily, beta member 2 Hs.298184 H14383 |
| 944 | KIAA1637: coactivator independent of AF-2 (CIA); KIAA1637 protein Hs.288140 AA521358 |
| 945 | ESTs: Hs.27379 H17455 |
| 946 | FLJ11323: hypothetical protein FLJ11323 Hs.25625 R49707 |
| 947 | SSP29: acidic protein rich in leucines Hs.84264 AA489201 |
| 948 | ESTs: Hs.69280 AA486011 |
| 949 | ADAMTS1: a disintegrin-like and metalloprotease (reprolysin type) with thrombospondin type 1 motif, 1 Hs.8230 AA057170 |
| 950 | ESTs: Hs.43466 N23889 |

TABLE 1-continued

Gene (Name and/or Symbol) or Number (EST, cDNA clone, or Accession)

951 MLLT4: myeloid/lymphoid or mixed-lineage leukemia (trithorax (*Drosophila*) homolog); translocated to, 4 Hs.100469 AA010818
952 ESTs: Hs.271034 AA406581
953 LMNB1: lamin B1 Hs.89497 AA983462
954 *Homo sapiens* cDNA FLJ13547 fis, clone PLACE1007053 Hs.7984 AA629264:
955 PTMS: parathymosin Hs.171814 R10451
956 H2AFL: H2A histone family, member L Hs.28777 AI268551
957 FLJ21603: hypothetical protein FLJ21603 Hs.129691 R72794
958 FLJ13287: hypothetical protein FLJ13287 Hs.53263 AA621725
959 CXCR4: chemokine (C—X—C motif), receptor 4 (fusin) Hs.89414 AA479357
960 INSM1: insulinoma-associated 1 Hs.89584 R38640
961 FREQ: frequenin (*Drosophila*) homolog Hs.301760 H16821
962 LOC58486: transposon-derived Buster1 transposase-like protein Hs.25726 AA868020
963 SMARCD1: SWI/SNF related, matrix associated, actin dependent regulator of chromatin, subfamily d, member 1 Hs.79335 H91691
964 ESTs: Hs.242998 T96522
965 INADL: PDZ domain protein (*Drosophila* inaD-like) Hs.321197 AA005153
966 ESTs,: Weakly similar to putative p150 [*H. sapiens*] Hs.37751 AA436174
967 MGC5338: hypothetical protein MGC5338 Hs.99598 H50550
968 W85890:
969 NUCKS: similar to rat nuclear ubiquitous casein kinase 2 Hs.118064 AI053436
970 *Homo sapiens* clone 25110 mRNA sequence Hs.27262 H18031:
971 AI333214:
972 GAS41: glioma-amplified sequence-41 Hs.4029 T62072
973 LOC51170: retinal short-chain dehydrogenase/reductase retSDR2 Hs.12150 N79745
974 H2BFG: **H2B histone family, member G Hs.182137 R98472
975 ABCC1: **ATP-binding cassette, sub-family C (CFTR/MRP), member 1 Hs.89433 AA424804
976 EFNA1: ephrin-A1 Hs.1624 AA857015
977 *Homo sapiens* mRNA; cDNA DKFZp434A1014 (from clone DKFZp434A1014); partial cds Hs.278531 H00596:
978 PPP2CA: protein phosphatase 2 (formerly 2A), catalytic subunit, alpha isoform Hs.91773 AA599092
979 ESTs,: Weakly similar to unnamed protein product [*H. sapiens*] Hs.118338 W85843
980 *Homo sapiens* cDNA FLJ11643 fis, clone HEMBA1004366 Hs.111496 AA598803:
981 ESTs,: Moderately similar to ALUE_HUMAN !!!! ALU CLASS E WARNING ENTRY !!! [*H. sapiens*] Hs.125407 AA878944
982 ESTs,: Moderately similar to ALU1_HUMAN ALU SUBFAMILY J SEQUENCE CONTAMINATION WARNING ENTRY [*H. sapiens*] Hs.144662 AI191290
983 KIAA0916: KIAA0916 protein Hs.151411 R91388
984 CDC25A: cell division cycle 25A Hs.1634 R09062
985 PRIM2A: primase, polypeptide 2A (58 kD) Hs.74519 R61073
986 DSP: desmoplakin (DPI, DPII) Hs.74316 H90899
987 KIAA0101: KIAA0101 gene product Hs.81892 W68219
988 ESTs,: Weakly similar to putative p150 [*H. sapiens*] Hs.268026 AA411454
989 ESTs: Hs.18140 T97707
990 H2AFL: H2A histone family, member L Hs.28777 AA457566
991 *Homo sapiens* mRNA for KIAA1700 protein, partial cds Hs.20281 H00287:
992 STAG3: stromal antigen 3 Hs.20132 AA453028
993 ZNF207: zinc finger protein 207 Hs.62112 N59119
994 BMP6: bone morphogenetic protein 6 Hs.285671 AA424833
995 ESTs,: Moderately similar to sertolin [*R. norvegicus*] Hs.91192 H60690
996 LOC51064: **glutathione S-transferase subunit 13 homolog Hs.279952 W88497
997 NUCKS: similar to rat nuclear ubiquitous casein kinase 2 Hs.118064 AA927182
998 ESTs,: Weakly similar to T00370 hypothetical protein KIAA0659 [*H. sapiens*] Hs.131899 W93155
999 FLJ13057: hypothetical protein FLJ13057 similar to germ cell-less Hs.243122 R23254
1000 ESTs: Hs.144796 AI219737
1001 FLJ10511: hypothetical protein FLJ10511 Hs.106768 R25877
1002 DKFZP564A122: DKFZP564A122 protein Hs.187991 N31577
1003 ODF2: outer dense fibre of sperm tails 2 Hs.129055 AA400407
1004 AMY2A: amylase, alpha 2A; pancreatic Hs.278399 R64129
1005 **ESTs,: Weakly similar to plakophilin 2b [*H. sapiens*] Hs.12705 N91589
1006 CYP1B1: cytochrome P450, subfamily I (dioxin-inducible), polypeptide 1 (glaucoma 3, primary infantile) Hs.154654 AA029776
1007 CAPN7: calpain 7 Hs.7145 N46420
1008 FLJ20069: hypothetical protein FLJ20069 Hs.273294 AA229966
1009 FLJ10618: hypothetical protein FLJ10618 Hs.42484 AA478847
1010 KIAA1637: **coactivator independent of AF-2 (CIA); KIAA1637 protein Hs.288140 AA452531
1011 FLJ20004: **hypothetical protein FLJ20004 Hs.17311 AA487895
1012 FLJ12892: hypothetical protein FLJ12892 Hs.17731 AA670363
1013 PLU-1: putative DNA/chromatin binding motif Hs.143323 AA464869
1014 **ESTs: Hs.36828 AA418448
1015 KIAA0586: KIAA0586 gene product Hs.77724 AA905278
1016 MTHFD2: methylene tetrahydrofolate dehydrogenase (NAD+ dependent), methenyltetrahydrofolate cyclohydrolase Hs.154672 AA480994
1017 BRF1: **butyrate response factor 1 (EGF-response factor 1) Hs.85155 AA424743

TABLE 1-continued

| Gene (Name and/or Symbol) or Number (EST, cDNA clone, or Accession) |
| --- |

1018 TFAP2A: transcription factor AP-2 alpha (activating enhancer-binding protein 2 alpha) Hs.18387 R38044
1019 VIL2: villin 2 (ezrin) Hs.155191 AA411440
1020 SDC1: syndecan 1 Hs.82109 AA074511
1021 RNTRE: related to the N terminus of tre Hs.278526 AA281057
1022 HSPC207: hypothetical protein Hs.75798 H99997
1023 FLJ22376: hypothetical protein FLJ22376 Hs.29341 AI199155
1024 RNF10: ring finger protein 10 Hs.5094 H73586
1025 PNN: pinin, desmosome associated protein Hs.44499 AA707321
1026 FLJ20516: hypothetical protein FLJ20516 Hs.70811 AA122393
1027 RPL13A: ribosomal protein L13a Hs.119122 AI254200
1028 H2BFB: H2B histone family, member B Hs.180779 AA885642
1029 OGT: O-linked N-acetylglucosamine (GlcNAc) transferase (UDP-N-acetylglucosamine:polypeptide-N-acetylglucosaminyl transferase) Hs.100293 R13317
1030 KIAA0155: KIAA0155 gene product Hs.173288 AA133684
1031 ILF2: interleukin enhancer binding factor 2, 45 kD Hs.75117 H95638
1032 Homo sapiens mRNA; cDNA DKFZp586I1518 (from clone DKFZp586I1518) Hs.21739 AA287917:
1033 PKNOX1: PBX/knotted 1 homeobox 1 Hs.158225 AI350546
1034 KMO: **kynurenine 3-monooxygenase (kynurenine 3-hydroxylase) Hs.107318 AA044326
1035 VCAM1: vascular cell adhesion molecule 1 Hs.109225 H16591 CD106 = VCAM-1
1036 N54811:
1037 KIAA0618: KIAA0618 gene product Hs.295112 H81940
1038 MAFG: v-maf musculoaponeurotic fibrosarcoma (avian) oncogene family, protein G Hs.252229 N21609 MafG = basic-leucine zipper transcription factor
1039 MATN2: matrilin 2 Hs.19368 AA071473
1040 HOXB4: homeo box B4 Hs.126666 AA918749
1041 FLJ10466: hypothetical protein FLJ10466 Hs.121073 AA453607
1042 FLJ22557: hypothetical protein FLJ22557 Hs.106101 AA127879
1043 EST: Hs.149260 AI247680
1044 KIAA0677: KIAA0677 gene product Hs.155983 AA026751
1045 EST: Hs.104123 AA197344
1046 UCP4: uncoupling protein 4 Hs.40510 H94680
1047 EST: Hs.144224 N93807
1048 GATA2: GATA-binding protein 2 Hs.760 H00625 GATA-binding protein 2
1049 ESTs: Hs.14743 H61082
1050 EST: Hs.116174 AA626786
1051 ITGB3: integrin, beta 3 (platelet glycoprotein IIIa, antigen CD61) Hs.87149 AA666269
1052 FLJ23399: hypothetical protein FLJ23399 Hs.299883 R19895
1053 ESTs: Hs.21734 N72976
1054 FLJ20425: hypothetical protein FLJ20425 Hs.71040 AA424566
1055 CUL4A: cullin 4A Hs.183874 AA598836
1056 PTP4A1: protein tyrosine phosphatase type IVA, member 1 Hs.227777 R61007 protein tyrosine phosphatase PTPCAAX1 (hPTPCAAX1)
1057 ESTs: Hs.7913 N35592
1058 GRO1: GRO1 oncogene (melanoma growth stimulating activity, alpha) Hs.789 W46900
1059 ESTs,: Moderately similar to NRD2 convertase [H. sapiens] Hs.309734 H78796
1060 FLJ10826: hypothetical protein FLJ10826 Hs.24809 AA486738
1061 TOM34: translocase of outer mitochondrial membrane 34 Hs.76927 AA457118
1062 H2AFL: H2A histone family, member L Hs.28777 AA452933
1063 D10S170: **DNA segment, single copy, probe pH4 (transforming sequence, thyroid-1, Hs.315591 N35493
1064 SCYA2: small inducible cytokine A2 (monocyte chemotactic protein 1, homologous to mouse Sig-je) Hs.303649 T77816 MCP-1 = MCAF = small inducible cytokine A2 = JE = chemokine
1065 FLJ10688: hypothetical protein FLJ10688 Hs.118793 AA465358
1066 PTD017: PTD017 protein Hs.274417 AA160498
1067 KIAA0026: MORF-related gene X Hs.173714 AA676604
1068 BMP2: bone morphogenetic protein 2 Hs.73853 AA489383
1069 MNT: MAX binding protein Hs.25497 AA455508
1070 KIAA1170: KIAA1170 protein Hs.268044 H80507
1071 CRYBA1: crystallin, beta A1 Hs.46275 AA487614
1072 KATNA1: katanin p60 (ATPase-containing) subunit A 1 Hs.289099 AA609740
1073 Homo sapiens cDNA FLJ20796 fis, clone COL00301 Hs.113994 N53458:
1074 CEP4: Cdc42 effector protein 4; binder of Rho GTPases 4 Hs.3903 W32509
1075 ESTs: Hs.117261 AA682521
1076 CYP1B1: cytochrome P450, subfamily I (dioxin-inducible), polypeptide 1 (glaucoma 3, primary infantile) Hs.154654 AA040872
1077 ALTE: Ac-like transposable element Hs.9933 AA630498
1078 RAD51: RAD51 (S. cerevisiae) homolog (E coli RecA homolog) Hs.23044 AA873056
1079 MAN1A2: mannosidase, alpha, class 1A, member 2 Hs.239114 R78501
1080 H53763:
1081 MET: met proto-oncogene (hepatocyte growth factor receptor) Hs.285754 AA410591
1082 DYRK1A: dual-specificity tyrosine-(Y)-phosphorylation regulated kinase 1A Hs.75842 AA676749

TABLE 1-continued

Gene (Name and/or Symbol) or Number (EST, cDNA clone, or Accession)

1083 ARHGAP8: **Rho GTPase activating protein 8 Hs.102336 AA037410
1084 LMO4: LIM domain only 4 Hs.3844 H27986
1085 ADCY6: adenylate cyclase 6 Hs.12373 AA148044
1086 EST: Hs.135448 AI078552
1087 NCOA3: nuclear receptor coactivator 3 Hs.225977 W46433
1088 DNAJB4: DnaJ (Hsp40) homolog, subfamily B, member 4 Hs.41693 AA081471
1089 NAB1: NGFI-A binding protein 1 (ERG1 binding protein 1) Hs.107474 AA486027
1090 ESTs,: Weakly similar to T08663 hypothetical protein DKFZp547G0910.1 [*H. sapiens*] Hs.172084 N63646
1091 KIAA0735: KIAA0735 gene product; synaptic vesicle protein 2B homolog Hs.8071 R56082
1092 GNB1: guanine nucleotide binding protein (G protein), beta polypeptide 1 Hs.215595 AA487912
1093 *Homo sapiens* mRNA for KIAA1716 protein, partial cds Hs.21446 R49763:
1094 KINESIN: HEAVY CHAIN
1095 CCND1: cyclin D1 (PRAD1: parathyroid adenomatosis 1) Hs.82932 AA487486
     Cyclin D1 = BCL1 = PRAD1 = Translocated in mantle cell leukemia
1096 ESTs: Hs.106129 R56716
1097 AA431931:
1098 PSEN1: presenilin 1 (Alzheimer disease 3) Hs.3260 AA403083
1099 ESTs: Hs.193804 AA010918
1100 DKFZp762P2111: hypothetical protein DKFZp762P2111 Hs.14217 AA429586
1101 KIAA1350: KIAA1350 protein Hs.101799 W37627
1102 FLJ20847: hypothetical protein FLJ20847 Hs.13479 H16996
1103 HDCMA18P: HDCMA18P protein Hs.278635 N64387
1104 FLJ12890: hypothetical protein FLJ12890 Hs.43299 N62475
1105 ESTs: Hs.127453 AA973625
1106 BAIAP2: BAI1-associated protein 2 Hs.7936 R60328
1107 ESTs: Hs.317584 AA191424
1108 DKFZP434J046: DKFZP434J046 protein Hs.116244 AI024401
1109 ESTs: Hs.114055 AA701352
1110 ESTs: Hs.44380 N93122
1111 ESTs: Hs.20142 AA625570
1112 UBL3: ubiquitin-like 3 Hs.173091 T82438
1113 H2AFL: H2A histone family, member L Hs.28777 N50797
1114 SUCLG2: **succinate-CoA ligase, GDP-forming, beta subunit Hs.247309 N68557
1115 ZWINT: ZW10 interactor Hs.42650 AA706968
1116 FLJ10583: hypothetical protein FLJ10583 Hs.105633 R00425
1117 FLJ20552: hypothetical protein FLJ20552 Hs.69554 AA463982
1118 FADD: Fas (TNFRSF6)-associated via death domain Hs.86131 AA430751
     FADD = MORT
1119 SFRS7: splicing factor, arginine/serine-rich 7 (35 kD) Hs.184167 AA418813
1120 RAD54L: RAD54 (*S. cerevisiae*)-like Hs.66718 AI372035
1121 MYLE: MYLE protein Hs.11902 T68845
1122 LOC51334: mesenchymal stem cell protein DSC54 Hs.157461 R63841
1123 PRIM2A: primase, polypeptide 2A (58 kD) Hs.74519 AA434404
1124 KIAA0056: KIAA0056 protein Hs.13421 AA430545
1125 ESTs,: Moderately similar to ALU7_HUMAN ALU SUBFAMILY SQ SEQUENCE CONTAMINATION WARNING ENTRY [*H. sapiens*] Hs.82590 N53024
1126 ESTs: Hs.117269 AA705050
1127 NSAP1: NS1-associated protein 1 Hs.155489 AA186327
1128 CEACAM5: carcinoembryonic antigen-related cell adhesion molecule 5 Hs.220529 AA130547
1129 FLJ11021: hypothetical protein FLJ11021 similar to splicing factor, arginine/serine-rich 4 Hs.81648 AA291183 Unknown UG Hs.202583 ESTs, Weakly similar to arginine-rich
1130 FOSL1: FOS-like antigen-1 Hs.283565 T82817 fra-1 = fos-related antigen 1
1131 U3-55K: U3 snoRNP-associated 55-kDa protein Hs.153768 AA465355
1132 DNAJC6: DnaJ (Hsp40) homolog, subfamily B, member 6 Hs.44896 AA455940
1133 KIAA1382: amino acid transporter 2 Hs.298275 R27255 Similar to transporter protein
1134 PCAF: p300/CBP-associated factor Hs.199061 N74637 P/CAF = p300/CBP-associated factor
1135 ESTs: Hs.130460 AA927252
1136 ESTs: Hs.112570 AI014667
1137 FLJ10209: hypothetical protein FLJ10209 Hs.260150 AA454626
1138 ESTs: Hs.99014 AA485679
1139 ESTs: Hs.99621 AA464707
1140 *Homo sapiens* cDNA FLJ11904 fis, clone HEMBB1000048 Hs.285519 N74617:
1141 AA928536:
1142 SQSTM1: **sequestosome 1 Hs.182248 AA931964
1143 ***Homo sapiens* cDNA FLJ13700 fis, clone PLACE2000216, highly similar to SPECTRIN BETA CHAIN, BRAIN Hs.324648 AA018591:
1144 SLC22A3: solute carrier family 22 (extraneuronal monoamine transporter), member 3 Hs.81086 AA460012
1145 FLJ22557: hypothetical protein FLJ22557 Hs.106101 H00595

TABLE 1-continued

| | Gene (Name and/or Symbol) or Number (EST, cDNA clone, or Accession) |
|---|---|
| 1146 | FLJ20539: hypothetical protein FLJ20539 Hs.118552 R36152 |
| 1147 | AA991624: |
| 1148 | TRAP150: thyroid hormone receptor-associated protein, 150 kDa subunit Hs.108319 W85832 |
| 1149 | ESTs: Hs.221847 R91557 |
| 1150 | TCFL1: transcription factor-like 1 Hs.2430 AA443950 |
| 1151 | ESTs,: Highly similar to oxytocinase splice variant 1 [*H. sapiens*] Hs.203271 AA487918 |
| 1152 | PLAB: prostate differentiation factor Hs.296638 AA450062 |
| 1153 | RBM14: RNA binding motif protein 14 Hs.11170 AA417283 |
| 1154 | EGFL5: EGF-like-domain, multiple 5 Hs.5599 W67981 |
| 1155 | H2AFO: H2A histone family, member O Hs.795 AA047260 |
| 1156 | ESTs,: Weakly similar to A46661 leukotriene B4 omega-hydroxylase [*H. sapiens*] Hs.169001 N45556 |
| 1157 | W78784: |
| 1158 | TOP3A: topoisomerase (DNA) III alpha Hs.91175 N21546 |
| 1159 | W73732: Host cell factor-1 = VP16 transactivator interacting protein |
| 1160 | CYP1B1: cytochrome P450, subfamily I (dioxin-inducible), polypeptide 1 (glaucoma 3, primary infantile) Hs.154654 AA448157 Cytochrome P450 IB1 (dioxin-inducible) |
| 1161 | ESTs: Hs.135276 AI092102 |
| 1162 | RHEB2: Ras homolog enriched in brain 2 Hs.279903 AA482117 |
| 1163 | ESTs,: Highly similar to EF-9 [*M. musculus*] Hs.8366 H94467 |
| 1164 | POLA: polymerase (DNA directed), alpha Hs.267289 AA707650 |
| 1165 | KIAA1008: KIAA1008 protein Hs.323346 AA863115 |
| 1166 | PIK3CD: phosphoinositide-3-kinase, catalytic, delta polypeptide Hs.162808 AA281652 |
| 1167 | T53625: |
| 1168 | ***Homo sapiens* mRNA; cDNA DKFZp434A1114 (from clone DKFZp434A1114) Hs.326292 AA417274: |
| 1169 | ESTs: Hs.26744 H16988 |
| 1170 | FLJ13912: hypothetical protein FLJ13912 Hs.47125 W74133 |
| 1171 | *Homo sapiens* mRNA; cDNA DKFZp762B195 (from clone DKFZp762B195) Hs.284158 AA625574: |
| 1172 | SSA2: Sjogren syndrome antigen A2 (60 kD, ribonucleoprotein autoantigen SS-A/Ro) Hs.554 AA010351 |
| 1173 | BK1048E9.5: hypothetical protein bK1048E9.5 Hs.6657 N68512 |
| 1174 | TOP1: topoisomerase (DNA) I Hs.317 AA232856 Topoisomerase I |
| 1175 | ESTs: Hs.15386 H18472 |
| 1176 | KPNB1: karyopherin (importin) beta 1 Hs.180446 AA121732 |
| 1177 | MGC861: hypothetical protein MGC861 Hs.208912 N69694 |
| 1178 | PMS2L8: **postmeiotic segregation increased 2-like 8 Hs.323954 T62577 |
| 1179 | TSC22: **transforming growth factor beta-stimulated protein TSC-22 Hs.114360 R16390 |
| 1180 | C8ORF1: chromosome 8 open reading frame 1 Hs.40539 AA278836 |
| 1181 | ESTs: Hs.129165 AA989211 |
| 1182 | DMTF: cyclin D binding Myb-like transcription factor 1 Hs.5671 AA129860 |
| 1183 | CDC7L1: CDC7 (cell division cycle 7, *S. cerevisiae*, homolog)-like 1 Hs.28853 N62245 Cdc7-related kinase |
| 1184 | LOC51700: cytochrome b5 reductase b5R.2 Hs.22142 AA425316 |
| 1185 | FLNA: filamin A, alpha (actin-binding protein-280) Hs.195464 AA598978 |
| 1186 | FLJ20257: hypothetical protein FLJ20257 Hs.178011 H78675 |
| 1187 | *Homo sapiens* cDNA FLJ13604 fis, clone PLACE1010401 Hs.23193 AA406599: |
| 1188 | ESTs: Hs.205227 R73480 |
| 1189 | SCYB14: small inducible cytokine subfamily B (Cys-X-Cys), member 14 (BRAK) Hs.24395 AA953842 |
| 1190 | MAPK8IP2: **mitogen-activated protein kinase 8 interacting protein 2 Hs.80545 AA418293 |
| 1191 | ZNF42: zinc finger protein 42 (myeloid-specific retinoic acid-responsive) Hs.169832 AA932642 |
| 1192 | ESTs: Hs.127054 AA862450 |
| 1193 | NUDT4: nudix (nucleoside diphosphate linked moiety X)-type motif 4 Hs.92381 AA425630 |
| 1194 | *Homo sapiens* cDNA FLJ10632 fis, clone NT2RP2005637 Hs.202596 H82421: |
| 1195 | LOC51042: zinc finger protein Hs.102419 AA033532 |
| 1196 | NUMA1: nuclear mitotic apparatus protein 1 Hs.301512 AA679293 |
| 1197 | ESTs,: Highly similar to A56429 I-kappa-B-related protein [*H. sapiens*] Hs.144614 AA293771 |
| 1198 | ESTs: Hs.127703 AA947258 |
| 1199 | *Homo sapiens* cDNA FLJ14214 fis, clone NT2RP3003576 Hs.321236 AA903913: |
| 1200 | NFKBIA: nuclear factor of kappa light polypeptide gene enhancer in B-cells inhibitor, alpha Hs.81328 W55872 IkB alpha |
| 1201 | ESTs: Hs.120029 AA707598 |
| 1202 | ESTs,: Moderately similar to A Chain A, Human Glucosamine-6-Phosphate Deaminase Isomerase At 1.75 A [*H. sapiens*] Hs.21398 AA172012 |
| 1203 | NFIA: nuclear factor I/A Hs.173933 AI912047 |
| 1204 | RECQL4: RecQ protein-like 4 Hs.31442 AA620446 |
| 1205 | **ESTs,: Weakly similar to ALU1_HUMAN ALU SUBFAMILY J SEQUENCE CONTAMINATION WARNING ENTRY [*H. sapiens*] Hs.318894 R96212 |

TABLE 1-continued

| Gene (Name and/or Symbol) or Number (EST, cDNA clone, or Accession) |
|---|

1206 *Homo sapiens* cDNA: FLJ21686 fis, clone COL09379 Hs.20787 R11371:
1207 LOC57168: similar to aspartate beta hydroxylase (ASPH) Hs.184390 H17272
1208 ESTs: Hs.26096 R54109
1209 *Homo sapiens* OSBP-related protein 6 mRNA, complete cds Hs.318775 AA680281:
1210 APACD: ATP binding protein associated with cell differentiation Hs.153884 N80741
1211 VIM: **vimentin Hs.297753 AI668662
1212 *Homo sapiens* cDNA FLJ13618 fis, clone PLACE1010925 Hs.17448 AA427980:
1213 NR3C1: nuclear receptor subfamily 3, group C, member 1 Hs.75772 N30428
    Glucocorticoid receptor
1214 *Homo sapiens* cDNA: FLJ21814 fis, clone HEP01068 Hs.289008 R12808:
1215 BRD7: bromodomain-containing 7 Hs.279762 AA488428
1216 MAP3K8: **mitogen-activated protein kinase kinase kinase 8 Hs.248 W42450
1217 ESTs: Hs.23213 H29336
1218 ESTs: Hs.122444 AA939019
1219 TUSP: tubby super-family protein Hs.102237 H78234
1220 KIAA1117: KIAA1117 protein Hs.278398 H01516
1221 Human: clone 137308 mRNA, partial cds Hs.322149 H91303
1222 ESTs: Hs.130214 AA456631
1223 RAB3A: RAB3A, member RAS oncogene family Hs.27744 H14230
1224 AA598795: Protein phosphatase 2 (formerly 2A), regulatory subunit B (P
1225 H2BFC: H2B histone family, member C Hs.137594 AI340654
1226 CFLAR: CASP8 and FADD-like apoptosis regulator Hs.195175 N94588
1227 CD24: CD24 antigen (small cell lung carcinoma cluster 4 antigen) Hs.286124 H59915
1228 EST: Hs.48532 N62402
1229 CCRK: cell cycle related kinase Hs.26322 H17616
1230 HECH: heterochromatin-like protein 1 Hs.278554 AI139106
1231 DKFZp547O146: hypothetical protein DKFZp547O146 Hs.91246 T80848
1232 ESTs: Hs.71574 AA135328
1233 HLXB9: homeo box HB9 Hs.37035 AI459915
1234 AA600222:
1235 SPINK5: serine protease inhibitor, Kazal type, 5 Hs.5476 W92134
1236 RNUT1: RNA, U transporter 1 Hs.21577 AA447799
1237 *Homo sapiens* cDNA: FLJ23013 fis, clone LNG00740 Hs.13075 AA464543:
1238 KIAA0063: KIAA0063 gene product Hs.3094 T82263
1239 DYRK2: dual-specificity tyrosine-(Y)-phosphorylation regulated kinase 2 Hs.173135
    R63622
1240 R94947:
1241 *Homo sapiens* cDNA FLJ14337 fis, clone PLACE4000494 Hs.180187 AA004903:
1242 FLJ20624: hypothetical protein FLJ20624 Hs.52256 AA431909
1243 ESTs: Hs.43838 R38261
1244 FLJ23053: hypothetical protein FLJ23053 Hs.94037 R25654
1245 MGC11266: hypothetical protein MGC11266 Hs.293943 AA400456
1246 ESTs,: Moderately similar to ALU8_HUMAN ALU SUBFAMILY SX SEQUENCE
    CONTAMINATION WARNING ENTRY [*H. sapiens*] Hs.34174 AA126603
1247 PLAUR: plasminogen activator, urokinase receptor Hs.179657 AA147962
1248 TSG101: tumor susceptibility gene 101 Hs.118910 AA670215
1249 HCNGP: transcriptional regulator protein Hs.27299 AA457232
1250 KIAA0978: KIAA0978 protein Hs.3686 AA857017
1251 ESTs: Hs.61708 AA033867
1252 ESTs: Hs.120734 AA827482
1253 ESTs: Hs.5909 AA972654
1254 CDH24: cadherin-like 24 Hs.155912 AI668564
1255 CCND1: cyclin D1 (PRAD1: parathyroid adenomatosis 1) Hs.82932 T77237
1256 ESTs: Hs.43148 AA284775
1257 ESTs: Hs.222566 T50982
1258 ESTs: Hs.194125 N52822
1259 EST: Hs.154621 AI138644
1260 MAN1A2: mannosidase, alpha, class 1A, member 2 Hs.239114 R22905
1261 MAN2A2: mannosidase, alpha, class 2A, member 2 Hs.295605 AA454175
1262 Human DNA sequence from clone 967N21 on chromosome 20p12.3-13. Contains the
    CHGB gene for chromogranin B (secretogranin 1, SCG1), a pseudogene similar to part
    of KIAA0172, the gene for a novel protein Hs.88959 W94690
1263 ESTs,: Highly similar to CIKG_HUMAN VOLTAGE-GATED POTASSIUM
    CHANNEL PROTEIN KV3.4 [*H. sapiens*] Hs.106486 H11376
1264 *Homo sapiens* HT023 mRNA, complete cds Hs.237225 AA169496:
1265 FLJ10339: **hypothetical protein FLJ10339 Hs.203963 H72354
1266 N66278:
1267 ESTs: Hs.6195 AA454745
1268 KIAA1404: KIAA1404 protein Hs.200317 W72798
1269 PMAIP1: phorbol-12-myristate-13-acetate-induced protein 1 Hs.96 AA458838
    APR = immediate-early-response gene = ATL-derived PMA-responsive
1270 G3BP: Ras-GTPase-activating protein SH3-domain-binding protein Hs.220689
    AA598628
1271 *Homo sapiens* cDNA: FLJ22807 fis, clone KAIA2887 Hs.261734 R26854:
1272 *Homo sapiens*, clone IMAGE: 3535294, mRNA, partial cds Hs.80449 T57359:
1273 CDC16: CDC16 (cell division cycle 16, *S. cerevisiae*, homolog) Hs.1592 AA410559
1274 FGA: **fibrinogen, A alpha polypeptide Hs.90765 AA026626
1275 ESTs: Hs.33446 N53560

TABLE 1-continued

Gene (Name and/or Symbol) or Number (EST, cDNA clone, or Accession)

1276 *Homo sapiens* cDNA FLJ14175 fis, clone NT2RP2002979 Hs.288613 AA054704:
1277 ESTs: Hs.44243 AA011390
1278 *Homo sapiens* mRNA full length insert cDNA clone EUROIMAGE 42408 Hs.284123 R61732:
1279 ESTs: Hs.53455 AA454165
1280 FLJ11264: hypothetical protein FLJ11264 Hs.11260 AI219094
1281 MBD4: methyl-CpG binding domain protein 4 Hs.35947 AA010492
1282 FLJ11305: hypothetical protein FLJ11305 Hs.7049 N94612
1283 *Homo sapiens*, Similar to CG5057 gene product, clone MGC: 5309, mRNA, complete cds Hs.13885 AA460004:
1284 ARHB: ras homolog gene family, member B Hs.204354 H88963
1285 ITPR3: inositol 1,4,5-triphosphate receptor, type 3 Hs.77515 AA865667
1286 HMG20B: high-mobility group 20B Hs.32317 AA775743
1287 ESTs: Hs.146276 AI214204
1288 PTPN9: protein tyrosine phosphatase, non-receptor type 9 Hs.147663 AA434420
1289 *Homo sapiens* clone FLB9213 PRO2474 mRNA, complete cds Hs.21321 AA486770:
1290 H21107:
1291 HSPC157: HSPC157 protein Hs.279842 N20480
1292 *Homo sapiens* mRNA; cDNA DKFZp564O2363 (from clone DKFZp564O2363) Hs.321403 AA406332:
1293 ESTs: Hs.150623 AA693532
1294 EST: Hs.188697 AA199733
1295 CLECSF2: C-type (calcium dependent, carbohydrate-recognition domain) lectin, superfamily member 2 (activation-induced) Hs.85201 H11732 AICL = activation-induced C-type lectin
1296 ITPR1: inositol 1,4,5-triphosphate receptor, type 1 Hs.198443 AA035450
1297 CHML: choroideremia-like (Rab escort protein 2) Hs.170129 R91881
1298 CDC42: cell division cycle 42 (GTP-binding protein, 25 kD) Hs.146409 AA668681
1299 FKBP5: **FK506-binding protein 5 Hs.7557 AA872767

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A method of treating prostate cancer in a patient comprising:
   (1) obtaining a sample comprising prostate cancer tumor tissue from said patient;
   (2) determining by quantitative real-time PCR of cDNA the expression of a panel of genes comprising ASF1B, ASPM, BIRC5, BUB1B, C18orf24, CDC2, CDC20, CDCA3, CDCA8, CDKN3, CENPF, CENPM, CEP55, DLGAP5, DTL, FOXM1, KIAA0101, KIF11, KIF20A, MCM10, NUSAP1, ORC6L, PBK, PLK1, PRC1, PTTG1, RAD51, RAD54L, RRM2, TK1 and TOP2A in said sample comprising prostate cancer tumor tissue;
   (3) prognosing said patient as having a decreased likelihood of prostate cancer progression when the average expression of the genes ASF1B, ASPM, BIRC5, BUB1B, C18orf24, CDC2, CDC20, CDCA3, CDCA8, CDKN3, CENPF, CENPM, CEP55, DLGAP5, DTL, FOXM1, KIAA0101, KIF11, KIF20A, MCM10, NUSAP1, ORC6L, PBK, PLK1, PRC1, PTTG1, RAD51, RAD54L, RRM2, TK1 and TOP2A is lower than a threshold index value; and
   (4) administering to said patient active surveillance based on the prognosis.

2. The method of claim 1, wherein said determining step further comprises determining the expression of one or more housekeeping genes in said sample.

3. The method of claim 2, wherein said determining step further comprises normalizing the expression of the genes ASF1B, ASPM, BIRC5, BUB1B, C18orf24, CDC2, CDC20, CDCA3, CDCA8, CDKN3, CENPF, CENPM, CEP55, DLGAP5, DTL, FOXM1, KIAA0101, KIF11, KIF20A, MCM10, NUSAP1, ORC6L, PBK, PLK1, PRC1, PTTG1, RAD51, RAD54L, RRM2, TK1 and TOP2A using the expression of the housekeeping genes.

4. The method of claim 3, wherein the housekeeping genes comprise the genes RPL38, UBA52, PSMC1, RPL4, RPL37, RPS29, SLC25A3, CLTC, TXNL1, PSMA1, RPL8, MMADHC, RPL13A, LOC728658, PPP2CA and MRFAP1.

5. A method of treating prostate cancer in a patient comprising:
   (1) obtaining a sample comprising prostate cancer tumor tissue from said patient;
   (2) determining by quantitative PCR of cDNA the expression of a panel of genes comprising ASF1B, ASPM, BIRC5, BUB1B, C18orf24, CDC2, CDC20, CDCA3, CDCA8, CDKN3, CENPF, CENPM, CEP55, DLGAP5, DTL, FOXM1, KIAA0101, KIF11, KIF20A, MCM10, NUSAP1, ORC6L, PBK, PLK1, PRC1, PTTG1, RAD51, RAD54L, RRM2, TK1 and TOP2A in said sample comprising prostate cancer tumor tissue;
   (3) prognosing said patient as having an increased likelihood of prostate cancer progression when the average expression of the genes ASF1B, ASPM, BIRC5, BUB1B, C18orf24, CDC2, CDC20, CDCA3, CDCA8, CDKN3, CENPF, CENPM, CEP55, DLGAP5, DTL, FOXM1, KIAA0101, KIF11, KIF20A, MCM10, NUSAP1, ORC6L, PBK, PLK1, PRC1, PTTG1, RAD51, RAD54L, RRM2, TK1 and TOP2A exceeds a threshold index value; and (4) administering to said patient one or more of chemotherapy, radiation therapy or surgery based on the prognosis.

6. The method of claim 5, wherein said determining step further comprises determining the expression of one or more housekeeping genes in said sample.

7. The method of claim 6, wherein said determining step further comprises normalizing the expression of the genes ASF1B, ASPM, BIRC5, BUB1B, C18orf24, CDC2, CDC20, CDCA3, CDCA8, CDKN3, CENPF, CENPM, CEP55, DLGAP5, DTL, FOXM1, KIAA0101, KIF11, KIF20A, MCM10, NUSAP1, ORC6L, PBK, PLK1, PRC1, PTTG1, RAD51, RAD54L, RRM2, TK1 and TOP2A using the expression of the housekeeping genes.

8. The method of claim 7, wherein the housekeeping genes comprise the genes RPL38, UBA52, PSMC1, RPL4, RPL37, RPS29, SLC25A3, CLTC, TXNL1, PSMA1, RPL8, MMADHC, RPL13A, LOC728658, PPP2CA and MRFAP1.

* * * * *

UNITED STATES PATENT AND TRADEMARK OFFICE
CERTIFICATE OF CORRECTION

PATENT NO. : 9,605,319 B2  
APPLICATION NO. : 13/819963  
DATED : March 28, 2017  
INVENTOR(S) : Stone et al.

Page 1 of 1

It is certified that error appears in the above-identified patent and that said Letters Patent is hereby corrected as shown below:

On the Title Page

Page 2, item (56) under Other Publications, Line 46-47 should read, "International Search Report and Written Opinion from Application No. PCT/US2013/040373, dated Apr. 1, 2014."

Page 3, item (56) under Other Publications, Line 53-54 should read, "International Search Report and Written Opinion from Application No. PCT/US2010/020397, dated Feb. 10, 2010."

Page 3, item (56) under Other Publications, Line 59-60 should read, "International Search Report and Written Opinion from Application No. PCT/US2012/051447, dated Feb. 21, 2013."

Signed and Sealed this  
Twenty-eighth Day of November, 2017

Joseph Matal  
*Performing the Functions and Duties of the*  
*Under Secretary of Commerce for Intellectual Property and*  
*Director of the United States Patent and Trademark Office*